(12) United States Patent
Jiménez et al.

(10) Patent No.: US 8,030,284 B2
(45) Date of Patent: Oct. 4, 2011

(54) TREATMENT OF EYE DISORDERS CHARACTERIZED BY AN ELEVATED INTRAOCULAR PRESSURE BY SIRNAS

(75) Inventors: Ana I. Jiménez, Madrid (ES); Ángela Sesto, Madrid (ES); José P. Roman, Vitoria (ES); Irene Gascón, Madrid (ES); Gonzalo González de Buitrago, Madrid (ES)

(73) Assignee: Sylentis S.A.U., Madrid (ES)

( * ) Notice: Subject to any disclaimer, the term of this patent is extended or adjusted under 35 U.S.C. 154(b) by 0 days.

(21) Appl. No.: 11/574,169

(22) PCT Filed: Aug. 23, 2005

(86) PCT No.: PCT/GB2005/050134
§ 371 (c)(1),
(2), (4) Date: Jul. 16, 2007

(87) PCT Pub. No.: WO2006/021817
PCT Pub. Date: Mar. 2, 2006

(65) Prior Publication Data
US 2007/0270365 A1    Nov. 22, 2007

(30) Foreign Application Priority Data

Aug. 23, 2004 (GB) .................................. 0418762.1
Feb. 18, 2005 (GB) .................................. 0503412.9

(51) Int. Cl.
*A61K 48/00* (2006.01)
*C07H 21/04* (2006.01)
(52) U.S. Cl. ............................. 514/44; 536/24.5
(58) Field of Classification Search ........................ None
See application file for complete search history.

(56) References Cited

U.S. PATENT DOCUMENTS

| | | | |
|---|---|---|---|
| 4,343,794 A | | 8/1982 | Podos et al. |
| 4,617,299 A | * | 10/1986 | Knepper ........................ 514/178 |
| 4,652,586 A | | 3/1987 | Nathanson |
| 4,757,089 A | * | 7/1988 | Epstein ........................ 514/571 |
| 4,812,448 A | * | 3/1989 | Knepper ........................ 514/178 |
| 5,075,323 A | * | 12/1991 | Fain et al. ........................ 514/338 |
| 5,242,943 A | | 9/1993 | Louis et al. |
| 5,260,059 A | * | 11/1993 | Acott et al. ................. 424/94.67 |
| 5,464,866 A | * | 11/1995 | Clark et al. ........................ 514/480 |
| 5,545,626 A | * | 8/1996 | Stein et al. ........................ 514/44 A |
| 5,585,401 A | * | 12/1996 | Brandt et al. ........................ 514/562 |
| 6,365,576 B1 | | 4/2002 | Carr |
| 6,372,249 B1 | * | 4/2002 | Smith et al. ........................ 424/450 |
| 6,489,307 B1 | | 12/2002 | Phillips et al. |
| 7,176,304 B2 | | 2/2007 | McSwiggen et al. |
| 7,294,504 B1 | | 11/2007 | Wang |
| 7,462,602 B2 | * | 12/2008 | Schultz et al. ........................ 514/44 R |
| 7,521,431 B2 | * | 4/2009 | Reich et al. ........................ 514/44 R |
| 7,579,457 B2 | | 8/2009 | Khvorova et al. |
| 7,592,324 B2 | | 9/2009 | Shepard et al. |
| 7,592,325 B2 | | 9/2009 | Jimenez et al. |

| | | |
|---|---|---|
| 2002/0055536 A1 | 5/2002 | DeWitte et al. |
| 2002/0114784 A1 | 8/2002 | Li et al. |
| 2002/0165158 A1 | 11/2002 | King |
| 2004/0115641 A1* | 6/2004 | Cowsert et al. .................... 435/6 |
| 2004/0167090 A1 | 8/2004 | Monahan et al. |
| 2004/0198640 A1 | 10/2004 | Leake et al. |
| 2004/0209832 A1 | 10/2004 | McSwiggen et al. |
| 2004/0224405 A1 | 11/2004 | Leake et al. |
| 2004/0235031 A1 | 11/2004 | Schultz et al. |
| 2004/0259247 A1 | 12/2004 | Tuschl et al. |
| 2004/0266707 A1 | 12/2004 | Leake et al. |
| 2005/0020521 A1 | 1/2005 | Rana |
| 2005/0171039 A1 | 8/2005 | McSwiggen et al. |
| 2006/0058266 A1 | 3/2006 | Manoharan et al. |
| 2006/0094032 A1 | 5/2006 | Fougerolles et al. |
| 2006/0172963 A1 | 8/2006 | Shepard et al. |
| 2006/0172965 A1 | 8/2006 | Shepard et al. |
| 2007/0093435 A1 | 4/2007 | Andrews et al. |
| 2007/0167384 A1 | 7/2007 | Leake et al. |
| 2009/0326044 A1 | 12/2009 | Shepard et al. |

FOREIGN PATENT DOCUMENTS

| | | |
|---|---|---|
| EP | 1 527 176 | 1/2007 |
| GB | 2406568 | 4/2005 |
| WO | WO 03/057840 | 7/2003 |
| WO | WO 03/070744 | 8/2003 |
| WO | 03/087367 | 10/2003 |
| WO | WO 2004/009794 | 1/2004 |
| WO | WO 2004/009796 | 1/2004 |
| WO | WO 2004/029212 | 4/2004 |
| WO | 2004/042024 | 5/2004 |
| WO | WO 2005/044976 | 5/2005 |
| WO | WO 2005/045037 | 5/2005 |
| WO | 2005/076998 | 8/2005 |
| WO | 2005/079815 | 9/2005 |
| WO | WO 2006/083945 | 8/2006 |
| WO | WO 2006/084217 | 8/2006 |
| WO | WO 2006/099353 | 9/2006 |

OTHER PUBLICATIONS

Denkert et al (Oncogene 22: 8653-8661, 2003).*
Gonzales et al (IOVS 41(2): 352-361, 2000).*
Vittal et al (IOVS 46(8): 2857-2868, 2005).* Diskin al (IOVS 47(4): 1491-1499, 2006).*
Rao et al (IOVS 42(5): 1029-1037, 2001).*
Madsen (Documenta ophthalmologica. Advances in ophthalmology, (May 14, 1971) vol. 29, No. 2, pp. 345-349).*
Herkel U et al., "Update on Topical Carbonic Anhydrase Inhibitors", Current Opinion in Ophthalmology, Apr. 2001, vol. 12, No. 2, pp. 88-93.
Woodward et al., "The Inflow and Outflow of Anti-Glaucoma Drugs", Trends in Pharmacological Sciences, vol. 25, No. 5, May 2004, pp. 238-241.
Jesús Pintor et al., "Adenosine Tetraphosphate, $Ap_4$, a Physiological Regulator of Intraocular Pressure in Normotensive Rabbit Eyes," The Journal of Pharmacology and Experimental Therapeutics, vol. 308, No. 2, pp. 468-473, 2004.

(Continued)

*Primary Examiner* — Richard Schnizer
(74) *Attorney, Agent, or Firm* — Kenneth H. Sonnenfeld; Margaret B. Brivanlou; King & Spalding LLP

(57) ABSTRACT

Sequences and protocols for treatment of eye conditions by use of RNA interference are disclosed. Target genes are selected from those responsible for aqueous flow or aqueous outflow, while particularly preferred conditions to be treated include glaucoma and uveitis.

7 Claims, 20 Drawing Sheets

OTHER PUBLICATIONS

Office Action dated Jul. 14, 2008 in corresponding U.S. Appl. No. 11/360,305.

Office Action dated Jan. 29, 2009 in corresponding U.S. Appl. No. 11/360,305.

Abrams et al., "Comparison of Three Tonometers for Measuring Intraocular Pressure in Rabbits," Invest Ophthalmol Vis Sci. Apr. 1996, 37(5):940-944.

Akashi et al., "Suppression of Gene Expression by RNA Interference in Cultured Plant Cells," Antisense Nucleic Acid Drug Dev, 2001, 11(6):359-367.

Ambion, Tech Notes 10(4) and siRNA Target Finder (http://www.ambion.com/techlib/misc/siRNA_finder.html, available to the public) retrieved on May 1, 2008, siRNA target hit for SEQ ID No. 139 included.

Banerjee et al., "Control of Developmental Timing by Small Temporal RNAs: a Paradigm for RNA-mediated Regulation of Gene Expression," Bioessays, 2002, 24(2):119-129.

Bhattacharya et al., "Cochlin Deposits in the Trabecular Meshwork of the Glaucomatous DBA/2J mouse," Exp Eye Res., May 2005a 80(5):741-744.

Bhattacharya et al., "Proteomics Reveal Cochlin Deposits Associated with Glaucomatous Trabecular Meshwork," J. Biol. Chem., Feb. 2005b, 18;280(7):6080-6084, Epub Dec. 3, 2004.

Bosher et al., "RNA Interference: Genetic Wand and Genetic Watchdog." Nat Cell Biol, 2000, 2(2):E31-6.

Braasch et al., "Novel Antisense and Peptide Nucleic Acid Strategies for Controlling Gene Expression," Biochemistry, 2002, 41(14):4503-4510.

Brummelkamp et al., "A System for Stable Expression of Short Interfering RNAs in Mammalian Cells," Science, American Association for the Advancement of Science, 2002, 296(5567):550-553.

Bunce et al., "Associations between the deletion polymorphism of the angiotensin 1-converting enzyme gene and ocular signs of primary open-angle glaucoma," Graefes Arch Clin Exp Ophthalmol., Apr. 2005 243(4):294-299. Epub Oct. 13, 2004.

Caplen et al., "Specific inhibition of Gene Expression by Small Double Stranded RNAs in Invertebrate and Vertebrate Systems," Proc. Natl. Acad. Sci. USA, 2001,98: 9742-9747.

Costagliola et al., "Effect of Oral Losartan Potassium Administration on Intraocular Pressure in Normotensive and Glaucomatous Human Subjects," Exp Eye Res., Aug. 2000, 71(2):167-171.

Costagliola et al., "Effect of Oral Captopril (SQ 14225) on Intraocular Pressure in Man," Eur. J. Opthalmol, Jan. 1995, 5(1):19-25.

Cullinane et al., "Renin-angiotensin System Expression and Secretory Function in Cultured human Ciliary Cody Nonpigmented Epithelium," Br J Ophthalmol. Jun. 2002, 86(6):6766-83.

Elabashir et al., "Duplexes of 21-Nucleotide RNAs mediate RNA interference in Cultured Mammalian Cells," Nature, May 24, 2001, 411(6836):494-498.

Elbashir et al., "RNA Interference is Mediated by 21- and 22-Nucleotide RNAs," Genes Dev, 2001, 15(2):188-200.

Fattal et al., "Ocular Delivery of Nucleic Acids: Antisense Oligonucleotides, Aptamers and siRNA," Advanced Drug Delivery Reviews, 2006, 58:1203-1223.

Fire et al., "Potent and Specific Genetic Interference by Double Stranded RNA in a *Caenorhabditis elegans*," Nature, 1998, 391(6669):806-11.

Ge et al., "RNA Interference of Influenza Virus Production by Directly Targeting mRNA for Degradation and Indirectly Inhibiting all Viral RNA Transcription," Proc Natl Acad Sci USA., 2003, 100(5):2718-2723.

Gil et al., "Induction of Apoptosis by the dsRNA-dependent Protein Kinase (PKR): Mechanism of Action," Apoptosis, 2000, 5(2)107-114.

Grosshans et al., "Micro-RNAs: Small is Plentiful," J Cell Bioi, 2002, 156(1):17-21.

Hammond et al., "Post-Transcriptional Gene Silencing By Double-Standed RNA," Nature, 2001, 2:110-119.

Hara et al., "Bunazosin, a Selective Alpha1-Adrenoceptor Antagonist, as an Anti-glaucoma Drug: Effects on Ocular Circulation and Retinal Neuronal Damage," Cardiovasc Drug Rev. 2005 Spring;23(1):43-56.

Khaw et al., "Glaucoma-1: Diagnosis," BMJ, 2004a, 328:97-99.

Khaw et al., "Glaucoma-2: Treatment," BMJ, 2004b, 328:156-158.

Kim et al., "Inhibition of Ocular Angiogenesis by Sirna Targeting Vascular Endothelial Growth Factor Pathway Genes Therapeutics Strategy for Herpetic Stromal Keratititis," American Journal of Pathology, Dec. 2004, 165(6):2177-285.

Krutzfeldt et al., "Silencing of microRNAs in vivo with 'Antagomirs'," Nature, 2005, 438(7068):685-689.

Mahato et al., "Modulation of Gene Expression by Antisense and Antigene Oligodeoxynucleotides and Small Interfering RNA," Expert Opinion on Drug Delivery, Jan. 2005, 2(1):3-28.

Miller et al., "Allele-specific Silencing of Dominant Disease Genes," Proceedings of the National Academy of Sciences of USA, Jun. 10, 2003, 100(12):7195-7200.

Osborne et al., "Some Current Ideas on the Pathogenesis and the Role of Neuroprotection in Glaucomatous Optic Neuropathy," Eur J Ophthalmol., Apr. 2003, 13Suppl. 3:S19-26.

Paddison et al., "Short hairpin RNAs (shRNAs) Induce Sequence-Specific Silencing in Mammalian Cells," Genes Dev, 2002, 16(8):948-958.

Reich et al., "Small Interfering RNA (siRNA) Targeting *VEGF* effectively Inhibits Ocular Neovascularization in a Mouse Model," Molecular Vision, 2003, 9:210-216.

Sakaguchi et al., "Chymase and Angiotensin Converting Enzyme Activities in a Hamster Model of Glaucoma Filtering Surgery," Curr Eye Res., May 2002, 24(5):325-331.

Scherer et al., "Approaches for the Sequence-Specific Knockdown of mRNA," Nat. Biotechnology, 2003, 21(12):1457-1465.

Shah et al., "Oculohypotensive Effect of Angiotensin-Converting Enzyme Inhibitors in Acute and Chronic Models of Glaucoma," J Cardiovasc Pharmacol. Aug. 2000, 36(2):169-175.

Tuschl et al., "Targeted mRNA degradation by double-stranded RNA in vitro," Genes Dev., 1999, 13(24):3191-3197.

Uprichard et al., The Therapeutic Potential of RNA Interference, FEBS Letters, Oct. 31, 2005 579(26):5996-6007.

Wang et al., Effect of C5-088, an Angiotensin AT1 Receptor Antagonist, on Intraocular Pressure in Glaucomatous Monkey Eyes, Exp Eye Res., May 2005 80(5):629-632. Epub Jan. 4, 2005.

Wetering et al., "Specific Inhibition of Gene Expression Using a Stably Integrated, Inducible Small-Interfering-RNA Vector," EMBO Reports, Jun. 2003, 4(6):609-615.

Wianny et al., "Specific Interference with Gene Function by Double-Stranded RNA in Early Mouse Development," Nat Cell Biol, 2000, 2(2):70-75.

Williams BR, "Role of the Double-Stranded RNA-activated Protein kinase (PKR) in Cell Regulation," Biochem Soc Trans, 1997, 25(2):509-513.

Wirtz et al., "The Genetic Loci of Open-Angle Glaucoma," Ophthalmol. Clin. North Am. 2003 16:505-514.

Wiznerowicz et al., "Conditional Suppression of Cellular Genes: Lentivirus Vector-Mediated Drug-Inducible RNA Interference," Journal of Virology, Aug. 2003, 77(16):8957-8961.

Xie et al., "Harnessing in vivo siRNA Delivery for Drug Discovery and Therapeutic Development," Drug Discovery Today, Jan. 2006, 11(1-2):67-73.

Yang-Feng et al., "Chromosomal Organization of Adrenergic Receptor Genes," PNAS, 1990, 87:1516-1520.

Achenbach et al., Oligonucleotide-Based Knockdown Technologies: Antisense Versus RNA Interference, ChemBioChem., 4, pp. 928-935, 2003.

Amaratunga et al., "Inhibition of Kinesin Synthesis and Rapid Anterograde Axonal Transport in Vivo by an Antisense Oligonucleotide," The Journal of Biological Chemistry, 268(23) pp. 17427-17430, Aug. 15, 1993.

Ambion, "The Basics: RNase Control," printout from website <<http://web.archive.org/web/20041207234247>>, dated 2004, retrieved on Sep. 17, 2009.

Banan et al., "The Ins and Outs of RNAi in Mammalian Cells," Current Pharmaceutical Biotechnology, 5, pp. 441-450, 2004.

Busch et al., "Adenylyl Cyclase in Human and Bovine Trabecular Meshwork," Investigative Ophthalmology & Visual Science, 34(10), pp. 3028-3034, Sep. 1993.

Cho et al., "Small Interfering RNA-Induced TLR3 Activation Inhibits Blood and Lymphatic Vessel Growth," PNAS, pp. 1-6, Dec. 5, 2008.

Crooke et al., "Nucleotides in Ocular Secretions: Their Role in Ocular Physiology," Pharmacology & Therapeutics, 119, pp. 55-73, 2008.

Diffen, DNA vs. RNA—Difference and Comparison, retrieved from <<http://www.diffen.com/difference/Dna_vs_Rna>> on May 21, 2009.

Elena et al., "Autoradiographic Localization of Beta-Adrenergic Receptors in Rabbit Eye," Investigative Ophthalmology & Visual Science, 28, pp. 1436-1441, Aug. 1987.

Horinouchi et al., "Pharmacological Evaluation of Ocular β-Adrenoceptors in Rabbit by Tissue Segment Binding Method," Life Sciences, 84, pp. 181-187, 2009.

Freier et al., "The Ups and Downs of Nucleic Acid Duplex Stability: Structure-Stability Studies on Chemically-Modified DNA:RNA Duplexes," Nucleic Acids Research, 25(22), pp. 4429-4443, 1997.

Jens Kurreck, "Antisense Technologies," Eur. J. Biochem., 270, pp. 1628-1644, 2003.

Jens Kurreck, "Antisense and RNA Interference Approaches to Target Validation in Pain Research," Current Opinion in Drug Discovery & Development, 7(2), pp. 179-187, 2004.

Kaplan et al., "Aqueous Humor Flow in Unilateral Carotid Stenosis," Journal of Glaucoma, 5, pp. 237-240, 1996.

Krohn et al., "Transcorneal Flux of Topical Pilocarpine to the Human Aqueous," Am. J. Ophthalmol., 87(1), pp. 50-56, Jan. 1979, Abstract retrieved from <<http://www.ncbi.nlm.nih.gov/pubmed/434053>> on Nov. 9, 2009.

Kwon et al., "Primary Open-Angle Glaucoma," The New England Journal of Medicine, 360(11), pp. 1113-1124, Mar. 12, 2009.

Lograno et al., "Receptor-Responses in Fresh Human Ciliary Muscle," Br. J. Pharmac., 87, pp. 379-385, 1986.

Meade et al., "Enhancing the Cellular Uptake of siRNA Duplexes Following Noncovalent Packaging with Protein Transduction Domain Peptides," Advanced Drug Delivery Reviews, 60, pp. 530-536, 2008.

Muratovska et al., "Conjugate for Efficient Delivery of Short Interfering RNA (siRNA) into Mammalian Cells," FEBS Letters, 558, pp. 63-68, 2004.

Office Action dated Nov. 3, 2009 in corresponding U.S. Appl. No. 12/170,078.

Office Action dated Oct. 15, 2009 in corresponding U.S. Appl. No. 12/170,104.

Office Action dated Oct. 30, 2009 in corresponding U.S. Appl. No. 12/170,116.

Office Action dated Oct. 30, 2009 in corresponding U.S. Appl. No. 12/170,132.

Office Action dated Oct. 19, 2009 in corresponding U.S. Appl. No. 12/170,148.

Office Action dated Oct. 15, 2009 in corresponding U.S. Appl. No. 12/170,157.

Valls et al., "Validation of a Device for Transcorneal Drug Permeation Measure," Journal of Pharmaceutical and Biomedical Analysis, 48, pp. 657-663, 2008.

U.S. Appl. No. 12/563,530, filed Sep. 21, 2009, Ana Jimenez et al.
U.S. Appl. No. 11/360,305, filed Feb. 22, 2006, Ana Jimenez et al.
U.S. Appl. No. 12/170,078, filed Jul. 9, 2008, Ana Jimenez et al.
U.S. Appl. No. 12/170,104, filed Jul. 9, 2008, Ana Jimenez et al.
U.S. Appl. No. 12/170,116, filed Jul. 9, 2008, Ana Jimenez et al.
U.S. Appl. No. 12/170,132, filed Jul. 9, 2008, Ana Jimenez et al.
U.S. Appl. No. 12/170,148, filed Jul. 9, 2008, Ana Jimenez et al.
U.S. Appl. No. 12/170,157, filed Jul. 9, 2008, Ana Jimenez et al.

Tan et al., "Recent Developments in Understanding the Pathophysiology of Elevated Intraocular Pressure," Current Opinion in Opthalmology, vol. 17, pp. 168-174, 2006.

Office Action dated Mar. 19, 2010 in corresponding U.S. Appl. No. 12/170,078.

Office Action dated Mar. 22, 2010 in corresponding U.S. Appl. No. 12/170,104.

Office Action dated Mar. 19, 2010 in corresponding U.S. Appl. No. 12/170,116.

Office Action dated Mar. 22, 2010 in corresponding U.S. Appl. No. 12/170,132.

Office Action dated Mar. 22, 2010 in corresponding U.S. Appl. No. 12/170,148.

Office Action dated Mar. 22, 2010 in corresponding U.S. Appl. No. 12/170,157.

Office Action dated Mar. 25, 2010 in corresponding U.S. Appl. No. 12/563,530.

Ghate D. and Edelhauser H.F., "Barriers to glaucoma drug delivery," *J. Glaucoma*, 17(2), 147-56, 2008.

Barar J. et al., "Ocular novel drug delivery" impacts of membranes and barriers, *Expert Opin. Drug Deliv.*, 5(5): 567-81, 2008.

Borrás, "Gene Expression in the Trabecular Meshwork and the Influence of Intraocular Pressure," *Progress in Retinal and Eye Research*, 22, 435-463, 2003.

Comes N. and Borrás T, "Functional delivery of synthetic naked siRNA to the human trabecular meshwork in perfused organ cultures," *Molec. Vision*, 13: 1363-74, 2007.

Caballero et al., "Inefficient Processing of an Olfactomedin-Deficient Myocilin Mutant: Potential Physiological Relevance to Glaucoma," *Biochemical and Biophysical Research Communications*, 282, 662-670, 2001.

Nie Y., et al., "The potential therapeutic of siRNA eye drops in ocular diseases," *Bioscience Hypotheses*, 2, 223-25, 2009.

Epstein et al., "*Effect of Iodoacetamide Perfusion on Outflow Facility and Metabolism of the Trabecular Meshwork*," Invest. Ophthalmol. Vis. Sci., 625-631, May 1981.

U.S. Appl. No. 12/874,928, filed Sep. 2, 2010, Ana Jimenez et al.

Ambati et al., "Transscleral Delivery of Bioactive Protein to the Choroid and Retina," Investigative Ophthalmology & Visual Science, vol. 41, No. 5, pp. 1186-1191, Apr. 2000.

Bass, "The Short Answer," Nature, vol. 411, pp. 428-429, 2001.

Bill, "Movement of Albumin and Dextran," Arch. Opthal., vol. 74, pp. 248-252, Aug. 1965.

Elbashir et al., "Functional Anatomy of siRNAs for Mediating Efficient RNAi in Drosophila Melanogaster Embryo Lysate," EMBO Journal, vol. 20, No. 23, pp. 6877-6888, 2001.

Hogeboom et al., "Angiotensin Converting Enzyme Inhibiting Therapy is Associated with Lower Vitreous Vascular Endothelial Growth Factor Concentrations in Patients with Proliferative Diabetic Retinopathy," Diabetologia, vol. 45, pp. 203-209, 2002.

Okabe et al., "Effect of Benzalkonium Chloride on Transscleral Drug Delivery," Investigative Ophthalmology & Visual Science, vol. 46, No. 2, pp. 703-708, Feb. 2005.

Olsen et al., "Human Scleral Permeability: Effects of Age, Cryotherapy, Transscleral Diode Laser, and Surgical Thinning," Investigative Ophthalmology & Visual Science, vol. 36, No. 9. pp. 1893-1903, Aug. 1995.

Stamer et al., "Isolation and Culture of Human Trabecular Meshwork Cells by Extracellular Matrix Digestion," Current Eye Research, pp. 611-617, Jan. 10, 1995.

Wax et al., "Vacuolar $H^+$-ATPase in Ocular Ciliary Epithelium," Proc. Natl. Acad. Sci., vol. 94, pp. 6752-6757, Jun. 1997.

Yang et al., "Early Growth Response Gene 1 Modulates Androgen Receptor Signaling in Prostate Carcinoma Cells," The Journal of Biological Chemistry, 278(41), pp. 39906-39911, 2003.

Office Action dated Sep. 23, 2010 in corresponding U.S. Appl. No. 12/170,078.

Office Action dated Sep. 23, 2010 in corresponding U.S. Appl. No. 12/170,104.

Office Action dated Sep. 23, 2010 in corresponding U.S. Appl. No. 12/170,116.

Office Action dated Sep. 23, 2010 in corresponding U.S. Appl. No. 12/170,132.

Office Action dated Sep. 23, 2010 in corresponding U.S. Appl. No. 12/170,148.

Office Action dated Sep. 23, 2010 in corresponding U.S. Appl. No. 12/170,157.

\* cited by examiner

Figure 1

| Gene name | Transcript accession numbers |
|---|---|
| Carbonic anhydrase IV (CA4) | NM_000717 |
| Carbonic anhydrase II (CA2) | NM_000067 |
| Adrenergic, beta-1-, receptor (ADRB1) | NM_000684 |
| Adrenergic, beta-2-, receptor (ADRB2) | NM_000024 |
| Acetylcholinesterase (ACHE) | NM_000665, NM_015831 |
| Selectin E (endothelial adhesion molecule 1) (SELE) | NM_000450 |
| Prostaglandin-endoperoxide synthase 1 (prostaglandin G/H synthase and cyclooxygenase) (PTGS1) | NM_000962, NM_080591 |
| Prostaglandin-endoperoxide synthase 2 (prostaglandin G/H synthase and cyclooxygenase) (PTGS2) | NM_000963 |
| Carbonic anhydrase XII (CA12) | NM_001218, NM_206925 |
| Adrenergic, alpha-1A-, receptor (ADRA1A) | NM_033302, NM_033303, NM_033304, NM_000680 |
| Adrenergic, alpha-1B-, receptor (ADRA1B) | NM_000679 |
| Adrenergic, alpha-1D-, receptor (ADRA1D) | NM_000678 |
| Angiotensinogen (AGT) | NM_000029 |
| Angiotensin II receptor, type 1 (AGTR1) | NM_000685, NM_009585, NM_004835, NM_031850, NM_032049 |
| Angiotensin II receptor, type 2 (AGTR2) | NM_000686 |
| Angiotensin I converting enzyme 1 (ACE1) | NM_000789, NM_152830, NM_152831 |
| Angiotensin I converting enzyme 2 (ACE2) | NM_021804 |
| Renin (REN) | NM_000537 |
| Coagulation factor C homolog, cochlin (COCH) | NM_004086 |
| ATPase, Na+/K+ transporting, alpha 1 polypeptide (ATP1A1) | NM_000701, NM_001001586 |
| ATPase, Na+/K+ transporting, alpha 2 (+) polypeptide (ATP1A2) | NM_000702 |
| ATPase, Na+/K+ transporting, alpha 3 polypeptide (ATP1A3) | NM_152296 |
| ATPase, Na+/K+ transporting, beta 1 polypeptide (ATP1B1) | NM_001677, NM_001001787 |
| ATPase, Na+/K+ transporting, beta 2 polypeptide (ATP1B2) | NM_001678 |

Figure 2A

| CA4 | |
|---|---|
| SEQ ID 1 | GCCGAGTCCTCCAACTACC |
| SEQ ID 2 | CTACCCCTGCTTGGTGCCA |
| SEQ ID 3 | GTGGGGTGGAAACTGCCAG |
| SEQ ID 4 | ACTGCCAGAAGGACCGCCA |
| SEQ ID 5 | CATCGTCACCACCAAGGCA |
| SEQ ID 6 | GGCAAAGGTGGACAAAAAA |
| SEQ ID 7 | AGGTGGACAAAAAACTGGG |
| SEQ ID 8 | GGTGGACAAAAAACTGGGA |
| SEQ ID 9 | AAAACTGGGACGCTTCTTC |
| SEQ ID 10 | AAACTGGGACGCTTCTTCT |
| SEQ ID 11 | AACTGGGACGCTTCTTCTT |
| SEQ ID 12 | ACTGGGACGCTTCTTCTTC |
| SEQ ID 13 | CTGGGACGCTTCTTCTTCT |
| SEQ ID 14 | GAAGCAAACGTGGACTGTC |
| SEQ ID 15 | GCAAACGTGGACTGTCCAA |
| SEQ ID 16 | ACGTGGACTGTCCAAAATA |
| SEQ ID 17 | CGTGGACTGTCCAAAATAA |
| SEQ ID 18 | AATAACGGGCACTCAGTGA |
| SEQ ID 19 | ATAACGGGCACTCAGTGAT |
| SEQ ID 20 | TAACGGGCACTCAGTGATG |
| SEQ ID 21 | CGGGCACTCAGTGATGATG |
| SEQ ID 22 | CAAGGCCAGCATTTCTGGA |
| SEQ ID 23 | GGCCAGCATTTCTGGAGGA |
| SEQ ID 24 | ACAGTTGCACCTGCACTGG |
| SEQ ID 25 | CAGTTGCACCTGCACTGGT |
| SEQ ID 26 | AGAGAAGGGGACATCGAGG |
| SEQ ID 27 | GAGAAGGGGACATCGAGGA |
| SEQ ID 28 | GGGGACATCGAGGAATGTG |
| SEQ ID 29 | TGTGAAAGAGGCCCAGGAC |
| SEQ ID 30 | AGAGGCCCAGGACCCTGAA |
| SEQ ID 31 | GACGAAATTGCGGTGCTGG |
| SEQ ID 32 | ATTGCGGTGCTGGCCTTTC |
| SEQ ID 33 | TTGCGGTGCTGGCCTTTCT |
| SEQ ID 34 | CCCAGGTGAACGAGGGCTT |
| SEQ ID 35 | TATCCCCAAACCTGAGATG |
| SEQ ID 36 | ACCTGAGATGAGCACTACG |
| SEQ ID 37 | CCTGAGATGAGCACTACGA |
| SEQ ID 38 | GGAGGAGAAACTGAGGCAC |
| SEQ ID 39 | ACTGAGGCACTACTTCCGC |
| SEQ ID 40 | CTGAGGCACTACTTCCGCT |
| SEQ ID 41 | GGTCGTCTGGACTGTGTTC |
| SEQ ID 42 | CAGATCCTGGCATTCTCTC |
| SEQ ID 43 | GCTGTACTACGACAAGGAA |
| SEQ ID 44 | GGAACAGACAGTGAGCATG |
| SEQ ID 45 | CAGACAGTGAGCATGAAGG |
| SEQ ID 46 | GGACAATGTCAGGCCCCTG |

| CA2 | |
|---|---|
| SEQ ID 47 | ACACAACGGACCTGAGCAC |

| SEQ ID 48 | CACAACGGACCTGAGCACT |
|---|---|
| SEQ ID 49 | CGGACCTGAGCACTGGCAT |
| SEQ ID 50 | GGACTTCCCCATTGCCAAG |
| SEQ ID 51 | GTATGACCCTTCCCTGAAG |
| SEQ ID 52 | GCCCCTGTCTGTTTCCTAT |
| SEQ ID 53 | GCAACTTCCCTGAGGATCC |
| SEQ ID 54 | CTTCCCTGAGGATCCTCAA |
| SEQ ID 55 | CAATGGTCATGCTTTCAAC |
| SEQ ID 56 | TGGTCATGCTTTCAACGTG |
| SEQ ID 57 | CGTGGAGTTTGATGACTCT |
| SEQ ID 58 | AGCAGTGCTCAAGGGAGGA |
| SEQ ID 59 | GCAGTGCTCAAGGGAGGAC |
| SEQ ID 60 | GGTTCAGAGCATACTGTGG |
| SEQ ID 61 | AAGAAATATGCTGCAGAAC |
| SEQ ID 62 | AGAAATATGCTGCAGAACT |
| SEQ ID 63 | GAAATATGCTGCAGAACTT |
| SEQ ID 64 | ATATGCTGCAGAACTTCAC |
| SEQ ID 65 | TATGCTGCAGAACTTCACT |
| SEQ ID 66 | CTTCACTTGGTTCACTGGA |
| SEQ ID 67 | CACCAAATATGGGGATTTT |
| SEQ ID 68 | ATATGGGGATTTTGGGAAA |
| SEQ ID 69 | TATGGGGATTTTGGGAAAG |
| SEQ ID 70 | AGCTGTGCAGCAACCTGAT |
| SEQ ID 71 | GCTGTGCAGCAACCTGATG |
| SEQ ID 72 | CCTGATGGACTGGCCGTTC |
| SEQ ID 73 | GGTTGGCAGCGCTAAACCG |
| SEQ ID 74 | ACCGGGCCTTCAGAAAGTT |
| SEQ ID 75 | CCGGGCCTTCAGAAAGTTG |
| SEQ ID 76 | AGTTGTTGATGTGCTGGAT |
| SEQ ID 77 | GTTGTTGATGTGCTGGATT |
| SEQ ID 78 | AACAAAGGGCAAGAGTGCT |
| SEQ ID 79 | ACAAAGGGCAAGAGTGCTG |
| SEQ ID 80 | CAAAGGGCAAGAGTGCTGA |
| SEQ ID 81 | AGGGCAAGAGTGCTGACTT |
| SEQ ID 82 | GGGCAAGAGTGCTGACTTC |
| SEQ ID 83 | GAGTGCTGACTTCACTAAC |
| SEQ ID 84 | GAGTGCTGACTTCACAAAC |
| SEQ ID 85 | ACTTTGCAGCTCGTGGCCT |
| SEQ ID 86 | CTTCGATCCTCGTGGCCTC |
| SEQ ID 87 | TCCCTGGATTACTGGACCT |
| SEQ ID 88 | TGTGTGACCTGGATTGTGC |
| SEQ ID 89 | GGAACCCATCAGCGTCAGC |
| SEQ ID 90 | ACTTAACTTCAATGGGGAG |
| SEQ ID 91 | CTTAACTTCAATGGGGAGG |
| SEQ ID 92 | CTTCAATGGGGAGGGTGAA |
| SEQ ID 93 | TGGGGAGGGTGAACCCGAA |
| SEQ ID 94 | CCCGAAGAACTGATGGTGG |
| SEQ ID 95 | GAACTGATGGTGGACAACT |
| SEQ ID 96 | CTGATGGTGGACAACTGGC |
| SEQ ID 97 | GAACAGGCAAATCAAAGCT |

Figure 2B

| | |
|---|---|
| SEQ ID 98 | CAGGCAAATCAAAGCTTCC |

ADRB1

| | |
|---|---|
| SEQ ID 99 | TGTGCTGGTGATCGTGGCC |
| SEQ ID 100 | CCTCTTCATCATGTCCCTG |
| SEQ ID 101 | GTGCTGCGACTTCGTCACC |
| SEQ ID 102 | GCAGGTGAAGAAGATCGAC |
| SEQ ID 103 | GAAGATCGACAGCTGCGAG |
| SEQ ID 104 | GACGCTGGGCATCATCATG |
| SEQ ID 105 | CGACCCCAAGTGCTGCGAC |
| SEQ ID 106 | CGTGGTGAAGGCCTTCCAC |
| SEQ ID 107 | CTCGGCCTTCAACCCCATC |
| SEQ ID 108 | CCCCATCATCTACTGCCGC |
| SEQ ID 109 | GAAGATCGACAGCTGTGAG |

ADRB2

| | |
|---|---|
| SEQ ID 110 | TAGAAGCCATGCGCCGGAC |
| SEQ ID 111 | TGTGCTGGTCATCACAGCC |
| SEQ ID 112 | GTTCGAGCGTCTGCAGACG |
| SEQ ID 113 | CTACTTCATCACTTCACTG |
| SEQ ID 114 | AATGTGGACTTTTGGCAAC |
| SEQ ID 115 | ATGTGGACTTTTGGCAACT |
| SEQ ID 116 | TGTGGACTTTTGGCAACTT |
| SEQ ID 117 | CTTCTGGTGCGAGTTTTGG |
| SEQ ID 118 | GTACCAGAGCCTGCTGACC |
| SEQ ID 119 | GAATAAGGCCCGGGTGATC |
| SEQ ID 120 | TAAGGCCCGGGTGATCATT |
| SEQ ID 121 | GGCCCGGGTGATCATTCTG |
| SEQ ID 122 | GCCATCAACTGCTATGCCA |
| SEQ ID 123 | CTGCTATGCCAATGAGACC |
| SEQ ID 124 | TGAGACCTGCTGTGACTTC |
| SEQ ID 125 | CCAAGCCTATGCCATTGCC |
| SEQ ID 126 | GCCTATGCCATTGCCTCTT |
| SEQ ID 127 | AAGGCAGCTCCAGAAGATT |
| SEQ ID 128 | AGGCAGCTCCAGAAGATTG |
| SEQ ID 129 | GGCAGCTCCAGAAGATTGA |
| SEQ ID 130 | GATTGACAAATCTGAGGGC |
| SEQ ID 131 | ATCTGAGGGCCGCTTCCAT |
| SEQ ID 132 | TCTGAGGGCCGCTTCCATG |
| SEQ ID 133 | CCTTAGCCAGGTGGAGCAG |
| SEQ ID 134 | GTTCTGCTTGAAGGAGCAC |
| SEQ ID 135 | GGAGCACAAAGCCCTCAAG |
| SEQ ID 136 | AGCCCTCAAGACGTTAGGC |
| SEQ ID 137 | GCCCTCAAGACGTTAGGCA |
| SEQ ID 138 | GACGTTAGGCATCATCATG |
| SEQ ID 139 | CATTGTGCATGTGATCCAG |
| SEQ ID 140 | CCTCATCCGTAAGGAAGTT |
| SEQ ID 141 | GGAAGTTTACATCCTCCTA |
| SEQ ID 142 | ATTGGATAGGCTATGTCAA |
| SEQ ID 143 | TTGGATAGGCTATGTCAAT |
| SEQ ID 144 | TTCTGGTTTCAATCCCCTT |
| SEQ ID 145 | TCCCCTTATCTACTGCCGG |
| SEQ ID 146 | GGCCTATGGGAATGGCTAC |

| | |
|---|---|
| SEQ ID 147 | TGGCTACTCCAGCAACGGC |
| SEQ ID 148 | CACAGGGGAGCAGAGTGGA |
| SEQ ID 149 | GAAAATAAACTGCTGTGTG |
| SEQ ID 150 | AATAAACTGCTGTGTGAAG |
| SEQ ID 151 | ATAAACTGCTGTGTGAAGA |
| SEQ ID 152 | TAAACTGCTGTGTGAAGAC |
| SEQ ID 153 | ACTGCTGTGTGAAGACCTC |
| SEQ ID 154 | CTGCTGTGTGAAGACCTCC |
| SEQ ID 155 | GACTTTGTGGGCCATCAAG |
| SEQ ID 156 | GGTACTGTGCCTAGCGATA |
| SEQ ID 157 | CATTGATTCACAAGGGAGG |
| SEQ ID 158 | GGGAGGAATTGTAGTACAA |
| SEQ ID 159 | GCCATCAACTGCTACGCCA |
| SEQ ID 160 | CATCGTGCACGTGATCCAG |

ACHE

| | |
|---|---|
| SEQ ID 161 | CCTTCCAGAGTGTCTGCTA |
| SEQ ID 162 | TATGTGGACACCCTATACC |
| SEQ ID 163 | CGTGTGGACACCATACCCC |
| SEQ ID 164 | CTACCGGGTGGGAGCCTTT |
| SEQ ID 165 | TGTGGGTCTCCTGGATCAG |
| SEQ ID 166 | TGACACAGAGCTGGTAGCC |
| SEQ ID 167 | CCACGAATGGCACGTGCTG |
| SEQ ID 168 | TGGCACGTGCTGCCTCAAG |
| SEQ ID 169 | GAAAGCGTCTTCCGGTTCT |
| SEQ ID 170 | AGCGTCTTCCGGTTCTCCT |
| SEQ ID 171 | GCGTCTTCCGGTTCTCCTT |
| SEQ ID 172 | GGATGAGGGCTCGTATTTT |
| SEQ ID 173 | AGACAACGAGTCTCTCATC |
| SEQ ID 174 | GACAACGAGTCTCTCATCA |
| SEQ ID 175 | CGAGTCTCTCATCAGCCGG |
| SEQ ID 176 | CACCGTGCTTCCACGCTCT |
| SEQ ID 177 | ACTACACGGCAGAGGAGAA |
| SEQ ID 178 | CTACACGGCAGAGGAGAAA |
| SEQ ID 179 | AATCTTCGCCCAGCGACTG |
| SEQ ID 180 | ATCTTCGCCCAGCGACTGA |
| SEQ ID 181 | TCTTCGCCCAGCGACTGAT |
| SEQ ID 182 | CTTTGCCCGCACAGGGGAT |
| SEQ ID 183 | CCGCTTCCTCCCCAAATTG |
| SEQ ID 184 | ATTGCTCAGCGCCACCGAC |
| SEQ ID 185 | TTGCTCAGCGCCACCGACA |
| SEQ ID 186 | GAACCAGTTCGACCACTAC |
| SEQ ID 187 | CCAGTTCGACCACTACAGC |
| SEQ ID 188 | GCAGGATCGCTGCTCAGAC |
| SEQ ID 189 | CCGTGAGCTGAGCGAGGAC |
| SEQ ID 190 | GAGAGGATCTTTGCCCAGA |

SELE

| | |
|---|---|
| SEQ ID 191 | AGAGAGTGGAGCCTGGTCT |
| SEQ ID 192 | GAGAGTGGAGCCTGGTCTT |
| SEQ ID 193 | CACCTCCACGGAAGCTATG |
| SEQ ID 194 | GCTATGACTTATGATGAGG |
| SEQ ID 195 | AGGTACACACACCTGGTTG |

Figure 2C

| SEQ ID | Sequence | SEQ ID | Sequence |
|---|---|---|---|
| SEQ ID 196 | GGTACACACACCTGGTTGC | SEQ ID 249 | TGTTTCCAAAACCCTGGAA |
| SEQ ID 197 | CAAAGAAGAGATTGAGTAC | SEQ ID 250 | AACCCTGGAAGCTTCCCAT |
| SEQ ID 198 | AGAAGAGATTGAGTACCTA | SEQ ID 251 | ACCCTGGAAGCTTCCCATG |
| SEQ ID 199 | GAAGAGATTGAGTACCTAA | SEQ ID 252 | CCCTGGAAGCTTCCCATGG |
| SEQ ID 200 | GAGATTGAGTACCTAAACT | SEQ ID 253 | GCTTCCCATGGAACACAAC |
| SEQ ID 201 | ACTCCATATTGAGCTATTC | SEQ ID 254 | CACAACCTGTACATTTGAC |
| SEQ ID 202 | CTCCATATTGAGCTATTCA | SEQ ID 255 | CCTGTACATTTGACTGTGA |
| SEQ ID 203 | AAGTCAACAATGTGTGGGT | SEQ ID 256 | GAAGGATTTGAACTAATGG |
| SEQ ID 204 | AGTCAACAATGTGTGGGTC | SEQ ID 257 | GGATTTGAACTAATGGGAG |
| SEQ ID 205 | GTCAACAATGTGTGGGTCT | SEQ ID 258 | CTAATGGGAGCCCAGAGCC |
| SEQ ID 206 | CAATGTGTGGGTCTGGGTA | SEQ ID 259 | TGGGAGCCCAGAGCCTTCA |
| SEQ ID 207 | TGTGTGGGTCTGGGTAGGA | SEQ ID 260 | TTGGGACAACGAGAAGCCA |
| SEQ ID 208 | CCCAGAAACCTCTGACAGA | SEQ ID 261 | CGAGAAGCCAACGTGTAAA |
| SEQ ID 209 | ACCTCTGACAGAAGAAGCC | SEQ ID 262 | GCCAACGTGTAAAGCTGTG |
| SEQ ID 210 | CCTCTGACAGAAGAAGCCA | SEQ ID 263 | CGTGTAAAGCTGTGACATG |
| SEQ ID 211 | GAAGCCAAGAACTGGGCTC | SEQ ID 264 | AGCTGTGACATGCAGGGCC |
| SEQ ID 212 | GCCAAGAACTGGGCTCCAG | SEQ ID 265 | TGGCTCTGTGAGGTGCAGC |
| SEQ ID 213 | GAACTGGGCTCCAGGTGAA | SEQ ID 266 | ATCATCCTGCAACTTCACC |
| SEQ ID 214 | CCCAACAATAGGCAAAAAG | SEQ ID 267 | TCATCCTGCAACTTCACCT |
| SEQ ID 215 | CAATAGGCAAAAAGATGAG | SEQ ID 268 | CTTCACCTGTGAGGAAGGC |
| SEQ ID 216 | TAGGCAAAAAGATGAGGAC | SEQ ID 269 | GGCTTCATGTTGCAGGGAC |
| SEQ ID 217 | AAAGATGAGGACTGCGTGG | SEQ ID 270 | TGCACCACTCAAGGGCAGT |
| SEQ ID 218 | AAGATGAGGACTGCGTGGA | SEQ ID 271 | GGGCAGTGGACACAGCAAA |
| SEQ ID 219 | AGATGAGGACTGCGTGGAG | SEQ ID 272 | ATCCCAGTTTGTGAAGCTT |
| SEQ ID 220 | GATGAGGACTGCGTGGAGA | SEQ ID 273 | TCCCAGTTTGTGAAGCTTT |
| SEQ ID 221 | GAGAGAAAAGATGTGGGC | SEQ ID 274 | GCTTTCCAGTGCACAGCCT |
| SEQ ID 222 | AAAGATGTGGGCATGTGGA | SEQ ID 275 | TTGTCTTCCTAGTGCTTCT |
| SEQ ID 223 | AAGATGTGGGCATGTGGAA | SEQ ID 276 | GGGATCCAAAAGGCTCCAA |
| SEQ ID 224 | AGATGTGGGCATGTGGAAT | SEQ ID 277 | AAGGCTCCAATGTGGCCCC |
| SEQ ID 225 | GATGTGGGCATGTGGAATG | SEQ ID 278 | AGGCTCCAATGTGGCCCCA |
| SEQ ID 226 | TGATGAGAGGTGCAGCAAG | SEQ ID 279 | CGAGAAGCCCACATGTGAA |
| SEQ ID 227 | GAAGAAGCTTGCCCTATGC | SEQ ID 280 | GCCCACATGTGAAGCTGTG |
| SEQ ID 228 | GAAGCTTGCCCTATGCTAC | SEQ ID 281 | GCTGTGAGATGCGATGCTG |
| SEQ ID 229 | GCTTGCCCTATGCTACACA | SEQ ID 282 | GGGTTTGGTGAGGTGTGCT |
| SEQ ID 230 | TACATCCTGCAGTGGCCAC | SEQ ID 283 | TTCACCTACAAGTCCTCTT |
| SEQ ID 231 | TGTGTAGAGACCATCAATA | SEQ ID 284 | GTCCTCTTGTGCCTTCAGC |
| SEQ ID 232 | TTACACTTGCAAGTGTGAC | SEQ ID 285 | CTCAACTTGAGTGCACATC |
| SEQ ID 233 | GTGTGACCCTGGCTTCAGT | SEQ ID 286 | CTTGAGTGCACATCTCAGG |
| SEQ ID 234 | GTGTGAGCAAATTGTGAAC | SEQ ID 287 | TGGACAGAAGAGGTTCCTT |
| SEQ ID 235 | ATTGTGAACTGTACAGCCC | SEQ ID 288 | GAGGTTCCTTCCTGCCAAG |
| SEQ ID 236 | TTGTGAACTGTACAGCCCT | SEQ ID 289 | GTGGTAAATGTTCAAGCC |
| SEQ ID 237 | CTGTACAGCCCTGGAATCC | SEQ ID 290 | AATGTTCAAGCCTGGCAGT |
| SEQ ID 238 | TCCCCTGAGCATGGAAGCC | SEQ ID 291 | ATGTTCAAGCCTGGCAGTT |
| SEQ ID 239 | GCCTGGTTTGCAGTCACCC | SEQ ID 292 | TGTTCAAGCCTGGCAGTTC |
| SEQ ID 240 | ACTTCAGCTACAATTCTTC | SEQ ID 293 | GCCTGGCAGTTCCGGGAAA |
| SEQ ID 241 | CTTCAGCTACAATTCTTCC | SEQ ID 294 | AGATCAACATGAGCTGCAG |
| SEQ ID 242 | TTCTTCCTGCTCTATCAGC | SEQ ID 295 | GATCAACATGAGCTGCAGT |
| SEQ ID 243 | GCAGCATGGAGACCATGCA | SEQ ID 296 | CATGAGCTGCAGTGGGGAG |
| SEQ ID 244 | TGGAGTGCTCCTATTCCAG | SEQ ID 297 | GTTCGCCTGTCCTGAAGGA |
| SEQ ID 245 | TGTGGTTGAGTGTGATGCT | SEQ ID 298 | GGATGGACGCTCAATGGCT |
| SEQ ID 246 | ATCCAGCCAATGGGTTCGT | SEQ ID 299 | TGGCTCTGCAGCTCGGACA |
| SEQ ID 247 | TCCAGCCAATGGGTTCGTG | SEQ ID 300 | GCTCCCACTGAGTCCAACA |
| SEQ ID 248 | TGGGTTCGTGGAATGTTTC | SEQ ID 301 | CATTCCCTTGGTAGCTGGA |

Figure 2D

| SEQ ID 302 | ATGCTTACGGAAAGCAAAG |
|---|---|
| SEQ ID 303 | TGCTTACGGAAAGCAAAGA |
| SEQ ID 304 | GCAAAGAAATTTGTTCCTG |
| SEQ ID 305 | AGAAATTTGTTCCTGCCAG |
| SEQ ID 306 | GAAATTTGTTCCTGCCAGC |
| SEQ ID 307 | ATTTGTTCCTGCCAGCAGC |
| SEQ ID 308 | TTTGTTCCTGCCAGCAGCT |
| SEQ ID 309 | AGCCTTGAATCAGACGGAA |
| SEQ ID 310 | GCCTTGAATCAGACGGAAG |
| SEQ ID 311 | TCAGACGGAAGCTACCAAA |
| SEQ ID 312 | GCTACCAAAAGCCTTCTTA |
| SEQ ID 313 | AAGCCTTCTTACATCCTTT |
| SEQ ID 314 | AGCCTTCTTACATCCTTTA |
| SEQ ID 315 | GCCTTCTTACATCCTTTAA |
| SEQ ID 316 | AGCCTTGAATCAGATGGAA |
| SEQ ID 317 | GCCTTGAATCAGATGGAAG |
| SEQ ID 318 | TCAGATGGAAGCTACCAAA |

PTGS1

| SEQ ID 319 | TCCCTGTTGTTACTATCCA |
|---|---|
| SEQ ID 320 | TGCCACCTTCATCCGAGAG |
| SEQ ID 321 | CTCAGCACATGACTACATC |
| SEQ ID 322 | CGTGAGCTATTACACTCGT |
| SEQ ID 323 | AGATTGCCCCACACCCATG |
| SEQ ID 324 | GATTGCCCCACACCCATGG |
| SEQ ID 325 | CCAAAGGGAAGAAGCAGTT |
| SEQ ID 326 | AGGGAAGAAGCAGTTGCCA |
| SEQ ID 327 | GGGAAGAAGCAGTTGCCAG |
| SEQ ID 328 | GAAGCAGTTGCCAGATGCC |
| SEQ ID 329 | GCAGTTGCCAGATGCCCAG |
| SEQ ID 330 | GTTCATACCTGACCCCCAA |
| SEQ ID 331 | GGCACCAACCTCATGTTTG |
| SEQ ID 332 | CCTCATGTTTGCCTTCTTT |
| SEQ ID 333 | CACTTCACCCACCAGTTCT |
| SEQ ID 334 | AACTTCTGGCAAGATGGGT |
| SEQ ID 335 | ACTTCTGGCAAGATGGGTC |
| SEQ ID 336 | CTTCTGGCAAGATGGGTCC |
| SEQ ID 337 | GATGGGTCCTGGCTTCACC |
| SEQ ID 338 | TCTGGAGCGTCAGTATCAA |
| SEQ ID 339 | CTGCGGCTCTTTAAGGATG |
| SEQ ID 340 | GGATGGGAAACTCAAGTAC |
| SEQ ID 341 | ACTCAAGTACCAGGTGCTG |
| SEQ ID 342 | CTCAAGTACCAGGTGCTGG |
| SEQ ID 343 | GTACCAGGTGCTGGATGGA |
| SEQ ID 344 | ATGTACCCGCCCTCGGTAG |
| SEQ ID 345 | TGTACCCGCCCTCGGTAGA |
| SEQ ID 346 | GAGGCGCCTGTGTTGATGC |
| SEQ ID 347 | CCGTGTGTGTGACCTGCTG |
| SEQ ID 348 | GATTGTCATCGAGGAGTAC |
| SEQ ID 349 | ATTTGACCCAGAGCTGCTG |
| SEQ ID 350 | TTTGACCCAGAGCTGCTGT |
| SEQ ID 351 | TACCGCAACCGCATTGCCA |
| SEQ ID 352 | CCGCATTGCCATGGAGTTC |

| SEQ ID 353 | CCATCTCTACCACTGGCAC |
|---|---|
| SEQ ID 354 | CACCTCCATGTTGGTGGAC |
| SEQ ID 355 | CATGGACCACCACATCCTG |
| SEQ ID 356 | TGAGTACCGCAAGAGGTTT |
| SEQ ID 357 | GAGGTTTGGCATGAAACCC |
| SEQ ID 358 | ACCCTACACCTCCTTCCAG |
| SEQ ID 359 | CCCTACACCTCCTTCCAGG |
| SEQ ID 360 | GGAGATGGCAGCAGAGTTG |
| SEQ ID 361 | TTGTATGGAGACATTGATG |
| SEQ ID 362 | AAGTGCCATCCAAACTCTA |
| SEQ ID 363 | AGTGCCATCCAAACTCTAT |
| SEQ ID 364 | GTGCCATCCAAACTCTATC |
| SEQ ID 365 | ACTCTATCTTTGGGGAGAG |
| SEQ ID 366 | CTCTATCTTTGGGGAGAGT |
| SEQ ID 367 | GGGTCTCCTAGGGAATCCC |
| SEQ ID 368 | TCCCATCTGTTCTCCGGAG |
| SEQ ID 369 | CATTGTCAAGACGGCCACA |
| SEQ ID 370 | GACGGCCACACTGAAGAAG |
| SEQ ID 371 | GAAGCTGGTCTGCCTCAAC |
| SEQ ID 372 | GCTGGTCTGCCTCAACACC |
| SEQ ID 373 | CACCAAGACCTGTCCCTAC |
| SEQ ID 374 | GACCTGTCCCTACGTTTCC |

PTGS2

| SEQ ID 375 | ATCCTTGCTGTTCCCACCC |
|---|---|
| SEQ ID 376 | TCCTTGCTGTTCCCACCCA |
| SEQ ID 377 | AACCGAGGTGTATGTATGA |
| SEQ ID 378 | ACCGAGGTGTATGTATGAG |
| SEQ ID 379 | CCGAGGTGTATGTATGAGT |
| SEQ ID 380 | GTGCGATTGTACCCGGACA |
| SEQ ID 381 | AACTGCTCAACACCGGAAT |
| SEQ ID 382 | ACTGCTCAACACCGGAATT |
| SEQ ID 383 | CTGCTCAACACCGGAATTT |
| SEQ ID 384 | CACCGGAATTTTTGACAAG |
| SEQ ID 385 | TTATTTCTGAAACCCACTC |
| SEQ ID 386 | ACCCACTCCAAACACAGTG |
| SEQ ID 387 | CCCACTCCAAACACAGTGC |
| SEQ ID 388 | ACACAGTGCACTACATACT |
| SEQ ID 389 | CACAGTGCACTACATACTT |
| SEQ ID 390 | GGGATTTTGGAACGTTGTG |
| SEQ ID 391 | CGTTGTGAATAACATTCCC |
| SEQ ID 392 | TAACATTCCCTTCCTTCGA |
| SEQ ID 393 | CATTCCCTTCCTTCGAAAT |
| SEQ ID 394 | CTTACAATGCTGACTATGG |
| SEQ ID 395 | TGCTGACTATGGCTACAAA |
| SEQ ID 396 | AAGCTGGGAAGCCTTCTCT |
| SEQ ID 397 | AGCTGGGAAGCCTTCTCTA |
| SEQ ID 398 | GCTGGGAAGCCTTCTCTAA |
| SEQ ID 399 | GCCTTCTCTAACCTCTCCT |
| SEQ ID 400 | CCTCTCCTATTATACTAGA |
| SEQ ID 401 | AGGTAAAAGCAGCTTCCT |
| SEQ ID 402 | GGTAAAAGCAGCTTCCTG |
| SEQ ID 403 | AAAGCAGCTTCCTGATTCA |

Figure 2E

| SEQ ID 404 | AAGCAGCTTCCTGATTCAA |
| --- | --- |
| SEQ ID 405 | AGCAGCTTCCTGATTCAAA |
| SEQ ID 406 | GCAGCTTCCTGATTCAAAT |
| SEQ ID 407 | GAAGAAAGTTCATCCCTGA |
| SEQ ID 408 | GAAAGTTCATCCCTGATCC |
| SEQ ID 409 | AGTTCATCCCTGATCCCCA |
| SEQ ID 410 | GTTCATCCCTGATCCCCAG |
| SEQ ID 411 | GACAGATCATAAGCGAGGG |
| SEQ ID 412 | ACTCTGGCTAGACAGCGTA |
| SEQ ID 413 | CTCTGGCTAGACAGCGTAA |
| SEQ ID 414 | ACTGCGCCTTTTCAAGGAT |
| SEQ ID 415 | CTGCGCCTTTTCAAGGATG |
| SEQ ID 416 | TTGATGGAGAGATGTATCC |
| SEQ ID 417 | AGATACTCAGGCAGAGATG |
| SEQ ID 418 | GATACTCAGGCAGAGATGA |
| SEQ ID 419 | GTCCCTGAGCATCTACGGT |
| SEQ ID 420 | TCTGGCTGCGGGAACACAA |
| SEQ ID 421 | CACAACAGAGTATGCGATG |
| SEQ ID 422 | CAGAGTATGCGATGTGCTT |
| SEQ ID 423 | ACAGGAGCATCCTGAATGG |
| SEQ ID 424 | CAGGAGCATCCTGAATGGG |
| SEQ ID 425 | TGGGGTGATGAGCAGTTGT |
| SEQ ID 426 | GCAGGCTAATACTGATAGG |
| SEQ ID 427 | TACTGATAGGAGAGACTAT |
| SEQ ID 428 | GATTATGTGCAACACTTGA |
| SEQ ID 429 | CACTTGAGTGGCTATCACT |
| SEQ ID 430 | ACTGAAATTTGACCCAGAA |
| SEQ ID 431 | CTGAAATTTGACCCAGAAC |
| SEQ ID 432 | ATTTGACCCAGAACTACTT |
| SEQ ID 433 | TTTGACCCAGAACTACTTT |
| SEQ ID 434 | CAAACAATTCCAGTACCAA |
| SEQ ID 435 | CAATTCCAGTACCAAAATC |
| SEQ ID 436 | TTCCAGTACCAAAATCGTA |
| SEQ ID 437 | AATCGTATTGCTGCTGAAT |
| SEQ ID 438 | ATCGTATTGCTGCTGAATT |
| SEQ ID 439 | TCGTATTGCTGCTGAATTT |
| SEQ ID 440 | TTTAACACCCTCTATCACT |
| SEQ ID 441 | CACCCTCTATCACTGGCAT |
| SEQ ID 442 | CAACTCTATATTGCTGGAA |
| SEQ ID 443 | CTCTATATTGCTGGAACAT |
| SEQ ID 444 | CATGGAATTACCCAGTTTG |
| SEQ ID 445 | TTACCCAGTTTGTTGAATC |
| SEQ ID 446 | TCATTCACCAGGCAAATTG |
| SEQ ID 447 | ATTGCTGGCAGGGTTGCTG |
| SEQ ID 448 | TTGCTGGCAGGGTTGCTGG |
| SEQ ID 449 | TGTTCCACCCGCAGTACAG |
| SEQ ID 450 | AGTATCACAGGCTTCCATT |
| SEQ ID 451 | GTATCACAGGCTTCCATTG |
| SEQ ID 452 | TGAGTACCGCAAACGCTTT |
| SEQ ID 453 | ACGCTTTATGCTGAAGCCC |
| SEQ ID 454 | CGCTTTATGCTGAAGCCCT |
| SEQ ID 455 | GCCCTATGAATCATTTGAA |
| SEQ ID 456 | GAACTTACAGGAGAAAAGG |
| SEQ ID 457 | CTTACAGGAGAAAAGGAAA |
| SEQ ID 458 | AAGGAAATGTCTGCAGAGT |
| SEQ ID 459 | AGGAAATGTCTGCAGAGTT |
| SEQ ID 460 | GGAAATGTCTGCAGAGTTG |
| SEQ ID 461 | ATGTCTGCAGAGTTGGAAG |
| SEQ ID 462 | TGTCTGCAGAGTTGGAAGC |
| SEQ ID 463 | GCACTCTATGGTGACATCG |
| SEQ ID 464 | AAGCCTCGGCCAGATGCCA |
| SEQ ID 465 | AGCCTCGGCCAGATGCCAT |
| SEQ ID 466 | ACCATGGTAGAAGTTGGAG |
| SEQ ID 467 | CCATGGTAGAAGTTGGAGC |
| SEQ ID 468 | GTTGGAGCACCATTCTCCT |
| SEQ ID 469 | AGGACTTATGGGTAATGTT |
| SEQ ID 470 | GGACTTATGGGTAATGTTA |
| SEQ ID 471 | TGTTATATGTTCTCCTGCC |
| SEQ ID 472 | GCCAAGCACTTTTGGTGGA |
| SEQ ID 473 | GCACTTTTGGTGGAGAAGT |
| SEQ ID 474 | GTGGGTTTTCAAATCATCA |
| SEQ ID 475 | ATCATCAACACTGCCTCAA |
| SEQ ID 476 | TCATCAACACTGCCTCAAT |
| SEQ ID 477 | CACTGCCTCAATTCAGTCT |
| SEQ ID 478 | TTCAGTCTCTCATCTGCAA |
| SEQ ID 479 | TAACGTGAAGGGCTGTCCC |
| SEQ ID 480 | CGTGAAGGGCTGTCCCTTT |
| SEQ ID 481 | GGGCTGTCCCTTTACTTCA |
| SEQ ID 482 | AACAGTCACCATCAATGCA |
| SEQ ID 483 | ACAGTCACCATCAATGCAA |
| SEQ ID 484 | CAGTCACCATCAATGCAAG |
| SEQ ID 485 | TGCAAGTTCTTCCCGCTCC |
| SEQ ID 486 | GTTCTTCCCGCTCCGGACT |
| SEQ ID 487 | TCCCACAGTACTACTAAAA |
| SEQ ID 488 | AAGAACGTTCGACTGAACT |
| SEQ ID 489 | AGAACGTTCGACTGAACTG |
| SEQ ID 490 | GAACGTTCGACTGAACTGT |
| SEQ ID 491 | CACAACAGAGTATGCGACG |

CA12

| SEQ ID 492 | AGGAACAGCCTTCCAGCCC |
| --- | --- |
| SEQ ID 493 | CGGTTCCAAGTGGACTTAT |
| SEQ ID 494 | GTGGACTTATTTTGGTCCT |
| SEQ ID 495 | TAGCTGGTCCAAGAAGTAC |
| SEQ ID 496 | GAAGTACCCGTCGTGTGGG |
| SEQ ID 497 | GGCTACAATCTGTCTGCCA |
| SEQ ID 498 | TCTGTCTGCCAACAAGCAG |
| SEQ ID 499 | CAAGCAGTTTCTCCTGACC |
| SEQ ID 500 | GCAGTTTCTCCTGACCAAC |
| SEQ ID 501 | CAATGGCCATTCAGTGAAG |
| SEQ ID 502 | TGGCCATTCAGTGAAGCTG |
| SEQ ID 503 | CTCAGACCTTTATCCTGAC |
| SEQ ID 504 | CAAGTCAGAAGGCCTCGCT |
| SEQ ID 505 | GTCAGAAGGCCTCGCTGTC |
| SEQ ID 506 | TCCGTCCTATGACAAGATC |
| SEQ ID 507 | GATCTTCAGTCACCTTCAA |

Figure 2F

| SEQ ID | Sequence | SEQ ID | Sequence |
|---|---|---|---|
| SEQ ID 508 | CATGTAAAGTACAAAGGCC | SEQ ID 559 | CAGCTGCATCAACCCCATC |
| SEQ ID 509 | AGTACAAAGGCCAGGAAGC | SEQ ID 560 | CCCCATCATATACCCATGC |
| SEQ ID 510 | GTACAAAGGCCAGGAAGCA | SEQ ID 561 | GAGTTCAAAAAGGCCTTTC |
| SEQ ID 511 | AGGCCAGGAAGCATTCGTC | SEQ ID 562 | AAAGGCCTTTCAGAATGTC |
| SEQ ID 512 | GGCCAGGAAGCATTCGTCC | SEQ ID 563 | AAGGCCTTTCAGAATGTCT |
| SEQ ID 513 | GCATTCGTCCCGGGATTCA | SEQ ID 564 | AGGCCTTTCAGAATGTCTT |
| SEQ ID 514 | CATTGAAGAGCTGCTTCCG | SEQ ID 565 | GGCCTTTCAGAATGTCTTG |
| SEQ ID 515 | GAGCTGCTTCCGGAGAGGA | SEQ ID 566 | TGTCTTGAGAATCCAGTGT |
| SEQ ID 516 | TATTACCGCTACCGGGGGT | SEQ ID 567 | TCCAGTGTCTCTGCAGAAA |
| SEQ ID 517 | CCCCACTGTGCTCTGGACA | SEQ ID 568 | TCCAGTGTCTCCGCAGAAA |
| SEQ ID 518 | ACCCCGTGCAAATTTCCCA | SEQ ID 569 | AGCAGTCTTCCAAACATGC |
| SEQ ID 519 | CCCCGTGCAAATTTCCCAG | SEQ ID 570 | GCAGTCTTCCAAACATGCC |
| SEQ ID 520 | ATTTCCCAGGAGCAGCTGC | SEQ ID 571 | ACATGCCCTGGGCTACACC |
| SEQ ID 521 | TTTCCCAGGAGCAGCTGCT | SEQ ID 572 | GGGCAACACAAGGACATGG |
| SEQ ID 522 | ATGATCAACAACTTCCGGC | SEQ ID 573 | CACAAGGACATGGTGCGCA |
| SEQ ID 523 | TGATCAACAACTTCCGGCA | SEQ ID 574 | GAGAGACCTTCTACAGGAT |
| SEQ ID 524 | CAACTTCCGGCAGGTCCAG | SEQ ID 575 | GACGGATGGCGTTTGTGAA |
| SEQ ID 525 | CTTCCGGCAGGTCCAGAAG | SEQ ID 576 | ATTTTTCTCTTCCATGCCC |
| SEQ ID 526 | GTTCGATGAGAGGCTGGTA | SEQ ID 577 | TTTTTCTCTTCCATGCCCC |
| SEQ ID 527 | GTGCAAGTCTGTACTGCGG | SEQ ID 578 | AGACCAATCCTCCTGTACC |
| SEQ ID 528 | GTCTGTACTGCGGCAGGAC | SEQ ID 579 | GACCAATCCTCCTGTACCA |
| SEQ ID 529 | GGAAGAGTATCAAAAAAGG | SEQ ID 580 | TCCTCCTGTACCACAGCCC |
| SEQ ID 530 | AAAAGGTGATAACAAGGGA | SEQ ID 581 | GTCTCGCTCTGTCACCAGG |
| SEQ ID 531 | AAAGGTGATAACAAGGGAG | SEQ ID 582 | GAGATTCTCCTGCCTCAGC |
| SEQ ID 532 | AAGGTGATAACAAGGGAGT | SEQ ID 583 | GAATTGCAGAGAGCATATC |
| SEQ ID 533 | AGGTGATAACAAGGGAGTC | SEQ ID 584 | TTGCAGAGAGCATATCAAG |
| SEQ ID 534 | GGTGATAACAAGGGAGTCA | SEQ ID 585 | TTTTATGATGCCACCGTGG |
| SEQ ID 535 | CAAGGGAGTCATTTACAAG | SEQ ID 586 | AGGGTCTAGAATGCTGATC |
| SEQ ID 536 | GGGAGTCATTTACAAGCCA | SEQ ID 587 | GGGTCTAGAATGCTGATCT |
| SEQ ID 537 | GCCAGCCACCAAGATGGAG | SEQ ID 588 | GTAAAAGCTTTTTGGAGGT |
| SEQ ID 538 | GATGGAGACTGAGGCCCAC | SEQ ID 589 | AAGCTTTTTGGAGGTCTGC |
| | | SEQ ID 590 | AGCTTTTTGGAGGTCTGCT |
| ADRA1A | | SEQ ID 591 | GCTTTTTGGAGGTCTGCTG |
| SEQ ID 539 | ATGCTTCCGACAGCTCCAA | SEQ ID 592 | CCCCCAGCCTTGACAAGAA |
| SEQ ID 540 | TGCTTCCGACAGCTCCAAC | SEQ ID 593 | GAACCATCAAGTTCCAACC |
| SEQ ID 541 | CATTTCCAAGGCCATTCTG | SEQ ID 594 | CCATCAAGTTCCAACCATT |
| SEQ ID 542 | CATCCTAGTGATCCTCTCC | SEQ ID 595 | GTTCCAACCATTAAGGTCC |
| SEQ ID 543 | CATCTGGGCGGCAGTGGAT | SEQ ID 596 | CCATTAAGGTCCACACCAT |
| SEQ ID 544 | CCATCGTCACCCAGAGGAG | SEQ ID 597 | GGTCCACACCATCTCCCTC |
| SEQ ID 545 | GTCTGGCCTCAAGACCGAC | SEQ ID 598 | CGGGGAGGAAGTCTAGGAC |
| SEQ ID 546 | GACCGACAAGTCGGACTCG | | |
| SEQ ID 547 | GTCGGACTCGGAGCAAGTG | ADRA1B | |
| SEQ ID 548 | GTGACGCTCCGCATCCATC | SEQ ID 599 | GATGAATCCCGACCTGGAC |
| SEQ ID 549 | GACCAAGACGCACTTCTCA | SEQ ID 600 | CACATCAGCACCTGCCCAC |
| SEQ ID 550 | GACGCACTTCTCAGTGAGG | SEQ ID 601 | AAATGCCAACTTCACTGGC |
| SEQ ID 551 | GTTCTCCCGGGAGAAGAAA | SEQ ID 602 | AATGCCAACTTCACTGGCC |
| SEQ ID 552 | GAAAGCGGCCAAAACGCTG | SEQ ID 603 | ATGCCAACTTCACTGGCCC |
| SEQ ID 553 | AACGCTGGGCATCGTGGTC | SEQ ID 604 | TGCCAACTTCACTGGCCCC |
| SEQ ID 554 | GCCCTCTGAAACAGTTTTT | SEQ ID 605 | CTTCACTGGCCCCAACCAG |
| SEQ ID 555 | AATAGTATTTTGGCTCGGA | SEQ ID 606 | CCAGACCTCGAGCAACTCC |
| SEQ ID 556 | ATAGTATTTTGGCTCGGAT | SEQ ID 607 | CATCCTAGTCATCTTGTCT |
| SEQ ID 557 | TAGTATTTTGGCTCGGATA | SEQ ID 608 | CTACTTCATTGTCAACCTG |
| SEQ ID 558 | ACAGCTGCATCAACCCCAT | SEQ ID 609 | CGATGACAAGGAGTGCGGG |

Figure 2G

| SEQ ID 610 | GAACCCTTCTATGCCCTCT |
|---|---|
| SEQ ID 611 | CCCTTCTATGCCCTCTTCT |
| SEQ ID 612 | GAGAACCACCAAGAACCTA |
| SEQ ID 613 | CCACCAAGAACCTAGAGGC |
| SEQ ID 614 | GAACCTAGAGGCAGGAGTC |
| SEQ ID 615 | CCTAGAGGCAGGAGTCATG |
| SEQ ID 616 | GGAGATGTCCAACTCCAAG |
| SEQ ID 617 | CTCCAAGGAGCTGACCCTG |
| SEQ ID 618 | GGAGCTGACCCTGAGGATC |
| SEQ ID 619 | GAACTTTCACGAGGACACC |
| SEQ ID 620 | CTTTCACGAGGACACCCTT |
| SEQ ID 621 | CCCCAGGAGTTCCATAGCT |
| SEQ ID 622 | ACTTTTTAAGTTCTCCAGG |
| SEQ ID 623 | CTTTTTAAGTTCTCCAGGG |
| SEQ ID 624 | GTTCTCCAGGGAAAAGAAA |
| SEQ ID 625 | AAGAAAGCAGCTAAGACGT |
| SEQ ID 626 | AGAAAGCAGCTAAGACGTT |
| SEQ ID 627 | GAAAGCAGCTAAGACGTTG |
| SEQ ID 628 | AGCAGCTAAGACGTTGGGC |
| SEQ ID 629 | GCAGCTAAGACGTTGGGCA |
| SEQ ID 630 | GACGTTGGGCATTGTGGTC |
| SEQ ID 631 | CAGCTGCCTCAACCCCATC |
| SEQ ID 632 | CCCCATCATCTACCCATGC |
| SEQ ID 633 | GGAGTTCAAGCGCGCTTTC |
| SEQ ID 634 | AAGCAACATGCCCCTGGCG |

| ADRA1D | |
|---|---|
| SEQ ID 635 | CCTGCTTGTCATCCTCTCA |
| SEQ ID 636 | CTATTTCATCGTGAACCTG |
| SEQ ID 637 | GTACCCAGCCATCATGACC |
| SEQ ID 638 | GTTCTCCCGTGAGAAGAAA |
| SEQ ID 639 | GAAAGCGGCCAAGACTCTG |
| SEQ ID 640 | GACTCTGGCCATCGTCGTG |
| SEQ ID 641 | GGTCATCTTCTGGCTCGGC |
| SEQ ID 642 | CCCGCTCATCTACCCCTGT |
| SEQ ID 643 | AGTCTCCAGCCTGTCGCAC |
| SEQ ID 644 | GTCTCCAGCCTGTCGCACA |
| SEQ ID 645 | TTGGCCGACTACAGCAACC |
| SEQ ID 646 | CCTACGGGAGACCGATATT |

| AGT | |
|---|---|
| SEQ ID 647 | TGAGAGTACCTGTGAGCAG |
| SEQ ID 648 | TGCCGGGAAGCCCAAAGAC |
| SEQ ID 649 | GCCCAAAGACCCCACCTTC |
| SEQ ID 650 | AGACCCCACCTTCATACCT |
| SEQ ID 651 | GACCCCACCTTCATACCTG |
| SEQ ID 652 | TTCAGGCCAAGACATCCCC |
| SEQ ID 653 | GACATCCCTGTGGATGAA |
| SEQ ID 654 | AAGGCCCTACAGGACCAGC |
| SEQ ID 655 | AGGCCCTACAGGACCAGCT |
| SEQ ID 656 | AACTTGACACCGAAGACAA |
| SEQ ID 657 | ACTTGACACCGAAGACAAG |
| SEQ ID 658 | CTTGACACCGAAGACAAGT |

| SEQ ID 659 | GACAAGTTGAGGGCCGCAA |
|---|---|
| SEQ ID 660 | GTTGAGGGCCGCAATGGTC |
| SEQ ID 661 | TGGTCGGGATGCTGGCCAA |
| SEQ ID 662 | CTTCTTGGGCTTCCGTATA |
| SEQ ID 663 | CGGCTGTCTTTGGCACCCT |
| SEQ ID 664 | TCCTGGGTGTTCCTTGGAA |
| SEQ ID 665 | GGACAAGAACTGCACCTCC |
| SEQ ID 666 | CTGGATGTTGCTGCTGAGA |
| SEQ ID 667 | GATTGACAGGTTCATGCAG |
| SEQ ID 668 | GACTGGCTGCTCCCTGATG |
| SEQ ID 669 | CACCTACGTCCACTTCCAA |
| SEQ ID 670 | GGGAAGATGAAGGGCTTCT |
| SEQ ID 671 | GATGAAGGGCTTCTCCCTG |
| SEQ ID 672 | CAGCACCTCAGTGTCTGTT |
| SEQ ID 673 | CTTCTCGGTGACTCAAGTG |
| SEQ ID 674 | GTGCCCTTCACTGAGAGCG |
| SEQ ID 675 | GGTGGAGGGTCTCACTTTC |
| SEQ ID 676 | AACTCCCTCAACTGGATGA |
| SEQ ID 677 | ACTCCCTCAACTGGATGAA |
| SEQ ID 678 | CTCCCTCAACTGGATGAAG |
| SEQ ID 679 | CTGGATGAAGAAACTGTCT |
| SEQ ID 680 | GAAACTGTCTCCCCGGACC |
| SEQ ID 681 | ACTGTCTCCCCGGACCATC |
| SEQ ID 682 | CTGGTGCTGCAAGGATCTT |
| SEQ ID 683 | GGATCTTATGACCTGCAGG |
| SEQ ID 684 | CCTGCAAAAATTGAGCAAT |
| SEQ ID 685 | AAATTGAGCAATGACCGCA |
| SEQ ID 686 | AATTGAGCAATGACCGCAT |
| SEQ ID 687 | ATTGAGCAATGACCGCATC |
| SEQ ID 688 | TTGAGCAATGACCGCATCA |
| SEQ ID 689 | GCGGATGAGAGAGAGCCCA |
| SEQ ID 690 | CAGCTTAACAAGCCTGAGG |
| SEQ ID 691 | CAAGCCTGAGGTCTTGGAG |
| SEQ ID 692 | GCCTGAGGTCTTGGAGGTG |
| SEQ ID 693 | CCGCCCATTCCTGTTTGCT |
| SEQ ID 694 | CCCGCTGAGCACAGCATGA |

| AGTR1 | |
|---|---|
| SEQ ID 695 | CTCTTCTACTGAAGATGGT |
| SEQ ID 696 | AGAATCCAAGATGATTGTC |
| SEQ ID 697 | GAATCCAAGATGATTGTCC |
| SEQ ID 698 | TCCAAGATGATTGTCCCAA |
| SEQ ID 699 | GATGATTGTCCCAAAGCTG |
| SEQ ID 700 | AGCTGGAAGGCATAATTAC |
| SEQ ID 701 | GCTGGAAGGCATAATTACA |
| SEQ ID 702 | TATTTGGAAACAGCTTGGT |
| SEQ ID 703 | ACAGCTTGGTGGTGATAGT |
| SEQ ID 704 | CAGCTTGGTGGTGATAGTC |
| SEQ ID 705 | GCTGAAGACTGTGGCCAGT |
| SEQ ID 706 | GACTGTGGCCAGTGTTTTT |
| SEQ ID 707 | TTTAGCACTGGCTGACTTA |
| SEQ ID 708 | TACCGCTGGCCCTTTGGCA |
| SEQ ID 709 | GATTGCTTCAGCCAGCGTC |

Figure 2H

| | |
|---|---|
| SEQ ID 710 | CCTGTACGCTAGTGTGTTT |
| SEQ ID 711 | TGAAGTCCCGCCTTCGACG |
| SEQ ID 712 | TGCTTGTAGCCAAAGTCAC |
| SEQ ID 713 | AGTCACCTGCATCATCATT |
| SEQ ID 714 | GTCACCTGCATCATCATTT |
| SEQ ID 715 | AATTCAACCCTTCCGATAG |
| SEQ ID 716 | ATTCAACCCTTCCGATAGG |
| SEQ ID 717 | TTCAACCCTTCCGATAGGG |
| SEQ ID 718 | AAATATACTGGGTTTCCTG |
| SEQ ID 719 | AATATACTGGGTTTCCTGT |
| SEQ ID 720 | ATATACTGGGTTTCCTGTT |
| SEQ ID 721 | TATACTGGGTTTCCTGTTT |
| SEQ ID 722 | GGCCCTAAAGAAGGCTTAT |
| SEQ ID 723 | GAAGGCTTATGAAATTCAG |
| SEQ ID 724 | GGCTTATGAAATTCAGAAG |
| SEQ ID 725 | TTCAGAAGAACAAACCAAG |
| SEQ ID 726 | CTAGGCATCATACGTGACT |
| SEQ ID 727 | TTGCAGATATTGTGGACAC |
| SEQ ID 728 | CAATTGCCTGAATCCTCTT |
| SEQ ID 729 | TTGCCTGAATCCTCTTTTT |
| SEQ ID 730 | AGATATTTTCTCCAGCTTC |
| SEQ ID 731 | GATATTTTCTCCAGCTTCT |
| SEQ ID 732 | AATATATTCCCCCAAAAGC |
| SEQ ID 733 | ATATATTCCCCCAAAAGCC |
| SEQ ID 734 | TATATTCCCCCAAAAGCCA |
| SEQ ID 735 | AAGCCAAATCCCACTCAAA |
| SEQ ID 736 | AGCCAAATCCCACTCAAAC |
| SEQ ID 737 | GCCAAATCCCACTCAAACC |
| SEQ ID 738 | ATCCCACTCAAACCTTTCA |
| SEQ ID 739 | TCCCACTCAAACCTTTCAA |
| SEQ ID 740 | CCTTTCAACAAAAATGAGC |
| SEQ ID 741 | CAAAAATGAGCACGCTTTC |
| SEQ ID 742 | AAATGAGCACGCTTTCCTA |
| SEQ ID 743 | AATGAGCACGCTTTCCTAC |
| SEQ ID 744 | ATGAGCACGCTTTCCTACC |
| SEQ ID 745 | TGAGCACGCTTTCCTACCG |
| SEQ ID 746 | TGTAAGCTCATCCACCAAG |
| SEQ ID 747 | GCTCATCCACCAAGAAGCC |
| SEQ ID 748 | GAAGCCTGCACCATGTTTT |
| SEQ ID 749 | GCCTGCACCATGTTTTGAG |

AGTR2

| | |
|---|---|
| SEQ ID 750 | TATGAAGGGCAACTCCACC |
| SEQ ID 751 | CTCCACCCTTGCCACTACT |
| SEQ ID 752 | AAACATTACCAGCGGTCTT |
| SEQ ID 753 | AACATTACCAGCGGTCTTC |
| SEQ ID 754 | ACATTACCAGCGGTCTTCA |
| SEQ ID 755 | CATTACCAGCGGTCTTCAC |
| SEQ ID 756 | CATCTCTGGCAACAATGAG |
| SEQ ID 757 | CAATGAGTCTACCTTGAAC |
| SEQ ID 758 | TGAGTCTACCTTGAACTGT |
| SEQ ID 759 | CTGTTCACAGAAACCATCA |
| SEQ ID 760 | CCATCAGATAAGCATTTAG |

| | |
|---|---|
| SEQ ID 761 | GCATTTAGATGCAATTCCT |
| SEQ ID 762 | TATTGTCGTGGTTACACTG |
| SEQ ID 763 | AAGGGTCCTAAAAAGGTTT |
| SEQ ID 764 | AGGGTCCTAAAAAGGTTTC |
| SEQ ID 765 | GGGTCCTAAAAAGGTTTCT |
| SEQ ID 766 | GGTTTCTAGCATATACATC |
| SEQ ID 767 | CCTCGCTGTGGCTGATTTA |
| SEQ ID 768 | TCTGTCATCTACCCCTTTC |
| SEQ ID 769 | AGAAGAAATCCCTGGCAAG |
| SEQ ID 770 | GAAGAAATCCCTGGCAAGC |
| SEQ ID 771 | GAAATCCCTGGCAAGCATC |
| SEQ ID 772 | ATCCCTGGCAAGCATCTTA |
| SEQ ID 773 | TCCCTGGCAAGCATCTTAT |
| SEQ ID 774 | GCATCTTATATAGTTCCCC |
| SEQ ID 775 | CCATTGAATACTTAGGAGT |
| SEQ ID 776 | TACTTAGGAGTGAATGCTT |
| SEQ ID 777 | TGCTTGCATTATGGCTTTC |
| SEQ ID 778 | ATATGCCCAATGGTCAGCT |
| SEQ ID 779 | TATGCCCAATGGTCAGCTG |
| SEQ ID 780 | TGGTCAGCTGGGATTGCCT |
| SEQ ID 781 | AACACTTACTGAAGACGAA |
| SEQ ID 782 | ACACTTACTGAAGACGAAT |
| SEQ ID 783 | CACTTACTGAAGACGAATA |
| SEQ ID 784 | GACGAATAGCTATGGGAAG |
| SEQ ID 785 | TAGCTATGGGAAGAACAGG |
| SEQ ID 786 | GAACAGGATAACCCGTGAC |
| SEQ ID 787 | CAGGATAACCCGTGACCAA |
| SEQ ID 788 | CCCGTGACCAAGTCCTGAA |
| SEQ ID 789 | GTCCTGAAGATGGCAGCTG |
| SEQ ID 790 | GATGGCAGCTGCTGTTGTT |
| SEQ ID 791 | TAGCTGCGAAGTTATAGCA |
| SEQ ID 792 | GTTATAGCAGTCATTGACC |
| SEQ ID 793 | CAGCTGCGTTAATCCGTTT |
| SEQ ID 794 | ACCGGTTCCAACAGAAGCT |
| SEQ ID 795 | CCGGTTCCAACAGAAGCTC |
| SEQ ID 796 | CAGAAGCTCCGCAGTGTGT |
| SEQ ID 797 | GCTCCGCAGTGTGTTTAGG |
| SEQ ID 798 | TTACTTGGCTCCAAGGGAA |
| SEQ ID 799 | GGGAAAAGAGAGAGTATGT |
| SEQ ID 800 | AAGAGAGTATGTCTTGC |
| SEQ ID 801 | AGAGAGAGTATGTCTTGCC |
| SEQ ID 802 | GAGAGAGTATGTCTTGCCG |
| SEQ ID 803 | AAGCAGTTCTCTTAGAGAA |
| SEQ ID 804 | AGCAGTTCTCTTAGAGAAA |
| SEQ ID 805 | GCAGTTCTCTTAGAGAAAT |
| SEQ ID 806 | ATGGAGACCTTTGTGTCTT |
| SEQ ID 807 | TGGAGACCTTTGTGTCTTA |

ACE1

| | |
|---|---|
| SEQ ID 808 | CTTTTCTGCTGACGAGGCC |
| SEQ ID 809 | CAGGTGCTGTTCCAGAGCG |
| SEQ ID 810 | CATCACCGCGGAGAATGCA |
| SEQ ID 811 | TGCAAGGCGCCAGGAGGAA |

Figure 2I

| SEQ ID 812 | GGCCAAGGAGCTGTATGAA | SEQ ID 865 | CGAGTATGCCGAGGCCAAC |
|---|---|---|---|
| SEQ ID 813 | GGAGCTGTATGAACCGATC | SEQ ID 866 | CTGGAACTACAACACCAAC |
| SEQ ID 814 | CCGATCTGGCAGAACTTCA | SEQ ID 867 | CTACAACACCAACATCACC |
| SEQ ID 815 | CGCCCTGCTAAGCAACATG | SEQ ID 868 | CACCAACATCACCACAGAG |
| SEQ ID 816 | GCAACATGAGCAGGATCTA | SEQ ID 869 | CATCACCACAGAGACCAGC |
| SEQ ID 817 | CATGAGCAGGATCTACTCC | SEQ ID 870 | GATTCTGCTGCAGAAGAAC |
| SEQ ID 818 | GGTCTGCCTCCCCAACAAG | SEQ ID 871 | GAACATGCAAATAGCCAAC |
| SEQ ID 819 | CAAGACTGCCACCTGCTGG | SEQ ID 872 | CATGCAAATAGCCAACCAC |
| SEQ ID 820 | CATCCTGGCTTCCTCGCGA | SEQ ID 873 | ATAGCCAACCACACCCTGA |
| SEQ ID 821 | GCTACGCCATGCTCCTGTT | SEQ ID 874 | TAGCCAACCACACCCTGAA |
| SEQ ID 822 | ACCGCTGTACGAGGATTTC | SEQ ID 875 | CCACACCCTGAAGTACGGC |
| SEQ ID 823 | CCGCTGTACGAGGATTTCA | SEQ ID 876 | GTTTGATGTGAACCAGTTG |
| SEQ ID 824 | TGAAGCCTACAAGCAGGAC | SEQ ID 877 | CCAGTTGCAGAACACCACT |
| SEQ ID 825 | GCCTACAAGCAGGACGGCT | SEQ ID 878 | CACCACTATCAAGCGGATC |
| SEQ ID 826 | GCAGGACGGCTTCACAGAC | SEQ ID 879 | GCGGATCATAAAGAAGGTT |
| SEQ ID 827 | CACCTCTACCAACAGCTAG | SEQ ID 880 | AGAAGGTTCAGGACCTAGA |
| SEQ ID 828 | CAGCTAGAGCCCCTCTACC | SEQ ID 881 | GAAGGTTCAGGACCTAGAA |
| SEQ ID 829 | AACATCTACGACATGGTGG | SEQ ID 882 | GGTTCAGGACCTAGAACGG |
| SEQ ID 830 | ACATCTACGACATGGTGGT | SEQ ID 883 | CAAGATCCTGTTGGATATG |
| SEQ ID 831 | CATCTACGACATGGTGGTG | SEQ ID 884 | GATCCTGTTGGATATGGAA |
| SEQ ID 832 | GCCCAACCTCGATGTCACC | SEQ ID 885 | ACCACCTACAGCGTGGCCA |
| SEQ ID 833 | CCTCGATGTCACCAGTACT | SEQ ID 886 | ATATGAAGACCTGTTATGG |
| SEQ ID 834 | GGGTCGATGCTGGAGAAGC | SEQ ID 887 | TATGAAGACCTGTTATGGG |
| SEQ ID 835 | CAGGAAAGACTTCAGGATC | SEQ ID 888 | GACCTGTTATGGGCATGGG |
| SEQ ID 836 | AGACTTCAGGATCAAGCAG | SEQ ID 889 | ATACGTGGAACTCATCAAC |
| SEQ ID 837 | GACTTCAGGATCAAGCAGT | SEQ ID 890 | TACGTGGAACTCATCAACC |
| SEQ ID 838 | CATCTGCACAAAATCGGCC | SEQ ID 891 | CTCATCAACCAGGCTGCCC |
| SEQ ID 839 | AATCGGCCTGCTGGACCGT | SEQ ID 892 | TGGCTATGTAGATGCAGGG |
| SEQ ID 840 | TGACACGGAAAGTGACATC | SEQ ID 893 | CATCTATGACTTGGTGGTG |
| SEQ ID 841 | AGTGACATCAATTACTTGC | SEQ ID 894 | GGAGGCTGATGATTTCTTC |
| SEQ ID 842 | GTGACATCAATTACTTGCT | SEQ ID 895 | CAAGTCGATGCTGGAGAAG |
| SEQ ID 843 | ATGGCACTGGAAAAAATTG | SEQ ID 896 | GTCGATGCTGGAGAAGCCA |
| SEQ ID 844 | TGGCACTGGAAAAAATTGC | SEQ ID 897 | CGGCAAGGACTTCCGGATC |
| SEQ ID 845 | AAAATTGCCTTCCTGCCCT | SEQ ID 898 | GGACTTCCGGATCAAGCAG |
| SEQ ID 846 | AAATTGCCTTCCTGCCCTT | SEQ ID 899 | GCAGTGCACCACCGTGAAC |
| SEQ ID 847 | AATTGCCTTCCTGCCCTTT | SEQ ID 900 | CTTGGAGGACCTGGTGGTG |
| SEQ ID 848 | ATTGCCTTCCTGCCCTTTG | SEQ ID 901 | ATGGGCCACATCCAGTATT |
| SEQ ID 849 | TTGCCTTCCTGCCCTTTGG | SEQ ID 902 | TGGGCCACATCCAGTATTT |
| SEQ ID 850 | CTTCGACTGGTGGTATCTT | SEQ ID 903 | AGACTTACCTGTGGCCTTG |
| SEQ ID 851 | CCAAGTATCAGGGGATCTG | SEQ ID 904 | GACTTACCTGTGGCCTTGA |
| SEQ ID 852 | GTATCAGGGGATCTGTCCT | SEQ ID 905 | GCACCTGCACAGTCTCAAC |
| SEQ ID 853 | ACGAAACCCACTTTGATGC | SEQ ID 906 | CCTGCTGAGCAGTGAGGGT |
| SEQ ID 854 | CGAAACCCACTTTGATGCT | SEQ ID 907 | CTTTCTGATGAAGATGGCC |
| SEQ ID 855 | ACCCACTTTGATGCTGGAG | SEQ ID 908 | GATGGCCCTTGACAAGATC |
| SEQ ID 856 | CCCACTTTGATGCTGGAGC | SEQ ID 909 | GATCGCCTTTATCCCCTTC |
| SEQ ID 857 | GTTTCATGTTCCAAATGTG | SEQ ID 910 | GCATCACCAAGGAGAACTA |
| SEQ ID 858 | ATGTGACACCATACATCAG | SEQ ID 911 | GGAGAACTATAACCAGGAG |
| SEQ ID 859 | TGTGACACCATACATCAGG | SEQ ID 912 | CTATAACCAGGAGTGGTGG |
| SEQ ID 860 | GGACATGGTCGGCTTAGAT | SEQ ID 913 | GGTGACTTTGACCCAGGGG |
| SEQ ID 861 | GTACTTCCAGCCAGTCACC | SEQ ID 914 | GTTCCACATTCCTTCTAGC |
| SEQ ID 862 | CTACCCGGAGGGCATAGAC | SEQ ID 915 | GTGTGACATCTACCAGTCC |
| SEQ ID 863 | GTTTGTGGAGGAATATGAC | SEQ ID 916 | GCCATGCAGCTGATCACGG |
| SEQ ID 864 | TATGACCGGACATCCCAGG | SEQ ID 917 | CGAGCTGCATGGGGAGAAG |

Figure 2J

| SEQ ID 918 | CAGGTGACAGTCACCCATG |
|---|---|
| SEQ ID 919 | GCAGCCAGGCAACAACCAG |
| SEQ ID 920 | CAACCAGCAGCCAGACAAC |
| SEQ ID 921 | CCAGCAGCCAGACAACCAC |
| SEQ ID 922 | ACCTGGTGACTGATGAGGC |
| SEQ ID 923 | CCTGGTGACTGATGAGGCT |
| SEQ ID 924 | CTGGACGCCGAACTCCGAT |
| SEQ ID 925 | CTCCGATGACTTCTACAAT |
| SEQ ID 926 | TGAGACCGAGACCAAGATC |
| SEQ ID 927 | GATCTTCCTGCAGTTTTAT |
| SEQ ID 928 | ACAGGGATTTGGGACCATG |
| SEQ ID 929 | CAGGGATTTGGGACCATGG |
| SEQ ID 930 | GCAAGAGGAACAAGGGAAG |
| SEQ ID 931 | GAGGAACAAGGGAAGCCCC |
| SEQ ID 932 | CAAGGGAAGCCCCAGTGTA |
| SEQ ID 933 | GGGAAGCCCCAGTGTACAT |
| SEQ ID 934 | GCCCCAGTGTACATGTCAA |
| SEQ ID 935 | AGAGGGCTGCAAGCTCTGG |
| SEQ ID 936 | GCCCTAAACTTCCTCCAGC |
| SEQ ID 937 | ACTTCCTCCAGCTGCACAA |
| SEQ ID 938 | CTTCCTCCAGCTGCACAAG |
| SEQ ID 939 | GGACATGGAGAGGTCCCAG |

ACE2

| SEQ ID 940 | GCTCTTCCTGGCTCCTTCT |
|---|---|
| SEQ ID 941 | CTGCTGCTCAGTCCACCAT |
| SEQ ID 942 | CAGGCCAAGACATTTTTGG |
| SEQ ID 943 | GTTTAACCACGAAGCCGAA |
| SEQ ID 944 | CCACGAAGCCGAAGACCTG |
| SEQ ID 945 | GCCGAAGACCTGTTCTATC |
| SEQ ID 946 | GACCTGTTCTATCAAAGTT |
| SEQ ID 947 | AGTTCACTTGCTTCTTGGA |
| SEQ ID 948 | GTTCACTTGCTTCTTGGAA |
| SEQ ID 949 | CACCAATATTACTGAAGAG |
| SEQ ID 950 | GAGAATGTCCAAAACATGA |
| SEQ ID 951 | AACATGAATAATGCTGGGG |
| SEQ ID 952 | ACATGAATAATGCTGGGGA |
| SEQ ID 953 | CATGAATAATGCTGGGGAC |
| SEQ ID 954 | TAATGCTGGGGACAAATGG |
| SEQ ID 955 | TGCTGGGGACAAATGGTCT |
| SEQ ID 956 | ATGGTCTGCCTTTTTAAAG |
| SEQ ID 957 | TGGTCTGCCTTTTTAAAGG |
| SEQ ID 958 | AGGAACAGTCCACACTTGC |
| SEQ ID 959 | GGAACAGTCCACACTTGCC |
| SEQ ID 960 | CAGTCCACACTTGCCCAAA |
| SEQ ID 961 | GAAATTCAGAATCTCACAG |
| SEQ ID 962 | ATTCAGAATCTCACAGTCA |
| SEQ ID 963 | TTCAGAATCTCACAGTCAA |
| SEQ ID 964 | TCTCACAGTCAAGCTTCAG |
| SEQ ID 965 | GCTTCAGCTGCAGGCTCTT |
| SEQ ID 966 | AATGGGTCTTCAGTGCTCT |
| SEQ ID 967 | ATGGGTCTTCAGTGCTCTC |
| SEQ ID 968 | TGGGTCTTCAGTGCTCTCA |

| SEQ ID 969 | GACAAGAGCAAACGGTTGA |
|---|---|
| SEQ ID 970 | GAGCAAACGGTTGAACACA |
| SEQ ID 971 | ACGGTTGAACACAATTCTA |
| SEQ ID 972 | CGGTTGAACACAATTCTAA |
| SEQ ID 973 | ATACAATGAGCACCATCTA |
| SEQ ID 974 | TACAATGAGCACCATCTAC |
| SEQ ID 975 | TGAGCACCATCTACAGTAC |
| SEQ ID 976 | GTTTGTAACCCAGATAATC |
| SEQ ID 977 | CCCAGATAATCCACAAGAA |
| SEQ ID 978 | TGCTTATTACTTGAACCAG |
| SEQ ID 979 | TGGCAAACAGTTTAGACTA |
| SEQ ID 980 | CAGTTTAGACTACAATGAG |
| SEQ ID 981 | TGAGAGGCTCTGGGCTTGG |
| SEQ ID 982 | AGCTGGAGATCTGAGGTCG |
| SEQ ID 983 | GCTGGAGATCTGAGGTCGG |
| SEQ ID 984 | GCAGCTGAGGCCATTATAT |
| SEQ ID 985 | GAGTATGTGGTCTTGAAAA |
| SEQ ID 986 | AAATGAGATGGCAAGAGCA |
| SEQ ID 987 | AATGAGATGGCAAGAGCAA |
| SEQ ID 988 | ATGAGATGGCAAGAGCAAA |
| SEQ ID 989 | TGAGATGGCAAGAGCAAAT |
| SEQ ID 990 | GAGCAAATCATTATGAGGA |
| SEQ ID 991 | ATCATTATGAGGACTATGG |
| SEQ ID 992 | TCATTATGAGGACTATGGG |
| SEQ ID 993 | GTAAATGGGGTAGATGGCT |
| SEQ ID 994 | ATGGGGTAGATGGCTATGA |
| SEQ ID 995 | TGGGGTAGATGGCTATGAC |
| SEQ ID 996 | GATGTGGAACATACCTTTG |
| SEQ ID 997 | CATCTTCATGCCTATGTGA |
| SEQ ID 998 | AGTTGATGAATGCCTATCC |
| SEQ ID 999 | GTTGATGAATGCCTATCCT |
| SEQ ID 1000 | TGCCTATCCTTCCTATATC |
| SEQ ID 1001 | TTGGATGCCTCCCTGCTCA |
| SEQ ID 1002 | ATCTGTACTCTTTGACAGT |
| SEQ ID 1003 | TCTGTACTCTTTGACAGTT |
| SEQ ID 1004 | CCAAACATAGATGTTACTG |
| SEQ ID 1005 | ACATAGATGTTACTGATGC |
| SEQ ID 1006 | CATAGATGTTACTGATGCA |
| SEQ ID 1007 | TATTCAAGGAGGCCGAGAA |
| SEQ ID 1008 | GGAGGCCGAGAAGTTCTTT |
| SEQ ID 1009 | GTTCTTTGTATCTGTTGGT |
| SEQ ID 1010 | TATGACTCAAGGATTCTGG |
| SEQ ID 1011 | GGATTCTGGGAAAATTCCA |
| SEQ ID 1012 | AATTCCATGCTAACGGACC |
| SEQ ID 1013 | ATTCCATGCTAACGGACCC |
| SEQ ID 1014 | TTCCATGCTAACGGACCCA |
| SEQ ID 1015 | CGGACCCAGGAAATGTTCA |
| SEQ ID 1016 | ATGTTCAGAAAGCAGTCTG |
| SEQ ID 1017 | TGTTCAGAAAGCAGTCTGC |
| SEQ ID 1018 | AGCAGTCTGCCATCCCACA |
| SEQ ID 1019 | GCAGTCTGCCATCCCACAG |
| SEQ ID 1020 | GGGCGACTTCAGGATCCTT |
| SEQ ID 1021 | AGGTGACAATGGACGACTT |

Figure 2K

| | | | |
|---|---|---|---|
| SEQ ID 1022 | GGTGACAATGGACGACTTC | SEQ ID 1075 | TATGCTGAGGCTTGGAAAA |
| SEQ ID 1023 | TGGACGACTTCCTGACAGC | SEQ ID 1076 | AATCAGAACCCTGGACCCT |
| SEQ ID 1024 | CCTTTTCTGCTAAGAAATG | SEQ ID 1077 | ATCAGAACCCTGGACCCTA |
| SEQ ID 1025 | GAAATGGAGCTAATGAAGG | SEQ ID 1078 | TCAGAACCCTGGACCCTAG |
| SEQ ID 1026 | ATGGAGCTAATGAAGGATT | SEQ ID 1079 | CCCTGGACCCTAGCATTGG |
| SEQ ID 1027 | TGGAGCTAATGAAGGATTC | SEQ ID 1080 | AATGTTGTAGGAGCAAAGA |
| SEQ ID 1028 | TGAAGGATTCCATGAAGCT | SEQ ID 1081 | ATGTTGTAGGAGCAAAGAA |
| SEQ ID 1029 | GGATTCCATGAAGCTGTTG | SEQ ID 1082 | TGTTGTAGGAGCAAAGAAC |
| SEQ ID 1030 | GCTGTTGGGGAAATCATGT | SEQ ID 1083 | AGAACATGAATGTAAGGCC |
| SEQ ID 1031 | ATCATGTCACTTTCTGCAG | SEQ ID 1084 | GAACATGAATGTAAGGCCA |
| SEQ ID 1032 | TCATGTCACTTTCTGCAGC | SEQ ID 1085 | CATGAATGTAAGGCCACTG |
| SEQ ID 1033 | AATCCATTGGTCTTCTGTC | SEQ ID 1086 | TGTAAGGCCACTGCTCAAC |
| SEQ ID 1034 | ATCCATTGGTCTTCTGTCA | SEQ ID 1087 | GGCCACTGCTCAACTACTT |
| SEQ ID 1035 | TCCATTGGTCTTCTGTCAC | SEQ ID 1088 | CTACTTTGAGCCCTTATTT |
| SEQ ID 1036 | ACAGAAATAAACTTCCTGC | SEQ ID 1089 | AGACCAGAACAAGAATTCT |
| SEQ ID 1037 | CAGAAATAAACTTCCTGCT | SEQ ID 1090 | GACCAGAACAAGAATTCTT |
| SEQ ID 1038 | ATAAACTTCCTGCTCAAAC | SEQ ID 1091 | CAAGAATTCTTTTGTGGGA |
| SEQ ID 1039 | TAAACTTCCTGCTCAAACA | SEQ ID 1092 | GAATTCTTTTGTGGGATGG |
| SEQ ID 1040 | ACTTCCTGCTCAAACAAGC | SEQ ID 1093 | TTCTTTTGTGGGATGGAGT |
| SEQ ID 1041 | CTTCCTGCTCAAACAAGCA | SEQ ID 1094 | AGCATCAAAGTGAGGATAA |
| SEQ ID 1042 | ACAAGCACTCACGATTGTT | SEQ ID 1095 | GCATCAAAGTGAGGATAAG |
| SEQ ID 1043 | CAAGCACTCACGATTGTTG | SEQ ID 1096 | AGTGAGGATAAGCCTAAAA |
| SEQ ID 1044 | GCACTCACGATTGTTGGGA | SEQ ID 1097 | GTGAGGATAAGCCTAAAAT |
| SEQ ID 1045 | GTGGAGGTGGATGGTCTTT | SEQ ID 1098 | GCCTAAAATCAGCTCTTGG |
| SEQ ID 1046 | AGGGGAAATTCCCAAAGAC | SEQ ID 1099 | AATCAGCTCTTGGAGATAA |
| SEQ ID 1047 | GGGGAAATTCCCAAAGACC | SEQ ID 1100 | ATCAGCTCTTGGAGATAAA |
| SEQ ID 1048 | ATTCCCAAAGACCAGTGGA | SEQ ID 1101 | TCAGCTCTTGGAGATAAAG |
| SEQ ID 1049 | TTCCCAAAGACCAGTGGAT | SEQ ID 1102 | AGCATATGAATGGAACGAC |
| SEQ ID 1050 | AGACCAGTGGATGAAAAAG | SEQ ID 1103 | GCATATGAATGGAACGACA |
| SEQ ID 1051 | GACCAGTGGATGAAAAAGT | SEQ ID 1104 | TGGAACGACAATGAAATGT |
| SEQ ID 1052 | AAAGTGGTGGGAGATGAAG | SEQ ID 1105 | CGACAATGAAATGTACCTG |
| SEQ ID 1053 | AAGTGGTGGGAGATGAAGC | SEQ ID 1106 | TGAAATGTACCTGTTCCGA |
| SEQ ID 1054 | AGTGGTGGGAGATGAAGCG | SEQ ID 1107 | ATGTACCTGTTCCGATCAT |
| SEQ ID 1055 | GTGGTGGGAGATGAAGCGA | SEQ ID 1108 | TGTACCTGTTCCGATCATC |
| SEQ ID 1056 | GCGAGAGATAGTTGGGGTG | SEQ ID 1109 | TCAGATGATTCTTTTTGGG |
| SEQ ID 1057 | CCTGTGCCCCATGATGAAA | SEQ ID 1110 | TTTGAAACCAAGAATCTCC |
| SEQ ID 1058 | ACATACTGTGACCCCGCAT | SEQ ID 1111 | TTTCTTTGTCACTGCACCT |
| SEQ ID 1059 | CATACTGTGACCCCGCATC | SEQ ID 1112 | ATGTGTCTGATATCATTCC |
| SEQ ID 1060 | GGACCCTTTACCAATTCCA | SEQ ID 1113 | TGTGTCTGATATCATTCCT |
| SEQ ID 1061 | TTCCAGTTTCAAGAAGCAC | SEQ ID 1114 | CTGAAGTTGAAAAGGCCAT |
| SEQ ID 1062 | GAAGCACTTTGTCAAGCAG | SEQ ID 1115 | GTTGAAAAGGCCATCAGGA |
| SEQ ID 1063 | GCACTTTGTCAAGCAGCTA | SEQ ID 1116 | AAGGCCATCAGGATGTCCC |
| SEQ ID 1064 | GCAGCTAAACATGAAGGCC | SEQ ID 1117 | AGGCCATCAGGATGTCCCG |
| SEQ ID 1065 | ACATGAAGGCCCTCTGCAC | SEQ ID 1118 | TGATGCTTTCCGTCTGAAT |
| SEQ ID 1066 | CATGAAGGCCCTCTGCACA | SEQ ID 1119 | TGACAACAGCCTAGAGTTT |
| SEQ ID 1067 | GGCCCTCTGCACAAATGTG | SEQ ID 1120 | CAGCCTAGAGTTTCTGGGG |
| SEQ ID 1068 | ATGTGACATCTCAAACTCT | SEQ ID 1121 | CACTTGGACCTCCTAACCA |
| SEQ ID 1069 | TGTGACATCTCAAACTCTA | SEQ ID 1122 | CCAGCCCCTGTTTCCATA |
| SEQ ID 1070 | ACTCTACAGAAGCTGGACA | SEQ ID 1123 | AATAAAGCAAGAAGTGGAG |
| SEQ ID 1071 | CTCTACAGAAGCTGGACAG | SEQ ID 1124 | ATAAAGCAAGAAGTGGAGA |
| SEQ ID 1072 | GCTGGACAGAAACTGTTCA | SEQ ID 1125 | TAAAGCAAGAAGTGGAGAA |
| SEQ ID 1073 | ACTGTTCAATATGCTGAGG | SEQ ID 1126 | AGCAAGAAGTGGAGAAAAT |
| SEQ ID 1074 | CTGTTCAATATGCTGAGGC | SEQ ID 1127 | GCAAGAAGTGGAGAAAATC |

Figure 2L

| SEQ ID | Sequence | SEQ ID | Sequence |
|---|---|---|---|
| SEQ ID 1128 | GAAGTGGAGAAAATCCTTA | SEQ ID 1179 | GACTGGTGTCTGGCAGATT |
| SEQ ID 1129 | GTGGAGAAAATCCTTATGC | SEQ ID 1180 | ATGAAGGGGGTGTCTGTGG |
| SEQ ID 1130 | AATCCTTATGCCTCCATCG | SEQ ID 1181 | TGAAGGGGGTGTCTGTGGG |
| SEQ ID 1131 | ATCCTTATGCCTCCATCGA | SEQ ID 1182 | GCTCATGGAGGCCTTGGGA |
| SEQ ID 1132 | TCCTTATGCCTCCATCGAT | SEQ ID 1183 | GAAGAGGCTGTTTGATTAT |
| SEQ ID 1133 | AGGAGAAAATAATCCAGGA | SEQ ID 1184 | GAGGCTGTTTGATTATGTC |
| SEQ ID 1134 | GGAGAAAATAATCCAGGAT | SEQ ID 1185 | GTGTAACGAGGGCCCTACA |
| SEQ ID 1135 | TAATCCAGGATTCCAAAAC | SEQ ID 1186 | AGAATACACGCTCACCAGC |
| SEQ ID 1136 | TCCAGGATTCCAAAACACT | SEQ ID 1187 | GAATACACGCTCACCAGCG |
| SEQ ID 1137 | AACACTGATGATGTTCAGA | SEQ ID 1188 | TCCTACAGTAGTAAAAAGC |
| SEQ ID 1138 | ACACTGATGATGTTCAGAC | SEQ ID 1189 | AAAGCTGTGCACACTGGCC |
| SEQ ID 1139 | CACTGATGATGTTCAGACC | SEQ ID 1190 | AAGCTGTGCACACTGGCCA |
| | | SEQ ID 1191 | AGCTGTGCACACTGGCCAT |
| REN | | SEQ ID 1192 | GCTGTGCACACTGGCCATC |
| SEQ ID 1140 | GCATGGATGGATGGAGAAG | SEQ ID 1193 | AGTTCTACACAGAGTTTGA |
| SEQ ID 1141 | ACGGATCTTCCTCAAGAGA | SEQ ID 1194 | GTTCTACACAGAGTTTGAT |
| SEQ ID 1142 | CGGATCTTCCTCAAGAGAA | SEQ ID 1195 | CAACCGCATTGGCTTCGCC |
| SEQ ID 1143 | GAGAATGCCCTCAATCCGA | SEQ ID 1196 | CCGCATTGGCTTCGCCTTG |
| SEQ ID 1144 | TGCCCTCAATCCGAGAAAG | | |
| SEQ ID 1145 | TCCGAGAAAGCCTGAAGGA | COCH | |
| SEQ ID 1146 | AGCCTGAAGGAACGAGGTG | SEQ ID 1197 | AGAGAAAGCAGATGTCCTC |
| SEQ ID 1147 | GCCTGAAGGAACGAGGTGT | SEQ ID 1198 | GAGAAAGCAGATGTCCTCT |
| SEQ ID 1148 | GGAACGAGGTGTGGACATG | SEQ ID 1199 | AGCAGATGTCCTCTGCCCA |
| SEQ ID 1149 | CGAGGTGTGGACATGGCCA | SEQ ID 1200 | GCAGATGTCCTCTGCCCAG |
| SEQ ID 1150 | CCCATGAAGAGGCTGACAC | SEQ ID 1201 | TTCTCTGTGTATGGGAACA |
| SEQ ID 1151 | GAGGCTGACACTTGGCAAC | SEQ ID 1202 | TCAGCAACTCAGGGGGACC |
| SEQ ID 1152 | CACCACCTCCTCCGTGATC | SEQ ID 1203 | CTCAGGGGGACCTGTACGA |
| SEQ ID 1153 | CTACATGGACACCCAGTAC | SEQ ID 1204 | AACTATTCCTCAGTAGATG |
| SEQ ID 1154 | ACCTTCAAAGTCGTCTTTG | SEQ ID 1205 | ACTATTCCTCAGTAGATGC |
| SEQ ID 1155 | CCTTCAAAGTCGTCTTTGA | SEQ ID 1206 | CTATTCCTCAGTAGATGCC |
| SEQ ID 1156 | AGTCGTCTTTGACACTGGT | SEQ ID 1207 | TGGCATCCAGTCTCAAATG |
| SEQ ID 1157 | GTCGTCTTTGACACTGGTT | SEQ ID 1208 | ATGCTTTCTAGATGGTCTG |
| SEQ ID 1158 | TGTTTGGGTGCCCTCCTCC | SEQ ID 1209 | TGCTTTCTAGATGGTCTGC |
| SEQ ID 1159 | GTGCAGCCGTCTCTACACT | SEQ ID 1210 | CTAAAGGCAAAAGTAGTAC |
| SEQ ID 1160 | GCTCTTCGATGCTTCGGAT | SEQ ID 1211 | AGGCAAAAGTAGTACACAG |
| SEQ ID 1161 | GCACAATGGAACAGAACTC | SEQ ID 1212 | GGCAAAAGTAGTACACAGG |
| SEQ ID 1162 | TGGAACAGAACTCACCCTC | SEQ ID 1213 | AAGTAGTACACAGGAGGCC |
| SEQ ID 1163 | CAGAACTCACCCTCCGCTA | SEQ ID 1214 | AGTAGTACACAGGAGGCCA |
| SEQ ID 1164 | CTCACCCTCCGCTATTCAA | SEQ ID 1215 | GTAGTACACAGGAGGCCAC |
| SEQ ID 1165 | CAGGGACAGTCAGTGGCTT | SEQ ID 1216 | GCAGTGTCCACAGCACATC |
| SEQ ID 1166 | TCACGGTGACACAGATGTT | SEQ ID 1217 | CAGGTAAACGACTAAAGAA |
| SEQ ID 1167 | CAGGCCATTGGCAGGGTCA | SEQ ID 1218 | ACGACTAAAGAAAACACCC |
| SEQ ID 1168 | CATCATCTCCCAAGGGGTG | SEQ ID 1219 | CGACTAAAGAAAACACCCG |
| SEQ ID 1169 | GGGGTGCTAAAAGAGGACG | SEQ ID 1220 | AGAAAACACCCGAGAAGAA |
| SEQ ID 1170 | AAGAGGACGTCTTCTCTTT | SEQ ID 1221 | GAAAACACCCGAGAAGAAA |
| SEQ ID 1171 | AGAGGACGTCTTCTCTTTC | SEQ ID 1222 | AACACCCGAGAAGAAAACT |
| SEQ ID 1172 | GAGGACGTCTTCTCTTTCT | SEQ ID 1223 | ACACCCGAGAAGAAAACTG |
| SEQ ID 1173 | CAGAGATTCCGAGAATTCC | SEQ ID 1224 | CACCCGAGAAGAAAACTGG |
| SEQ ID 1174 | TTCCCAATCGCTGGGAGGA | SEQ ID 1225 | GATTGTAAAGCAGACATTG |
| SEQ ID 1175 | TCGCTGGGAGGACAGATTG | SEQ ID 1226 | AGCAGACATTGCATTTCTG |
| SEQ ID 1176 | GGGAATTTCCACTATATCA | SEQ ID 1227 | GCAGACATTGCATTTCTGA |
| SEQ ID 1177 | TTTCCACTATATCAACCTC | SEQ ID 1228 | GCTTTAATATTGGGCAGCG |
| SEQ ID 1178 | CCTCATCAAGACTGGTGTC | SEQ ID 1229 | TATTGGGCAGCGCCGATTT |

Figure 2M

| SEQ ID 1230 | TTTTGTTGGAAAAGTGGCT |
|---|---|
| SEQ ID 1231 | AAGTGGCTCTAATGTTGGG |
| SEQ ID 1232 | AGTGGCTCTAATGTTGGGA |
| SEQ ID 1233 | GTGGCTCTAATGTTGGGAA |
| SEQ ID 1234 | TGTTGGGAATTGGAACAGA |
| SEQ ID 1235 | TTGGAACAGAAGGACCACA |
| SEQ ID 1236 | CAGAAGGACCACATGTGGG |
| SEQ ID 1237 | GGACCACATGTGGGCCTTG |
| SEQ ID 1238 | GCCAGTGAACATCCCAAAA |
| SEQ ID 1239 | AACTTTACATCAGCCAAAG |
| SEQ ID 1240 | ACTTTACATCAGCCAAAGA |
| SEQ ID 1241 | CTTTACATCAGCCAAAGAT |
| SEQ ID 1242 | AGGAAGTAGGTTTCAGAGG |
| SEQ ID 1243 | GGAAGTAGGTTTCAGAGGG |
| SEQ ID 1244 | GTAGGTTTCAGAGGGGGTA |
| SEQ ID 1245 | TTCCAATACAGGAAAAGCC |
| SEQ ID 1246 | TACAGGAAAAGCCTTGAAG |
| SEQ ID 1247 | AAGCCTTGAAGCATACTGC |
| SEQ ID 1248 | AGCCTTGAAGCATACTGCT |
| SEQ ID 1249 | GCCTTGAAGCATACTGCTC |
| SEQ ID 1250 | GCATACTGCTCAGAAATTC |
| SEQ ID 1251 | ATTCTTCACGGTAGATGCT |
| SEQ ID 1252 | TTCTTCACGGTAGATGCTG |
| SEQ ID 1253 | GAAAAGGGATCCCCAAAGT |
| SEQ ID 1254 | AAGGGATCCCCAAAGTGGT |
| SEQ ID 1255 | AGGGATCCCCAAAGTGGTG |
| SEQ ID 1256 | GGGATCCCCAAAGTGGTGG |
| SEQ ID 1257 | AGTGGTGGTGGTATTTATT |
| SEQ ID 1258 | GTGGTGGTGGTATTTATTG |
| SEQ ID 1259 | GCAGGCATTGTGGCCAGAG |
| SEQ ID 1260 | GCCTATCCCTGAAGAACTG |
| SEQ ID 1261 | GAACTGGGGATGGTTCAGG |
| SEQ ID 1262 | CTGGGGATGGTTCAGGATG |
| SEQ ID 1263 | GGCTGTCTGTCGGAATAAT |
| SEQ ID 1264 | TAATGGCTTCTTCTCTTAC |
| SEQ ID 1265 | TGGCTTCTTCTCTTACCAC |
| SEQ ID 1266 | CTGGTTTGGCACCACAAAA |
| SEQ ID 1267 | AATACGTAAAGCCTCTGGT |
| SEQ ID 1268 | ATACGTAAAGCCTCTGGTA |
| SEQ ID 1269 | TACGTAAAGCCTCTGGTAC |
| SEQ ID 1270 | AGCCTCTGGTACAGAAGCT |
| SEQ ID 1271 | GCCTCTGGTACAGAAGCTG |
| SEQ ID 1272 | GCTGTGCACTCATGAACAA |
| SEQ ID 1273 | CAAATGATGTGCAGCAAGA |
| SEQ ID 1274 | ATGATGTGCAGCAAGACCT |
| SEQ ID 1275 | TGATGTGCAGCAAGACCTG |
| SEQ ID 1276 | GACCTGTTATAACTCAGTG |
| SEQ ID 1277 | CTCAGTGAACATTGCCTTT |
| SEQ ID 1278 | TTGATGGCTCCAGCAGTGT |
| SEQ ID 1279 | TTTCCGCCTCATGCTTGAA |
| SEQ ID 1280 | TTTGTTTCCAACATAGCCA |
| SEQ ID 1281 | CATAGCCAAGACTTTTGAA |
| SEQ ID 1282 | GACTTTTGAAATCTCGGAC |
| SEQ ID 1283 | ATCTCGGACATTGGTGCCA |
| SEQ ID 1284 | TCTCGGACATTGGTGCCAA |
| SEQ ID 1285 | GATAGCTGCTGTACAGTTT |
| SEQ ID 1286 | AGAGAATGTCCTAGCTGTC |
| SEQ ID 1287 | GAGAATGTCCTAGCTGTCA |
| SEQ ID 1288 | TGTCCTAGCTGTCATCAGA |
| SEQ ID 1289 | ACATCCGCTATATGAGTGG |
| SEQ ID 1290 | CATCCGCTATATGAGTGGT |
| SEQ ID 1291 | CAGCTACTGGTGATGCCAT |
| SEQ ID 1292 | ATGTGTTTGGCCCTATAAG |
| SEQ ID 1293 | TGTGTTTGGCCCTATAAGG |
| SEQ ID 1294 | GGGAGAGCCCCAACAAGAA |
| SEQ ID 1295 | GAACTTCCTAGTAATTGTC |
| SEQ ID 1296 | CTTCCTAGTAATTGTCACA |
| SEQ ID 1297 | TTGTCACAGATGGGCAGTC |
| SEQ ID 1298 | TCACTATCTTCTCTGTTGG |
| SEQ ID 1299 | AGATATGGCTTCTAAACCG |
| SEQ ID 1300 | GATATGGCTTCTAAACCGA |
| SEQ ID 1301 | ACCGAAGGAGTCTCATGCT |
| SEQ ID 1302 | CCGAAGGAGTCTCATGCTT |
| SEQ ID 1303 | GGAGTCTCATGCTTTCTTC |
| SEQ ID 1304 | GAGAGTTCACAGGATTAGA |
| SEQ ID 1305 | CCAATTGTTTCTGATGTCA |
| SEQ ID 1306 | TTGTTTCTGATGTCATCAG |
| SEQ ID 1307 | TCCCAGCAATAATGGTAAC |

ATP1A1

| SEQ ID 1308 | GGCAATGGACCTATGAGCA |
|---|---|
| SEQ ID 1309 | TGGACCTATGAGCAGAGGA |
| SEQ ID 1310 | GGGGGTTGGACGTGATAAG |
| SEQ ID 1311 | GTATGAGCCTGCAGCTGTT |
| SEQ ID 1312 | CAAGGTGATAAAAAGGGCA |
| SEQ ID 1313 | GGTGATAAAAAGGGCAAAA |
| SEQ ID 1314 | AAAGGGCAAAAAGGGCAAA |
| SEQ ID 1315 | AAGGGCAAAAAGGGCAAAA |
| SEQ ID 1316 | AGGGCAAAAAGGGCAAAAA |
| SEQ ID 1317 | GGGCAAAAAGGGCAAAAAA |
| SEQ ID 1318 | AAAGGGCAAAAAGACAGG |
| SEQ ID 1319 | AAGGGCAAAAAGACAGGG |
| SEQ ID 1320 | AGGGCAAAAAGACAGGGA |
| SEQ ID 1321 | GGGCAAAAAGACAGGGAC |
| SEQ ID 1322 | AAAAGACAGGGACATGGAT |
| SEQ ID 1323 | AAAGACAGGGACATGGATG |
| SEQ ID 1324 | AAGACAGGGACATGGATGA |
| SEQ ID 1325 | AGACAGGGACATGGATGAA |
| SEQ ID 1326 | GACAGGGACATGGATGAAC |
| SEQ ID 1327 | GAAGTTTCTATGGATGATC |
| SEQ ID 1328 | ACTTAGCCTTGATGAACTT |
| SEQ ID 1329 | CTTAGCCTTGATGAACTTC |
| SEQ ID 1330 | ATATGGAACAGACTTGAGC |
| SEQ ID 1331 | TATGGAACAGACTTGAGCC |
| SEQ ID 1332 | CAGACTTGAGCCGGGGATT |
| SEQ ID 1333 | CATCTGCTCGTGCAGCTGA |

Figure 2N

| SEQ ID 1334 | TGGATCAAGTTTTGTCGGC |
|---|---|
| SEQ ID 1335 | GTTTTGTCGGCAGCTCTTT |
| SEQ ID 1336 | TGTTACTGTGGATTGGAGC |
| SEQ ID 1337 | GCTGCTACAGAAGAGGAAC |
| SEQ ID 1338 | GAGGAACCTCAAAACGATA |
| SEQ ID 1339 | CCTCAAAACGATAATCTGT |
| SEQ ID 1340 | AACGATAATCTGTACCTGG |
| SEQ ID 1341 | ACGATAATCTGTACCTGGG |
| SEQ ID 1342 | CGATAATCTGTACCTGGGT |
| SEQ ID 1343 | TCTGTACCTGGGTGTGGTG |
| SEQ ID 1344 | TCATAACTGGTTGCTTCTC |
| SEQ ID 1345 | CTGGTTGCTTCTCCTACTA |
| SEQ ID 1346 | GTTCAAAGATCATGGAATC |
| SEQ ID 1347 | AGATCATGGAATCCTTCAA |
| SEQ ID 1348 | GATCATGGAATCCTTCAAA |
| SEQ ID 1349 | TCCTTCAAAAACATGGTCC |
| SEQ ID 1350 | AAACATGGTCCCTCAGCAA |
| SEQ ID 1351 | AACATGGTCCCTCAGCAAG |
| SEQ ID 1352 | ACATGGTCCCTCAGCAAGC |
| SEQ ID 1353 | CATGGTCCCTCAGCAAGCC |
| SEQ ID 1354 | GCCCTTGTGATTCGAAATG |
| SEQ ID 1355 | ATGGTGAGAAAATGAGCAT |
| SEQ ID 1356 | TGGTGAGAAAATGAGCATA |
| SEQ ID 1357 | AATGAGCATAAATGCGGAG |
| SEQ ID 1358 | ATGAGCATAAATGCGGAGG |
| SEQ ID 1359 | TGAGCATAAATGCGGAGGA |
| SEQ ID 1360 | ATGCGGAGGAAGTTGTGGT |
| SEQ ID 1361 | TGCGGAGGAAGTTGTGGTT |
| SEQ ID 1362 | GTTGTGGTTGGGGATCTGG |
| SEQ ID 1363 | GTAAAAGGAGGAGACCGAA |
| SEQ ID 1364 | AAGGAGGAGACCGAATTCC |
| SEQ ID 1365 | AGGAGGAGACCGAATTCCT |
| SEQ ID 1366 | GGAGGAGACCGAATTCCTG |
| SEQ ID 1367 | TTCCTGCTGACCTCAGAAT |
| SEQ ID 1368 | TCATATCTGCAAATGGCTG |
| SEQ ID 1369 | ATGGCTGCAAGGTGGATAA |
| SEQ ID 1370 | TGGCTGCAAGGTGGATAAC |
| SEQ ID 1371 | GGTGGATAACTCCTCGCTC |
| SEQ ID 1372 | CTCCTCGCTCACTGGTGAA |
| SEQ ID 1373 | TCAGAACCCCAGACTAGGT |
| SEQ ID 1374 | CCCCAGACTAGGTCTCCAG |
| SEQ ID 1375 | ATGAAAACCCCCTGGAGAC |
| SEQ ID 1376 | TGAAAACCCCCTGGAGACG |
| SEQ ID 1377 | AACCCCCTGGAGACGAGGA |
| SEQ ID 1378 | ACCCCCTGGAGACGAGGAA |
| SEQ ID 1379 | CATTGCCTTCTTTTCAACC |
| SEQ ID 1380 | CCAATTGTGTTGAAGGCAC |
| SEQ ID 1381 | TTGTGTTGAAGGCACCGCA |
| SEQ ID 1382 | GGCACCGCACGTGGTATTG |
| SEQ ID 1383 | GAATTGCCACACTTGCTTC |
| SEQ ID 1384 | TTGCCACACTTGCTTCTGG |
| SEQ ID 1385 | TGTGCCGGAAGGTTTGCTG |
| SEQ ID 1386 | GGTTTGCTGGCCACTGTCA |
| SEQ ID 1387 | ACGCATGGCAAGGAAAAAC |
| SEQ ID 1388 | CGCATGGCAAGGAAAAACT |
| SEQ ID 1389 | GGAAAAACTGCTTAGTGAA |
| SEQ ID 1390 | AAACTGCTTAGTGAAGAAC |
| SEQ ID 1391 | AACTGCTTAGTGAAGAACT |
| SEQ ID 1392 | ACTGCTTAGTGAAGAACTT |
| SEQ ID 1393 | CTGCTTAGTGAAGAACTTA |
| SEQ ID 1394 | GAACTTAGAAGCTGTGGAG |
| SEQ ID 1395 | CTTAGAAGCTGTGGAGACC |
| SEQ ID 1396 | GCTGTGGAGACCTTGGGGT |
| SEQ ID 1397 | AACTGGAACTCTGACTCAG |
| SEQ ID 1398 | ACTGGAACTCTGACTCAGA |
| SEQ ID 1399 | CTGGAACTCTGACTCAGAA |
| SEQ ID 1400 | CTCTGACTCAGAACCGGAT |
| SEQ ID 1401 | TCAAATCCATGAAGCTGAT |
| SEQ ID 1402 | ATCCATGAAGCTGATACGA |
| SEQ ID 1403 | TCCATGAAGCTGATACGAC |
| SEQ ID 1404 | GCTGATACGACAGAGAATC |
| SEQ ID 1405 | TCAGAGTGGTGTCTCTTTT |
| SEQ ID 1406 | GACTTCAGCTACCTGGCTT |
| SEQ ID 1407 | TTGCAGGTCTTTGTAACAG |
| SEQ ID 1408 | CAGGGCAGTGTTTCAGGCT |
| SEQ ID 1409 | CCAGGAAAACCTACCTATT |
| SEQ ID 1410 | AACCTACCTATTCTTAAGC |
| SEQ ID 1411 | ACCTACCTATTCTTAAGCG |
| SEQ ID 1412 | CCTACCTATTCTTAAGCGG |
| SEQ ID 1413 | GCGGGCAGTTGCAGGAGAT |
| SEQ ID 1414 | AGTGCATAGAGCTGTGCTG |
| SEQ ID 1415 | GTGCATAGAGCTGTGCTGT |
| SEQ ID 1416 | GGAGATGAGAGAAAGATAC |
| SEQ ID 1417 | AGATACGCCAAAATCGTCG |
| SEQ ID 1418 | GATACGCCAAAATCGTCGA |
| SEQ ID 1419 | AATCGTCGAGATACCCTTC |
| SEQ ID 1420 | ATCGTCGAGATACCCTTCA |
| SEQ ID 1421 | TCGTCGAGATACCCTTCAA |
| SEQ ID 1422 | CTCCACCAACAAGTACCAG |
| SEQ ID 1423 | CAAGTACCAGTTGTCTATT |
| SEQ ID 1424 | GTACCAGTTGTCTATTCAT |
| SEQ ID 1425 | GAACCCCAACACATCGGAG |
| SEQ ID 1426 | CACATCGGAGCCCCAACAC |
| SEQ ID 1427 | CACCTGTTGGTGATGAAGG |
| SEQ ID 1428 | AGGATCCTAGACCGTTGCA |
| SEQ ID 1429 | GGATCCTAGACCGTTGCAG |
| SEQ ID 1430 | AGACGCCTTTCAGAACGCC |
| SEQ ID 1431 | GACGCCTTTCAGAACGCCT |
| SEQ ID 1432 | CGCCTATTTGGAGCTGGGG |
| SEQ ID 1433 | CGAGTCCTAGGTTTCTGCC |
| SEQ ID 1434 | CAGTTTCCTGAAGGGTTCC |
| SEQ ID 1435 | GGGTTCCAGTTTGACACTG |
| SEQ ID 1436 | TTTCCCTATCGATAATCTG |
| SEQ ID 1437 | TCTGTGCTTTGTTGGGCTC |
| SEQ ID 1438 | ATGTCGAAGTGCTGGAATT |
| SEQ ID 1439 | TGTCGAAGTGCTGGAATTA |

Figure 2O

| SEQ ID 1440 | GTGCTGGAATTAAGGTCAT |
|---|---|
| SEQ ID 1441 | TTAAGGTCATCATGGTCAC |
| SEQ ID 1442 | GGTCATCATGGTCACAGGA |
| SEQ ID 1443 | TCACAGCTAAAGCTATTGC |
| SEQ ID 1444 | AGCTATTGCCAAAGGTGTG |
| SEQ ID 1445 | GCTATTGCCAAAGGTGTGG |
| SEQ ID 1446 | AGGTGTGGGCATCATCTCA |
| SEQ ID 1447 | GGTGTGGGCATCATCTCAG |
| SEQ ID 1448 | GGCAATGAGACCGTGGAAG |
| SEQ ID 1449 | TGAGACCGTGGAAGACATT |
| SEQ ID 1450 | GACATTGCTGCCCGCCTCA |
| SEQ ID 1451 | CATCCCAGTCAGCCAGGTG |
| SEQ ID 1452 | AGGACATGACCTCCGAGCA |
| SEQ ID 1453 | GGACATGACCTCCGAGCAG |
| SEQ ID 1454 | GTACCACACTGAGATAGTG |
| SEQ ID 1455 | GCTCATCATTGTGGAAGGC |
| SEQ ID 1456 | GGCTGCCAAAGACAGGGTG |
| SEQ ID 1457 | AGACAGGGTGCTATCGTGG |
| SEQ ID 1458 | GACAGGGTGCTATCGTGGC |
| SEQ ID 1459 | TGACTCTCCAGCTTTGAAG |
| SEQ ID 1460 | GAAAGCAGACATTGGGGTT |
| SEQ ID 1461 | AGCAGACATTGGGGTTGCT |
| SEQ ID 1462 | GCAGACATTGGGGTTGCTA |
| SEQ ID 1463 | GCAAGCTGCTGACATGATT |
| SEQ ID 1464 | GCTGCTGACATGATTCTTC |
| SEQ ID 1465 | CTTTGCCTCAATTGTGACT |
| SEQ ID 1466 | TTGTGACTGGAGTAGAGGA |
| SEQ ID 1467 | GGTCGTCTGATCTTTGATA |
| SEQ ID 1468 | CTTGAAGAAATCCATTGCT |
| SEQ ID 1469 | GAAATCCATTGCTTATACC |
| SEQ ID 1470 | CCAGTAACATTCCCGAGAT |
| SEQ ID 1471 | CATTCCCGAGATCACCCCG |
| SEQ ID 1472 | ACATTCCACTACCACTGGG |
| SEQ ID 1473 | CATTCCACTACCACTGGGG |
| SEQ ID 1474 | GAGACAGCCCAGAAATCCC |
| SEQ ID 1475 | ATCCCAAAACAGACAAACT |
| SEQ ID 1476 | TCCCAAAACAGACAAACTT |
| SEQ ID 1477 | ACAGACAAACTTGTGAATG |
| SEQ ID 1478 | CAGACAAACTTGTGAATGA |
| SEQ ID 1479 | ACTTGTGAATGAGCGGCTG |
| SEQ ID 1480 | CTTGTGAATGAGCGGCTGA |
| SEQ ID 1481 | TGAGCGGCTGATCAGCATG |
| SEQ ID 1482 | CGGCTTCCTCCCAATTCAC |
| SEQ ID 1483 | TTCACCTGTTGGGCCTCCG |
| SEQ ID 1484 | CGATGTGGAAGACAGCTAC |
| SEQ ID 1485 | GACAGCTACGGGCAGCAGT |
| SEQ ID 1486 | AATCGTGGAGTTCACCTGC |
| SEQ ID 1487 | ATCGTGGAGTTCACCTGCC |
| SEQ ID 1488 | TCGTGGAGTTCACCTGCCA |
| SEQ ID 1489 | GACCAGGAGGAATTCGGTC |
| SEQ ID 1490 | TTCGGTCTTCCAGCAGGGG |
| SEQ ID 1491 | CAAGATCTTGATATTTGGC |
| SEQ ID 1492 | GATCTTGATATTTGGCCTC |

| SEQ ID 1493 | GAGACAGCCCTGGCTGCTT |
|---|---|
| SEQ ID 1494 | TGGGTGTTGCTCTTAGGAT |
| SEQ ID 1495 | ACCTACCTGGTGGTTCTGT |
| SEQ ID 1496 | CCTACCTGGTGGTTCTGTG |
| SEQ ID 1497 | GTCAGAAAACTCATCATCA |
| SEQ ID 1498 | AACTCATCATCAGGCGACG |
| SEQ ID 1499 | ACTCATCATCAGGCGACGC |
| SEQ ID 1500 | CTCATCATCAGGCGACGCC |

ATP1A2

| SEQ ID 1501 | TGGGGGCGGCAAGAAGAAA |
|---|---|
| SEQ ID 1502 | GAAGAAACAGAAGGAGAAG |
| SEQ ID 1503 | GAAACAGAAGGAGAAGGAA |
| SEQ ID 1504 | ACAGAAGGAGAAGGAACTG |
| SEQ ID 1505 | CAGAAGGAGAAGGAACTGG |
| SEQ ID 1506 | GGAGAAGGAACTGGATGAG |
| SEQ ID 1507 | GGAACTGGATGAGCTGAAG |
| SEQ ID 1508 | CTGGATGAGCTGAAGAAGG |
| SEQ ID 1509 | GAAGGAGGTGGCAATGGAT |
| SEQ ID 1510 | GGAGGTGGCAATGGATGAC |
| SEQ ID 1511 | TGGATGACCACAAGCTGTC |
| SEQ ID 1512 | GCTGTCCTTGGATGAGCTG |
| SEQ ID 1513 | ATACCAAGTGGACCTGTCC |
| SEQ ID 1514 | TACCAAGTGGACCTGTCCA |
| SEQ ID 1515 | CCCCTGAGTGGGTCAAGTT |
| SEQ ID 1516 | GTTCTGCCGTCAGCTTTTC |
| SEQ ID 1517 | CCATCCAACGACAATCTAT |
| SEQ ID 1518 | CGACAATCTATATCTGGGT |
| SEQ ID 1519 | TCTATATCTGGGTGTGGTG |
| SEQ ID 1520 | GAGCTCCAAGATCATGGAT |
| SEQ ID 1521 | GATCATGGATTCCTTCAAG |
| SEQ ID 1522 | GAACATGGTACCTCAGCAA |
| SEQ ID 1523 | CATGGTACCTCAGCAAGCC |
| SEQ ID 1524 | GATGCAGATCAACGCAGAG |
| SEQ ID 1525 | CGCAGAGGAAGTGGTGGTG |
| SEQ ID 1526 | GGTGGATAACTCATCCTTA |
| SEQ ID 1527 | CTCATCCTTAACAGGAGAG |
| SEQ ID 1528 | TATCTGTTTCTTCTCCACC |
| SEQ ID 1529 | CTGTGTTGAAGGCACTGCC |
| SEQ ID 1530 | TGGAGATTGAACACTTCAT |
| SEQ ID 1531 | CACTTCATCCAGCTGATCA |
| SEQ ID 1532 | GCGCATGGCACGGAAGAAC |
| SEQ ID 1533 | GAACTGCCTGGTGAAGAAC |
| SEQ ID 1534 | CTGCCTGGTGAAGAACCTG |
| SEQ ID 1535 | CCAAATCCATGAGGCTGAC |
| SEQ ID 1536 | ATCCATGAGGCTGACACCA |
| SEQ ID 1537 | TCCATGAGGCTGACACCAC |
| SEQ ID 1538 | GATCAGTCTGGGCCACTT |
| SEQ ID 1539 | ACGATCCCTACGTGGACG |
| SEQ ID 1540 | TTGCTGGTCTCTGCAACCG |
| SEQ ID 1541 | GGCAGGACAGGAGAACATC |
| SEQ ID 1542 | CATCTCCGTGTCTAAGCGG |
| SEQ ID 1543 | GCGGGACACAGCTGGTGAT |

Figure 2P

| SEQ ID | Sequence |
|---|---|
| SEQ ID 1544 | GTGCATTGAGCTCTCCTGT |
| SEQ ID 1545 | AATGAGAGACAGAAACCCC |
| SEQ ID 1546 | ATGAGAGACAGAAACCCCA |
| SEQ ID 1547 | TGAGAGACAGAAACCCCAA |
| SEQ ID 1548 | ACCCCAAGGTGGCAGAGAT |
| SEQ ID 1549 | CCCCAAGGTGGCAGAGATT |
| SEQ ID 1550 | GGTGGCAGAGATTCCTTTC |
| SEQ ID 1551 | CTCTACCAACAAGTACCAG |
| SEQ ID 1552 | CAAGTACCAGCTGTCTATC |
| SEQ ID 1553 | GTACCAGCTGTCTATCCAC |
| SEQ ID 1554 | GGAGATCCCGCTCGACAAG |
| SEQ ID 1555 | GGAGATGCAAGATGCCTTT |
| SEQ ID 1556 | GATGCCTTTCAAAATGCCT |
| SEQ ID 1557 | AATGCCTACATGGAGCTGG |
| SEQ ID 1558 | ATGCCTACATGGAGCTGGG |
| SEQ ID 1559 | TGCCTACATGGAGCTGGGG |
| SEQ ID 1560 | CTGAATCTGCCATCTGGAA |
| SEQ ID 1561 | TCTGCCATCTGGAAAGTTT |
| SEQ ID 1562 | AGTTTCCTCGGGGCTTCAA |
| SEQ ID 1563 | GTTTCCTCGGGGCTTCAAA |
| SEQ ID 1564 | ATTCGACACGGATGAGCTG |
| SEQ ID 1565 | TTCGACACGGATGAGCTGA |
| SEQ ID 1566 | CTTTCCCACGGAGAAGCTT |
| SEQ ID 1567 | GCTTTGCTTTGTGGGGCTC |
| SEQ ID 1568 | GCGCAGGCATCAAGGTGAT |
| SEQ ID 1569 | GGTGATCATGGTAACCGGG |
| SEQ ID 1570 | CCGGGGATCACCCTATCAC |
| SEQ ID 1571 | GGCCATTGCCAAAGGCGTG |
| SEQ ID 1572 | AGGCGTGGGCATCATATCA |
| SEQ ID 1573 | GGCGTGGGCATCATATCAG |
| SEQ ID 1574 | CGAGACTGTGGAGGACATT |
| SEQ ID 1575 | CATTCCCATGAGTCAAGTC |
| SEQ ID 1576 | GTCAACCCCAGAGAAGCCA |
| SEQ ID 1577 | CCCCAGAGAAGCCAAGGCA |
| SEQ ID 1578 | GGACATGACATCGGAGCAG |
| SEQ ID 1579 | GAACCACACAGAGGATCGTC |
| SEQ ID 1580 | CCACACAGAGATCGTCTTT |
| SEQ ID 1581 | CGTCTCCCCAGCAGAAGCT |
| SEQ ID 1582 | GCTCATCATTGTGGAGGGA |
| SEQ ID 1583 | CGACTCCCTGCATTGAAG |
| SEQ ID 1584 | GAAGGCTGACATTGGCATT |
| SEQ ID 1585 | GGCTGACATTGGCATTGCC |
| SEQ ID 1586 | GCAGGCAGCCGACATGATC |
| SEQ ID 1587 | CTTTGCCTCCATCGTCACG |
| SEQ ID 1588 | CTTGAAGAAATCCATCGCC |
| SEQ ID 1589 | GAAATCCATCGCCTACACC |
| SEQ ID 1590 | ATCCATCGCCTACACCCTG |
| SEQ ID 1591 | TCCATCGCCTACACCCTGA |
| SEQ ID 1592 | ACTCCCAGACGGACAAGCT |
| SEQ ID 1593 | CTCCCAGACGGACAAGCTG |
| SEQ ID 1594 | GCTGGTGAATGAGAGGCT |
| SEQ ID 1595 | TGAGAGGCTCATCAGCATG |
| SEQ ID 1596 | CGGTTTCCTGCCATCACGG |
| SEQ ID 1597 | TCCGCCTCGACTGGGATGA |
| SEQ ID 1598 | TGATCTGGAGGACAGCTAT |
| SEQ ID 1599 | GGTGGTGGAGTTCACGTGC |
| SEQ ID 1600 | CTCAGTCTTCCAGCAGGGC |
| SEQ ID 1601 | CAAGATCCTGATTTTTGGG |
| SEQ ID 1602 | GATCCTGATTTTTGGGCTC |
| SEQ ID 1603 | AGTCACCTGGTGGTTCTGC |
| SEQ ID 1604 | GTCACCTGGTGGTTCTGCG |
| SEQ ID 1605 | AGCTCATCCTGCGGCGGTA |
| SEQ ID 1606 | GCTCATCCTGCGGCGGTAT |

ATP1A3

| SEQ ID | Sequence |
|---|---|
| SEQ ID 1607 | GATGGGGGACAAGAAAGAT |
| SEQ ID 1608 | GAAAGATGACAAGGACTCA |
| SEQ ID 1609 | AGATGACAAGGACTCACCC |
| SEQ ID 1610 | GATGACAAGGACTCACCCA |
| SEQ ID 1611 | GGACTCACCCAAGAAGAAC |
| SEQ ID 1612 | GAAGAACAAGGGCAAGGAG |
| SEQ ID 1613 | GAACAAGGGCAAGGAGCGC |
| SEQ ID 1614 | GAAGGAGGTGGCTATGACA |
| SEQ ID 1615 | GGAGGTGGCTATGACAGAG |
| SEQ ID 1616 | GATGTCAGTGGAAGAGGTC |
| SEQ ID 1617 | GAGGTCTGCCGGAAATACA |
| SEQ ID 1618 | ATACAACACAGACTGTGTG |
| SEQ ID 1619 | TACAACACAGACTGTGTGC |
| SEQ ID 1620 | CACAGACTGTGTGCAGGGT |
| SEQ ID 1621 | GTTTTGCCGGCAGCTCTTC |
| SEQ ID 1622 | CCTGTACCTGGGCATCGTG |
| SEQ ID 1623 | GAGCTCCAAGATCATGGAG |
| SEQ ID 1624 | GATCATGGAGTCCTTCAAG |
| SEQ ID 1625 | GAACATGGTGCCCCAGCAA |
| SEQ ID 1626 | GGTGAGAAGATGCAGGTGA |
| SEQ ID 1627 | GATGCAGGTGAACGCTGAG |
| SEQ ID 1628 | GGTGGACAACTCCTCCCTG |
| SEQ ID 1629 | CTCCTCCCTGACTGGCGAA |
| SEQ ID 1630 | CCCCTTGGAGACTCGGAAC |
| SEQ ID 1631 | CATCACCTTCTTTTCCACC |
| SEQ ID 1632 | CTGTGTGGAAGGCACGGCT |
| SEQ ID 1633 | TGTCCCAGAGGGTCTGCTG |
| SEQ ID 1634 | GAACTGCCTGGTGAAGAAC |
| SEQ ID 1635 | CTGCCTGGTGAAGAACCTG |
| SEQ ID 1636 | GAACCTGGAGGCTGTAGAA |
| SEQ ID 1637 | CCTGGAGGCTGTAGAAACC |
| SEQ ID 1638 | GACAGGGACCCTCACTCAG |
| SEQ ID 1639 | CCAGATCCACGAGGCTGAC |
| SEQ ID 1640 | GAGTTCGCACACCTGGGTG |
| SEQ ID 1641 | TCGCGCTGTCTTCAAGGGT |
| SEQ ID 1642 | GGGTGGTCAGGACAACATC |
| SEQ ID 1643 | CATCCCTGTGCTCAAGAGG |
| SEQ ID 1644 | GAGGGATGTGGCTGGGGAT |
| SEQ ID 1645 | GTGCATCGAGCTGTCCTCT |
| SEQ ID 1646 | GCTGATGCGTGAACGCAAC |
| SEQ ID 1647 | CGCAACAAGAAAGTGGCTG |

Figure 2Q

| SEQ ID | Sequence | SEQ ID | Sequence |
|---|---|---|---|
| SEQ ID 1648 | CAAGAAAGTGGCTGAGATT | SEQ ID 1701 | ATCCGCAAACTCATCCTGC |
| SEQ ID 1649 | GAAAGTGGCTGAGATTCCC | SEQ ID 1702 | TCCGCAAACTCATCCTGCG |
| SEQ ID 1650 | AGTGGCTGAGATTCCCTTC | SEQ ID 1703 | ACTCATCCTGCGCAGGAAC |
| SEQ ID 1651 | GTGGCTGAGATTCCCTTCA | SEQ ID 1704 | CTCATCCTGCGCAGGAACC |
| SEQ ID 1652 | TTCCACCAACAAATACCAG | SEQ ID 1705 | GGAAACCTACTACTGACCT |
| SEQ ID 1653 | CAAATACCAGCTCTCCATC | | |
| SEQ ID 1654 | ATACCAGCTCTCCATCCAT | ATP1B1 | |
| SEQ ID 1655 | TACCAGCTCTCCATCCATG | SEQ ID 1706 | AAATTAAATTTTAAGTGAC |
| SEQ ID 1656 | CGACAACCGATACCTGCTG | SEQ ID 1707 | AATTAAATTTTAAGTGACA |
| SEQ ID 1657 | CCGATACCTGCTGGTGATG | SEQ ID 1708 | ATTAAATTTTAAGTGACAC |
| SEQ ID 1658 | ATGAAGGAGGCCTTCCAGA | SEQ ID 1709 | TTAAATTTTAAGTGACACT |
| SEQ ID 1659 | TGAAGGAGGCCTTCCAGAA | SEQ ID 1710 | GAAATTCATCTGGAACTCA |
| SEQ ID 1660 | GGAGGCCTTCCAGAATGCC | SEQ ID 1711 | ATTCATCTGGAACTCAGAG |
| SEQ ID 1661 | TGCCTACCTTGAGCTCGGT | SEQ ID 1712 | TTCATCTGGAACTCAGAGA |
| SEQ ID 1662 | GGGCTTTGCCTTCGACTGT | SEQ ID 1713 | CTCAGAGAAGAAGGAGTTT |
| SEQ ID 1663 | CTTCACCACGGACAACCTC | SEQ ID 1714 | GAAGGAGTTTCTGGGCAGG |
| SEQ ID 1664 | CCTCTGCTTTGTGGGCCTC | SEQ ID 1715 | GGAGTTTCTGGGCAGGACC |
| SEQ ID 1665 | GGTCATCATGGTCACCGGC | SEQ ID 1716 | GATCCTTCTATTCTACGTA |
| SEQ ID 1666 | GGCCATTGCCAAGGGTGTG | SEQ ID 1717 | TATTTTATGGCTGCCTGGC |
| SEQ ID 1667 | GGGTGTGGGCATCATCTCT | SEQ ID 1718 | CCATCCAAGTGATGCTGCT |
| SEQ ID 1668 | CGAGACTGTGGAGGACATC | SEQ ID 1719 | GTGATGCTGCTCACCATCA |
| SEQ ID 1669 | CATTCCCGTCAGCCAGGTT | SEQ ID 1720 | TTTAAGCCCACATATCAGG |
| SEQ ID 1670 | GGACTTCACCTCCGAGCAA | SEQ ID 1721 | GCCCACATATCAGGACCGA |
| SEQ ID 1671 | ATCGACGAGATCCTGCAGA | SEQ ID 1722 | CACAGATTCCTCAGATCCA |
| SEQ ID 1672 | TCGACGAGATCCTGCAGAA | SEQ ID 1723 | GACTGAAATTCCTTTCGT |
| SEQ ID 1673 | TCACACCGAGATCGTCTTC | SEQ ID 1724 | ATTTCCTTTCGTCCTAATG |
| SEQ ID 1674 | GCTCATCATTGTGGAGGGC | SEQ ID 1725 | TTTCCTTTCGTCCTAATGA |
| SEQ ID 1675 | TTGTGGCTGTGACCGGGGA | SEQ ID 1726 | TGATCCCAAGAGCTATGAG |
| SEQ ID 1676 | GAAGGCCGACATTGGGGTG | SEQ ID 1727 | GAGCTATGAGGCATATGTA |
| SEQ ID 1677 | GCAGGCAGCTGACATGATC | SEQ ID 1728 | CATAGTTAGGTTCCTGGAA |
| SEQ ID 1678 | CTTTGCCTCCATCGTCACA | SEQ ID 1729 | AAGTACAAAGATTCAGCCC |
| SEQ ID 1679 | CCTAAAGAAGTCCATTGCC | SEQ ID 1730 | AGTACAAAGATTCAGCCCA |
| SEQ ID 1680 | AGAAGTCCATTGCCTACAC | SEQ ID 1731 | GTACAAAGATTCAGCCCAG |
| SEQ ID 1681 | GAAGTCCATTGCCTACACC | SEQ ID 1732 | AGATTCAGCCCAGAGGGAT |
| SEQ ID 1682 | GTCCATTGCCTACACCCTG | SEQ ID 1733 | GATTCAGCCCAGAGGGATG |
| SEQ ID 1683 | TATCCCGGAGATCACGCCC | SEQ ID 1734 | GATTGTGGCGATGTGCCCA |
| SEQ ID 1684 | AGCGACATCATGAAGAGAC | SEQ ID 1735 | CCGAAAGAACGAGGAGACT |
| SEQ ID 1685 | GCGACATCATGAAGAGACA | SEQ ID 1736 | AGAACGAGGAGACTTTAAT |
| SEQ ID 1686 | CCCGCGGACGGACAAATTG | SEQ ID 1737 | GAACGAGGAGACTTTAATC |
| SEQ ID 1687 | ATTGGTCAATGAGAGACTC | SEQ ID 1738 | CGAGGAGACTTTAATCATG |
| SEQ ID 1688 | TTGGTCAATGAGAGACTCA | SEQ ID 1739 | TCATGAACGAGGAGAGCGA |
| SEQ ID 1689 | TGAGAGACTCATCAGCATG | SEQ ID 1740 | CGAGGAGAGCGAAAGGTCT |
| SEQ ID 1690 | TGATCCAGGCTCTCGGTGG | SEQ ID 1741 | AGGTCTGCAGATTCAAGCT |
| SEQ ID 1691 | AATGGCTTCTTGCCCGGCA | SEQ ID 1742 | GGTCTGCAGATTCAAGCTT |
| SEQ ID 1692 | ATGGCTTCTTGCCCGGCAA | SEQ ID 1743 | GCTTGAATGGCTGGGAAAT |
| SEQ ID 1693 | TGGCTTCTTGCCCGGCAAC | SEQ ID 1744 | TGGCTGGGAAATTGCTCTG |
| SEQ ID 1694 | TGACCTGGAAGACAGTTAC | SEQ ID 1745 | TGATGAAACTTATGGCTAC |
| SEQ ID 1695 | GACAGTTACGGGCAGCAGT | SEQ ID 1746 | ACTTATGGCTACAAGAGG |
| SEQ ID 1696 | GGTGGTGGAGTTCACCTGC | SEQ ID 1747 | CTTATGGCTACAAAGAGGG |
| SEQ ID 1697 | GAACAAGATCCTGATCTTC | SEQ ID 1748 | AGAGGGCAAACCGTGCATT |
| SEQ ID 1698 | CAAGATCCTGATCTTCGGG | SEQ ID 1749 | GAGGGCAAACCGTGCATTA |
| SEQ ID 1699 | GATCCTGATCTTCGGGCTG | SEQ ID 1750 | CCGTGCATTATTATAAAGC |
| SEQ ID 1700 | GCCCAGCTGGTGGTTCTGT | SEQ ID 1751 | AGCTCAACCGAGTTCTAGG |

Figure 2R

| SEQ ID 1752 | GCTCAACCGAGTTCTAGGC |
|---|---|
| SEQ ID 1753 | CCGAGTTCTAGGCTTCAAA |
| SEQ ID 1754 | ACCTAAGCCTCCCAAGAAT |
| SEQ ID 1755 | CCTAAGCCTCCCAAGAATG |
| SEQ ID 1756 | GCCTCCCAAGAATGAGTCC |
| SEQ ID 1757 | GAATGAGTCCTTGGAGACT |
| SEQ ID 1758 | TGAGTCCTTGGAGACTTAC |
| SEQ ID 1759 | GTATAACCCAAATGTCCTT |
| SEQ ID 1760 | CCCAAATGTCCTTCCCGTT |
| SEQ ID 1761 | ATGTCCTTCCCGTTCAGTG |
| SEQ ID 1762 | TGTCCTTCCCGTTCAGTGC |
| SEQ ID 1763 | GCGAGATGAAGATAAGGAT |
| SEQ ID 1764 | GGATAAAGTTGGAAATGTG |
| SEQ ID 1765 | AGTTGGAAATGTGGAGTAT |
| SEQ ID 1766 | GTTGGAAATGTGGAGTATT |
| SEQ ID 1767 | ATGTGGAGTATTTTGGACT |
| SEQ ID 1768 | TGTGGAGTATTTTGGACTG |
| SEQ ID 1769 | CTCCCCTGGTTTTCCTCTG |
| SEQ ID 1770 | ACTCCTGCAGCCCAAATAC |
| SEQ ID 1771 | CTCCTGCAGCCCAAATACC |
| SEQ ID 1772 | ATACCTGCAGCCCCTGCTG |
| SEQ ID 1773 | TCTTACCATGGACACTGAA |
| SEQ ID 1774 | ATTCGCATAGAGTGTAAGG |
| SEQ ID 1775 | TTCGCATAGAGTGTAAGGC |
| SEQ ID 1776 | GGCGTACGGTGAGAACATT |
| SEQ ID 1777 | CATTGGGTACAGTGAGAAA |
| SEQ ID 1778 | AGACCGTTTTCAGGGACGT |
| SEQ ID 1779 | GACCGTTTTCAGGGACGTT |
| SEQ ID 1780 | TTGAAGTTAAGAGCTGATC |

| ATP1B2 | |
|---|---|
| SEQ ID 1781 | GATGGTCATCCAGAAAGAG |
| SEQ ID 1782 | AGAGAAGAAGAGCTGCGGG |
| SEQ ID 1783 | GAGAAGAAGAGCTGCGGGC |
| SEQ ID 1784 | GGAGTTCGTGTGGAACCCG |
| SEQ ID 1785 | CCCGAGGACGCACCAGTTT |
| SEQ ID 1786 | GACTGAGAACCTTGATGTC |
| SEQ ID 1787 | CCTTGATGTCATTGTCAAT |
| SEQ ID 1788 | TGTCAGTGACACTGAAAGC |
| SEQ ID 1789 | AGCTGGGACCAGCATGTTC |
| SEQ ID 1790 | GCTGGGACCAGCATGTTCA |
| SEQ ID 1791 | GCTCAACAAGTTCTTGGAG |
| SEQ ID 1792 | CAAGTTCTTGGAGCCTTAC |
| SEQ ID 1793 | GTTCTTGGAGCCTTACAAC |
| SEQ ID 1794 | CGACTCTATCCAAGCCCAA |
| SEQ ID 1795 | GCCCAAAAGAATGATGTCT |
| SEQ ID 1796 | AAGAATGATGTCTGCCGCC |
| SEQ ID 1797 | AGAATGATGTCTGCCGCCC |
| SEQ ID 1798 | GAATGATGTCTGCCGCCCT |
| SEQ ID 1799 | CAGCCAGATAATGGAGTCC |
| SEQ ID 1800 | TGGAGTCCTCAACTACCCC |
| SEQ ID 1801 | CTACCCCAAACGTGCCTGC |
| SEQ ID 1802 | ACGTGCCTGCCAATTCAAC |

| SEQ ID 1803 | CGTGCCTGCCAATTCAACC |
|---|---|
| SEQ ID 1804 | TTCAACCGGACCCAGCTGG |
| SEQ ID 1805 | GATGAACCGGGTCATCAAC |
| SEQ ID 1806 | CCGGGTCATCAACTTCTAT |
| SEQ ID 1807 | CTTCTATGCAGGAGCAAAC |
| SEQ ID 1808 | ACCAGAGCATGAATGTTAC |
| SEQ ID 1809 | CCAGAGCATGAATGTTACC |
| SEQ ID 1810 | TGTTACCTGTGCTGGGAAG |
| SEQ ID 1811 | GCGAGATGAAGATGCTGAG |
| SEQ ID 1812 | GATGCTGAGAATCTCGGCA |
| SEQ ID 1813 | TCTCGGCAACTTCGTCATG |
| SEQ ID 1814 | CTTCGTCATGTTCCCCGCC |
| SEQ ID 1815 | CGGCAACATCGACCTCATG |
| SEQ ID 1816 | CATCGACCTCATGTACTTC |
| SEQ ID 1817 | AAAGTTCCACGTGAACTAC |
| SEQ ID 1818 | AAGTTCCACGTGAACTACA |
| SEQ ID 1819 | AGTTCCACGTGAACTACAC |
| SEQ ID 1820 | GTTCCACGTGAACTACACA |
| SEQ ID 1821 | CTACACACAGCCCCTGGTG |
| SEQ ID 1822 | GTTCCTGAATGTGACCCCC |
| SEQ ID 1823 | TGTGACCCCCAACGTGGAG |
| SEQ ID 1824 | CGTGGAGGTGAATGTAGAA |
| SEQ ID 1825 | TGTAGAATGTCGCATCAAC |
| SEQ ID 1826 | TGTCGCATCAACGCCGCCA |
| SEQ ID 1827 | CATCGCCACAGACGATGAG |
| SEQ ID 1828 | ACTCCGCATCAACAAAACC |
| SEQ ID 1829 | CTCCGCATCAACAAAACCT |

SEQUENCE LISTING

<160> NUMBER OF SEQ ID NOS: 1829

<210> SEQ ID NO 1
<211> LENGTH: 19
<212> TYPE: DNA
<213> ORGANISM: Homo sapiens

<400> SEQUENCE: 1
gccgagtcct ccaactacc                                                    19

<210> SEQ ID NO 2
<211> LENGTH: 19
<212> TYPE: DNA
<213> ORGANISM: Homo sapiens

<400> SEQUENCE: 2 ctaccctgc ttggtgcca                                                     19

<210> SEQ ID NO 3
<211> LENGTH: 19
<212> TYPE: DNA
<213> ORGANISM: Homo sapiens

<400> SEQUENCE: 3
gtggggtgga aactgccag                                                    19

<210> SEQ ID NO 4
<211> LENGTH: 19
<212> TYPE: DNA
<213> ORGANISM: Homo sapiens

<400> SEQUENCE: 4
actgccagaa ggaccgcca                                                    19

<210> SEQ ID NO 5
<211> LENGTH: 19
<212> TYPE: DNA
<213> ORGANISM: Homo sapiens

<400> SEQUENCE: 5
catcgtcacc accaaggca                                                    19

<210> SEQ ID NO 6
<211> LENGTH: 19
<212> TYPE: DNA
<213> ORGANISM: Homo sapiens

<400> SEQUENCE: 6
ggcaaaggtg gacaaaaaa                                                    19

<210> SEQ ID NO 7
<211> LENGTH: 19
<212> TYPE: DNA
<213> ORGANISM: Homo sapiens

<400> SEQUENCE: 7
aggtggacaa aaaactggg                                                    19

<210> SEQ ID NO 8
<211> LENGTH: 19
<212> TYPE: DNA
<213> ORGANISM: Homo sapiens

```
<400> SEQUENCE: 8
ggtggacaaa aaactggga                                              19

<210> SEQ ID NO 9
<211> LENGTH: 19
<212> TYPE: DNA
<213> ORGANISM: Homo sapiens

<400> SEQUENCE: 9
aaaactggga cgcttcttc                                              19

<210> SEQ ID NO 10
<211> LENGTH: 19
<212> TYPE: DNA
<213> ORGANISM: Homo sapiens

<400> SEQUENCE: 10
aaactgggac gcttcttct                                              19

<210> SEQ ID NO 11
<211> LENGTH: 19
<212> TYPE: DNA
<213> ORGANISM: Homo sapiens

<400> SEQUENCE: 11
aactgggacg cttcttctt                                              19

<210> SEQ ID NO 12
<211> LENGTH: 19
<212> TYPE: DNA
<213> ORGANISM: Homo sapiens

<400> SEQUENCE: 12
actgggacgc ttcttcttc                                              19

<210> SEQ ID NO 13
<211> LENGTH: 19
<212> TYPE: DNA
<213> ORGANISM: Homo sapiens

<400> SEQUENCE: 13
ctgggacgct tcttcttct                                              19

<210> SEQ ID NO 14
<211> LENGTH: 19
<212> TYPE: DNA
<213> ORGANISM: Homo sapiens

<400> SEQUENCE: 14
gaagcaaacg tggactgtc                                              19

<210> SEQ ID NO 15
<211> LENGTH: 19
<212> TYPE: DNA
<213> ORGANISM: Homo sapiens

<400> SEQUENCE: 15
gcaaacgtgg actgtccaa                                              19

<210> SEQ ID NO 16
<211> LENGTH: 19
<212> TYPE: DNA
<213> ORGANISM: Homo sapiens
```

```
<400> SEQUENCE: 16
acgtggactg tccaaaata                                                19

<210> SEQ ID NO 17
<211> LENGTH: 19
<212> TYPE: DNA
<213> ORGANISM: Homo sapiens

<400> SEQUENCE: 17
cgtggactgt ccaaaataa                                                19

<210> SEQ ID NO 18
<211> LENGTH: 19
<212> TYPE: DNA
<213> ORGANISM: Homo sapiens

<400> SEQUENCE: 18
aataacgggc actcagtga                                                19

<210> SEQ ID NO 19
<211> LENGTH: 19
<212> TYPE: DNA
<213> ORGANISM: Homo sapiens

<400> SEQUENCE: 19
ataacgggca ctcagtgat                                                19

<210> SEQ ID NO 20
<211> LENGTH: 19
<212> TYPE: DNA
<213> ORGANISM: Homo sapiens

<400> SEQUENCE: 20
taacgggcac tcagtgatg                                                19

<210> SEQ ID NO 21
<211> LENGTH: 19
<212> TYPE: DNA
<213> ORGANISM: Homo sapiens

<400> SEQUENCE: 21
cgggcactca gtgatgatg                                                19

<210> SEQ ID NO 22
<211> LENGTH: 19
<212> TYPE: DNA
<213> ORGANISM: Homo sapiens

<400> SEQUENCE: 22
caaggccagc atttctgga                                                19

<210> SEQ ID NO 23
<211> LENGTH: 19
<212> TYPE: DNA
<213> ORGANISM: Homo sapiens

<400> SEQUENCE: 23
ggccagcatt tctggagga                                                19

<210> SEQ ID NO 24
<211> LENGTH: 19
<212> TYPE: DNA
<213> ORGANISM: Homo sapiens
```

```
<400> SEQUENCE: 24
acagttgcac ctgcactgg                                                  19

<210> SEQ ID NO 25
<211> LENGTH: 19
<212> TYPE: DNA
<213> ORGANISM: Homo sapiens

<400> SEQUENCE: 25
cagttgcacc tgcactggt                                                  19

<210> SEQ ID NO 26
<211> LENGTH: 19
<212> TYPE: DNA
<213> ORGANISM: Homo sapiens

<400> SEQUENCE: 26
agagaagggg acatcgagg                                                  19

<210> SEQ ID NO 27
<211> LENGTH: 19
<212> TYPE: DNA
<213> ORGANISM: Homo sapiens

<400> SEQUENCE: 27
gagaagggga catcgagga                                                  19

<210> SEQ ID NO 28
<211> LENGTH: 19
<212> TYPE: DNA
<213> ORGANISM: Homo sapiens

<400> SEQUENCE: 28
ggggacatcg aggaatgtg                                                  19

<210> SEQ ID NO 29
<211> LENGTH: 19
<212> TYPE: DNA
<213> ORGANISM: Homo sapiens

<400> SEQUENCE: 29
tgtgaaagag gcccaggac                                                  19

<210> SEQ ID NO 30
<211> LENGTH: 19
<212> TYPE: DNA
<213> ORGANISM: Homo sapiens

<400> SEQUENCE: 30
agaggcccag gaccctgaa                                                  19

<210> SEQ ID NO 31
<211> LENGTH: 19
<212> TYPE: DNA
<213> ORGANISM: Homo sapiens

<400> SEQUENCE: 31
gacgaaattg cggtgctgg                                                  19

<210> SEQ ID NO 32
<211> LENGTH: 19
<212> TYPE: DNA
<213> ORGANISM: Homo sapiens
```

```
<400> SEQUENCE: 32
attgcggtgc tggcctttc                                                 19

<210> SEQ ID NO 33
<211> LENGTH: 19
<212> TYPE: DNA
<213> ORGANISM: Homo sapiens

<400> SEQUENCE: 33
ttgcggtgct ggcctttct                                                 19

<210> SEQ ID NO 34
<211> LENGTH: 19
<212> TYPE: DNA
<213> ORGANISM: Homo sapiens

<400> SEQUENCE: 34
cccaggtgaa cgagggctt                                                 19

<210> SEQ ID NO 35
<211> LENGTH: 19
<212> TYPE: DNA
<213> ORGANISM: Homo sapiens

<400> SEQUENCE: 35
tatccccaaa cctgagatg                                                 19

<210> SEQ ID NO 36
<211> LENGTH: 19
<212> TYPE: DNA
<213> ORGANISM: Homo sapiens

<400> SEQUENCE: 36
acctgagatg agcactacg                                                 19

<210> SEQ ID NO 37
<211> LENGTH: 19
<212> TYPE: DNA
<213> ORGANISM: Homo sapiens

<400> SEQUENCE: 37
cctgagatga gcactacga                                                 19

<210> SEQ ID NO 38
<211> LENGTH: 19
<212> TYPE: DNA
<213> ORGANISM: Homo sapiens

<400> SEQUENCE: 38
ggaggagaaa ctgaggcac                                                 19

<210> SEQ ID NO 39
<211> LENGTH: 19
<212> TYPE: DNA
<213> ORGANISM: Homo sapiens

<400> SEQUENCE: 39
actgaggcac tacttccgc                                                 19

<210> SEQ ID NO 40
<211> LENGTH: 19
<212> TYPE: DNA
<213> ORGANISM: Homo sapiens
```

```
<400> SEQUENCE: 40
ctgaggcact acttccgct                                               19

<210> SEQ ID NO 41
<211> LENGTH: 19
<212> TYPE: DNA
<213> ORGANISM: Homo sapiens

<400> SEQUENCE: 41
ggtcgtctgg actgtgttc                                               19

<210> SEQ ID NO 42
<211> LENGTH: 19
<212> TYPE: DNA
<213> ORGANISM: Homo sapiens

<400> SEQUENCE: 42
cagatcctgg cattctctc                                               19

<210> SEQ ID NO 43
<211> LENGTH: 19
<212> TYPE: DNA
<213> ORGANISM: Homo sapiens

<400> SEQUENCE: 43
gctgtactac gacaaggaa                                               19

<210> SEQ ID NO 44
<211> LENGTH: 19
<212> TYPE: DNA
<213> ORGANISM: Homo sapiens

<400> SEQUENCE: 44
ggaacagaca gtgagcatg                                               19

<210> SEQ ID NO 45
<211> LENGTH: 19
<212> TYPE: DNA
<213> ORGANISM: Homo sapiens

<400> SEQUENCE: 45
cagacagtga gcatgaagg                                               19

<210> SEQ ID NO 46
<211> LENGTH: 19
<212> TYPE: DNA
<213> ORGANISM: Homo sapiens

<400> SEQUENCE: 46
ggacaatgtc aggcccctg                                               19

<210> SEQ ID NO 47
<211> LENGTH: 19
<212> TYPE: DNA
<213> ORGANISM: Homo sapiens

<400> SEQUENCE: 47
acacaacgga cctgagcac                                               19

<210> SEQ ID NO 48
<211> LENGTH: 19
<212> TYPE: DNA
<213> ORGANISM: Homo sapiens
```

```
<400> SEQUENCE: 48
cacaacggac ctgagcact                                               19

<210> SEQ ID NO 49
<211> LENGTH: 19
<212> TYPE: DNA
<213> ORGANISM: Homo sapiens

<400> SEQUENCE: 49
cggacctgag cactggcat                                               19

<210> SEQ ID NO 50
<211> LENGTH: 19
<212> TYPE: DNA
<213> ORGANISM: Homo sapiens

<400> SEQUENCE: 50
ggacttcccc attgccaag                                               19

<210> SEQ ID NO 51
<211> LENGTH: 19
<212> TYPE: DNA
<213> ORGANISM: Homo sapiens

<400> SEQUENCE: 51
gtatgaccct tccctgaag                                               19

<210> SEQ ID NO 52
<211> LENGTH: 19
<212> TYPE: DNA
<213> ORGANISM: Homo sapiens

<400> SEQUENCE: 52
gcccctgtct gtttcctat                                               19

<210> SEQ ID NO 53
<211> LENGTH: 19
<212> TYPE: DNA
<213> ORGANISM: Homo sapiens

<400> SEQUENCE: 53
gcaacttccc tgaggatcc                                               19

<210> SEQ ID NO 54
<211> LENGTH: 19
<212> TYPE: DNA
<213> ORGANISM: Homo sapiens

<400> SEQUENCE: 54
cttccctgag gatcctcaa                                               19

<210> SEQ ID NO 55
<211> LENGTH: 19
<212> TYPE: DNA
<213> ORGANISM: Homo sapiens

<400> SEQUENCE: 55
caatggtcat gctttcaac                                               19

<210> SEQ ID NO 56
<211> LENGTH: 19
<212> TYPE: DNA
<213> ORGANISM: Homo sapiens
```

```
<400> SEQUENCE: 56
tggtcatgct ttcaacgtg                                              19

<210> SEQ ID NO 57
<211> LENGTH: 19
<212> TYPE: DNA
<213> ORGANISM: Homo sapiens

<400> SEQUENCE: 57
cgtggagttt gatgactct                                              19

<210> SEQ ID NO 58
<211> LENGTH: 19
<212> TYPE: DNA
<213> ORGANISM: Homo sapiens

<400> SEQUENCE: 58
agcagtgctc aagggagga                                              19

<210> SEQ ID NO 59
<211> LENGTH: 19
<212> TYPE: DNA
<213> ORGANISM: Homo sapiens

<400> SEQUENCE: 59
gcagtgctca agggaggac                                              19

<210> SEQ ID NO 60
<211> LENGTH: 19
<212> TYPE: DNA
<213> ORGANISM: Homo sapiens

<400> SEQUENCE: 60
ggttcagagc atactgtgg                                              19

<210> SEQ ID NO 61
<211> LENGTH: 19
<212> TYPE: DNA
<213> ORGANISM: Homo sapiens

<400> SEQUENCE: 61
aagaaatatg ctgcagaac                                              19

<210> SEQ ID NO 62
<211> LENGTH: 19
<212> TYPE: DNA
<213> ORGANISM: Homo sapiens

<400> SEQUENCE: 62
agaaatatgc tgcagaact                                              19

<210> SEQ ID NO 63
<211> LENGTH: 19
<212> TYPE: DNA
<213> ORGANISM: Homo sapiens

<400> SEQUENCE: 63
gaaatatgct gcagaactt                                              19

<210> SEQ ID NO 64
<211> LENGTH: 19
<212> TYPE: DNA
<213> ORGANISM: Homo sapiens
```

```
<400> SEQUENCE: 64
atatgctgca gaacttcac                                              19

<210> SEQ ID NO 65
<211> LENGTH: 19
<212> TYPE: DNA
<213> ORGANISM: Homo sapiens

<400> SEQUENCE: 65
tatgctgcag aacttcact                                              19

<210> SEQ ID NO 66
<211> LENGTH: 19
<212> TYPE: DNA
<213> ORGANISM: Homo sapiens

<400> SEQUENCE: 66
cttcacttgg ttcactgga                                              19

<210> SEQ ID NO 67
<211> LENGTH: 19
<212> TYPE: DNA
<213> ORGANISM: Homo sapiens

<400> SEQUENCE: 67
caccaaatat ggggatttt                                              19

<210> SEQ ID NO 68
<211> LENGTH: 19
<212> TYPE: DNA
<213> ORGANISM: Homo sapiens

<400> SEQUENCE: 68 atatgggat tttgggaaa                                               19

<210> SEQ ID NO 69
<211> LENGTH: 19
<212> TYPE: DNA
<213> ORGANISM: Homo sapiens

<400> SEQUENCE: 69
tatggggatt tgggaaag                                               19

<210> SEQ ID NO 70
<211> LENGTH: 19
<212> TYPE: DNA
<213> ORGANISM: Homo sapiens

<400> SEQUENCE: 70
agctgtgcag caacctgat                                              19

<210> SEQ ID NO 71
<211> LENGTH: 19
<212> TYPE: DNA
<213> ORGANISM: Homo sapiens

<400> SEQUENCE: 71
gctgtgcagc aacctgatg                                              19

<210> SEQ ID NO 72
<211> LENGTH: 19
<212> TYPE: DNA
<213> ORGANISM: Homo sapiens
```

```
<400> SEQUENCE: 72
cctgatggac tggccgttc                                                19

<210> SEQ ID NO 73
<211> LENGTH: 19
<212> TYPE: DNA
<213> ORGANISM: Homo sapiens

<400> SEQUENCE: 73
ggttggcagc gctaaaccg                                                19

<210> SEQ ID NO 74
<211> LENGTH: 19
<212> TYPE: DNA
<213> ORGANISM: Homo sapiens

<400> SEQUENCE: 74
accgggcctt cagaaagtt                                                19

<210> SEQ ID NO 75
<211> LENGTH: 19
<212> TYPE: DNA
<213> ORGANISM: Homo sapiens

<400> SEQUENCE: 75
ccgggccttc agaaagttg                                                19

<210> SEQ ID NO 76
<211> LENGTH: 19
<212> TYPE: DNA
<213> ORGANISM: Homo sapiens

<400> SEQUENCE: 76
agttgttgat gtgctggat                                                19

<210> SEQ ID NO 77
<211> LENGTH: 19
<212> TYPE: DNA
<213> ORGANISM: Homo sapiens

<400> SEQUENCE: 77
gttgttgatg tgctggatt                                                19

<210> SEQ ID NO 78
<211> LENGTH: 19
<212> TYPE: DNA
<213> ORGANISM: Homo sapiens

<400> SEQUENCE: 78
aacaaagggc aagagtgct                                                19

<210> SEQ ID NO 79
<211> LENGTH: 19
<212> TYPE: DNA
<213> ORGANISM: Homo sapiens

<400> SEQUENCE: 79
acaaagggca agagtgctg                                                19

<210> SEQ ID NO 80
<211> LENGTH: 19
<212> TYPE: DNA
<213> ORGANISM: Homo sapiens
```

<400> SEQUENCE: 80
caaagggcaa gagtgctga                                        19

<210> SEQ ID NO 81
<211> LENGTH: 19
<212> TYPE: DNA
<213> ORGANISM: Homo sapiens

<400> SEQUENCE: 81
agggcaagag tgctgactt                                        19

<210> SEQ ID NO 82
<211> LENGTH: 19
<212> TYPE: DNA
<213> ORGANISM: Homo sapiens

<400> SEQUENCE: 82
gggcaagagt gctgacttc                                        19

<210> SEQ ID NO 83
<211> LENGTH: 19
<212> TYPE: DNA
<213> ORGANISM: Homo sapiens

<400> SEQUENCE: 83
gagtgctgac ttcactaac                                        19

<210> SEQ ID NO 84
<211> LENGTH: 19
<212> TYPE: DNA
<213> ORGANISM: Homo sapiens

<400> SEQUENCE: 84
gagtgctgac ttcacaaac                                        19

<210> SEQ ID NO 85
<211> LENGTH: 19
<212> TYPE: DNA
<213> ORGANISM: Homo sapiens

<400> SEQUENCE: 85
actttgcagc tcgtggcct                                        19

<210> SEQ ID NO 86
<211> LENGTH: 19
<212> TYPE: DNA
<213> ORGANISM: Homo sapiens

<400> SEQUENCE: 86
cttcgatcct cgtggcctc                                        19

<210> SEQ ID NO 87
<211> LENGTH: 19
<212> TYPE: DNA
<213> ORGANISM: Homo sapiens

<400> SEQUENCE: 87
tccctggatt actggacct                                        19

<210> SEQ ID NO 88
<211> LENGTH: 19
<212> TYPE: DNA
<213> ORGANISM: Homo sapiens

```
<400> SEQUENCE: 88
tgtgtgacct ggattgtgc                                                  19

<210> SEQ ID NO 89
<211> LENGTH: 19
<212> TYPE: DNA
<213> ORGANISM: Homo sapiens

<400> SEQUENCE: 89
ggaacccatc agcgtcagc                                                  19

<210> SEQ ID NO 90
<211> LENGTH: 19
<212> TYPE: DNA
<213> ORGANISM: Homo sapiens

<400> SEQUENCE: 90
acttaacttc aatggggag                                                  19

<210> SEQ ID NO 91
<211> LENGTH: 19
<212> TYPE: DNA
<213> ORGANISM: Homo sapiens

<400> SEQUENCE: 91
cttaacttca atggggagg                                                  19

<210> SEQ ID NO 92
<211> LENGTH: 19
<212> TYPE: DNA
<213> ORGANISM: Homo sapiens

<400> SEQUENCE: 92
cttcaatggg gagggtgaa                                                  19

<210> SEQ ID NO 93
<211> LENGTH: 19
<212> TYPE: DNA
<213> ORGANISM: Homo sapiens

<400> SEQUENCE: 93
tggggagggt gaacccgaa                                                  19

<210> SEQ ID NO 94
<211> LENGTH: 19
<212> TYPE: DNA
<213> ORGANISM: Homo sapiens

<400> SEQUENCE: 94
cccgaagaac tgatggtgg                                                  19

<210> SEQ ID NO 95
<211> LENGTH: 19
<212> TYPE: DNA
<213> ORGANISM: Homo sapiens

<400> SEQUENCE: 95
gaactgatgg tggacaact                                                  19

<210> SEQ ID NO 96
<211> LENGTH: 19
<212> TYPE: DNA
<213> ORGANISM: Homo sapiens
```

```
<400> SEQUENCE: 96
ctgatggtgg acaactggc                                               19

<210> SEQ ID NO 97
<211> LENGTH: 19
<212> TYPE: DNA
<213> ORGANISM: Homo sapiens

<400> SEQUENCE: 97
gaacaggcaa atcaaagct                                               19

<210> SEQ ID NO 98
<211> LENGTH: 19
<212> TYPE: DNA
<213> ORGANISM: Homo sapiens

<400> SEQUENCE: 98
caggcaaatc aaagcttcc                                               19

<210> SEQ ID NO 99
<211> LENGTH: 19
<212> TYPE: DNA
<213> ORGANISM: Homo sapiens

<400> SEQUENCE: 99
tgtgctggtg atcgtggcc                                               19

<210> SEQ ID NO 100
<211> LENGTH: 19
<212> TYPE: DNA
<213> ORGANISM: Homo sapiens

<400> SEQUENCE: 100
cctcttcatc atgtccctg                                               19

<210> SEQ ID NO 101
<211> LENGTH: 19
<212> TYPE: DNA
<213> ORGANISM: Homo sapiens

<400> SEQUENCE: 101
gtgctgcgac ttcgtcacc                                               19

<210> SEQ ID NO 102
<211> LENGTH: 19
<212> TYPE: DNA
<213> ORGANISM: Homo sapiens

<400> SEQUENCE: 102
gcaggtgaag aagatcgac                                               19

<210> SEQ ID NO 103
<211> LENGTH: 19
<212> TYPE: DNA
<213> ORGANISM: Homo sapiens

<400> SEQUENCE: 103
gaagatcgac agctgcgag                                               19

<210> SEQ ID NO 104
<211> LENGTH: 19
<212> TYPE: DNA
<213> ORGANISM: Homo sapiens
```

```
<400> SEQUENCE: 104
gacgctgggc atcatcatg                                          19

<210> SEQ ID NO 105
<211> LENGTH: 19
<212> TYPE: DNA
<213> ORGANISM: Homo sapiens

<400> SEQUENCE: 105
cgaccccaag tgctgcgac                                          19

<210> SEQ ID NO 106
<211> LENGTH: 19
<212> TYPE: DNA
<213> ORGANISM: Homo sapiens

<400> SEQUENCE: 106
cgtggtgaag gccttccac                                          19

<210> SEQ ID NO 107
<211> LENGTH: 19
<212> TYPE: DNA
<213> ORGANISM: Homo sapiens

<400> SEQUENCE: 107
ctcggccttc aacccatc                                           19

<210> SEQ ID NO 108
<211> LENGTH: 19
<212> TYPE: DNA
<213> ORGANISM: Homo sapiens

<400> SEQUENCE: 108
ccccatcatc tactgccgc                                          19

<210> SEQ ID NO 109
<211> LENGTH: 19
<212> TYPE: DNA
<213> ORGANISM: Homo sapiens

<400> SEQUENCE: 109
gaagatcgac agctgtgag                                          19

<210> SEQ ID NO 110
<211> LENGTH: 19
<212> TYPE: DNA
<213> ORGANISM: Homo sapiens

<400> SEQUENCE: 110
tagaagccat gcgccggac                                          19

<210> SEQ ID NO 111
<211> LENGTH: 19
<212> TYPE: DNA
<213> ORGANISM: Homo sapiens

<400> SEQUENCE: 111
tgtgctggtc atcacagcc                                          19

<210> SEQ ID NO 112
<211> LENGTH: 19
<212> TYPE: DNA
<213> ORGANISM: Homo sapiens
```

```
<400> SEQUENCE: 112
gttcgagcgt ctgcagacg                                                  19

<210> SEQ ID NO 113
<211> LENGTH: 19
<212> TYPE: DNA
<213> ORGANISM: Homo sapiens

<400> SEQUENCE: 113
ctacttcatc acttcactg                                                  19

<210> SEQ ID NO 114
<211> LENGTH: 19
<212> TYPE: DNA
<213> ORGANISM: Homo sapiens

<400> SEQUENCE: 114
aatgtggact tttggcaac                                                  19

<210> SEQ ID NO 115
<211> LENGTH: 19
<212> TYPE: DNA
<213> ORGANISM: Homo sapiens

<400> SEQUENCE: 115
atgtggactt ttggcaact                                                  19

<210> SEQ ID NO 116
<211> LENGTH: 19
<212> TYPE: DNA
<213> ORGANISM: Homo sapiens

<400> SEQUENCE: 116
tgtggacttt tggcaactt                                                  19

<210> SEQ ID NO 117
<211> LENGTH: 19
<212> TYPE: DNA
<213> ORGANISM: Homo sapiens

<400> SEQUENCE: 117
cttctggtgc gagttttgg                                                  19

<210> SEQ ID NO 118
<211> LENGTH: 19
<212> TYPE: DNA
<213> ORGANISM: Homo sapiens

<400> SEQUENCE: 118
gtaccagagc ctgctgacc                                                  19

<210> SEQ ID NO 119
<211> LENGTH: 19
<212> TYPE: DNA
<213> ORGANISM: Homo sapiens

<400> SEQUENCE: 119
gaataaggcc cgggtgatc                                                  19

<210> SEQ ID NO 120
<211> LENGTH: 19
<212> TYPE: DNA
<213> ORGANISM: Homo sapiens
```

<400> SEQUENCE: 120
taaggcccgg gtgatcatt                                                    19

<210> SEQ ID NO 121
<211> LENGTH: 19
<212> TYPE: DNA
<213> ORGANISM: Homo sapiens

<400> SEQUENCE: 121
ggcccgggtg atcattctg                                                    19

<210> SEQ ID NO 122
<211> LENGTH: 19
<212> TYPE: DNA
<213> ORGANISM: Homo sapiens

<400> SEQUENCE: 122
gccatcaact gctatgcca                                                    19

<210> SEQ ID NO 123
<211> LENGTH: 19
<212> TYPE: DNA
<213> ORGANISM: Homo sapiens

<400> SEQUENCE: 123
ctgctatgcc aatgagacc                                                    19

<210> SEQ ID NO 124
<211> LENGTH: 19
<212> TYPE: DNA
<213> ORGANISM: Homo sapiens

<400> SEQUENCE: 124
tgagacctgc tgtgacttc                                                    19

<210> SEQ ID NO 125
<211> LENGTH: 19
<212> TYPE: DNA
<213> ORGANISM: Homo sapiens

<400> SEQUENCE: 125
ccaagcctat gccattgcc                                                    19

<210> SEQ ID NO 126
<211> LENGTH: 19
<212> TYPE: DNA
<213> ORGANISM: Homo sapiens

<400> SEQUENCE: 126
gcctatgcca ttgcctctt                                                    19

<210> SEQ ID NO 127
<211> LENGTH: 19
<212> TYPE: DNA
<213> ORGANISM: Homo sapiens

<400> SEQUENCE: 127
aaggcagctc cagaagatt                                                    19

<210> SEQ ID NO 128
<211> LENGTH: 19
<212> TYPE: DNA
<213> ORGANISM: Homo sapiens -continued

```
<400> SEQUENCE: 128
aggcagctcc agaagattg                                              19

<210> SEQ ID NO 129
<211> LENGTH: 19
<212> TYPE: DNA
<213> ORGANISM: Homo sapiens

<400> SEQUENCE: 129
ggcagctcca gaagattga                                              19

<210> SEQ ID NO 130
<211> LENGTH: 19
<212> TYPE: DNA
<213> ORGANISM: Homo sapiens

<400> SEQUENCE: 130
gattgacaaa tctgagggc                                              19

<210> SEQ ID NO 131
<211> LENGTH: 19
<212> TYPE: DNA
<213> ORGANISM: Homo sapiens

<400> SEQUENCE: 131
atctgagggc cgcttccat                                              19

<210> SEQ ID NO 132
<211> LENGTH: 19
<212> TYPE: DNA
<213> ORGANISM: Homo sapiens

<400> SEQUENCE: 132
tctgagggcc gcttccatg                                              19

<210> SEQ ID NO 133
<211> LENGTH: 19
<212> TYPE: DNA
<213> ORGANISM: Homo sapiens

<400> SEQUENCE: 133
ccttagccag gtggagcag                                              19

<210> SEQ ID NO 134
<211> LENGTH: 19
<212> TYPE: DNA
<213> ORGANISM: Homo sapiens

<400> SEQUENCE: 134
gttctgcttg aaggagcac                                              19

<210> SEQ ID NO 135
<211> LENGTH: 19
<212> TYPE: DNA
<213> ORGANISM: Homo sapiens

<400> SEQUENCE: 135
ggagcacaaa gccctcaag                                              19

<210> SEQ ID NO 136
<211> LENGTH: 19
<212> TYPE: DNA
<213> ORGANISM: Homo sapiens
```

```
<400> SEQUENCE: 136
agccctcaag acgttaggc                                                19

<210> SEQ ID NO 137
<211> LENGTH: 19
<212> TYPE: DNA
<213> ORGANISM: Homo sapiens

<400> SEQUENCE: 137
gccctcaaga cgttaggca                                                19

<210> SEQ ID NO 138
<211> LENGTH: 19
<212> TYPE: DNA
<213> ORGANISM: Homo sapiens

<400> SEQUENCE: 138
gacgttaggc atcatcatg                                                19

<210> SEQ ID NO 139
<211> LENGTH: 19
<212> TYPE: DNA
<213> ORGANISM: Homo sapiens

<400> SEQUENCE: 139
cattgtgcat gtgatccag                                                19

<210> SEQ ID NO 140
<211> LENGTH: 19
<212> TYPE: DNA
<213> ORGANISM: Homo sapiens

<400> SEQUENCE: 140
cctcatccgt aaggaagtt                                                19

<210> SEQ ID NO 141
<211> LENGTH: 19
<212> TYPE: DNA
<213> ORGANISM: Homo sapiens

<400> SEQUENCE: 141
ggaagtttac atcctccta                                                19

<210> SEQ ID NO 142
<211> LENGTH: 19
<212> TYPE: DNA
<213> ORGANISM: Homo sapiens

<400> SEQUENCE: 142
attggatagg ctatgtcaa                                                19

<210> SEQ ID NO 143
<211> LENGTH: 19
<212> TYPE: DNA
<213> ORGANISM: Homo sapiens

<400> SEQUENCE: 143
ttggataggc tatgtcaat                                                19

<210> SEQ ID NO 144
<211> LENGTH: 19
<212> TYPE: DNA
<213> ORGANISM: Homo sapiens
```

```
<400> SEQUENCE: 144
ttctggtttc aatcccctt                                          19

<210> SEQ ID NO 145
<211> LENGTH: 19
<212> TYPE: DNA
<213> ORGANISM: Homo sapiens

<400> SEQUENCE: 145
tccccttatc tactgccgg                                          19

<210> SEQ ID NO 146
<211> LENGTH: 19
<212> TYPE: DNA
<213> ORGANISM: Homo sapiens

<400> SEQUENCE: 146
ggcctatggg aatggctac                                          19

<210> SEQ ID NO 147
<211> LENGTH: 19
<212> TYPE: DNA
<213> ORGANISM: Homo sapiens

<400> SEQUENCE: 147
tggctactcc agcaacggc                                          19

<210> SEQ ID NO 148
<211> LENGTH: 19
<212> TYPE: DNA
<213> ORGANISM: Homo sapiens

<400> SEQUENCE: 148
cacaggggag cagagtgga                                          19

<210> SEQ ID NO 149
<211> LENGTH: 19
<212> TYPE: DNA
<213> ORGANISM: Homo sapiens

<400> SEQUENCE: 149
gaaaataaac tgctgtgtg                                          19

<210> SEQ ID NO 150
<211> LENGTH: 19
<212> TYPE: DNA
<213> ORGANISM: Homo sapiens

<400> SEQUENCE: 150
aataaactgc tgtgtgaag                                          19

<210> SEQ ID NO 151
<211> LENGTH: 19
<212> TYPE: DNA
<213> ORGANISM: Homo sapiens

<400> SEQUENCE: 151
ataaactgct gtgtgaaga                                          19

<210> SEQ ID NO 152
<211> LENGTH: 19
<212> TYPE: DNA
<213> ORGANISM: Homo sapiens
```

```
<400> SEQUENCE: 152
taaactgctg tgtgaagac                                              19

<210> SEQ ID NO 153
<211> LENGTH: 19
<212> TYPE: DNA
<213> ORGANISM: Homo sapiens

<400> SEQUENCE: 153
actgctgtgt gaagacctc                                              19

<210> SEQ ID NO 154
<211> LENGTH: 19
<212> TYPE: DNA
<213> ORGANISM: Homo sapiens

<400> SEQUENCE: 154
ctgctgtgtg aagacctcc                                              19

<210> SEQ ID NO 155
<211> LENGTH: 19
<212> TYPE: DNA
<213> ORGANISM: Homo sapiens

<400> SEQUENCE: 155
gactttgtgg gccatcaag                                              19

<210> SEQ ID NO 156
<211> LENGTH: 19
<212> TYPE: DNA
<213> ORGANISM: Homo sapiens

<400> SEQUENCE: 156
ggtactgtgc ctagcgata                                              19

<210> SEQ ID NO 157
<211> LENGTH: 19
<212> TYPE: DNA
<213> ORGANISM: Homo sapiens

<400> SEQUENCE: 157
cattgattca caagggagg                                              19

<210> SEQ ID NO 158
<211> LENGTH: 19
<212> TYPE: DNA
<213> ORGANISM: Homo sapiens

<400> SEQUENCE: 158
gggaggaatt gtagtacaa                                              19

<210> SEQ ID NO 159
<211> LENGTH: 19
<212> TYPE: DNA
<213> ORGANISM: Homo sapiens

<400> SEQUENCE: 159
gccatcaact gctacgcca                                              19

<210> SEQ ID NO 160
<211> LENGTH: 19
<212> TYPE: DNA
<213> ORGANISM: Homo sapiens
```

```
<400> SEQUENCE: 160
catcgtgcac gtgatccag                                               19

<210> SEQ ID NO 161
<211> LENGTH: 19
<212> TYPE: DNA
<213> ORGANISM: Homo sapiens

<400> SEQUENCE: 161
ccttccagag tgtctgcta                                               19

<210> SEQ ID NO 162
<211> LENGTH: 19
<212> TYPE: DNA
<213> ORGANISM: Homo sapiens

<400> SEQUENCE: 162
tatgtggaca ccctatacc                                               19

<210> SEQ ID NO 163
<211> LENGTH: 19
<212> TYPE: DNA
<213> ORGANISM: Homo sapiens

<400> SEQUENCE: 163
cgtgtggaca ccatacccc                                               19

<210> SEQ ID NO 164
<211> LENGTH: 19
<212> TYPE: DNA
<213> ORGANISM: Homo sapiens

<400> SEQUENCE: 164
ctaccgggtg ggagccttt                                               19

<210> SEQ ID NO 165
<211> LENGTH: 19
<212> TYPE: DNA
<213> ORGANISM: Homo sapiens

<400> SEQUENCE: 165
tgtgggtctc ctggatcag                                               19

<210> SEQ ID NO 166
<211> LENGTH: 19
<212> TYPE: DNA
<213> ORGANISM: Homo sapiens

<400> SEQUENCE: 166
tgacacagag ctggtagcc                                               19

<210> SEQ ID NO 167
<211> LENGTH: 19
<212> TYPE: DNA
<213> ORGANISM: Homo sapiens

<400> SEQUENCE: 167
ccacgaatgg cacgtgctg                                               19

<210> SEQ ID NO 168
<211> LENGTH: 19
<212> TYPE: DNA
<213> ORGANISM: Homo sapiens
```

```
<400> SEQUENCE: 168
tggcacgtgc tgcctcaag                                            19

<210> SEQ ID NO 169
<211> LENGTH: 19
<212> TYPE: DNA
<213> ORGANISM: Homo sapiens

<400> SEQUENCE: 169
gaaagcgtct tccggttct                                            19

<210> SEQ ID NO 170
<211> LENGTH: 19
<212> TYPE: DNA
<213> ORGANISM: Homo sapiens

<400> SEQUENCE: 170
agcgtcttcc ggttctcct                                            19

<210> SEQ ID NO 171
<211> LENGTH: 19
<212> TYPE: DNA
<213> ORGANISM: Homo sapiens

<400> SEQUENCE: 171
gcgtcttccg gttctcctt                                            19

<210> SEQ ID NO 172
<211> LENGTH: 19
<212> TYPE: DNA
<213> ORGANISM: Homo sapiens

<400> SEQUENCE: 172
ggatgagggc tcgtatttt                                            19

<210> SEQ ID NO 173
<211> LENGTH: 19
<212> TYPE: DNA
<213> ORGANISM: Homo sapiens

<400> SEQUENCE: 173
agacaacgag tctctcatc                                            19

<210> SEQ ID NO 174
<211> LENGTH: 19
<212> TYPE: DNA
<213> ORGANISM: Homo sapiens

<400> SEQUENCE: 174
gacaacgagt ctctcatca                                            19

<210> SEQ ID NO 175
<211> LENGTH: 19
<212> TYPE: DNA
<213> ORGANISM: Homo sapiens

<400> SEQUENCE: 175
cgagtctctc atcagccgg                                            19

<210> SEQ ID NO 176
<211> LENGTH: 19
<212> TYPE: DNA
<213> ORGANISM: Homo sapiens
```

<400> SEQUENCE: 176
caccgtgctt ccacgctct                                                    19

<210> SEQ ID NO 177
<211> LENGTH: 19
<212> TYPE: DNA
<213> ORGANISM: Homo sapiens

<400> SEQUENCE: 177
actacacggc agaggagaa                                                    19

<210> SEQ ID NO 178
<211> LENGTH: 19
<212> TYPE: DNA
<213> ORGANISM: Homo sapiens

<400> SEQUENCE: 178
ctacacggca gaggagaaa                                                    19

<210> SEQ ID NO 179
<211> LENGTH: 19
<212> TYPE: DNA
<213> ORGANISM: Homo sapiens

<400> SEQUENCE: 179
aatcttcgcc cagcgactg                                                    19

<210> SEQ ID NO 180
<211> LENGTH: 19
<212> TYPE: DNA
<213> ORGANISM: Homo sapiens

<400> SEQUENCE: 180
atcttcgccc agcgactga                                                    19

<210> SEQ ID NO 181
<211> LENGTH: 19
<212> TYPE: DNA
<213> ORGANISM: Homo sapiens

<400> SEQUENCE: 181
tcttcgccca gcgactgat                                                    19

<210> SEQ ID NO 182
<211> LENGTH: 19
<212> TYPE: DNA
<213> ORGANISM: Homo sapiens

<400> SEQUENCE: 182
ctttgcccgc acaggggat                                                    19

<210> SEQ ID NO 183
<211> LENGTH: 19
<212> TYPE: DNA
<213> ORGANISM: Homo sapiens

<400> SEQUENCE: 183
ccgcttcctc cccaaattg                                                    19

<210> SEQ ID NO 184
<211> LENGTH: 19
<212> TYPE: DNA
<213> ORGANISM: Homo sapiens

```
<400> SEQUENCE: 184
attgctcagc gccaccgac                                           19

<210> SEQ ID NO 185
<211> LENGTH: 19
<212> TYPE: DNA
<213> ORGANISM: Homo sapiens

<400> SEQUENCE: 185
ttgctcagcg ccaccgaca                                           19

<210> SEQ ID NO 186
<211> LENGTH: 19
<212> TYPE: DNA
<213> ORGANISM: Homo sapiens

<400> SEQUENCE: 186
gaaccagttc gaccactac                                           19

<210> SEQ ID NO 187
<211> LENGTH: 19
<212> TYPE: DNA
<213> ORGANISM: Homo sapiens

<400> SEQUENCE: 187
ccagttcgac cactacagc                                           19

<210> SEQ ID NO 188
<211> LENGTH: 19
<212> TYPE: DNA
<213> ORGANISM: Homo sapiens

<400> SEQUENCE: 188
gcaggatcgc tgctcagac                                           19

<210> SEQ ID NO 189
<211> LENGTH: 19
<212> TYPE: DNA
<213> ORGANISM: Homo sapiens

<400> SEQUENCE: 189
ccgtgagctg agcgaggac                                           19

<210> SEQ ID NO 190
<211> LENGTH: 19
<212> TYPE: DNA
<213> ORGANISM: Homo sapiens

<400> SEQUENCE: 190
gagaggatct ttgcccaga                                           19

<210> SEQ ID NO 191
<211> LENGTH: 19
<212> TYPE: DNA
<213> ORGANISM: Homo sapiens

<400> SEQUENCE: 191
agagagtgga gcctggtct                                           19

<210> SEQ ID NO 192
<211> LENGTH: 19
<212> TYPE: DNA
<213> ORGANISM: Homo sapiens
```

```
<400> SEQUENCE: 192
gagagtggag cctggtctt                                                    19

<210> SEQ ID NO 193
<211> LENGTH: 19
<212> TYPE: DNA
<213> ORGANISM: Homo sapiens

<400> SEQUENCE: 193
cacctccacg gaagctatg                                                    19

<210> SEQ ID NO 194
<211> LENGTH: 19
<212> TYPE: DNA
<213> ORGANISM: Homo sapiens

<400> SEQUENCE: 194
gctatgactt atgatgagg                                                    19

<210> SEQ ID NO 195
<211> LENGTH: 19
<212> TYPE: DNA
<213> ORGANISM: Homo sapiens

<400> SEQUENCE: 195
aggtacacac acctggttg                                                    19

<210> SEQ ID NO 196
<211> LENGTH: 19
<212> TYPE: DNA
<213> ORGANISM: Homo sapiens

<400> SEQUENCE: 196
ggtacacaca cctggttgc                                                    19

<210> SEQ ID NO 197
<211> LENGTH: 19
<212> TYPE: DNA
<213> ORGANISM: Homo sapiens

<400> SEQUENCE: 197
caaagaagag attgagtac                                                    19

<210> SEQ ID NO 198
<211> LENGTH: 19
<212> TYPE: DNA
<213> ORGANISM: Homo sapiens

<400> SEQUENCE: 198
agaagagatt gagtaccta                                                    19

<210> SEQ ID NO 199
<211> LENGTH: 19
<212> TYPE: DNA
<213> ORGANISM: Homo sapiens

<400> SEQUENCE: 199
gaagagattg agtacctaa                                                    19

<210> SEQ ID NO 200
<211> LENGTH: 19
<212> TYPE: DNA
<213> ORGANISM: Homo sapiens
```

```
<400> SEQUENCE: 200
gagattgagt acctaaact                                              19

<210> SEQ ID NO 201
<211> LENGTH: 19
<212> TYPE: DNA
<213> ORGANISM: Homo sapiens

<400> SEQUENCE: 201
actccatatt gagctattc                                              19

<210> SEQ ID NO 202
<211> LENGTH: 19
<212> TYPE: DNA
<213> ORGANISM: Homo sapiens

<400> SEQUENCE: 202
ctccatattg agctattca                                              19

<210> SEQ ID NO 203
<211> LENGTH: 19
<212> TYPE: DNA
<213> ORGANISM: Homo sapiens

<400> SEQUENCE: 203
aagtcaacaa tgtgtgggt                                              19

<210> SEQ ID NO 204
<211> LENGTH: 19
<212> TYPE: DNA
<213> ORGANISM: Homo sapiens

<400> SEQUENCE: 204
agtcaacaat gtgtgggtc                                              19

<210> SEQ ID NO 205
<211> LENGTH: 19
<212> TYPE: DNA
<213> ORGANISM: Homo sapiens

<400> SEQUENCE: 205
gtcaacaatg tgtgggtct                                              19

<210> SEQ ID NO 206
<211> LENGTH: 19
<212> TYPE: DNA
<213> ORGANISM: Homo sapiens

<400> SEQUENCE: 206
caatgtgtgg gtctgggta                                              19

<210> SEQ ID NO 207
<211> LENGTH: 19
<212> TYPE: DNA
<213> ORGANISM: Homo sapiens

<400> SEQUENCE: 207
tgtgtgggtc tgggtagga                                              19

<210> SEQ ID NO 208
<211> LENGTH: 19
<212> TYPE: DNA
<213> ORGANISM: Homo sapiens
```

```
<400> SEQUENCE: 208
cccagaaacc tctgacaga                                                19

<210> SEQ ID NO 209
<211> LENGTH: 19
<212> TYPE: DNA
<213> ORGANISM: Homo sapiens

<400> SEQUENCE: 209
acctctgaca gaagaagcc                                                19

<210> SEQ ID NO 210
<211> LENGTH: 19
<212> TYPE: DNA
<213> ORGANISM: Homo sapiens

<400> SEQUENCE: 210
cctctgacag aagaagcca                                                19

<210> SEQ ID NO 211
<211> LENGTH: 19
<212> TYPE: DNA
<213> ORGANISM: Homo sapiens

<400> SEQUENCE: 211
gaagccaaga actgggctc                                                19

<210> SEQ ID NO 212
<211> LENGTH: 19
<212> TYPE: DNA
<213> ORGANISM: Homo sapiens

<400> SEQUENCE: 212
gccaagaact gggctccag                                                19

<210> SEQ ID NO 213
<211> LENGTH: 19
<212> TYPE: DNA
<213> ORGANISM: Homo sapiens

<400> SEQUENCE: 213
gaactgggct ccaggtgaa                                                19

<210> SEQ ID NO 214
<211> LENGTH: 19
<212> TYPE: DNA
<213> ORGANISM: Homo sapiens

<400> SEQUENCE: 214
cccaacaata ggcaaaaag                                                19

<210> SEQ ID NO 215
<211> LENGTH: 19
<212> TYPE: DNA
<213> ORGANISM: Homo sapiens

<400> SEQUENCE: 215
caataggcaa aaagatgag                                                19

<210> SEQ ID NO 216
<211> LENGTH: 19
<212> TYPE: DNA
<213> ORGANISM: Homo sapiens
```

```
<400> SEQUENCE: 216
taggcaaaaa gatgaggac                                                    19

<210> SEQ ID NO 217
<211> LENGTH: 19
<212> TYPE: DNA
<213> ORGANISM: Homo sapiens

<400> SEQUENCE: 217
aaagatgagg actgcgtgg                                                    19

<210> SEQ ID NO 218
<211> LENGTH: 19
<212> TYPE: DNA
<213> ORGANISM: Homo sapiens

<400> SEQUENCE: 218
aagatgagga ctgcgtgga                                                    19

<210> SEQ ID NO 219
<211> LENGTH: 19
<212> TYPE: DNA
<213> ORGANISM: Homo sapiens

<400> SEQUENCE: 219
agatgaggac tgcgtggag                                                    19

<210> SEQ ID NO 220
<211> LENGTH: 19
<212> TYPE: DNA
<213> ORGANISM: Homo sapiens

<400> SEQUENCE: 220
gatgaggact gcgtggaga                                                    19

<210> SEQ ID NO 221
<211> LENGTH: 19
<212> TYPE: DNA
<213> ORGANISM: Homo sapiens

<400> SEQUENCE: 221
gagagaaaaa gatgtgggc                                                    19

<210> SEQ ID NO 222
<211> LENGTH: 19
<212> TYPE: DNA
<213> ORGANISM: Homo sapiens

<400> SEQUENCE: 222
aaagatgtgg gcatgtgga                                                    19

<210> SEQ ID NO 223
<211> LENGTH: 19
<212> TYPE: DNA
<213> ORGANISM: Homo sapiens

<400> SEQUENCE: 223
aagatgtggg catgtggaa                                                    19

<210> SEQ ID NO 224
<211> LENGTH: 19
<212> TYPE: DNA
<213> ORGANISM: Homo sapiens
```

<400> SEQUENCE: 224
agatgtgggc atgtggaat                                                19

<210> SEQ ID NO 225
<211> LENGTH: 19
<212> TYPE: DNA
<213> ORGANISM: Homo sapiens

<400> SEQUENCE: 225
gatgtgggca tgtggaatg                                                19

<210> SEQ ID NO 226
<211> LENGTH: 19
<212> TYPE: DNA
<213> ORGANISM: Homo sapiens

<400> SEQUENCE: 226
tgatgagagg tgcagcaag                                                19

<210> SEQ ID NO 227
<211> LENGTH: 19
<212> TYPE: DNA
<213> ORGANISM: Homo sapiens

<400> SEQUENCE: 227
gaagaagctt gccctatgc                                                19

<210> SEQ ID NO 228
<211> LENGTH: 19
<212> TYPE: DNA
<213> ORGANISM: Homo sapiens

<400> SEQUENCE: 228
gaagcttgcc ctatgctac                                                19

<210> SEQ ID NO 229
<211> LENGTH: 19
<212> TYPE: DNA
<213> ORGANISM: Homo sapiens

<400> SEQUENCE: 229
gcttgcccta tgctacaca                                                19

<210> SEQ ID NO 230
<211> LENGTH: 19
<212> TYPE: DNA
<213> ORGANISM: Homo sapiens

<400> SEQUENCE: 230
tacatcctgc agtggccac                                                19

<210> SEQ ID NO 231
<211> LENGTH: 19
<212> TYPE: DNA
<213> ORGANISM: Homo sapiens

<400> SEQUENCE: 231
tgtgtagaga ccatcaata                                                19

<210> SEQ ID NO 232
<211> LENGTH: 19
<212> TYPE: DNA
<213> ORGANISM: Homo sapiens

<400> SEQUENCE: 232
ttacacttgc aagtgtgac               19

<210> SEQ ID NO 233
<211> LENGTH: 19
<212> TYPE: DNA
<213> ORGANISM: Homo sapiens

<400> SEQUENCE: 233
gtgtgaccct ggcttcagt               19

<210> SEQ ID NO 234
<211> LENGTH: 19
<212> TYPE: DNA
<213> ORGANISM: Homo sapiens

<400> SEQUENCE: 234
gtgtgagcaa attgtgaac               19

<210> SEQ ID NO 235
<211> LENGTH: 19
<212> TYPE: DNA
<213> ORGANISM: Homo sapiens

<400> SEQUENCE: 235
attgtgaact gtacagccc               19

<210> SEQ ID NO 236
<211> LENGTH: 19
<212> TYPE: DNA
<213> ORGANISM: Homo sapiens

<400> SEQUENCE: 236
ttgtgaactg tacagccct               19

<210> SEQ ID NO 237
<211> LENGTH: 19
<212> TYPE: DNA
<213> ORGANISM: Homo sapiens

<400> SEQUENCE: 237
ctgtacagcc ctggaatcc               19

<210> SEQ ID NO 238
<211> LENGTH: 19
<212> TYPE: DNA
<213> ORGANISM: Homo sapiens

<400> SEQUENCE: 238 tccctgagc atggaagcc                19

<210> SEQ ID NO 239
<211> LENGTH: 19
<212> TYPE: DNA
<213> ORGANISM: Homo sapiens

<400> SEQUENCE: 239
gcctggtttg cagtcaccc               19

<210> SEQ ID NO 240
<211> LENGTH: 19
<212> TYPE: DNA
<213> ORGANISM: Homo sapiens

```
<400> SEQUENCE: 240
acttcagcta caattcttc                                                19

<210> SEQ ID NO 241
<211> LENGTH: 19
<212> TYPE: DNA
<213> ORGANISM: Homo sapiens

<400> SEQUENCE: 241
cttcagctac aattcttcc                                                19

<210> SEQ ID NO 242
<211> LENGTH: 19
<212> TYPE: DNA
<213> ORGANISM: Homo sapiens

<400> SEQUENCE: 242
ttcttcctgc tctatcagc                                                19

<210> SEQ ID NO 243
<211> LENGTH: 19
<212> TYPE: DNA
<213> ORGANISM: Homo sapiens

<400> SEQUENCE: 243
gcagcatgga gaccatgca                                                19

<210> SEQ ID NO 244
<211> LENGTH: 19
<212> TYPE: DNA
<213> ORGANISM: Homo sapiens

<400> SEQUENCE: 244
tggagtgctc ctattccag                                                19

<210> SEQ ID NO 245
<211> LENGTH: 19
<212> TYPE: DNA
<213> ORGANISM: Homo sapiens

<400> SEQUENCE: 245
tgtggttgag tgtgatgct                                                19

<210> SEQ ID NO 246
<211> LENGTH: 19
<212> TYPE: DNA
<213> ORGANISM: Homo sapiens

<400> SEQUENCE: 246
atccagccaa tgggttcgt                                                19

<210> SEQ ID NO 247
<211> LENGTH: 19
<212> TYPE: DNA
<213> ORGANISM: Homo sapiens

<400> SEQUENCE: 247
tccagccaat gggttcgtg                                                19

<210> SEQ ID NO 248
<211> LENGTH: 19
<212> TYPE: DNA
<213> ORGANISM: Homo sapiens
```

```
<400> SEQUENCE: 248
tgggttcgtg gaatgtttc                                                    19

<210> SEQ ID NO 249
<211> LENGTH: 19
<212> TYPE: DNA
<213> ORGANISM: Homo sapiens

<400> SEQUENCE: 249
tgtttccaaa accctggaa                                                    19

<210> SEQ ID NO 250
<211> LENGTH: 19
<212> TYPE: DNA
<213> ORGANISM: Homo sapiens

<400> SEQUENCE: 250
aaccctggaa gcttcccat                                                    19

<210> SEQ ID NO 251
<211> LENGTH: 19
<212> TYPE: DNA
<213> ORGANISM: Homo sapiens

<400> SEQUENCE: 251
accctggaag cttcccatg                                                    19

<210> SEQ ID NO 252
<211> LENGTH: 19
<212> TYPE: DNA
<213> ORGANISM: Homo sapiens

<400> SEQUENCE: 252
ccctggaagc ttcccatgg                                                    19

<210> SEQ ID NO 253
<211> LENGTH: 19
<212> TYPE: DNA
<213> ORGANISM: Homo sapiens

<400> SEQUENCE: 253
gcttcccatg gaacacaac                                                    19

<210> SEQ ID NO 254
<211> LENGTH: 19
<212> TYPE: DNA
<213> ORGANISM: Homo sapiens

<400> SEQUENCE: 254
cacaacctgt acatttgac                                                    19

<210> SEQ ID NO 255
<211> LENGTH: 19
<212> TYPE: DNA
<213> ORGANISM: Homo sapiens

<400> SEQUENCE: 255
cctgtacatt tgactgtga                                                    19

<210> SEQ ID NO 256
<211> LENGTH: 19
<212> TYPE: DNA
<213> ORGANISM: Homo sapiens
```

```
<400> SEQUENCE: 256
gaaggatttg aactaatgg                                                19

<210> SEQ ID NO 257
<211> LENGTH: 19
<212> TYPE: DNA
<213> ORGANISM: Homo sapiens

<400> SEQUENCE: 257
ggatttgaac taatgggag                                                19

<210> SEQ ID NO 258
<211> LENGTH: 19
<212> TYPE: DNA
<213> ORGANISM: Homo sapiens

<400> SEQUENCE: 258
ctaatgggag cccagagcc                                                19

<210> SEQ ID NO 259
<211> LENGTH: 19
<212> TYPE: DNA
<213> ORGANISM: Homo sapiens

<400> SEQUENCE: 259
tgggagccca gagccttca                                                19

<210> SEQ ID NO 260
<211> LENGTH: 19
<212> TYPE: DNA
<213> ORGANISM: Homo sapiens

<400> SEQUENCE: 260
ttgggacaac gagaagcca                                                19

<210> SEQ ID NO 261
<211> LENGTH: 19
<212> TYPE: DNA
<213> ORGANISM: Homo sapiens

<400> SEQUENCE: 261
cgagaagcca acgtgtaaa                                                19

<210> SEQ ID NO 262
<211> LENGTH: 19
<212> TYPE: DNA
<213> ORGANISM: Homo sapiens

<400> SEQUENCE: 262
gccaacgtgt aaagctgtg                                                19

<210> SEQ ID NO 263
<211> LENGTH: 19
<212> TYPE: DNA
<213> ORGANISM: Homo sapiens

<400> SEQUENCE: 263
cgtgtaaagc tgtgacatg                                                19

<210> SEQ ID NO 264
<211> LENGTH: 19
<212> TYPE: DNA
<213> ORGANISM: Homo sapiens
```

-continued

<400> SEQUENCE: 264
agctgtgaca tgcagggcc                                              19

<210> SEQ ID NO 265
<211> LENGTH: 19
<212> TYPE: DNA
<213> ORGANISM: Homo sapiens

<400> SEQUENCE: 265
tggctctgtg aggtgcagc                                              19

<210> SEQ ID NO 266
<211> LENGTH: 19
<212> TYPE: DNA
<213> ORGANISM: Homo sapiens

<400> SEQUENCE: 266
atcatcctgc aacttcacc                                              19

<210> SEQ ID NO 267
<211> LENGTH: 19
<212> TYPE: DNA
<213> ORGANISM: Homo sapiens

<400> SEQUENCE: 267
tcatcctgca acttcacct                                              19

<210> SEQ ID NO 268
<211> LENGTH: 19
<212> TYPE: DNA
<213> ORGANISM: Homo sapiens

<400> SEQUENCE: 268
cttcacctgt gaggaaggc                                              19

<210> SEQ ID NO 269
<211> LENGTH: 19
<212> TYPE: DNA
<213> ORGANISM: Homo sapiens

<400> SEQUENCE: 269
ggcttcatgt tgcagggac                                              19

<210> SEQ ID NO 270
<211> LENGTH: 19
<212> TYPE: DNA
<213> ORGANISM: Homo sapiens

<400> SEQUENCE: 270
tgcaccactc aagggcagt                                              19

<210> SEQ ID NO 271
<211> LENGTH: 19
<212> TYPE: DNA
<213> ORGANISM: Homo sapiens

<400> SEQUENCE: 271
gggcagtgga cacagcaaa                                              19

<210> SEQ ID NO 272
<211> LENGTH: 19
<212> TYPE: DNA
<213> ORGANISM: Homo sapiens

```
<400> SEQUENCE: 272
atcccagttt gtgaagctt                                                  19

<210> SEQ ID NO 273
<211> LENGTH: 19
<212> TYPE: DNA
<213> ORGANISM: Homo sapiens

<400> SEQUENCE: 273
tcccagtttg tgaagcttt                                                  19

<210> SEQ ID NO 274
<211> LENGTH: 19
<212> TYPE: DNA
<213> ORGANISM: Homo sapiens

<400> SEQUENCE: 274
gctttccagt gcacagcct                                                  19

<210> SEQ ID NO 275
<211> LENGTH: 19
<212> TYPE: DNA
<213> ORGANISM: Homo sapiens

<400> SEQUENCE: 275
ttgtcttcct agtgcttct                                                  19

<210> SEQ ID NO 276
<211> LENGTH: 19
<212> TYPE: DNA
<213> ORGANISM: Homo sapiens

<400> SEQUENCE: 276
gggatccaaa aggctccaa                                                  19

<210> SEQ ID NO 277
<211> LENGTH: 19
<212> TYPE: DNA
<213> ORGANISM: Homo sapiens

<400> SEQUENCE: 277
aaggctccaa tgtggcccc                                                  19

<210> SEQ ID NO 278
<211> LENGTH: 19
<212> TYPE: DNA
<213> ORGANISM: Homo sapiens

<400> SEQUENCE: 278
aggctccaat gtggccca                                                   19

<210> SEQ ID NO 279
<211> LENGTH: 19
<212> TYPE: DNA
<213> ORGANISM: Homo sapiens

<400> SEQUENCE: 279
cgagaagccc acatgtgaa                                                  19

<210> SEQ ID NO 280
<211> LENGTH: 19
<212> TYPE: DNA
<213> ORGANISM: Homo sapiens
```

<400> SEQUENCE: 280
gcccacatgt gaagctgtg                                                    19

<210> SEQ ID NO 281
<211> LENGTH: 19
<212> TYPE: DNA
<213> ORGANISM: Homo sapiens

<400> SEQUENCE: 281
gctgtgagat gcgatgctg                                                    19

<210> SEQ ID NO 282
<211> LENGTH: 19
<212> TYPE: DNA
<213> ORGANISM: Homo sapiens

<400> SEQUENCE: 282
gggtttggtg aggtgtgct                                                    19

<210> SEQ ID NO 283
<211> LENGTH: 19
<212> TYPE: DNA
<213> ORGANISM: Homo sapiens

<400> SEQUENCE: 283
ttcacctaca agtcctctt                                                    19

<210> SEQ ID NO 284
<211> LENGTH: 19
<212> TYPE: DNA
<213> ORGANISM: Homo sapiens

<400> SEQUENCE: 284
gtcctcttgt gccttcagc                                                    19

<210> SEQ ID NO 285
<211> LENGTH: 19
<212> TYPE: DNA
<213> ORGANISM: Homo sapiens

<400> SEQUENCE: 285
ctcaacttga gtgcacatc                                                    19

<210> SEQ ID NO 286
<211> LENGTH: 19
<212> TYPE: DNA
<213> ORGANISM: Homo sapiens

<400> SEQUENCE: 286
cttgagtgca catctcagg                                                    19

<210> SEQ ID NO 287
<211> LENGTH: 19
<212> TYPE: DNA
<213> ORGANISM: Homo sapiens

<400> SEQUENCE: 287
tggacagaag aggttcctt                                                    19

<210> SEQ ID NO 288
<211> LENGTH: 19
<212> TYPE: DNA
<213> ORGANISM: Homo sapiens

```
<400> SEQUENCE: 288
gaggttcctt cctgccaag                                              19

<210> SEQ ID NO 289
<211> LENGTH: 19
<212> TYPE: DNA
<213> ORGANISM: Homo sapiens

<400> SEQUENCE: 289
gtggtaaaat gttcaagcc                                              19

<210> SEQ ID NO 290
<211> LENGTH: 19
<212> TYPE: DNA
<213> ORGANISM: Homo sapiens

<400> SEQUENCE: 290
aatgttcaag cctggcagt                                              19

<210> SEQ ID NO 291
<211> LENGTH: 19
<212> TYPE: DNA
<213> ORGANISM: Homo sapiens

<400> SEQUENCE: 291
atgttcaagc ctggcagtt                                              19

<210> SEQ ID NO 292
<211> LENGTH: 19
<212> TYPE: DNA
<213> ORGANISM: Homo sapiens

<400> SEQUENCE: 292
tgttcaagcc tggcagttc                                              19

<210> SEQ ID NO 293
<211> LENGTH: 19
<212> TYPE: DNA
<213> ORGANISM: Homo sapiens

<400> SEQUENCE: 293
gcctggcagt tccgggaaa                                              19

<210> SEQ ID NO 294
<211> LENGTH: 19
<212> TYPE: DNA
<213> ORGANISM: Homo sapiens

<400> SEQUENCE: 294
agatcaacat gagctgcag                                              19

<210> SEQ ID NO 295
<211> LENGTH: 19
<212> TYPE: DNA
<213> ORGANISM: Homo sapiens

<400> SEQUENCE: 295
gatcaacatg agctgcagt                                              19

<210> SEQ ID NO 296
<211> LENGTH: 19
<212> TYPE: DNA
<213> ORGANISM: Homo sapiens
```

```
<400> SEQUENCE: 296
catgagctgc agtggggag                                              19

<210> SEQ ID NO 297
<211> LENGTH: 19
<212> TYPE: DNA
<213> ORGANISM: Homo sapiens

<400> SEQUENCE: 297
gttcgcctgt cctgaagga                                              19

<210> SEQ ID NO 298
<211> LENGTH: 19
<212> TYPE: DNA
<213> ORGANISM: Homo sapiens

<400> SEQUENCE: 298
ggatggacgc tcaatggct                                              19

<210> SEQ ID NO 299
<211> LENGTH: 19
<212> TYPE: DNA
<213> ORGANISM: Homo sapiens

<400> SEQUENCE: 299
tggctctgca gctcggaca                                              19

<210> SEQ ID NO 300
<211> LENGTH: 19
<212> TYPE: DNA
<213> ORGANISM: Homo sapiens

<400> SEQUENCE: 300
gctcccactg agtccaaca                                              19

<210> SEQ ID NO 301
<211> LENGTH: 19
<212> TYPE: DNA
<213> ORGANISM: Homo sapiens

<400> SEQUENCE: 301
cattcccttg gtagctgga                                              19

<210> SEQ ID NO 302
<211> LENGTH: 19
<212> TYPE: DNA
<213> ORGANISM: Homo sapiens

<400> SEQUENCE: 302
atgcttacgg aaagcaaag                                              19

<210> SEQ ID NO 303
<211> LENGTH: 19
<212> TYPE: DNA
<213> ORGANISM: Homo sapiens

<400> SEQUENCE: 303
tgcttacgga aagcaaaga                                              19

<210> SEQ ID NO 304
<211> LENGTH: 19
<212> TYPE: DNA
<213> ORGANISM: Homo sapiens
```

```
<400> SEQUENCE: 304
gcaaagaaat tgttcctg                                                   19

<210> SEQ ID NO 305
<211> LENGTH: 19
<212> TYPE: DNA
<213> ORGANISM: Homo sapiens

<400> SEQUENCE: 305
agaaatttgt tcctgccag                                                  19

<210> SEQ ID NO 306
<211> LENGTH: 19
<212> TYPE: DNA
<213> ORGANISM: Homo sapiens

<400> SEQUENCE: 306
gaaatttgtt cctgccagc                                                  19

<210> SEQ ID NO 307
<211> LENGTH: 19
<212> TYPE: DNA
<213> ORGANISM: Homo sapiens

<400> SEQUENCE: 307
atttgttcct gccagcagc                                                  19

<210> SEQ ID NO 308
<211> LENGTH: 19
<212> TYPE: DNA
<213> ORGANISM: Homo sapiens

<400> SEQUENCE: 308
tttgttcctg ccagcagct                                                  19

<210> SEQ ID NO 309
<211> LENGTH: 19
<212> TYPE: DNA
<213> ORGANISM: Homo sapiens

<400> SEQUENCE: 309
agccttgaat cagacggaa                                                  19

<210> SEQ ID NO 310
<211> LENGTH: 19
<212> TYPE: DNA
<213> ORGANISM: Homo sapiens

<400> SEQUENCE: 310
gccttgaatc agacggaag                                                  19

<210> SEQ ID NO 311
<211> LENGTH: 19
<212> TYPE: DNA
<213> ORGANISM: Homo sapiens

<400> SEQUENCE: 311
tcagacggaa gctaccaaa                                                  19

<210> SEQ ID NO 312
<211> LENGTH: 19
<212> TYPE: DNA
<213> ORGANISM: Homo sapiens
```

```
<400> SEQUENCE: 312
gctaccaaaa gccttctta                                              19

<210> SEQ ID NO 313
<211> LENGTH: 19
<212> TYPE: DNA
<213> ORGANISM: Homo sapiens

<400> SEQUENCE: 313
aagccttctt acatccttt                                              19

<210> SEQ ID NO 314
<211> LENGTH: 19
<212> TYPE: DNA
<213> ORGANISM: Homo sapiens

<400> SEQUENCE: 314
agccttctta catcctta                                               19

<210> SEQ ID NO 315
<211> LENGTH: 19
<212> TYPE: DNA
<213> ORGANISM: Homo sapiens

<400> SEQUENCE: 315
gccttcttac atccttaa                                               19

<210> SEQ ID NO 316
<211> LENGTH: 19
<212> TYPE: DNA
<213> ORGANISM: Homo sapiens

<400> SEQUENCE: 316
agccttgaat cagatggaa                                              19

<210> SEQ ID NO 317
<211> LENGTH: 19
<212> TYPE: DNA
<213> ORGANISM: Homo sapiens

<400> SEQUENCE: 317
gccttgaatc agatggaag                                              19

<210> SEQ ID NO 318
<211> LENGTH: 19
<212> TYPE: DNA
<213> ORGANISM: Homo sapiens

<400> SEQUENCE: 318
tcagatggaa gctaccaaa                                              19

<210> SEQ ID NO 319
<211> LENGTH: 19
<212> TYPE: DNA
<213> ORGANISM: Homo sapiens

<400> SEQUENCE: 319
tccctgttgt tactatcca                                              19

<210> SEQ ID NO 320
<211> LENGTH: 19
<212> TYPE: DNA
<213> ORGANISM: Homo sapiens
```

```
<400> SEQUENCE: 320
tgccaccttc atccgagag                                                    19

<210> SEQ ID NO 321
<211> LENGTH: 19
<212> TYPE: DNA
<213> ORGANISM: Homo sapiens

<400> SEQUENCE: 321
ctcagcacat gactacatc                                                    19

<210> SEQ ID NO 322
<211> LENGTH: 19
<212> TYPE: DNA
<213> ORGANISM: Homo sapiens

<400> SEQUENCE: 322
cgtgagctat tacactcgt                                                    19

<210> SEQ ID NO 323
<211> LENGTH: 19
<212> TYPE: DNA
<213> ORGANISM: Homo sapiens

<400> SEQUENCE: 323
agattgcccc acacccatg                                                    19

<210> SEQ ID NO 324
<211> LENGTH: 19
<212> TYPE: DNA
<213> ORGANISM: Homo sapiens

<400> SEQUENCE: 324
gattgcccca cacccatgg                                                    19

<210> SEQ ID NO 325
<211> LENGTH: 19
<212> TYPE: DNA
<213> ORGANISM: Homo sapiens

<400> SEQUENCE: 325
ccaaagggaa gaagcagtt                                                    19

<210> SEQ ID NO 326
<211> LENGTH: 19
<212> TYPE: DNA
<213> ORGANISM: Homo sapiens

<400> SEQUENCE: 326
agggaagaag cagttgcca                                                    19

<210> SEQ ID NO 327
<211> LENGTH: 19
<212> TYPE: DNA
<213> ORGANISM: Homo sapiens

<400> SEQUENCE: 327
gggaagaagc agttgccag                                                    19

<210> SEQ ID NO 328
<211> LENGTH: 19
<212> TYPE: DNA
<213> ORGANISM: Homo sapiens
```

```
<400> SEQUENCE: 328
gaagcagttg ccagatgcc                                                  19

<210> SEQ ID NO 329
<211> LENGTH: 19
<212> TYPE: DNA
<213> ORGANISM: Homo sapiens

<400> SEQUENCE: 329
gcagttgcca gatgcccag                                                  19

<210> SEQ ID NO 330
<211> LENGTH: 19
<212> TYPE: DNA
<213> ORGANISM: Homo sapiens

<400> SEQUENCE: 330
gttcatacct gacccccaa                                                  19

<210> SEQ ID NO 331
<211> LENGTH: 19
<212> TYPE: DNA
<213> ORGANISM: Homo sapiens

<400> SEQUENCE: 331
ggcaccaacc tcatgtttg                                                  19

<210> SEQ ID NO 332
<211> LENGTH: 19
<212> TYPE: DNA
<213> ORGANISM: Homo sapiens

<400> SEQUENCE: 332
cctcatgttt gccttcttt                                                  19

<210> SEQ ID NO 333
<211> LENGTH: 19
<212> TYPE: DNA
<213> ORGANISM: Homo sapiens

<400> SEQUENCE: 333
cacttcaccc accagttct                                                  19

<210> SEQ ID NO 334
<211> LENGTH: 19
<212> TYPE: DNA
<213> ORGANISM: Homo sapiens

<400> SEQUENCE: 334
aacttctggc aagatgggt                                                  19

<210> SEQ ID NO 335
<211> LENGTH: 19
<212> TYPE: DNA
<213> ORGANISM: Homo sapiens

<400> SEQUENCE: 335
acttctggca agatgggtc                                                  19

<210> SEQ ID NO 336
<211> LENGTH: 19
<212> TYPE: DNA
<213> ORGANISM: Homo sapiens
```

-continued

<400> SEQUENCE: 336
cttctggcaa gatgggtcc                                              19

<210> SEQ ID NO 337
<211> LENGTH: 19
<212> TYPE: DNA
<213> ORGANISM: Homo sapiens

<400> SEQUENCE: 337
gatgggtcct ggcttcacc                                              19

<210> SEQ ID NO 338
<211> LENGTH: 19
<212> TYPE: DNA
<213> ORGANISM: Homo sapiens

<400> SEQUENCE: 338
tctggagcgt cagtatcaa                                              19

<210> SEQ ID NO 339
<211> LENGTH: 19
<212> TYPE: DNA
<213> ORGANISM: Homo sapiens

<400> SEQUENCE: 339
ctgcggctct ttaaggatg                                              19

<210> SEQ ID NO 340
<211> LENGTH: 19
<212> TYPE: DNA
<213> ORGANISM: Homo sapiens

<400> SEQUENCE: 340
ggatgggaaa ctcaagtac                                              19

<210> SEQ ID NO 341
<211> LENGTH: 19
<212> TYPE: DNA
<213> ORGANISM: Homo sapiens

<400> SEQUENCE: 341
actcaagtac caggtgctg                                              19

<210> SEQ ID NO 342
<211> LENGTH: 19
<212> TYPE: DNA
<213> ORGANISM: Homo sapiens

<400> SEQUENCE: 342
ctcaagtacc aggtgctgg                                              19

<210> SEQ ID NO 343
<211> LENGTH: 19
<212> TYPE: DNA
<213> ORGANISM: Homo sapiens

<400> SEQUENCE: 343
gtaccaggtg ctggatgga                                              19

<210> SEQ ID NO 344
<211> LENGTH: 19
<212> TYPE: DNA
<213> ORGANISM: Homo sapiens

```
<400> SEQUENCE: 344
atgtacccgc cctcggtag                                              19

<210> SEQ ID NO 345
<211> LENGTH: 19
<212> TYPE: DNA
<213> ORGANISM: Homo sapiens

<400> SEQUENCE: 345
tgtacccgcc ctcggtaga                                              19

<210> SEQ ID NO 346
<211> LENGTH: 19
<212> TYPE: DNA
<213> ORGANISM: Homo sapiens

<400> SEQUENCE: 346
gaggcgcctg tgttgatgc                                              19

<210> SEQ ID NO 347
<211> LENGTH: 19
<212> TYPE: DNA
<213> ORGANISM: Homo sapiens

<400> SEQUENCE: 347
ccgtgtgtgt gacctgctg                                              19

<210> SEQ ID NO 348
<211> LENGTH: 19
<212> TYPE: DNA
<213> ORGANISM: Homo sapiens

<400> SEQUENCE: 348
gattgtcatc gaggagtac                                              19

<210> SEQ ID NO 349
<211> LENGTH: 19
<212> TYPE: DNA
<213> ORGANISM: Homo sapiens

<400> SEQUENCE: 349
atttgaccca gagctgctg                                              19

<210> SEQ ID NO 350
<211> LENGTH: 19
<212> TYPE: DNA
<213> ORGANISM: Homo sapiens

<400> SEQUENCE: 350
tttgacccag agctgctgt                                              19

<210> SEQ ID NO 351
<211> LENGTH: 19
<212> TYPE: DNA
<213> ORGANISM: Homo sapiens

<400> SEQUENCE: 351
taccgcaacc gcattgcca                                              19

<210> SEQ ID NO 352
<211> LENGTH: 19
<212> TYPE: DNA
<213> ORGANISM: Homo sapiens
```

```
<400> SEQUENCE: 352
ccgcattgcc atggagttc                                              19

<210> SEQ ID NO 353
<211> LENGTH: 19
<212> TYPE: DNA
<213> ORGANISM: Homo sapiens

<400> SEQUENCE: 353
ccatctctac cactggcac                                              19

<210> SEQ ID NO 354
<211> LENGTH: 19
<212> TYPE: DNA
<213> ORGANISM: Homo sapiens

<400> SEQUENCE: 354
cacctccatg ttggtggac                                              19

<210> SEQ ID NO 355
<211> LENGTH: 19
<212> TYPE: DNA
<213> ORGANISM: Homo sapiens

<400> SEQUENCE: 355
catggaccac cacatcctg                                              19

<210> SEQ ID NO 356
<211> LENGTH: 19
<212> TYPE: DNA
<213> ORGANISM: Homo sapiens

<400> SEQUENCE: 356
tgagtaccgc aagaggttt                                              19

<210> SEQ ID NO 357
<211> LENGTH: 19
<212> TYPE: DNA
<213> ORGANISM: Homo sapiens

<400> SEQUENCE: 357
gaggtttggc atgaaaccc                                              19

<210> SEQ ID NO 358
<211> LENGTH: 19
<212> TYPE: DNA
<213> ORGANISM: Homo sapiens

<400> SEQUENCE: 358
accctacacc tccttccag                                              19

<210> SEQ ID NO 359
<211> LENGTH: 19
<212> TYPE: DNA
<213> ORGANISM: Homo sapiens

<400> SEQUENCE: 359
ccctacacct ccttccagg                                              19

<210> SEQ ID NO 360
<211> LENGTH: 19
<212> TYPE: DNA
<213> ORGANISM: Homo sapiens
```

```
<400> SEQUENCE: 360
ggagatggca gcagagttg                                                    19

<210> SEQ ID NO 361
<211> LENGTH: 19
<212> TYPE: DNA
<213> ORGANISM: Homo sapiens

<400> SEQUENCE: 361
ttgtatggag acattgatg                                                    19

<210> SEQ ID NO 362
<211> LENGTH: 19
<212> TYPE: DNA
<213> ORGANISM: Homo sapiens

<400> SEQUENCE: 362
aagtgccatc caaactcta                                                    19

<210> SEQ ID NO 363
<211> LENGTH: 19
<212> TYPE: DNA
<213> ORGANISM: Homo sapiens

<400> SEQUENCE: 363
agtgccatcc aaactctat                                                    19

<210> SEQ ID NO 364
<211> LENGTH: 19
<212> TYPE: DNA
<213> ORGANISM: Homo sapiens

<400> SEQUENCE: 364
gtgccatcca aactctatc                                                    19

<210> SEQ ID NO 365
<211> LENGTH: 19
<212> TYPE: DNA
<213> ORGANISM: Homo sapiens

<400> SEQUENCE: 365
actctatctt tggggagag                                                    19

<210> SEQ ID NO 366
<211> LENGTH: 19
<212> TYPE: DNA
<213> ORGANISM: Homo sapiens

<400> SEQUENCE: 366
ctctatcttt ggggagagt                                                    19

<210> SEQ ID NO 367
<211> LENGTH: 19
<212> TYPE: DNA
<213> ORGANISM: Homo sapiens

<400> SEQUENCE: 367
gggtctccta gggaatccc                                                    19

<210> SEQ ID NO 368
<211> LENGTH: 19
<212> TYPE: DNA
<213> ORGANISM: Homo sapiens
```

-continued

```
<400> SEQUENCE: 368
tcccatctgt tctccggag                                              19

<210> SEQ ID NO 369
<211> LENGTH: 19
<212> TYPE: DNA
<213> ORGANISM: Homo sapiens

<400> SEQUENCE: 369
cattgtcaag acggccaca                                              19

<210> SEQ ID NO 370
<211> LENGTH: 19
<212> TYPE: DNA
<213> ORGANISM: Homo sapiens

<400> SEQUENCE: 370
gacggccaca ctgaagaag                                              19

<210> SEQ ID NO 371
<211> LENGTH: 19
<212> TYPE: DNA
<213> ORGANISM: Homo sapiens

<400> SEQUENCE: 371
gaagctggtc tgcctcaac                                              19

<210> SEQ ID NO 372
<211> LENGTH: 19
<212> TYPE: DNA
<213> ORGANISM: Homo sapiens

<400> SEQUENCE: 372
gctggtctgc ctcaacacc                                              19

<210> SEQ ID NO 373
<211> LENGTH: 19
<212> TYPE: DNA
<213> ORGANISM: Homo sapiens

<400> SEQUENCE: 373
caccaagacc tgtccctac                                              19

<210> SEQ ID NO 374
<211> LENGTH: 19
<212> TYPE: DNA
<213> ORGANISM: Homo sapiens

<400> SEQUENCE: 374
gacctgtccc tacgtttcc                                              19

<210> SEQ ID NO 375
<211> LENGTH: 19
<212> TYPE: DNA
<213> ORGANISM: Homo sapiens

<400> SEQUENCE: 375
atccttgctg ttcccaccc                                              19

<210> SEQ ID NO 376
<211> LENGTH: 19
<212> TYPE: DNA
<213> ORGANISM: Homo sapiens
```

```
<400> SEQUENCE: 376
tccttgctgt tcccaccca                                              19

<210> SEQ ID NO 377
<211> LENGTH: 19
<212> TYPE: DNA
<213> ORGANISM: Homo sapiens

<400> SEQUENCE: 377
aaccgaggtg tatgtatga                                              19

<210> SEQ ID NO 378
<211> LENGTH: 19
<212> TYPE: DNA
<213> ORGANISM: Homo sapiens

<400> SEQUENCE: 378
accgaggtgt atgtatgag                                              19

<210> SEQ ID NO 379
<211> LENGTH: 19
<212> TYPE: DNA
<213> ORGANISM: Homo sapiens

<400> SEQUENCE: 379
ccgaggtgta tgtatgagt                                              19

<210> SEQ ID NO 380
<211> LENGTH: 19
<212> TYPE: DNA
<213> ORGANISM: Homo sapiens

<400> SEQUENCE: 380
gtgcgattgt acccggaca                                              19

<210> SEQ ID NO 381
<211> LENGTH: 19
<212> TYPE: DNA
<213> ORGANISM: Homo sapiens

<400> SEQUENCE: 381
aactgctcaa caccggaat                                              19

<210> SEQ ID NO 382
<211> LENGTH: 19
<212> TYPE: DNA
<213> ORGANISM: Homo sapiens

<400> SEQUENCE: 382
actgctcaac accggaatt                                              19

<210> SEQ ID NO 383
<211> LENGTH: 19
<212> TYPE: DNA
<213> ORGANISM: Homo sapiens

<400> SEQUENCE: 383
ctgctcaaca ccggaattt                                              19

<210> SEQ ID NO 384
<211> LENGTH: 19
<212> TYPE: DNA
<213> ORGANISM: Homo sapiens
```

```
<400> SEQUENCE: 384
caccggaatt tttgacaag                                            19

<210> SEQ ID NO 385
<211> LENGTH: 19
<212> TYPE: DNA
<213> ORGANISM: Homo sapiens

<400> SEQUENCE: 385
ttatttctga aacccactc                                            19

<210> SEQ ID NO 386
<211> LENGTH: 19
<212> TYPE: DNA
<213> ORGANISM: Homo sapiens

<400> SEQUENCE: 386
acccactcca aacacagtg                                            19

<210> SEQ ID NO 387
<211> LENGTH: 19
<212> TYPE: DNA
<213> ORGANISM: Homo sapiens

<400> SEQUENCE: 387
cccactccaa acacagtgc                                            19

<210> SEQ ID NO 388
<211> LENGTH: 19
<212> TYPE: DNA
<213> ORGANISM: Homo sapiens

<400> SEQUENCE: 388
acacagtgca ctacatact                                            19

<210> SEQ ID NO 389
<211> LENGTH: 19
<212> TYPE: DNA
<213> ORGANISM: Homo sapiens

<400> SEQUENCE: 389
cacagtgcac tacatactt                                            19

<210> SEQ ID NO 390
<211> LENGTH: 19
<212> TYPE: DNA
<213> ORGANISM: Homo sapiens

<400> SEQUENCE: 390
gggattttgg aacgttgtg                                            19

<210> SEQ ID NO 391
<211> LENGTH: 19
<212> TYPE: DNA
<213> ORGANISM: Homo sapiens

<400> SEQUENCE: 391
cgttgtgaat aacattccc                                            19

<210> SEQ ID NO 392
<211> LENGTH: 19
<212> TYPE: DNA
<213> ORGANISM: Homo sapiens
```

```
<400> SEQUENCE: 392
taacattccc ttccttcga                                            19

<210> SEQ ID NO 393
<211> LENGTH: 19
<212> TYPE: DNA
<213> ORGANISM: Homo sapiens

<400> SEQUENCE: 393
cattcccttc cttcgaaat                                            19

<210> SEQ ID NO 394
<211> LENGTH: 19
<212> TYPE: DNA
<213> ORGANISM: Homo sapiens

<400> SEQUENCE: 394
cttacaatgc tgactatgg                                            19

<210> SEQ ID NO 395
<211> LENGTH: 19
<212> TYPE: DNA
<213> ORGANISM: Homo sapiens

<400> SEQUENCE: 395
tgctgactat ggctacaaa                                            19

<210> SEQ ID NO 396
<211> LENGTH: 19
<212> TYPE: DNA
<213> ORGANISM: Homo sapiens

<400> SEQUENCE: 396
aagctgggaa gccttctct                                            19

<210> SEQ ID NO 397
<211> LENGTH: 19
<212> TYPE: DNA
<213> ORGANISM: Homo sapiens

<400> SEQUENCE: 397
agctgggaag ccttctcta                                            19

<210> SEQ ID NO 398
<211> LENGTH: 19
<212> TYPE: DNA
<213> ORGANISM: Homo sapiens

<400> SEQUENCE: 398
gctgggaagc cttctctaa                                            19

<210> SEQ ID NO 399
<211> LENGTH: 19
<212> TYPE: DNA
<213> ORGANISM: Homo sapiens

<400> SEQUENCE: 399
gccttctcta acctctcct                                            19

<210> SEQ ID NO 400
<211> LENGTH: 19
<212> TYPE: DNA
<213> ORGANISM: Homo sapiens
```

```
<400> SEQUENCE: 400
cctctcctat tatactaga                                               19

<210> SEQ ID NO 401
<211> LENGTH: 19
<212> TYPE: DNA
<213> ORGANISM: Homo sapiens

<400> SEQUENCE: 401
aggtaaaaag cagcttcct                                               19

<210> SEQ ID NO 402
<211> LENGTH: 19
<212> TYPE: DNA
<213> ORGANISM: Homo sapiens

<400> SEQUENCE: 402
ggtaaaaagc agcttcctg                                               19

<210> SEQ ID NO 403
<211> LENGTH: 19
<212> TYPE: DNA
<213> ORGANISM: Homo sapiens

<400> SEQUENCE: 403
aaagcagctt cctgattca                                               19

<210> SEQ ID NO 404
<211> LENGTH: 19
<212> TYPE: DNA
<213> ORGANISM: Homo sapiens

<400> SEQUENCE: 404
aagcagcttc ctgattcaa                                               19

<210> SEQ ID NO 405
<211> LENGTH: 19
<212> TYPE: DNA
<213> ORGANISM: Homo sapiens

<400> SEQUENCE: 405
agcagcttcc tgattcaaa                                               19

<210> SEQ ID NO 406
<211> LENGTH: 19
<212> TYPE: DNA
<213> ORGANISM: Homo sapiens

<400> SEQUENCE: 406
gcagcttcct gattcaaat                                               19

<210> SEQ ID NO 407
<211> LENGTH: 19
<212> TYPE: DNA
<213> ORGANISM: Homo sapiens

<400> SEQUENCE: 407
gaagaaagtt catccctga                                               19

<210> SEQ ID NO 408
<211> LENGTH: 19
<212> TYPE: DNA
<213> ORGANISM: Homo sapiens
```

<400> SEQUENCE: 408
gaaagttcat ccctgatcc                                                  19

<210> SEQ ID NO 409
<211> LENGTH: 19
<212> TYPE: DNA
<213> ORGANISM: Homo sapiens

<400> SEQUENCE: 409
agttcatccc tgatcccca                                                  19

<210> SEQ ID NO 410
<211> LENGTH: 19
<212> TYPE: DNA
<213> ORGANISM: Homo sapiens

<400> SEQUENCE: 410
gttcatccct gatccccag                                                  19

<210> SEQ ID NO 411
<211> LENGTH: 19
<212> TYPE: DNA
<213> ORGANISM: Homo sapiens

<400> SEQUENCE: 411
gacagatcat aagcgaggg                                                  19

<210> SEQ ID NO 412
<211> LENGTH: 19
<212> TYPE: DNA
<213> ORGANISM: Homo sapiens

<400> SEQUENCE: 412
actctggcta gacagcgta                                                  19

<210> SEQ ID NO 413
<211> LENGTH: 19
<212> TYPE: DNA
<213> ORGANISM: Homo sapiens

<400> SEQUENCE: 413
ctctggctag acagcgtaa                                                  19

<210> SEQ ID NO 414
<211> LENGTH: 19
<212> TYPE: DNA
<213> ORGANISM: Homo sapiens

<400> SEQUENCE: 414
actgcgcctt ttcaaggat                                                  19

<210> SEQ ID NO 415
<211> LENGTH: 19
<212> TYPE: DNA
<213> ORGANISM: Homo sapiens

<400> SEQUENCE: 415
ctgcgccttt tcaaggatg                                                  19

<210> SEQ ID NO 416
<211> LENGTH: 19
<212> TYPE: DNA
<213> ORGANISM: Homo sapiens

```
<400> SEQUENCE: 416
ttgatggaga gatgtatcc                                              19

<210> SEQ ID NO 417
<211> LENGTH: 19
<212> TYPE: DNA
<213> ORGANISM: Homo sapiens

<400> SEQUENCE: 417
agatactcag gcagagatg                                              19

<210> SEQ ID NO 418
<211> LENGTH: 19
<212> TYPE: DNA
<213> ORGANISM: Homo sapiens

<400> SEQUENCE: 418
gatactcagg cagagatga                                              19

<210> SEQ ID NO 419
<211> LENGTH: 19
<212> TYPE: DNA
<213> ORGANISM: Homo sapiens

<400> SEQUENCE: 419
gtccctgagc atctacggt                                              19

<210> SEQ ID NO 420
<211> LENGTH: 19
<212> TYPE: DNA
<213> ORGANISM: Homo sapiens

<400> SEQUENCE: 420
tctggctgcg ggaacacaa                                              19

<210> SEQ ID NO 421
<211> LENGTH: 19
<212> TYPE: DNA
<213> ORGANISM: Homo sapiens

<400> SEQUENCE: 421
cacaacagag tatgcgatg                                              19

<210> SEQ ID NO 422
<211> LENGTH: 19
<212> TYPE: DNA
<213> ORGANISM: Homo sapiens

<400> SEQUENCE: 422
cagagtatgc gatgtgctt                                              19

<210> SEQ ID NO 423
<211> LENGTH: 19
<212> TYPE: DNA
<213> ORGANISM: Homo sapiens

<400> SEQUENCE: 423
acaggagcat cctgaatgg                                              19

<210> SEQ ID NO 424
<211> LENGTH: 19
<212> TYPE: DNA
<213> ORGANISM: Homo sapiens
```

```
<400> SEQUENCE: 424
caggagcatc ctgaatggg                                                19

<210> SEQ ID NO 425
<211> LENGTH: 19
<212> TYPE: DNA
<213> ORGANISM: Homo sapiens

<400> SEQUENCE: 425
tggggtgatg agcagttgt                                                19

<210> SEQ ID NO 426
<211> LENGTH: 19
<212> TYPE: DNA
<213> ORGANISM: Homo sapiens

<400> SEQUENCE: 426
gcaggctaat actgatagg                                                19

<210> SEQ ID NO 427
<211> LENGTH: 19
<212> TYPE: DNA
<213> ORGANISM: Homo sapiens

<400> SEQUENCE: 427
tactgatagg agagactat                                                19

<210> SEQ ID NO 428
<211> LENGTH: 19
<212> TYPE: DNA
<213> ORGANISM: Homo sapiens

<400> SEQUENCE: 428
gattatgtgc aacacttga                                                19

<210> SEQ ID NO 429
<211> LENGTH: 19
<212> TYPE: DNA
<213> ORGANISM: Homo sapiens

<400> SEQUENCE: 429
cacttgagtg gctatcact                                                19

<210> SEQ ID NO 430
<211> LENGTH: 19
<212> TYPE: DNA
<213> ORGANISM: Homo sapiens

<400> SEQUENCE: 430
actgaaattt gacccagaa                                                19

<210> SEQ ID NO 431
<211> LENGTH: 19
<212> TYPE: DNA
<213> ORGANISM: Homo sapiens

<400> SEQUENCE: 431
ctgaaatttg acccagaac                                                19

<210> SEQ ID NO 432
<211> LENGTH: 19
<212> TYPE: DNA
<213> ORGANISM: Homo sapiens
```

```
<400> SEQUENCE: 432
atttgaccca gaactactt                                          19

<210> SEQ ID NO 433
<211> LENGTH: 19
<212> TYPE: DNA
<213> ORGANISM: Homo sapiens

<400> SEQUENCE: 433
tttgacccag aactacttt                                          19

<210> SEQ ID NO 434
<211> LENGTH: 19
<212> TYPE: DNA
<213> ORGANISM: Homo sapiens

<400> SEQUENCE: 434
caaacaattc cagtaccaa                                          19

<210> SEQ ID NO 435
<211> LENGTH: 19
<212> TYPE: DNA
<213> ORGANISM: Homo sapiens

<400> SEQUENCE: 435
caattccagt accaaaatc                                          19

<210> SEQ ID NO 436
<211> LENGTH: 19
<212> TYPE: DNA
<213> ORGANISM: Homo sapiens

<400> SEQUENCE: 436
ttccagtacc aaaatcgta                                          19

<210> SEQ ID NO 437
<211> LENGTH: 19
<212> TYPE: DNA
<213> ORGANISM: Homo sapiens

<400> SEQUENCE: 437
aatcgtattg ctgctgaat                                          19

<210> SEQ ID NO 438
<211> LENGTH: 19
<212> TYPE: DNA
<213> ORGANISM: Homo sapiens

<400> SEQUENCE: 438
atcgtattgc tgctgaatt                                          19

<210> SEQ ID NO 439
<211> LENGTH: 19
<212> TYPE: DNA
<213> ORGANISM: Homo sapiens

<400> SEQUENCE: 439
tcgtattgct gctgaattt                                          19

<210> SEQ ID NO 440
<211> LENGTH: 19
<212> TYPE: DNA
<213> ORGANISM: Homo sapiens
```

```
<400> SEQUENCE: 440
tttaacaccc tctatcact                                                19

<210> SEQ ID NO 441
<211> LENGTH: 19
<212> TYPE: DNA
<213> ORGANISM: Homo sapiens

<400> SEQUENCE: 441
caccctctat cactggcat                                                19

<210> SEQ ID NO 442
<211> LENGTH: 19
<212> TYPE: DNA
<213> ORGANISM: Homo sapiens

<400> SEQUENCE: 442
caactctata ttgctggaa                                                19

<210> SEQ ID NO 443
<211> LENGTH: 19
<212> TYPE: DNA
<213> ORGANISM: Homo sapiens

<400> SEQUENCE: 443
ctctatattg ctggaacat                                                19

<210> SEQ ID NO 444
<211> LENGTH: 19
<212> TYPE: DNA
<213> ORGANISM: Homo sapiens

<400> SEQUENCE: 444
catggaatta cccagtttg                                                19

<210> SEQ ID NO 445
<211> LENGTH: 19
<212> TYPE: DNA
<213> ORGANISM: Homo sapiens

<400> SEQUENCE: 445
ttacccagtt tgttgaatc                                                19

<210> SEQ ID NO 446
<211> LENGTH: 19
<212> TYPE: DNA
<213> ORGANISM: Homo sapiens

<400> SEQUENCE: 446
tcattcacca ggcaaattg                                                19

<210> SEQ ID NO 447
<211> LENGTH: 19
<212> TYPE: DNA
<213> ORGANISM: Homo sapiens

<400> SEQUENCE: 447
attgctggca gggttgctg                                                19

<210> SEQ ID NO 448
<211> LENGTH: 19
<212> TYPE: DNA
<213> ORGANISM: Homo sapiens
```

```
<400> SEQUENCE: 448
ttgctggcag ggttgctgg                                               19

<210> SEQ ID NO 449
<211> LENGTH: 19
<212> TYPE: DNA
<213> ORGANISM: Homo sapiens

<400> SEQUENCE: 449
tgttccaccc gcagtacag                                               19

<210> SEQ ID NO 450
<211> LENGTH: 19
<212> TYPE: DNA
<213> ORGANISM: Homo sapiens

<400> SEQUENCE: 450
agtatcacag gcttccatt                                               19

<210> SEQ ID NO 451
<211> LENGTH: 19
<212> TYPE: DNA
<213> ORGANISM: Homo sapiens

<400> SEQUENCE: 451
gtatcacagg cttccattg                                               19

<210> SEQ ID NO 452
<211> LENGTH: 19
<212> TYPE: DNA
<213> ORGANISM: Homo sapiens

<400> SEQUENCE: 452
tgagtaccgc aaacgcttt                                               19

<210> SEQ ID NO 453
<211> LENGTH: 19
<212> TYPE: DNA
<213> ORGANISM: Homo sapiens

<400> SEQUENCE: 453
acgctttatg ctgaagccc                                               19

<210> SEQ ID NO 454
<211> LENGTH: 19
<212> TYPE: DNA
<213> ORGANISM: Homo sapiens

<400> SEQUENCE: 454
cgctttatgc tgaagccct                                               19

<210> SEQ ID NO 455
<211> LENGTH: 19
<212> TYPE: DNA
<213> ORGANISM: Homo sapiens

<400> SEQUENCE: 455
gccctatgaa tcatttgaa                                               19

<210> SEQ ID NO 456
<211> LENGTH: 19
<212> TYPE: DNA
<213> ORGANISM: Homo sapiens
```

```
<400> SEQUENCE: 456
gaacttacag gagaaaagg                                               19

<210> SEQ ID NO 457
<211> LENGTH: 19
<212> TYPE: DNA
<213> ORGANISM: Homo sapiens

<400> SEQUENCE: 457
cttacaggag aaaaggaaa                                               19

<210> SEQ ID NO 458
<211> LENGTH: 19
<212> TYPE: DNA
<213> ORGANISM: Homo sapiens

<400> SEQUENCE: 458
aaggaaatgt ctgcagagt                                               19

<210> SEQ ID NO 459
<211> LENGTH: 19
<212> TYPE: DNA
<213> ORGANISM: Homo sapiens

<400> SEQUENCE: 459
aggaaatgtc tgcagagtt                                               19

<210> SEQ ID NO 460
<211> LENGTH: 19
<212> TYPE: DNA
<213> ORGANISM: Homo sapiens

<400> SEQUENCE: 460
ggaaatgtct gcagagttg                                               19

<210> SEQ ID NO 461
<211> LENGTH: 19
<212> TYPE: DNA
<213> ORGANISM: Homo sapiens

<400> SEQUENCE: 461
atgtctgcag agttggaag                                               19

<210> SEQ ID NO 462
<211> LENGTH: 19
<212> TYPE: DNA
<213> ORGANISM: Homo sapiens

<400> SEQUENCE: 462
tgtctgcaga gttggaagc                                               19

<210> SEQ ID NO 463
<211> LENGTH: 19
<212> TYPE: DNA
<213> ORGANISM: Homo sapiens

<400> SEQUENCE: 463
gcactctatg gtgacatcg                                               19

<210> SEQ ID NO 464
<211> LENGTH: 19
<212> TYPE: DNA
<213> ORGANISM: Homo sapiens
```

```
<400> SEQUENCE: 464
aagcctcggc cagatgcca                                               19

<210> SEQ ID NO 465
<211> LENGTH: 19
<212> TYPE: DNA
<213> ORGANISM: Homo sapiens

<400> SEQUENCE: 465
agcctcggcc agatgccat                                               19

<210> SEQ ID NO 466
<211> LENGTH: 19
<212> TYPE: DNA
<213> ORGANISM: Homo sapiens

<400> SEQUENCE: 466
accatggtag aagttggag                                               19

<210> SEQ ID NO 467
<211> LENGTH: 19
<212> TYPE: DNA
<213> ORGANISM: Homo sapiens

<400> SEQUENCE: 467
ccatggtaga agttggagc                                               19

<210> SEQ ID NO 468
<211> LENGTH: 19
<212> TYPE: DNA
<213> ORGANISM: Homo sapiens

<400> SEQUENCE: 468
gttggagcac cattctcct                                               19

<210> SEQ ID NO 469
<211> LENGTH: 19
<212> TYPE: DNA
<213> ORGANISM: Homo sapiens

<400> SEQUENCE: 469
aggacttatg ggtaatgtt                                               19

<210> SEQ ID NO 470
<211> LENGTH: 19
<212> TYPE: DNA
<213> ORGANISM: Homo sapiens

<400> SEQUENCE: 470
ggacttatgg gtaatgtta                                               19

<210> SEQ ID NO 471
<211> LENGTH: 19
<212> TYPE: DNA
<213> ORGANISM: Homo sapiens

<400> SEQUENCE: 471
tgttatatgt tctcctgcc                                               19

<210> SEQ ID NO 472
<211> LENGTH: 19
<212> TYPE: DNA
<213> ORGANISM: Homo sapiens
```

```
<400> SEQUENCE: 472
gccaagcact tttggtgga                                                19

<210> SEQ ID NO 473
<211> LENGTH: 19
<212> TYPE: DNA
<213> ORGANISM: Homo sapiens

<400> SEQUENCE: 473
gcactttggg tggagaagt                                                19

<210> SEQ ID NO 474
<211> LENGTH: 19
<212> TYPE: DNA
<213> ORGANISM: Homo sapiens

<400> SEQUENCE: 474
gtgggttttc aaatcatca                                                19

<210> SEQ ID NO 475
<211> LENGTH: 19
<212> TYPE: DNA
<213> ORGANISM: Homo sapiens

<400> SEQUENCE: 475
atcatcaaca ctgcctcaa                                                19

<210> SEQ ID NO 476
<211> LENGTH: 19
<212> TYPE: DNA
<213> ORGANISM: Homo sapiens

<400> SEQUENCE: 476
tcatcaacac tgcctcaat                                                19

<210> SEQ ID NO 477
<211> LENGTH: 19
<212> TYPE: DNA
<213> ORGANISM: Homo sapiens

<400> SEQUENCE: 477
cactgcctca attcagtct                                                19

<210> SEQ ID NO 478
<211> LENGTH: 19
<212> TYPE: DNA
<213> ORGANISM: Homo sapiens

<400> SEQUENCE: 478
ttcagtctct catctgcaa                                                19

<210> SEQ ID NO 479
<211> LENGTH: 19
<212> TYPE: DNA
<213> ORGANISM: Homo sapiens

<400> SEQUENCE: 479
taacgtgaag ggctgtccc                                                19

<210> SEQ ID NO 480
<211> LENGTH: 19
<212> TYPE: DNA
<213> ORGANISM: Homo sapiens
```

```
<400> SEQUENCE: 480
cgtgaagggc tgtcccttt                                              19

<210> SEQ ID NO 481
<211> LENGTH: 19
<212> TYPE: DNA
<213> ORGANISM: Homo sapiens

<400> SEQUENCE: 481
gggctgtccc tttacttca                                              19

<210> SEQ ID NO 482
<211> LENGTH: 19
<212> TYPE: DNA
<213> ORGANISM: Homo sapiens

<400> SEQUENCE: 482
aacagtcacc atcaatgca                                              19

<210> SEQ ID NO 483
<211> LENGTH: 19
<212> TYPE: DNA
<213> ORGANISM: Homo sapiens

<400> SEQUENCE: 483
acagtcacca tcaatgcaa                                              19

<210> SEQ ID NO 484
<211> LENGTH: 19
<212> TYPE: DNA
<213> ORGANISM: Homo sapiens

<400> SEQUENCE: 484
cagtcaccat caatgcaag                                              19

<210> SEQ ID NO 485
<211> LENGTH: 19
<212> TYPE: DNA
<213> ORGANISM: Homo sapiens

<400> SEQUENCE: 485
tgcaagttct tcccgctcc                                              19

<210> SEQ ID NO 486
<211> LENGTH: 19
<212> TYPE: DNA
<213> ORGANISM: Homo sapiens

<400> SEQUENCE: 486
gttcttcccg ctccggact                                              19

<210> SEQ ID NO 487
<211> LENGTH: 19
<212> TYPE: DNA
<213> ORGANISM: Homo sapiens

<400> SEQUENCE: 487
tcccacagta ctactaaaa                                              19

<210> SEQ ID NO 488
<211> LENGTH: 19
<212> TYPE: DNA
<213> ORGANISM: Homo sapiens
```

```
<400> SEQUENCE: 488
aagaacgttc gactgaact                                            19

<210> SEQ ID NO 489
<211> LENGTH: 19
<212> TYPE: DNA
<213> ORGANISM: Homo sapiens

<400> SEQUENCE: 489
agaacgttcg actgaactg                                            19

<210> SEQ ID NO 490
<211> LENGTH: 19
<212> TYPE: DNA
<213> ORGANISM: Homo sapiens

<400> SEQUENCE: 490
gaacgttcga ctgaactgt                                            19

<210> SEQ ID NO 491
<211> LENGTH: 19
<212> TYPE: DNA
<213> ORGANISM: Homo sapiens

<400> SEQUENCE: 491
cacaacagag tatgcgacg                                            19

<210> SEQ ID NO 492
<211> LENGTH: 19
<212> TYPE: DNA
<213> ORGANISM: Homo sapiens

<400> SEQUENCE: 492
aggaacagcc ttccagccc                                            19

<210> SEQ ID NO 493
<211> LENGTH: 19
<212> TYPE: DNA
<213> ORGANISM: Homo sapiens

<400> SEQUENCE: 493
cggttccaag tggacttat                                            19

<210> SEQ ID NO 494
<211> LENGTH: 19
<212> TYPE: DNA
<213> ORGANISM: Homo sapiens

<400> SEQUENCE: 494
gtggacttat tttggtcct                                            19

<210> SEQ ID NO 495
<211> LENGTH: 19
<212> TYPE: DNA
<213> ORGANISM: Homo sapiens

<400> SEQUENCE: 495
tagctggtcc aagaagtac                                            19

<210> SEQ ID NO 496
<211> LENGTH: 19
<212> TYPE: DNA
<213> ORGANISM: Homo sapiens
```

```
<400> SEQUENCE: 496
gaagtacccg tcgtgtggg                                                19

<210> SEQ ID NO 497
<211> LENGTH: 19
<212> TYPE: DNA
<213> ORGANISM: Homo sapiens

<400> SEQUENCE: 497
ggctacaatc tgtctgcca                                                19

<210> SEQ ID NO 498
<211> LENGTH: 19
<212> TYPE: DNA
<213> ORGANISM: Homo sapiens

<400> SEQUENCE: 498
tctgtctgcc aacaagcag                                                19

<210> SEQ ID NO 499
<211> LENGTH: 19
<212> TYPE: DNA
<213> ORGANISM: Homo sapiens

<400> SEQUENCE: 499
caagcagttt ctcctgacc                                                19

<210> SEQ ID NO 500
<211> LENGTH: 19
<212> TYPE: DNA
<213> ORGANISM: Homo sapiens

<400> SEQUENCE: 500
gcagtttctc ctgaccaac                                                19

<210> SEQ ID NO 501
<211> LENGTH: 19
<212> TYPE: DNA
<213> ORGANISM: Homo sapiens

<400> SEQUENCE: 501
caatggccat tcagtgaag                                                19

<210> SEQ ID NO 502
<211> LENGTH: 19
<212> TYPE: DNA
<213> ORGANISM: Homo sapiens

<400> SEQUENCE: 502
tggccattca gtgaagctg                                                19

<210> SEQ ID NO 503
<211> LENGTH: 19
<212> TYPE: DNA
<213> ORGANISM: Homo sapiens

<400> SEQUENCE: 503
ctcagacctt tatcctgac                                                19

<210> SEQ ID NO 504
<211> LENGTH: 19
<212> TYPE: DNA
<213> ORGANISM: Homo sapiens
```

```
<400> SEQUENCE: 504
caagtcagaa ggcctcgct                                              19

<210> SEQ ID NO 505
<211> LENGTH: 19
<212> TYPE: DNA
<213> ORGANISM: Homo sapiens

<400> SEQUENCE: 505
gtcagaaggc ctcgctgtc                                              19

<210> SEQ ID NO 506
<211> LENGTH: 19
<212> TYPE: DNA
<213> ORGANISM: Homo sapiens

<400> SEQUENCE: 506
tccgtcctat gacaagatc                                              19

<210> SEQ ID NO 507
<211> LENGTH: 19
<212> TYPE: DNA
<213> ORGANISM: Homo sapiens

<400> SEQUENCE: 507
gatcttcagt caccttcaa                                              19

<210> SEQ ID NO 508
<211> LENGTH: 19
<212> TYPE: DNA
<213> ORGANISM: Homo sapiens

<400> SEQUENCE: 508
catgtaaagt acaaaggcc                                              19

<210> SEQ ID NO 509
<211> LENGTH: 19
<212> TYPE: DNA
<213> ORGANISM: Homo sapiens

<400> SEQUENCE: 509
agtacaaagg ccaggaagc                                              19

<210> SEQ ID NO 510
<211> LENGTH: 19
<212> TYPE: DNA
<213> ORGANISM: Homo sapiens

<400> SEQUENCE: 510
gtacaaaggc caggaagca                                              19

<210> SEQ ID NO 511
<211> LENGTH: 19
<212> TYPE: DNA
<213> ORGANISM: Homo sapiens

<400> SEQUENCE: 511
aggccaggaa gcattcgtc                                              19

<210> SEQ ID NO 512
<211> LENGTH: 19
<212> TYPE: DNA
<213> ORGANISM: Homo sapiens
```

<400> SEQUENCE: 512
ggccaggaag cattcgtcc                                                19

<210> SEQ ID NO 513
<211> LENGTH: 19
<212> TYPE: DNA
<213> ORGANISM: Homo sapiens

<400> SEQUENCE: 513
gcattcgtcc cgggattca                                                19

<210> SEQ ID NO 514
<211> LENGTH: 19
<212> TYPE: DNA
<213> ORGANISM: Homo sapiens

<400> SEQUENCE: 514
cattgaagag ctgcttccg                                                19

<210> SEQ ID NO 515
<211> LENGTH: 19
<212> TYPE: DNA
<213> ORGANISM: Homo sapiens

<400> SEQUENCE: 515
gagctgcttc cggagagga                                                19

<210> SEQ ID NO 516
<211> LENGTH: 19
<212> TYPE: DNA
<213> ORGANISM: Homo sapiens

<400> SEQUENCE: 516
tattaccgct accgggggt                                                19

<210> SEQ ID NO 517
<211> LENGTH: 19
<212> TYPE: DNA
<213> ORGANISM: Homo sapiens

<400> SEQUENCE: 517
ccccactgtg ctctggaca                                                19

<210> SEQ ID NO 518
<211> LENGTH: 19
<212> TYPE: DNA
<213> ORGANISM: Homo sapiens

<400> SEQUENCE: 518
accccgtgca aatttccca                                                19

<210> SEQ ID NO 519
<211> LENGTH: 19
<212> TYPE: DNA
<213> ORGANISM: Homo sapiens

<400> SEQUENCE: 519
ccccgtgcaa atttcccag                                                19

<210> SEQ ID NO 520
<211> LENGTH: 19
<212> TYPE: DNA
<213> ORGANISM: Homo sapiens

```
<400> SEQUENCE: 520
atttcccagg agcagctgc                                        19

<210> SEQ ID NO 521
<211> LENGTH: 19
<212> TYPE: DNA
<213> ORGANISM: Homo sapiens

<400> SEQUENCE: 521
tttcccagga gcagctgct                                        19

<210> SEQ ID NO 522
<211> LENGTH: 19
<212> TYPE: DNA
<213> ORGANISM: Homo sapiens

<400> SEQUENCE: 522
atgatcaaca acttccggc                                        19

<210> SEQ ID NO 523
<211> LENGTH: 19
<212> TYPE: DNA
<213> ORGANISM: Homo sapiens

<400> SEQUENCE: 523
tgatcaacaa cttccggca                                        19

<210> SEQ ID NO 524
<211> LENGTH: 19
<212> TYPE: DNA
<213> ORGANISM: Homo sapiens

<400> SEQUENCE: 524
caacttccgg caggtccag                                        19

<210> SEQ ID NO 525
<211> LENGTH: 19
<212> TYPE: DNA
<213> ORGANISM: Homo sapiens

<400> SEQUENCE: 525
cttccggcag gtccagaag                                        19

<210> SEQ ID NO 526
<211> LENGTH: 19
<212> TYPE: DNA
<213> ORGANISM: Homo sapiens

<400> SEQUENCE: 526
gttcgatgag aggctggta                                        19

<210> SEQ ID NO 527
<211> LENGTH: 19
<212> TYPE: DNA
<213> ORGANISM: Homo sapiens

<400> SEQUENCE: 527
gtgcaagtct gtactgcgg                                        19

<210> SEQ ID NO 528
<211> LENGTH: 19
<212> TYPE: DNA
<213> ORGANISM: Homo sapiens
```

```
<400> SEQUENCE: 528
gtctgtactg cggcaggac                                                19

<210> SEQ ID NO 529
<211> LENGTH: 19
<212> TYPE: DNA
<213> ORGANISM: Homo sapiens

<400> SEQUENCE: 529
ggaagagtat caaaaaagg                                                19

<210> SEQ ID NO 530
<211> LENGTH: 19
<212> TYPE: DNA
<213> ORGANISM: Homo sapiens

<400> SEQUENCE: 530
aaaaggtgat aacaaggga                                                19

<210> SEQ ID NO 531
<211> LENGTH: 19
<212> TYPE: DNA
<213> ORGANISM: Homo sapiens

<400> SEQUENCE: 531
aaaggtgata acaagggag                                                19

<210> SEQ ID NO 532
<211> LENGTH: 19
<212> TYPE: DNA
<213> ORGANISM: Homo sapiens

<400> SEQUENCE: 532
aaggtgataa caagggagt                                                19

<210> SEQ ID NO 533
<211> LENGTH: 19
<212> TYPE: DNA
<213> ORGANISM: Homo sapiens

<400> SEQUENCE: 533
aggtgataac aagggagtc                                                19

<210> SEQ ID NO 534
<211> LENGTH: 19
<212> TYPE: DNA
<213> ORGANISM: Homo sapiens

<400> SEQUENCE: 534
ggtgataaca agggagtca                                                19

<210> SEQ ID NO 535
<211> LENGTH: 19
<212> TYPE: DNA
<213> ORGANISM: Homo sapiens

<400> SEQUENCE: 535
caagggagtc atttacaag                                                19

<210> SEQ ID NO 536
<211> LENGTH: 19
<212> TYPE: DNA
<213> ORGANISM: Homo sapiens
```

-continued

```
<400> SEQUENCE: 536
gggagtcatt tacaagcca                                              19

<210> SEQ ID NO 537
<211> LENGTH: 19
<212> TYPE: DNA
<213> ORGANISM: Homo sapiens

<400> SEQUENCE: 537
gccagccacc aagatggag                                              19

<210> SEQ ID NO 538
<211> LENGTH: 19
<212> TYPE: DNA
<213> ORGANISM: Homo sapiens

<400> SEQUENCE: 538
gatggagact gaggcccac                                              19

<210> SEQ ID NO 539
<211> LENGTH: 19
<212> TYPE: DNA
<213> ORGANISM: Homo sapiens

<400> SEQUENCE: 539
atgcttccga cagctccaa                                              19

<210> SEQ ID NO 540
<211> LENGTH: 19
<212> TYPE: DNA
<213> ORGANISM: Homo sapiens

<400> SEQUENCE: 540
tgcttccgac agctccaac                                              19

<210> SEQ ID NO 541
<211> LENGTH: 19
<212> TYPE: DNA
<213> ORGANISM: Homo sapiens

<400> SEQUENCE: 541
catttccaag gccattctg                                              19

<210> SEQ ID NO 542
<211> LENGTH: 19
<212> TYPE: DNA
<213> ORGANISM: Homo sapiens

<400> SEQUENCE: 542
catcctagtg atcctctcc                                              19

<210> SEQ ID NO 543
<211> LENGTH: 19
<212> TYPE: DNA
<213> ORGANISM: Homo sapiens

<400> SEQUENCE: 543
catctgggcg gcagtggat                                              19

<210> SEQ ID NO 544
<211> LENGTH: 19
<212> TYPE: DNA
<213> ORGANISM: Homo sapiens
```

```
<400> SEQUENCE: 544
ccatcgtcac ccagaggag                                                    19

<210> SEQ ID NO 545
<211> LENGTH: 19
<212> TYPE: DNA
<213> ORGANISM: Homo sapiens

<400> SEQUENCE: 545
gtctggcctc aagaccgac                                                    19

<210> SEQ ID NO 546
<211> LENGTH: 19
<212> TYPE: DNA
<213> ORGANISM: Homo sapiens

<400> SEQUENCE: 546
gaccgacaag tcggactcg                                                    19

<210> SEQ ID NO 547
<211> LENGTH: 19
<212> TYPE: DNA
<213> ORGANISM: Homo sapiens

<400> SEQUENCE: 547
gtcggactcg gagcaagtg                                                    19

<210> SEQ ID NO 548
<211> LENGTH: 19
<212> TYPE: DNA
<213> ORGANISM: Homo sapiens

<400> SEQUENCE: 548
gtgacgctcc gcatccatc                                                    19

<210> SEQ ID NO 549
<211> LENGTH: 19
<212> TYPE: DNA
<213> ORGANISM: Homo sapiens

<400> SEQUENCE: 549
gaccaagacg cacttctca                                                    19

<210> SEQ ID NO 550
<211> LENGTH: 19
<212> TYPE: DNA
<213> ORGANISM: Homo sapiens

<400> SEQUENCE: 550
gacgcacttc tcagtgagg                                                    19

<210> SEQ ID NO 551
<211> LENGTH: 19
<212> TYPE: DNA
<213> ORGANISM: Homo sapiens

<400> SEQUENCE: 551
gttctcccgg gagaagaaa                                                    19

<210> SEQ ID NO 552
<211> LENGTH: 19
<212> TYPE: DNA
<213> ORGANISM: Homo sapiens
```

-continued

```
<400> SEQUENCE: 552
gaaagcggcc aaaacgctg                                                   19

<210> SEQ ID NO 553
<211> LENGTH: 19
<212> TYPE: DNA
<213> ORGANISM: Homo sapiens

<400> SEQUENCE: 553
aacgctgggc atcgtggtc                                                   19

<210> SEQ ID NO 554
<211> LENGTH: 19
<212> TYPE: DNA
<213> ORGANISM: Homo sapiens

<400> SEQUENCE: 554
gccctctgaa acagttttt                                                   19

<210> SEQ ID NO 555
<211> LENGTH: 19
<212> TYPE: DNA
<213> ORGANISM: Homo sapiens

<400> SEQUENCE: 555
aatagtattt tggctcgga                                                   19

<210> SEQ ID NO 556
<211> LENGTH: 19
<212> TYPE: DNA
<213> ORGANISM: Homo sapiens

<400> SEQUENCE: 556
atagtatttt ggctcggat                                                   19

<210> SEQ ID NO 557
<211> LENGTH: 19
<212> TYPE: DNA
<213> ORGANISM: Homo sapiens

<400> SEQUENCE: 557
tagtattttg gctcggata                                                   19

<210> SEQ ID NO 558
<211> LENGTH: 19
<212> TYPE: DNA
<213> ORGANISM: Homo sapiens

<400> SEQUENCE: 558
acagctgcat caacccat                                                    19

<210> SEQ ID NO 559
<211> LENGTH: 19
<212> TYPE: DNA
<213> ORGANISM: Homo sapiens

<400> SEQUENCE: 559
cagctgcatc aaccccatc                                                   19

<210> SEQ ID NO 560
<211> LENGTH: 19
<212> TYPE: DNA
<213> ORGANISM: Homo sapiens
```

```
<400> SEQUENCE: 560
ccccatcata tacccatgc                                                 19

<210> SEQ ID NO 561
<211> LENGTH: 19
<212> TYPE: DNA
<213> ORGANISM: Homo sapiens

<400> SEQUENCE: 561
gagttcaaaa aggcctttc                                                 19

<210> SEQ ID NO 562
<211> LENGTH: 19
<212> TYPE: DNA
<213> ORGANISM: Homo sapiens

<400> SEQUENCE: 562
aaaggccttt cagaatgtc                                                 19

<210> SEQ ID NO 563
<211> LENGTH: 19
<212> TYPE: DNA
<213> ORGANISM: Homo sapiens

<400> SEQUENCE: 563
aaggcctttc agaatgtct                                                 19

<210> SEQ ID NO 564
<211> LENGTH: 19
<212> TYPE: DNA
<213> ORGANISM: Homo sapiens

<400> SEQUENCE: 564
aggcctttca gaatgtctt                                                 19

<210> SEQ ID NO 565
<211> LENGTH: 19
<212> TYPE: DNA
<213> ORGANISM: Homo sapiens

<400> SEQUENCE: 565
ggcctttcag aatgtcttg                                                 19

<210> SEQ ID NO 566
<211> LENGTH: 19
<212> TYPE: DNA
<213> ORGANISM: Homo sapiens

<400> SEQUENCE: 566
tgtcttgaga atccagtgt                                                 19

<210> SEQ ID NO 567
<211> LENGTH: 19
<212> TYPE: DNA
<213> ORGANISM: Homo sapiens

<400> SEQUENCE: 567
tccagtgtct ctgcagaaa                                                 19

<210> SEQ ID NO 568
<211> LENGTH: 19
<212> TYPE: DNA
<213> ORGANISM: Homo sapiens
```

```
<400> SEQUENCE: 568
tccagtgtct ccgcagaaa                                                  19

<210> SEQ ID NO 569
<211> LENGTH: 19
<212> TYPE: DNA
<213> ORGANISM: Homo sapiens

<400> SEQUENCE: 569
agcagtcttc caaacatgc                                                  19

<210> SEQ ID NO 570
<211> LENGTH: 19
<212> TYPE: DNA
<213> ORGANISM: Homo sapiens

<400> SEQUENCE: 570
gcagtcttcc aaacatgcc                                                  19

<210> SEQ ID NO 571
<211> LENGTH: 19
<212> TYPE: DNA
<213> ORGANISM: Homo sapiens

<400> SEQUENCE: 571
acatgccctg ggctacacc                                                  19

<210> SEQ ID NO 572
<211> LENGTH: 19
<212> TYPE: DNA
<213> ORGANISM: Homo sapiens

<400> SEQUENCE: 572
gggcaacaca aggacatgg                                                  19

<210> SEQ ID NO 573
<211> LENGTH: 19
<212> TYPE: DNA
<213> ORGANISM: Homo sapiens

<400> SEQUENCE: 573
cacaaggaca tggtgcgca                                                  19

<210> SEQ ID NO 574
<211> LENGTH: 19
<212> TYPE: DNA
<213> ORGANISM: Homo sapiens

<400> SEQUENCE: 574
gagagacctt ctacaggat                                                  19

<210> SEQ ID NO 575
<211> LENGTH: 19
<212> TYPE: DNA
<213> ORGANISM: Homo sapiens

<400> SEQUENCE: 575
gacggatggc gtttgtgaa                                                  19

<210> SEQ ID NO 576
<211> LENGTH: 19
<212> TYPE: DNA
<213> ORGANISM: Homo sapiens
```

```
<400> SEQUENCE: 576
atttttctct tccatgccc                                              19

<210> SEQ ID NO 577
<211> LENGTH: 19
<212> TYPE: DNA
<213> ORGANISM: Homo sapiens

<400> SEQUENCE: 577
tttttctctt ccatgcccc                                              19

<210> SEQ ID NO 578
<211> LENGTH: 19
<212> TYPE: DNA
<213> ORGANISM: Homo sapiens

<400> SEQUENCE: 578
agaccaatcc tcctgtacc                                              19

<210> SEQ ID NO 579
<211> LENGTH: 19
<212> TYPE: DNA
<213> ORGANISM: Homo sapiens

<400> SEQUENCE: 579
gaccaatcct cctgtacca                                              19

<210> SEQ ID NO 580
<211> LENGTH: 19
<212> TYPE: DNA
<213> ORGANISM: Homo sapiens

<400> SEQUENCE: 580
tcctcctgta ccacagccc                                              19

<210> SEQ ID NO 581
<211> LENGTH: 19
<212> TYPE: DNA
<213> ORGANISM: Homo sapiens

<400> SEQUENCE: 581
gtctcgctct gtcaccagg                                              19

<210> SEQ ID NO 582
<211> LENGTH: 19
<212> TYPE: DNA
<213> ORGANISM: Homo sapiens

<400> SEQUENCE: 582
gagattctcc tgcctcagc                                              19

<210> SEQ ID NO 583
<211> LENGTH: 19
<212> TYPE: DNA
<213> ORGANISM: Homo sapiens

<400> SEQUENCE: 583
gaattgcaga gagcatatc                                              19

<210> SEQ ID NO 584
<211> LENGTH: 19
<212> TYPE: DNA
<213> ORGANISM: Homo sapiens
```

```
<400> SEQUENCE: 584
ttgcagagag catatcaag                                              19

<210> SEQ ID NO 585
<211> LENGTH: 19
<212> TYPE: DNA
<213> ORGANISM: Homo sapiens

<400> SEQUENCE: 585
ttttatgatg ccaccgtgg                                              19

<210> SEQ ID NO 586
<211> LENGTH: 19
<212> TYPE: DNA
<213> ORGANISM: Homo sapiens

<400> SEQUENCE: 586
agggtctaga atgctgatc                                              19

<210> SEQ ID NO 587
<211> LENGTH: 19
<212> TYPE: DNA
<213> ORGANISM: Homo sapiens

<400> SEQUENCE: 587
gggtctagaa tgctgatct                                              19

<210> SEQ ID NO 588
<211> LENGTH: 19
<212> TYPE: DNA
<213> ORGANISM: Homo sapiens

<400> SEQUENCE: 588
gtaaaagctt tttggaggt                                              19

<210> SEQ ID NO 589
<211> LENGTH: 19
<212> TYPE: DNA
<213> ORGANISM: Homo sapiens

<400> SEQUENCE: 589
aagctttttg gaggtctgc                                              19

<210> SEQ ID NO 590
<211> LENGTH: 19
<212> TYPE: DNA
<213> ORGANISM: Homo sapiens

<400> SEQUENCE: 590
agcttttggg aggtctgct                                              19

<210> SEQ ID NO 591
<211> LENGTH: 19
<212> TYPE: DNA
<213> ORGANISM: Homo sapiens

<400> SEQUENCE: 591 gcttttgga ggtctgctg                                               19

<210> SEQ ID NO 592
<211> LENGTH: 19
<212> TYPE: DNA
<213> ORGANISM: Homo sapiens
```

```
<400> SEQUENCE: 592
cccccagcct tgacaagaa                                                 19

<210> SEQ ID NO 593
<211> LENGTH: 19
<212> TYPE: DNA
<213> ORGANISM: Homo sapiens

<400> SEQUENCE: 593
gaaccatcaa gttccaacc                                                 19

<210> SEQ ID NO 594
<211> LENGTH: 19
<212> TYPE: DNA
<213> ORGANISM: Homo sapiens

<400> SEQUENCE: 594
ccatcaagtt ccaaccatt                                                 19

<210> SEQ ID NO 595
<211> LENGTH: 19
<212> TYPE: DNA
<213> ORGANISM: Homo sapiens

<400> SEQUENCE: 595
gttccaacca ttaaggtcc                                                 19

<210> SEQ ID NO 596
<211> LENGTH: 19
<212> TYPE: DNA
<213> ORGANISM: Homo sapiens

<400> SEQUENCE: 596
ccattaaggt ccacaccat                                                 19

<210> SEQ ID NO 597
<211> LENGTH: 19
<212> TYPE: DNA
<213> ORGANISM: Homo sapiens

<400> SEQUENCE: 597
ggtccacacc atctccctc                                                 19

<210> SEQ ID NO 598
<211> LENGTH: 19
<212> TYPE: DNA
<213> ORGANISM: Homo sapiens

<400> SEQUENCE: 598
cggggaggaa gtctaggac                                                 19

<210> SEQ ID NO 599
<211> LENGTH: 19
<212> TYPE: DNA
<213> ORGANISM: Homo sapiens

<400> SEQUENCE: 599
gatgaatccc gacctggac                                                 19

<210> SEQ ID NO 600
<211> LENGTH: 19
<212> TYPE: DNA
<213> ORGANISM: Homo sapiens
```

```
<400> SEQUENCE: 600
cacatcagca cctgcccac                                              19

<210> SEQ ID NO 601
<211> LENGTH: 19
<212> TYPE: DNA
<213> ORGANISM: Homo sapiens

<400> SEQUENCE: 601
aaatgccaac ttcactggc                                              19

<210> SEQ ID NO 602
<211> LENGTH: 19
<212> TYPE: DNA
<213> ORGANISM: Homo sapiens

<400> SEQUENCE: 602
aatgccaact tcactggcc                                              19

<210> SEQ ID NO 603
<211> LENGTH: 19
<212> TYPE: DNA
<213> ORGANISM: Homo sapiens

<400> SEQUENCE: 603
atgccaactt cactggccc                                              19

<210> SEQ ID NO 604
<211> LENGTH: 19
<212> TYPE: DNA
<213> ORGANISM: Homo sapiens

<400> SEQUENCE: 604
tgccaacttc actggcccc                                              19

<210> SEQ ID NO 605
<211> LENGTH: 19
<212> TYPE: DNA
<213> ORGANISM: Homo sapiens

<400> SEQUENCE: 605
cttcactggc cccaaccag                                              19

<210> SEQ ID NO 606
<211> LENGTH: 19
<212> TYPE: DNA
<213> ORGANISM: Homo sapiens

<400> SEQUENCE: 606
ccagacctcg agcaactcc                                              19

<210> SEQ ID NO 607
<211> LENGTH: 19
<212> TYPE: DNA
<213> ORGANISM: Homo sapiens

<400> SEQUENCE: 607
catcctagtc atcttgtct                                              19

<210> SEQ ID NO 608
<211> LENGTH: 19
<212> TYPE: DNA
<213> ORGANISM: Homo sapiens
```

```
<400> SEQUENCE: 608
ctacttcatt gtcaacctg                                              19

<210> SEQ ID NO 609
<211> LENGTH: 19
<212> TYPE: DNA
<213> ORGANISM: Homo sapiens

<400> SEQUENCE: 609
cgatgacaag gagtgcggg                                              19

<210> SEQ ID NO 610
<211> LENGTH: 19
<212> TYPE: DNA
<213> ORGANISM: Homo sapiens

<400> SEQUENCE: 610
gaacccttct atgccctct                                              19

<210> SEQ ID NO 611
<211> LENGTH: 19
<212> TYPE: DNA
<213> ORGANISM: Homo sapiens

<400> SEQUENCE: 611
cccttctatg ccctcttct                                              19

<210> SEQ ID NO 612
<211> LENGTH: 19
<212> TYPE: DNA
<213> ORGANISM: Homo sapiens

<400> SEQUENCE: 612
gagaaccacc aagaaccta                                              19

<210> SEQ ID NO 613
<211> LENGTH: 19
<212> TYPE: DNA
<213> ORGANISM: Homo sapiens

<400> SEQUENCE: 613
ccaccaagaa cctagaggc                                              19

<210> SEQ ID NO 614
<211> LENGTH: 19
<212> TYPE: DNA
<213> ORGANISM: Homo sapiens

<400> SEQUENCE: 614
gaacctagag gcaggagtc                                              19

<210> SEQ ID NO 615
<211> LENGTH: 19
<212> TYPE: DNA
<213> ORGANISM: Homo sapiens

<400> SEQUENCE: 615
cctagaggca ggagtcatg                                              19

<210> SEQ ID NO 616
<211> LENGTH: 19
<212> TYPE: DNA
<213> ORGANISM: Homo sapiens
```

-continued

```
<400> SEQUENCE: 616
ggagatgtcc aactccaag                                                19

<210> SEQ ID NO 617
<211> LENGTH: 19
<212> TYPE: DNA
<213> ORGANISM: Homo sapiens

<400> SEQUENCE: 617
ctccaaggag ctgaccctg                                                19

<210> SEQ ID NO 618
<211> LENGTH: 19
<212> TYPE: DNA
<213> ORGANISM: Homo sapiens

<400> SEQUENCE: 618
ggagctgacc ctgaggatc                                                19

<210> SEQ ID NO 619
<211> LENGTH: 19
<212> TYPE: DNA
<213> ORGANISM: Homo sapiens

<400> SEQUENCE: 619
gaactttcac gaggacacc                                                19

<210> SEQ ID NO 620
<211> LENGTH: 19
<212> TYPE: DNA
<213> ORGANISM: Homo sapiens

<400> SEQUENCE: 620
ctttcacgag gacaccctt                                                19

<210> SEQ ID NO 621
<211> LENGTH: 19
<212> TYPE: DNA
<213> ORGANISM: Homo sapiens

<400> SEQUENCE: 621
ccccaggagt tccatagct                                                19

<210> SEQ ID NO 622
<211> LENGTH: 19
<212> TYPE: DNA
<213> ORGANISM: Homo sapiens

<400> SEQUENCE: 622 acttttaag ttctccagg                                                 19

<210> SEQ ID NO 623
<211> LENGTH: 19
<212> TYPE: DNA
<213> ORGANISM: Homo sapiens

<400> SEQUENCE: 623 cttttaagt tctccaggg                                                 19

<210> SEQ ID NO 624
<211> LENGTH: 19
<212> TYPE: DNA
<213> ORGANISM: Homo sapiens
```

```
<400> SEQUENCE: 624
gttctccagg gaaaagaaa                                              19

<210> SEQ ID NO 625
<211> LENGTH: 19
<212> TYPE: DNA
<213> ORGANISM: Homo sapiens

<400> SEQUENCE: 625
aagaaagcag ctaagacgt                                              19

<210> SEQ ID NO 626
<211> LENGTH: 19
<212> TYPE: DNA
<213> ORGANISM: Homo sapiens

<400> SEQUENCE: 626
agaaagcagc taagacgtt                                              19

<210> SEQ ID NO 627
<211> LENGTH: 19
<212> TYPE: DNA
<213> ORGANISM: Homo sapiens

<400> SEQUENCE: 627
gaaagcagct aagacgttg                                              19

<210> SEQ ID NO 628
<211> LENGTH: 19
<212> TYPE: DNA
<213> ORGANISM: Homo sapiens

<400> SEQUENCE: 628
agcagctaag acgttgggc                                              19

<210> SEQ ID NO 629
<211> LENGTH: 19
<212> TYPE: DNA
<213> ORGANISM: Homo sapiens

<400> SEQUENCE: 629
gcagctaaga cgttgggca                                              19

<210> SEQ ID NO 630
<211> LENGTH: 19
<212> TYPE: DNA
<213> ORGANISM: Homo sapiens

<400> SEQUENCE: 630
gacgttgggc attgtggtc                                              19

<210> SEQ ID NO 631
<211> LENGTH: 19
<212> TYPE: DNA
<213> ORGANISM: Homo sapiens

<400> SEQUENCE: 631
cagctgcctc aaccccatc                                              19

<210> SEQ ID NO 632
<211> LENGTH: 19
<212> TYPE: DNA
<213> ORGANISM: Homo sapiens
```

<400> SEQUENCE: 632
ccccatcatc tacccatgc                                              19

<210> SEQ ID NO 633
<211> LENGTH: 19
<212> TYPE: DNA
<213> ORGANISM: Homo sapiens

<400> SEQUENCE: 633
ggagttcaag cgcgctttc                                              19

<210> SEQ ID NO 634
<211> LENGTH: 19
<212> TYPE: DNA
<213> ORGANISM: Homo sapiens

<400> SEQUENCE: 634
aagcaacatg cccctggcg                                              19

<210> SEQ ID NO 635
<211> LENGTH: 19
<212> TYPE: DNA
<213> ORGANISM: Homo sapiens

<400> SEQUENCE: 635
cctgcttgtc atcctctca                                              19

<210> SEQ ID NO 636
<211> LENGTH: 19
<212> TYPE: DNA
<213> ORGANISM: Homo sapiens

<400> SEQUENCE: 636
ctatttcatc gtgaacctg                                              19

<210> SEQ ID NO 637
<211> LENGTH: 19
<212> TYPE: DNA
<213> ORGANISM: Homo sapiens

<400> SEQUENCE: 637
gtacccagcc atcatgacc                                              19

<210> SEQ ID NO 638
<211> LENGTH: 19
<212> TYPE: DNA
<213> ORGANISM: Homo sapiens

<400> SEQUENCE: 638
gttctcccgt gagaagaaa                                              19

<210> SEQ ID NO 639
<211> LENGTH: 19
<212> TYPE: DNA
<213> ORGANISM: Homo sapiens

<400> SEQUENCE: 639
gaaagcggcc aagactctg                                              19

<210> SEQ ID NO 640
<211> LENGTH: 19
<212> TYPE: DNA
<213> ORGANISM: Homo sapiens

```
<400> SEQUENCE: 640
gactctggcc atcgtcgtg                                              19

<210> SEQ ID NO 641
<211> LENGTH: 19
<212> TYPE: DNA
<213> ORGANISM: Homo sapiens

<400> SEQUENCE: 641
ggtcatcttc tggctcggc                                              19

<210> SEQ ID NO 642
<211> LENGTH: 19
<212> TYPE: DNA
<213> ORGANISM: Homo sapiens

<400> SEQUENCE: 642
cccgctcatc tacccctgt                                              19

<210> SEQ ID NO 643
<211> LENGTH: 19
<212> TYPE: DNA
<213> ORGANISM: Homo sapiens

<400> SEQUENCE: 643
agtctccagc ctgtcgcac                                              19

<210> SEQ ID NO 644
<211> LENGTH: 19
<212> TYPE: DNA
<213> ORGANISM: Homo sapiens

<400> SEQUENCE: 644
gtctccagcc tgtcgcaca                                              19

<210> SEQ ID NO 645
<211> LENGTH: 19
<212> TYPE: DNA
<213> ORGANISM: Homo sapiens

<400> SEQUENCE: 645
ttggccgact acagcaacc                                              19

<210> SEQ ID NO 646
<211> LENGTH: 19
<212> TYPE: DNA
<213> ORGANISM: Homo sapiens

<400> SEQUENCE: 646
cctacgggag accgatatt                                              19

<210> SEQ ID NO 647
<211> LENGTH: 19
<212> TYPE: DNA
<213> ORGANISM: Homo sapiens

<400> SEQUENCE: 647
tgagagtacc tgtgagcag                                              19

<210> SEQ ID NO 648
<211> LENGTH: 19
<212> TYPE: DNA
<213> ORGANISM: Homo sapiens
```

```
<400> SEQUENCE: 648
tgccgggaag cccaaagac                                             19

<210> SEQ ID NO 649
<211> LENGTH: 19
<212> TYPE: DNA
<213> ORGANISM: Homo sapiens

<400> SEQUENCE: 649
gcccaaagac cccaccttc                                             19

<210> SEQ ID NO 650
<211> LENGTH: 19
<212> TYPE: DNA
<213> ORGANISM: Homo sapiens

<400> SEQUENCE: 650
agaccccacc ttcatacct                                             19

<210> SEQ ID NO 651
<211> LENGTH: 19
<212> TYPE: DNA
<213> ORGANISM: Homo sapiens

<400> SEQUENCE: 651
gaccccacct tcatacctg                                             19

<210> SEQ ID NO 652
<211> LENGTH: 19
<212> TYPE: DNA
<213> ORGANISM: Homo sapiens

<400> SEQUENCE: 652
ttcaggccaa gacatcccc                                             19

<210> SEQ ID NO 653
<211> LENGTH: 19
<212> TYPE: DNA
<213> ORGANISM: Homo sapiens

<400> SEQUENCE: 653
gacatcccct gtggatgaa                                             19

<210> SEQ ID NO 654
<211> LENGTH: 19
<212> TYPE: DNA
<213> ORGANISM: Homo sapiens

<400> SEQUENCE: 654
aaggccctac aggaccagc                                             19

<210> SEQ ID NO 655
<211> LENGTH: 19
<212> TYPE: DNA
<213> ORGANISM: Homo sapiens

<400> SEQUENCE: 655
aggccctaca ggaccagct                                             19

<210> SEQ ID NO 656
<211> LENGTH: 19
<212> TYPE: DNA
<213> ORGANISM: Homo sapiens
```

<400> SEQUENCE: 656
aacttgacac cgaagacaa                                                    19

<210> SEQ ID NO 657
<211> LENGTH: 19
<212> TYPE: DNA
<213> ORGANISM: Homo sapiens

<400> SEQUENCE: 657
acttgacacc gaagacaag                                                    19

<210> SEQ ID NO 658
<211> LENGTH: 19
<212> TYPE: DNA
<213> ORGANISM: Homo sapiens

<400> SEQUENCE: 658
cttgacaccg aagacaagt                                                    19

<210> SEQ ID NO 659
<211> LENGTH: 19
<212> TYPE: DNA
<213> ORGANISM: Homo sapiens

<400> SEQUENCE: 659
gacaagttga gggccgcaa                                                    19

<210> SEQ ID NO 660
<211> LENGTH: 19
<212> TYPE: DNA
<213> ORGANISM: Homo sapiens

<400> SEQUENCE: 660
gttgagggcc gcaatggtc                                                    19

<210> SEQ ID NO 661
<211> LENGTH: 19
<212> TYPE: DNA
<213> ORGANISM: Homo sapiens

<400> SEQUENCE: 661
tggtcgggat gctggccaa                                                    19

<210> SEQ ID NO 662
<211> LENGTH: 19
<212> TYPE: DNA
<213> ORGANISM: Homo sapiens

<400> SEQUENCE: 662
cttcttgggc ttccgtata                                                    19

<210> SEQ ID NO 663
<211> LENGTH: 19
<212> TYPE: DNA
<213> ORGANISM: Homo sapiens

<400> SEQUENCE: 663
cggctgtctt tggcaccct                                                    19

<210> SEQ ID NO 664
<211> LENGTH: 19
<212> TYPE: DNA
<213> ORGANISM: Homo sapiens

<400> SEQUENCE: 664
tcctgggtgt tccttggaa                                              19

<210> SEQ ID NO 665
<211> LENGTH: 19
<212> TYPE: DNA
<213> ORGANISM: Homo sapiens

<400> SEQUENCE: 665
ggacaagaac tgcacctcc                                              19

<210> SEQ ID NO 666
<211> LENGTH: 19
<212> TYPE: DNA
<213> ORGANISM: Homo sapiens

<400> SEQUENCE: 666
ctggatgttg ctgctgaga                                              19

<210> SEQ ID NO 667
<211> LENGTH: 19
<212> TYPE: DNA
<213> ORGANISM: Homo sapiens

<400> SEQUENCE: 667
gattgacagg ttcatgcag                                              19

<210> SEQ ID NO 668
<211> LENGTH: 19
<212> TYPE: DNA
<213> ORGANISM: Homo sapiens

<400> SEQUENCE: 668
gactggctgc tccctgatg                                              19

<210> SEQ ID NO 669
<211> LENGTH: 19
<212> TYPE: DNA
<213> ORGANISM: Homo sapiens

<400> SEQUENCE: 669
cacctacgtc cacttccaa                                              19

<210> SEQ ID NO 670
<211> LENGTH: 19
<212> TYPE: DNA
<213> ORGANISM: Homo sapiens

<400> SEQUENCE: 670
gggaagatga agggcttct                                              19

<210> SEQ ID NO 671
<211> LENGTH: 19
<212> TYPE: DNA
<213> ORGANISM: Homo sapiens

<400> SEQUENCE: 671
gatgaagggc ttctccctg                                              19

<210> SEQ ID NO 672
<211> LENGTH: 19
<212> TYPE: DNA
<213> ORGANISM: Homo sapiens

```
<400> SEQUENCE: 672
cagcacctca gtgtctgtt                                              19

<210> SEQ ID NO 673
<211> LENGTH: 19
<212> TYPE: DNA
<213> ORGANISM: Homo sapiens

<400> SEQUENCE: 673
cttctcggtg actcaagtg                                              19

<210> SEQ ID NO 674
<211> LENGTH: 19
<212> TYPE: DNA
<213> ORGANISM: Homo sapiens

<400> SEQUENCE: 674
gtgcccttca ctgagagcg                                              19

<210> SEQ ID NO 675
<211> LENGTH: 19
<212> TYPE: DNA
<213> ORGANISM: Homo sapiens

<400> SEQUENCE: 675
ggtggagggt ctcactttc                                              19

<210> SEQ ID NO 676
<211> LENGTH: 19
<212> TYPE: DNA
<213> ORGANISM: Homo sapiens

<400> SEQUENCE: 676
aactccctca actggatga                                              19

<210> SEQ ID NO 677
<211> LENGTH: 19
<212> TYPE: DNA
<213> ORGANISM: Homo sapiens

<400> SEQUENCE: 677
actccctcaa ctggatgaa                                              19

<210> SEQ ID NO 678
<211> LENGTH: 19
<212> TYPE: DNA
<213> ORGANISM: Homo sapiens

<400> SEQUENCE: 678
ctccctcaac tggatgaag                                              19

<210> SEQ ID NO 679
<211> LENGTH: 19
<212> TYPE: DNA
<213> ORGANISM: Homo sapiens

<400> SEQUENCE: 679
ctggatgaag aaactgtct                                              19

<210> SEQ ID NO 680
<211> LENGTH: 19
<212> TYPE: DNA
<213> ORGANISM: Homo sapiens
```

```
<400> SEQUENCE: 680
gaaactgtct ccccggacc                                                19

<210> SEQ ID NO 681
<211> LENGTH: 19
<212> TYPE: DNA
<213> ORGANISM: Homo sapiens

<400> SEQUENCE: 681
actgtctccc cggaccatc                                                19

<210> SEQ ID NO 682
<211> LENGTH: 19
<212> TYPE: DNA
<213> ORGANISM: Homo sapiens

<400> SEQUENCE: 682
ctggtgctgc aaggatctt                                                19

<210> SEQ ID NO 683
<211> LENGTH: 19
<212> TYPE: DNA
<213> ORGANISM: Homo sapiens

<400> SEQUENCE: 683
ggatcttatg acctgcagg                                                19

<210> SEQ ID NO 684
<211> LENGTH: 19
<212> TYPE: DNA
<213> ORGANISM: Homo sapiens

<400> SEQUENCE: 684
cctgcaaaaa ttgagcaat                                                19

<210> SEQ ID NO 685
<211> LENGTH: 19
<212> TYPE: DNA
<213> ORGANISM: Homo sapiens

<400> SEQUENCE: 685
aaattgagca atgaccgca                                                19

<210> SEQ ID NO 686
<211> LENGTH: 19
<212> TYPE: DNA
<213> ORGANISM: Homo sapiens

<400> SEQUENCE: 686
aattgagcaa tgaccgcat                                                19

<210> SEQ ID NO 687
<211> LENGTH: 19
<212> TYPE: DNA
<213> ORGANISM: Homo sapiens

<400> SEQUENCE: 687
attgagcaat gaccgcatc                                                19

<210> SEQ ID NO 688
<211> LENGTH: 19
<212> TYPE: DNA
<213> ORGANISM: Homo sapiens
```

```
<400> SEQUENCE: 688
ttgagcaatg accgcatca                                           19

<210> SEQ ID NO 689
<211> LENGTH: 19
<212> TYPE: DNA
<213> ORGANISM: Homo sapiens

<400> SEQUENCE: 689
gcggatgaga gagagccca                                           19

<210> SEQ ID NO 690
<211> LENGTH: 19
<212> TYPE: DNA
<213> ORGANISM: Homo sapiens

<400> SEQUENCE: 690
cagcttaaca agcctgagg                                           19

<210> SEQ ID NO 691
<211> LENGTH: 19
<212> TYPE: DNA
<213> ORGANISM: Homo sapiens

<400> SEQUENCE: 691
caagcctgag gtcttggag                                           19

<210> SEQ ID NO 692
<211> LENGTH: 19
<212> TYPE: DNA
<213> ORGANISM: Homo sapiens

<400> SEQUENCE: 692
gcctgaggtc ttggaggtg                                           19

<210> SEQ ID NO 693
<211> LENGTH: 19
<212> TYPE: DNA
<213> ORGANISM: Homo sapiens

<400> SEQUENCE: 693
ccgcccattc ctgtttgct                                           19

<210> SEQ ID NO 694
<211> LENGTH: 19
<212> TYPE: DNA
<213> ORGANISM: Homo sapiens

<400> SEQUENCE: 694
cccgctgagc acagcatga                                           19

<210> SEQ ID NO 695
<211> LENGTH: 19
<212> TYPE: DNA
<213> ORGANISM: Homo sapiens

<400> SEQUENCE: 695
ctcttctact gaagatggt                                           19

<210> SEQ ID NO 696
<211> LENGTH: 19
<212> TYPE: DNA
<213> ORGANISM: Homo sapiens
```

-continued

```
<400> SEQUENCE: 696
agaatccaag atgattgtc                                              19

<210> SEQ ID NO 697
<211> LENGTH: 19
<212> TYPE: DNA
<213> ORGANISM: Homo sapiens

<400> SEQUENCE: 697
gaatccaaga tgattgtcc                                              19

<210> SEQ ID NO 698
<211> LENGTH: 19
<212> TYPE: DNA
<213> ORGANISM: Homo sapiens

<400> SEQUENCE: 698
tccaagatga ttgtcccaa                                              19

<210> SEQ ID NO 699
<211> LENGTH: 19
<212> TYPE: DNA
<213> ORGANISM: Homo sapiens

<400> SEQUENCE: 699
gatgattgtc ccaaagctg                                              19

<210> SEQ ID NO 700
<211> LENGTH: 19
<212> TYPE: DNA
<213> ORGANISM: Homo sapiens

<400> SEQUENCE: 700
agctggaagg cataattac                                              19

<210> SEQ ID NO 701
<211> LENGTH: 19
<212> TYPE: DNA
<213> ORGANISM: Homo sapiens

<400> SEQUENCE: 701
gctggaaggc ataattaca                                              19

<210> SEQ ID NO 702
<211> LENGTH: 19
<212> TYPE: DNA
<213> ORGANISM: Homo sapiens

<400> SEQUENCE: 702
tatttggaaa cagcttggt                                              19

<210> SEQ ID NO 703
<211> LENGTH: 19
<212> TYPE: DNA
<213> ORGANISM: Homo sapiens

<400> SEQUENCE: 703
acagcttggt ggtgatagt                                              19

<210> SEQ ID NO 704
<211> LENGTH: 19
<212> TYPE: DNA
<213> ORGANISM: Homo sapiens
```

```
<400> SEQUENCE: 704
cagcttggtg gtgatagtc                                          19

<210> SEQ ID NO 705
<211> LENGTH: 19
<212> TYPE: DNA
<213> ORGANISM: Homo sapiens

<400> SEQUENCE: 705
gctgaagact gtggccagt                                          19

<210> SEQ ID NO 706
<211> LENGTH: 19
<212> TYPE: DNA
<213> ORGANISM: Homo sapiens

<400> SEQUENCE: 706
gactgtggcc agtgttttt                                          19

<210> SEQ ID NO 707
<211> LENGTH: 19
<212> TYPE: DNA
<213> ORGANISM: Homo sapiens

<400> SEQUENCE: 707
tttagcactg gctgactta                                          19

<210> SEQ ID NO 708
<211> LENGTH: 19
<212> TYPE: DNA
<213> ORGANISM: Homo sapiens

<400> SEQUENCE: 708
taccgctggc cctttggca                                          19

<210> SEQ ID NO 709
<211> LENGTH: 19
<212> TYPE: DNA
<213> ORGANISM: Homo sapiens

<400> SEQUENCE: 709
gattgcttca gccagcgtc                                          19

<210> SEQ ID NO 710
<211> LENGTH: 19
<212> TYPE: DNA
<213> ORGANISM: Homo sapiens

<400> SEQUENCE: 710
cctgtacgct agtgtgttt                                          19

<210> SEQ ID NO 711
<211> LENGTH: 19
<212> TYPE: DNA
<213> ORGANISM: Homo sapiens

<400> SEQUENCE: 711
tgaagtcccg ccttcgacg                                          19

<210> SEQ ID NO 712
<211> LENGTH: 19
<212> TYPE: DNA
<213> ORGANISM: Homo sapiens
```

```
<400> SEQUENCE: 712
tgcttgtagc caaagtcac                                                19

<210> SEQ ID NO 713
<211> LENGTH: 19
<212> TYPE: DNA
<213> ORGANISM: Homo sapiens

<400> SEQUENCE: 713
agtcacctgc atcatcatt                                                19

<210> SEQ ID NO 714
<211> LENGTH: 19
<212> TYPE: DNA
<213> ORGANISM: Homo sapiens

<400> SEQUENCE: 714
gtcacctgca tcatcattt                                                19

<210> SEQ ID NO 715
<211> LENGTH: 19
<212> TYPE: DNA
<213> ORGANISM: Homo sapiens

<400> SEQUENCE: 715
aattcaaccc ttccgatag                                                19

<210> SEQ ID NO 716
<211> LENGTH: 19
<212> TYPE: DNA
<213> ORGANISM: Homo sapiens

<400> SEQUENCE: 716
attcaaccct tccgatagg                                                19

<210> SEQ ID NO 717
<211> LENGTH: 19
<212> TYPE: DNA
<213> ORGANISM: Homo sapiens

<400> SEQUENCE: 717 ttcaacccctt ccgatagggg                                              19

<210> SEQ ID NO 718
<211> LENGTH: 19
<212> TYPE: DNA
<213> ORGANISM: Homo sapiens

<400> SEQUENCE: 718
aaatatactg ggtttcctg                                                19

<210> SEQ ID NO 719
<211> LENGTH: 19
<212> TYPE: DNA
<213> ORGANISM: Homo sapiens

<400> SEQUENCE: 719
aatatactgg gtttcctgt                                                19

<210> SEQ ID NO 720
<211> LENGTH: 19
<212> TYPE: DNA
<213> ORGANISM: Homo sapiens
```

<400> SEQUENCE: 720
atatactggg tttcctgtt        19

<210> SEQ ID NO 721
<211> LENGTH: 19
<212> TYPE: DNA
<213> ORGANISM: Homo sapiens

<400> SEQUENCE: 721
tatactgggt ttcctgttt        19

<210> SEQ ID NO 722
<211> LENGTH: 19
<212> TYPE: DNA
<213> ORGANISM: Homo sapiens

<400> SEQUENCE: 722
ggccctaaag aaggcttat        19

<210> SEQ ID NO 723
<211> LENGTH: 19
<212> TYPE: DNA
<213> ORGANISM: Homo sapiens

<400> SEQUENCE: 723
gaaggcttat gaaattcag        19

<210> SEQ ID NO 724
<211> LENGTH: 19
<212> TYPE: DNA
<213> ORGANISM: Homo sapiens

<400> SEQUENCE: 724
ggcttatgaa attcagaag        19

<210> SEQ ID NO 725
<211> LENGTH: 19
<212> TYPE: DNA
<213> ORGANISM: Homo sapiens

<400> SEQUENCE: 725
ttcagaagaa caaaccaag        19

<210> SEQ ID NO 726
<211> LENGTH: 19
<212> TYPE: DNA
<213> ORGANISM: Homo sapiens

<400> SEQUENCE: 726
ctaggcatca tacgtgact        19

<210> SEQ ID NO 727
<211> LENGTH: 19
<212> TYPE: DNA
<213> ORGANISM: Homo sapiens

<400> SEQUENCE: 727
ttgcagatat tgtggacac        19

<210> SEQ ID NO 728
<211> LENGTH: 19
<212> TYPE: DNA
<213> ORGANISM: Homo sapiens -continued

```
<400> SEQUENCE: 728
caattgcctg aatcctctt                                                    19

<210> SEQ ID NO 729
<211> LENGTH: 19
<212> TYPE: DNA
<213> ORGANISM: Homo sapiens

<400> SEQUENCE: 729
ttgcctgaat cctctttt                                                     19

<210> SEQ ID NO 730
<211> LENGTH: 19
<212> TYPE: DNA
<213> ORGANISM: Homo sapiens

<400> SEQUENCE: 730
agatattttc tccagcttc                                                    19

<210> SEQ ID NO 731
<211> LENGTH: 19
<212> TYPE: DNA
<213> ORGANISM: Homo sapiens

<400> SEQUENCE: 731
gatattttct ccagcttct                                                    19

<210> SEQ ID NO 732
<211> LENGTH: 19
<212> TYPE: DNA
<213> ORGANISM: Homo sapiens

<400> SEQUENCE: 732
aatatattcc cccaaaagc                                                    19

<210> SEQ ID NO 733
<211> LENGTH: 19
<212> TYPE: DNA
<213> ORGANISM: Homo sapiens

<400> SEQUENCE: 733
atatattccc ccaaaagcc                                                    19

<210> SEQ ID NO 734
<211> LENGTH: 19
<212> TYPE: DNA
<213> ORGANISM: Homo sapiens

<400> SEQUENCE: 734
tatattcccc caaaagcca                                                    19

<210> SEQ ID NO 735
<211> LENGTH: 19
<212> TYPE: DNA
<213> ORGANISM: Homo sapiens

<400> SEQUENCE: 735
aagccaaatc ccactcaaa                                                    19

<210> SEQ ID NO 736
<211> LENGTH: 19
<212> TYPE: DNA
<213> ORGANISM: Homo sapiens
```

<400> SEQUENCE: 736
agccaaatcc cactcaaac                                               19

<210> SEQ ID NO 737
<211> LENGTH: 19
<212> TYPE: DNA
<213> ORGANISM: Homo sapiens

<400> SEQUENCE: 737
gccaaatccc actcaaacc                                               19

<210> SEQ ID NO 738
<211> LENGTH: 19
<212> TYPE: DNA
<213> ORGANISM: Homo sapiens

<400> SEQUENCE: 738
atcccactca aacctttca                                               19

<210> SEQ ID NO 739
<211> LENGTH: 19
<212> TYPE: DNA
<213> ORGANISM: Homo sapiens

<400> SEQUENCE: 739
tcccactcaa acctttcaa                                               19

<210> SEQ ID NO 740
<211> LENGTH: 19
<212> TYPE: DNA
<213> ORGANISM: Homo sapiens

<400> SEQUENCE: 740
cctttcaaca aaaatgagc                                               19

<210> SEQ ID NO 741
<211> LENGTH: 19
<212> TYPE: DNA
<213> ORGANISM: Homo sapiens

<400> SEQUENCE: 741
caaaaatgag cacgctttc                                               19

<210> SEQ ID NO 742
<211> LENGTH: 19
<212> TYPE: DNA
<213> ORGANISM: Homo sapiens

<400> SEQUENCE: 742
aaatgagcac gctttccta                                               19

<210> SEQ ID NO 743
<211> LENGTH: 19
<212> TYPE: DNA
<213> ORGANISM: Homo sapiens

<400> SEQUENCE: 743
aatgagcacg ctttcctac                                               19

<210> SEQ ID NO 744
<211> LENGTH: 19
<212> TYPE: DNA
<213> ORGANISM: Homo sapiens

```
<400> SEQUENCE: 744
atgagcacgc tttcctacc                                                  19

<210> SEQ ID NO 745
<211> LENGTH: 19
<212> TYPE: DNA
<213> ORGANISM: Homo sapiens

<400> SEQUENCE: 745
tgagcacgct ttcctaccg                                                  19

<210> SEQ ID NO 746
<211> LENGTH: 19
<212> TYPE: DNA
<213> ORGANISM: Homo sapiens

<400> SEQUENCE: 746
tgtaagctca tccaccaag                                                  19

<210> SEQ ID NO 747
<211> LENGTH: 19
<212> TYPE: DNA
<213> ORGANISM: Homo sapiens

<400> SEQUENCE: 747
gctcatccac caagaagcc                                                  19

<210> SEQ ID NO 748
<211> LENGTH: 19
<212> TYPE: DNA
<213> ORGANISM: Homo sapiens

<400> SEQUENCE: 748
gaagcctgca ccatgtttt                                                  19

<210> SEQ ID NO 749
<211> LENGTH: 19
<212> TYPE: DNA
<213> ORGANISM: Homo sapiens

<400> SEQUENCE: 749
gcctgcacca tgttttgag                                                  19

<210> SEQ ID NO 750
<211> LENGTH: 19
<212> TYPE: DNA
<213> ORGANISM: Homo sapiens

<400> SEQUENCE: 750
tatgaagggc aactccacc                                                  19

<210> SEQ ID NO 751
<211> LENGTH: 19
<212> TYPE: DNA
<213> ORGANISM: Homo sapiens

<400> SEQUENCE: 751 ctccacccctt gccactact                                                 19

<210> SEQ ID NO 752
<211> LENGTH: 19
<212> TYPE: DNA
<213> ORGANISM: Homo sapiens
```

```
<400> SEQUENCE: 752
aaacattacc agcggtctt                                                    19

<210> SEQ ID NO 753
<211> LENGTH: 19
<212> TYPE: DNA
<213> ORGANISM: Homo sapiens

<400> SEQUENCE: 753
aacattacca gcggtcttc                                                    19

<210> SEQ ID NO 754
<211> LENGTH: 19
<212> TYPE: DNA
<213> ORGANISM: Homo sapiens

<400> SEQUENCE: 754
acattaccag cggtcttca                                                    19

<210> SEQ ID NO 755
<211> LENGTH: 19
<212> TYPE: DNA
<213> ORGANISM: Homo sapiens

<400> SEQUENCE: 755
cattaccagc ggtcttcac                                                    19

<210> SEQ ID NO 756
<211> LENGTH: 19
<212> TYPE: DNA
<213> ORGANISM: Homo sapiens

<400> SEQUENCE: 756
catctctggc aacaatgag                                                    19

<210> SEQ ID NO 757
<211> LENGTH: 19
<212> TYPE: DNA
<213> ORGANISM: Homo sapiens

<400> SEQUENCE: 757
caatgagtct accttgaac                                                    19

<210> SEQ ID NO 758
<211> LENGTH: 19
<212> TYPE: DNA
<213> ORGANISM: Homo sapiens

<400> SEQUENCE: 758
tgagtctacc ttgaactgt                                                    19

<210> SEQ ID NO 759
<211> LENGTH: 19
<212> TYPE: DNA
<213> ORGANISM: Homo sapiens

<400> SEQUENCE: 759
ctgttcacag aaaccatca                                                    19

<210> SEQ ID NO 760
<211> LENGTH: 19
<212> TYPE: DNA
<213> ORGANISM: Homo sapiens
```

```
<400> SEQUENCE: 760
ccatcagata agcatttag                                            19

<210> SEQ ID NO 761
<211> LENGTH: 19
<212> TYPE: DNA
<213> ORGANISM: Homo sapiens

<400> SEQUENCE: 761
gcatttagat gcaattcct                                            19

<210> SEQ ID NO 762
<211> LENGTH: 19
<212> TYPE: DNA
<213> ORGANISM: Homo sapiens

<400> SEQUENCE: 762
tattgtcgtg gttacactg                                            19

<210> SEQ ID NO 763
<211> LENGTH: 19
<212> TYPE: DNA
<213> ORGANISM: Homo sapiens

<400> SEQUENCE: 763
aagggtccta aaaaggttt                                            19

<210> SEQ ID NO 764
<211> LENGTH: 19
<212> TYPE: DNA
<213> ORGANISM: Homo sapiens

<400> SEQUENCE: 764
agggtcctaa aaaggtttc                                            19

<210> SEQ ID NO 765
<211> LENGTH: 19
<212> TYPE: DNA
<213> ORGANISM: Homo sapiens

<400> SEQUENCE: 765
gggtcctaaa aaggtttct                                            19

<210> SEQ ID NO 766
<211> LENGTH: 19
<212> TYPE: DNA
<213> ORGANISM: Homo sapiens

<400> SEQUENCE: 766
ggtttctagc atatacatc                                            19

<210> SEQ ID NO 767
<211> LENGTH: 19
<212> TYPE: DNA
<213> ORGANISM: Homo sapiens

<400> SEQUENCE: 767
cctcgctgtg gctgattta                                            19

<210> SEQ ID NO 768
<211> LENGTH: 19
<212> TYPE: DNA
<213> ORGANISM: Homo sapiens
```

```
<400> SEQUENCE: 768
tctgtcatct accccttc                                                    19

<210> SEQ ID NO 769
<211> LENGTH: 19
<212> TYPE: DNA
<213> ORGANISM: Homo sapiens

<400> SEQUENCE: 769
agaagaaatc cctggcaag                                                   19

<210> SEQ ID NO 770
<211> LENGTH: 19
<212> TYPE: DNA
<213> ORGANISM: Homo sapiens

<400> SEQUENCE: 770
gaagaaatcc ctggcaagc                                                   19

<210> SEQ ID NO 771
<211> LENGTH: 19
<212> TYPE: DNA
<213> ORGANISM: Homo sapiens

<400> SEQUENCE: 771
gaaatccctg gcaagcatc                                                   19

<210> SEQ ID NO 772
<211> LENGTH: 19
<212> TYPE: DNA
<213> ORGANISM: Homo sapiens

<400> SEQUENCE: 772
atccctggca agcatctta                                                   19

<210> SEQ ID NO 773
<211> LENGTH: 19
<212> TYPE: DNA
<213> ORGANISM: Homo sapiens

<400> SEQUENCE: 773
tccctggcaa gcatcttat                                                   19

<210> SEQ ID NO 774
<211> LENGTH: 19
<212> TYPE: DNA
<213> ORGANISM: Homo sapiens

<400> SEQUENCE: 774
gcatcttata tagttcccc                                                   19

<210> SEQ ID NO 775
<211> LENGTH: 19
<212> TYPE: DNA
<213> ORGANISM: Homo sapiens

<400> SEQUENCE: 775
ccattgaata cttaggagt                                                   19

<210> SEQ ID NO 776
<211> LENGTH: 19
<212> TYPE: DNA
<213> ORGANISM: Homo sapiens
```

```
<400> SEQUENCE: 776
tacttaggag tgaatgctt                                    19

<210> SEQ ID NO 777
<211> LENGTH: 19
<212> TYPE: DNA
<213> ORGANISM: Homo sapiens

<400> SEQUENCE: 777
tgcttgcatt atggctttc                                    19

<210> SEQ ID NO 778
<211> LENGTH: 19
<212> TYPE: DNA
<213> ORGANISM: Homo sapiens

<400> SEQUENCE: 778
atatgcccaa tggtcagct                                    19

<210> SEQ ID NO 779
<211> LENGTH: 19
<212> TYPE: DNA
<213> ORGANISM: Homo sapiens

<400> SEQUENCE: 779
tatgcccaat ggtcagctg                                    19

<210> SEQ ID NO 780
<211> LENGTH: 19
<212> TYPE: DNA
<213> ORGANISM: Homo sapiens

<400> SEQUENCE: 780
tggtcagctg ggattgcct                                    19

<210> SEQ ID NO 781
<211> LENGTH: 19
<212> TYPE: DNA
<213> ORGANISM: Homo sapiens

<400> SEQUENCE: 781
aacacttact gaagacgaa                                    19

<210> SEQ ID NO 782
<211> LENGTH: 19
<212> TYPE: DNA
<213> ORGANISM: Homo sapiens

<400> SEQUENCE: 782
acacttactg aagacgaat                                    19

<210> SEQ ID NO 783
<211> LENGTH: 19
<212> TYPE: DNA
<213> ORGANISM: Homo sapiens

<400> SEQUENCE: 783
cacttactga agacgaata                                    19

<210> SEQ ID NO 784
<211> LENGTH: 19
<212> TYPE: DNA
<213> ORGANISM: Homo sapiens
```

<400> SEQUENCE: 784
gacgaatagc tatgggaag					19

<210> SEQ ID NO 785
<211> LENGTH: 19
<212> TYPE: DNA
<213> ORGANISM: Homo sapiens

<400> SEQUENCE: 785
tagctatggg aagaacagg					19

<210> SEQ ID NO 786
<211> LENGTH: 19
<212> TYPE: DNA
<213> ORGANISM: Homo sapiens

<400> SEQUENCE: 786
gaacaggata acccgtgac					19

<210> SEQ ID NO 787
<211> LENGTH: 19
<212> TYPE: DNA
<213> ORGANISM: Homo sapiens

<400> SEQUENCE: 787
caggataacc cgtgaccaa					19

<210> SEQ ID NO 788
<211> LENGTH: 19
<212> TYPE: DNA
<213> ORGANISM: Homo sapiens

<400> SEQUENCE: 788
cccgtgacca agtcctgaa					19

<210> SEQ ID NO 789
<211> LENGTH: 19
<212> TYPE: DNA
<213> ORGANISM: Homo sapiens

<400> SEQUENCE: 789
gtcctgaaga tggcagctg					19

<210> SEQ ID NO 790
<211> LENGTH: 19
<212> TYPE: DNA
<213> ORGANISM: Homo sapiens

<400> SEQUENCE: 790
gatggcagct gctgttgtt					19

<210> SEQ ID NO 791
<211> LENGTH: 19
<212> TYPE: DNA
<213> ORGANISM: Homo sapiens

<400> SEQUENCE: 791
tagctgcgaa gttatagca					19

<210> SEQ ID NO 792
<211> LENGTH: 19
<212> TYPE: DNA
<213> ORGANISM: Homo sapiens

```
<400> SEQUENCE: 792
gttatagcag tcattgacc                                            19

<210> SEQ ID NO 793
<211> LENGTH: 19
<212> TYPE: DNA
<213> ORGANISM: Homo sapiens

<400> SEQUENCE: 793
cagctgcgtt aatccgttt                                            19

<210> SEQ ID NO 794
<211> LENGTH: 19
<212> TYPE: DNA
<213> ORGANISM: Homo sapiens

<400> SEQUENCE: 794
accggttcca acagaagct                                            19

<210> SEQ ID NO 795
<211> LENGTH: 19
<212> TYPE: DNA
<213> ORGANISM: Homo sapiens

<400> SEQUENCE: 795
ccggttccaa cagaagctc                                            19

<210> SEQ ID NO 796
<211> LENGTH: 19
<212> TYPE: DNA
<213> ORGANISM: Homo sapiens

<400> SEQUENCE: 796
cagaagctcc gcagtgtgt                                            19

<210> SEQ ID NO 797
<211> LENGTH: 19
<212> TYPE: DNA
<213> ORGANISM: Homo sapiens

<400> SEQUENCE: 797
gctccgcagt gtgtttagg                                            19

<210> SEQ ID NO 798
<211> LENGTH: 19
<212> TYPE: DNA
<213> ORGANISM: Homo sapiens

<400> SEQUENCE: 798
ttacttggct ccaagggaa                                            19

<210> SEQ ID NO 799
<211> LENGTH: 19
<212> TYPE: DNA
<213> ORGANISM: Homo sapiens

<400> SEQUENCE: 799
gggaaaagag agagtatgt                                            19

<210> SEQ ID NO 800
<211> LENGTH: 19
<212> TYPE: DNA
<213> ORGANISM: Homo sapiens
```

```
<400> SEQUENCE: 800
aagagagagt atgtcttgc                                              19

<210> SEQ ID NO 801
<211> LENGTH: 19
<212> TYPE: DNA
<213> ORGANISM: Homo sapiens

<400> SEQUENCE: 801
agagagagta tgtcttgcc                                              19

<210> SEQ ID NO 802
<211> LENGTH: 19
<212> TYPE: DNA
<213> ORGANISM: Homo sapiens

<400> SEQUENCE: 802
gagagagtat gtcttgccg                                              19

<210> SEQ ID NO 803
<211> LENGTH: 19
<212> TYPE: DNA
<213> ORGANISM: Homo sapiens

<400> SEQUENCE: 803
aagcagttct cttagagaa                                              19

<210> SEQ ID NO 804
<211> LENGTH: 19
<212> TYPE: DNA
<213> ORGANISM: Homo sapiens

<400> SEQUENCE: 804
agcagttctc ttagagaaa                                              19

<210> SEQ ID NO 805
<211> LENGTH: 19
<212> TYPE: DNA
<213> ORGANISM: Homo sapiens

<400> SEQUENCE: 805
gcagttctct tagagaaat                                              19

<210> SEQ ID NO 806
<211> LENGTH: 19
<212> TYPE: DNA
<213> ORGANISM: Homo sapiens

<400> SEQUENCE: 806
atggagacct ttgtgtctt                                              19

<210> SEQ ID NO 807
<211> LENGTH: 19
<212> TYPE: DNA
<213> ORGANISM: Homo sapiens

<400> SEQUENCE: 807
tggagacctt tgtgtctta                                              19

<210> SEQ ID NO 808
<211> LENGTH: 19
<212> TYPE: DNA
<213> ORGANISM: Homo sapiens
```

```
<400> SEQUENCE: 808
cttttctgct gacgaggcc                                           19

<210> SEQ ID NO 809
<211> LENGTH: 19
<212> TYPE: DNA
<213> ORGANISM: Homo sapiens

<400> SEQUENCE: 809
caggtgctgt tccagagcg                                           19

<210> SEQ ID NO 810
<211> LENGTH: 19
<212> TYPE: DNA
<213> ORGANISM: Homo sapiens

<400> SEQUENCE: 810
catcaccgcg gagaatgca                                           19

<210> SEQ ID NO 811
<211> LENGTH: 19
<212> TYPE: DNA
<213> ORGANISM: Homo sapiens

<400> SEQUENCE: 811
tgcaaggcgc caggaggaa                                           19

<210> SEQ ID NO 812
<211> LENGTH: 19
<212> TYPE: DNA
<213> ORGANISM: Homo sapiens

<400> SEQUENCE: 812
ggccaaggag ctgtatgaa                                           19

<210> SEQ ID NO 813
<211> LENGTH: 19
<212> TYPE: DNA
<213> ORGANISM: Homo sapiens

<400> SEQUENCE: 813
ggagctgtat gaaccgatc                                           19

<210> SEQ ID NO 814
<211> LENGTH: 19
<212> TYPE: DNA
<213> ORGANISM: Homo sapiens

<400> SEQUENCE: 814
ccgatctggc agaacttca                                           19

<210> SEQ ID NO 815
<211> LENGTH: 19
<212> TYPE: DNA
<213> ORGANISM: Homo sapiens

<400> SEQUENCE: 815
cgccctgcta agcaacatg                                           19

<210> SEQ ID NO 816
<211> LENGTH: 19
<212> TYPE: DNA
<213> ORGANISM: Homo sapiens
```

<400> SEQUENCE: 816
gcaacatgag caggatcta                                              19

<210> SEQ ID NO 817
<211> LENGTH: 19
<212> TYPE: DNA
<213> ORGANISM: Homo sapiens

<400> SEQUENCE: 817
catgagcagg atctactcc                                              19

<210> SEQ ID NO 818
<211> LENGTH: 19
<212> TYPE: DNA
<213> ORGANISM: Homo sapiens

<400> SEQUENCE: 818
ggtctgcctc cccaacaag                                              19

<210> SEQ ID NO 819
<211> LENGTH: 19
<212> TYPE: DNA
<213> ORGANISM: Homo sapiens

<400> SEQUENCE: 819
caagactgcc acctgctgg                                              19

<210> SEQ ID NO 820
<211> LENGTH: 19
<212> TYPE: DNA
<213> ORGANISM: Homo sapiens

<400> SEQUENCE: 820
catcctggct tcctcgcga                                              19

<210> SEQ ID NO 821
<211> LENGTH: 19
<212> TYPE: DNA
<213> ORGANISM: Homo sapiens

<400> SEQUENCE: 821
gctacgccat gctcctgtt                                              19

<210> SEQ ID NO 822
<211> LENGTH: 19
<212> TYPE: DNA
<213> ORGANISM: Homo sapiens

<400> SEQUENCE: 822
accgctgtac gaggatttc                                              19

<210> SEQ ID NO 823
<211> LENGTH: 19
<212> TYPE: DNA
<213> ORGANISM: Homo sapiens

<400> SEQUENCE: 823
ccgctgtacg aggatttca                                              19

<210> SEQ ID NO 824
<211> LENGTH: 19
<212> TYPE: DNA
<213> ORGANISM: Homo sapiens

```
<400> SEQUENCE: 824
tgaagcctac aagcaggac                                              19

<210> SEQ ID NO 825
<211> LENGTH: 19
<212> TYPE: DNA
<213> ORGANISM: Homo sapiens

<400> SEQUENCE: 825
gcctacaagc aggacggct                                              19

<210> SEQ ID NO 826
<211> LENGTH: 19
<212> TYPE: DNA
<213> ORGANISM: Homo sapiens

<400> SEQUENCE: 826
gcaggacggc ttcacagac                                              19

<210> SEQ ID NO 827
<211> LENGTH: 19
<212> TYPE: DNA
<213> ORGANISM: Homo sapiens

<400> SEQUENCE: 827
cacctctacc aacagctag                                              19

<210> SEQ ID NO 828
<211> LENGTH: 19
<212> TYPE: DNA
<213> ORGANISM: Homo sapiens

<400> SEQUENCE: 828
cagctagagc ccctctacc                                              19

<210> SEQ ID NO 829
<211> LENGTH: 19
<212> TYPE: DNA
<213> ORGANISM: Homo sapiens

<400> SEQUENCE: 829
aacatctacg acatggtgg                                              19

<210> SEQ ID NO 830
<211> LENGTH: 19
<212> TYPE: DNA
<213> ORGANISM: Homo sapiens

<400> SEQUENCE: 830
acatctacga catggtggt                                              19

<210> SEQ ID NO 831
<211> LENGTH: 19
<212> TYPE: DNA
<213> ORGANISM: Homo sapiens

<400> SEQUENCE: 831
catctacgac atggtggtg                                              19

<210> SEQ ID NO 832
<211> LENGTH: 19
<212> TYPE: DNA
<213> ORGANISM: Homo sapiens
```

```
<400> SEQUENCE: 832
gcccaacctc gatgtcacc                                              19

<210> SEQ ID NO 833
<211> LENGTH: 19
<212> TYPE: DNA
<213> ORGANISM: Homo sapiens

<400> SEQUENCE: 833
cctcgatgtc accagtact                                              19

<210> SEQ ID NO 834
<211> LENGTH: 19
<212> TYPE: DNA
<213> ORGANISM: Homo sapiens

<400> SEQUENCE: 834
gggtcgatgc tggagaagc                                              19

<210> SEQ ID NO 835
<211> LENGTH: 19
<212> TYPE: DNA
<213> ORGANISM: Homo sapiens

<400> SEQUENCE: 835
caggaaagac ttcaggatc                                              19

<210> SEQ ID NO 836
<211> LENGTH: 19
<212> TYPE: DNA
<213> ORGANISM: Homo sapiens

<400> SEQUENCE: 836
agacttcagg atcaagcag                                              19

<210> SEQ ID NO 837
<211> LENGTH: 19
<212> TYPE: DNA
<213> ORGANISM: Homo sapiens

<400> SEQUENCE: 837
gacttcagga tcaagcagt                                              19

<210> SEQ ID NO 838
<211> LENGTH: 19
<212> TYPE: DNA
<213> ORGANISM: Homo sapiens

<400> SEQUENCE: 838
catctgcaca aaatcggcc                                              19

<210> SEQ ID NO 839
<211> LENGTH: 19
<212> TYPE: DNA
<213> ORGANISM: Homo sapiens

<400> SEQUENCE: 839
aatcggcctg ctggaccgt                                              19

<210> SEQ ID NO 840
<211> LENGTH: 19
<212> TYPE: DNA
<213> ORGANISM: Homo sapiens
```

<400> SEQUENCE: 840
tgacacggaa agtgacatc                                        19

<210> SEQ ID NO 841
<211> LENGTH: 19
<212> TYPE: DNA
<213> ORGANISM: Homo sapiens

<400> SEQUENCE: 841
agtgacatca attacttgc                                        19

<210> SEQ ID NO 842
<211> LENGTH: 19
<212> TYPE: DNA
<213> ORGANISM: Homo sapiens

<400> SEQUENCE: 842
gtgacatcaa ttacttgct                                        19

<210> SEQ ID NO 843
<211> LENGTH: 19
<212> TYPE: DNA
<213> ORGANISM: Homo sapiens

<400> SEQUENCE: 843
atggcactgg aaaaaattg                                        19

<210> SEQ ID NO 844
<211> LENGTH: 19
<212> TYPE: DNA
<213> ORGANISM: Homo sapiens

<400> SEQUENCE: 844
tggcactgga aaaaattgc                                        19

<210> SEQ ID NO 845
<211> LENGTH: 19
<212> TYPE: DNA
<213> ORGANISM: Homo sapiens

<400> SEQUENCE: 845
aaaattgcct tcctgccct                                        19

<210> SEQ ID NO 846
<211> LENGTH: 19
<212> TYPE: DNA
<213> ORGANISM: Homo sapiens

<400> SEQUENCE: 846
aaattgcctt cctgccctt                                        19

<210> SEQ ID NO 847
<211> LENGTH: 19
<212> TYPE: DNA
<213> ORGANISM: Homo sapiens

<400> SEQUENCE: 847
aattgccttc ctgcccttt                                        19

<210> SEQ ID NO 848
<211> LENGTH: 19
<212> TYPE: DNA
<213> ORGANISM: Homo sapiens

```
<400> SEQUENCE: 848
attgccttcc tgcccttttg                                              19

<210> SEQ ID NO 849
<211> LENGTH: 19
<212> TYPE: DNA
<213> ORGANISM: Homo sapiens

<400> SEQUENCE: 849
ttgccttcct gcccttttgg                                              19

<210> SEQ ID NO 850
<211> LENGTH: 19
<212> TYPE: DNA
<213> ORGANISM: Homo sapiens

<400> SEQUENCE: 850
cttcgactgg tggtatctt                                               19

<210> SEQ ID NO 851
<211> LENGTH: 19
<212> TYPE: DNA
<213> ORGANISM: Homo sapiens

<400> SEQUENCE: 851
ccaagtatca ggggatctg                                               19

<210> SEQ ID NO 852
<211> LENGTH: 19
<212> TYPE: DNA
<213> ORGANISM: Homo sapiens

<400> SEQUENCE: 852
gtatcagggg atctgtcct                                               19

<210> SEQ ID NO 853
<211> LENGTH: 19
<212> TYPE: DNA
<213> ORGANISM: Homo sapiens

<400> SEQUENCE: 853
acgaaaccca ctttgatgc                                               19

<210> SEQ ID NO 854
<211> LENGTH: 19
<212> TYPE: DNA
<213> ORGANISM: Homo sapiens

<400> SEQUENCE: 854
cgaaacccac tttgatgct                                               19

<210> SEQ ID NO 855
<211> LENGTH: 19
<212> TYPE: DNA
<213> ORGANISM: Homo sapiens

<400> SEQUENCE: 855
acccactttg atgctggag                                               19

<210> SEQ ID NO 856
<211> LENGTH: 19
<212> TYPE: DNA
<213> ORGANISM: Homo sapiens
```

```
<400> SEQUENCE: 856
cccactttga tgctggagc                                              19

<210> SEQ ID NO 857
<211> LENGTH: 19
<212> TYPE: DNA
<213> ORGANISM: Homo sapiens

<400> SEQUENCE: 857
gtttcatgtt ccaaatgtg                                              19

<210> SEQ ID NO 858
<211> LENGTH: 19
<212> TYPE: DNA
<213> ORGANISM: Homo sapiens

<400> SEQUENCE: 858
atgtgacacc atacatcag                                              19

<210> SEQ ID NO 859
<211> LENGTH: 19
<212> TYPE: DNA
<213> ORGANISM: Homo sapiens

<400> SEQUENCE: 859
tgtgacacca tacatcagg                                              19

<210> SEQ ID NO 860
<211> LENGTH: 19
<212> TYPE: DNA
<213> ORGANISM: Homo sapiens

<400> SEQUENCE: 860
ggacatggtc ggcttagat                                              19

<210> SEQ ID NO 861
<211> LENGTH: 19
<212> TYPE: DNA
<213> ORGANISM: Homo sapiens

<400> SEQUENCE: 861
gtacttccag ccagtcacc                                              19

<210> SEQ ID NO 862
<211> LENGTH: 19
<212> TYPE: DNA
<213> ORGANISM: Homo sapiens

<400> SEQUENCE: 862
ctacccggag ggcatagac                                              19

<210> SEQ ID NO 863
<211> LENGTH: 19
<212> TYPE: DNA
<213> ORGANISM: Homo sapiens

<400> SEQUENCE: 863
gtttgtggag gaatatgac                                              19

<210> SEQ ID NO 864
<211> LENGTH: 19
<212> TYPE: DNA
<213> ORGANISM: Homo sapiens
```

```
<400> SEQUENCE: 864
tatgaccgga catcccagg                                              19

<210> SEQ ID NO 865
<211> LENGTH: 19
<212> TYPE: DNA
<213> ORGANISM: Homo sapiens

<400> SEQUENCE: 865
cgagtatgcc gaggccaac                                              19

<210> SEQ ID NO 866
<211> LENGTH: 19
<212> TYPE: DNA
<213> ORGANISM: Homo sapiens

<400> SEQUENCE: 866
ctggaactac aacaccaac                                              19

<210> SEQ ID NO 867
<211> LENGTH: 19
<212> TYPE: DNA
<213> ORGANISM: Homo sapiens

<400> SEQUENCE: 867
ctacaacacc aacatcacc                                              19

<210> SEQ ID NO 868
<211> LENGTH: 19
<212> TYPE: DNA
<213> ORGANISM: Homo sapiens

<400> SEQUENCE: 868
caccaacatc accacagag                                              19

<210> SEQ ID NO 869
<211> LENGTH: 19
<212> TYPE: DNA
<213> ORGANISM: Homo sapiens

<400> SEQUENCE: 869
catcaccaca gagaccagc                                              19

<210> SEQ ID NO 870
<211> LENGTH: 19
<212> TYPE: DNA
<213> ORGANISM: Homo sapiens

<400> SEQUENCE: 870
gattctgctg cagaagaac                                              19

<210> SEQ ID NO 871
<211> LENGTH: 19
<212> TYPE: DNA
<213> ORGANISM: Homo sapiens

<400> SEQUENCE: 871
gaacatgcaa atagccaac                                              19

<210> SEQ ID NO 872
<211> LENGTH: 19
<212> TYPE: DNA
<213> ORGANISM: Homo sapiens
```

```
<400> SEQUENCE: 872
catgcaaata gccaaccac                                              19

<210> SEQ ID NO 873
<211> LENGTH: 19
<212> TYPE: DNA
<213> ORGANISM: Homo sapiens

<400> SEQUENCE: 873
atagccaacc acaccctga                                              19

<210> SEQ ID NO 874
<211> LENGTH: 19
<212> TYPE: DNA
<213> ORGANISM: Homo sapiens

<400> SEQUENCE: 874
tagccaacca caccctgaa                                              19

<210> SEQ ID NO 875
<211> LENGTH: 19
<212> TYPE: DNA
<213> ORGANISM: Homo sapiens

<400> SEQUENCE: 875
ccacaccctg aagtacggc                                              19

<210> SEQ ID NO 876
<211> LENGTH: 19
<212> TYPE: DNA
<213> ORGANISM: Homo sapiens

<400> SEQUENCE: 876
gtttgatgtg aaccagttg                                              19

<210> SEQ ID NO 877
<211> LENGTH: 19
<212> TYPE: DNA
<213> ORGANISM: Homo sapiens

<400> SEQUENCE: 877
ccagttgcag aacaccact                                              19

<210> SEQ ID NO 878
<211> LENGTH: 19
<212> TYPE: DNA
<213> ORGANISM: Homo sapiens

<400> SEQUENCE: 878
caccactatc aagcggatc                                              19

<210> SEQ ID NO 879
<211> LENGTH: 19
<212> TYPE: DNA
<213> ORGANISM: Homo sapiens

<400> SEQUENCE: 879
gcggatcata aagaaggtt                                              19

<210> SEQ ID NO 880
<211> LENGTH: 19
<212> TYPE: DNA
<213> ORGANISM: Homo sapiens
```

<400> SEQUENCE: 880
agaaggttca ggacctaga                                    19

<210> SEQ ID NO 881
<211> LENGTH: 19
<212> TYPE: DNA
<213> ORGANISM: Homo sapiens

<400> SEQUENCE: 881
gaaggttcag gacctagaa                                    19

<210> SEQ ID NO 882
<211> LENGTH: 19
<212> TYPE: DNA
<213> ORGANISM: Homo sapiens

<400> SEQUENCE: 882
ggttcaggac ctagaacgg                                    19

<210> SEQ ID NO 883
<211> LENGTH: 19
<212> TYPE: DNA
<213> ORGANISM: Homo sapiens

<400> SEQUENCE: 883
caagatcctg ttggatatg                                    19

<210> SEQ ID NO 884
<211> LENGTH: 19
<212> TYPE: DNA
<213> ORGANISM: Homo sapiens

<400> SEQUENCE: 884
gatcctgttg gatatggaa                                    19

<210> SEQ ID NO 885
<211> LENGTH: 19
<212> TYPE: DNA
<213> ORGANISM: Homo sapiens

<400> SEQUENCE: 885
accacctaca gcgtggcca                                    19

<210> SEQ ID NO 886
<211> LENGTH: 19
<212> TYPE: DNA
<213> ORGANISM: Homo sapiens

<400> SEQUENCE: 886
atatgaagac ctgttatgg                                    19

<210> SEQ ID NO 887
<211> LENGTH: 19
<212> TYPE: DNA
<213> ORGANISM: Homo sapiens

<400> SEQUENCE: 887
tatgaagacc tgttatggg                                    19

<210> SEQ ID NO 888
<211> LENGTH: 19
<212> TYPE: DNA
<213> ORGANISM: Homo sapiens

```
<400> SEQUENCE: 888
gacctgttat gggcatggg                                              19

<210> SEQ ID NO 889
<211> LENGTH: 19
<212> TYPE: DNA
<213> ORGANISM: Homo sapiens

<400> SEQUENCE: 889
atacgtggaa ctcatcaac                                              19

<210> SEQ ID NO 890
<211> LENGTH: 19
<212> TYPE: DNA
<213> ORGANISM: Homo sapiens

<400> SEQUENCE: 890
tacgtggaac tcatcaacc                                              19

<210> SEQ ID NO 891
<211> LENGTH: 19
<212> TYPE: DNA
<213> ORGANISM: Homo sapiens

<400> SEQUENCE: 891
ctcatcaacc aggctgccc                                              19

<210> SEQ ID NO 892
<211> LENGTH: 19
<212> TYPE: DNA
<213> ORGANISM: Homo sapiens

<400> SEQUENCE: 892
tggctatgta gatgcaggg                                              19

<210> SEQ ID NO 893
<211> LENGTH: 19
<212> TYPE: DNA
<213> ORGANISM: Homo sapiens

<400> SEQUENCE: 893
catctatgac ttggtggtg                                              19

<210> SEQ ID NO 894
<211> LENGTH: 19
<212> TYPE: DNA
<213> ORGANISM: Homo sapiens

<400> SEQUENCE: 894
ggaggctgat gatttcttc                                              19

<210> SEQ ID NO 895
<211> LENGTH: 19
<212> TYPE: DNA
<213> ORGANISM: Homo sapiens

<400> SEQUENCE: 895
caagtcgatg ctggagaag                                              19

<210> SEQ ID NO 896
<211> LENGTH: 19
<212> TYPE: DNA
<213> ORGANISM: Homo sapiens
```

```
<400> SEQUENCE: 896
gtcgatgctg gagaagcca                                              19

<210> SEQ ID NO 897
<211> LENGTH: 19
<212> TYPE: DNA
<213> ORGANISM: Homo sapiens

<400> SEQUENCE: 897
cggcaaggac ttccggatc                                              19

<210> SEQ ID NO 898
<211> LENGTH: 19
<212> TYPE: DNA
<213> ORGANISM: Homo sapiens

<400> SEQUENCE: 898
ggacttccgg atcaagcag                                              19

<210> SEQ ID NO 899
<211> LENGTH: 19
<212> TYPE: DNA
<213> ORGANISM: Homo sapiens

<400> SEQUENCE: 899
gcagtgcacc accgtgaac                                              19

<210> SEQ ID NO 900
<211> LENGTH: 19
<212> TYPE: DNA
<213> ORGANISM: Homo sapiens

<400> SEQUENCE: 900
cttggaggac ctggtggtg                                              19

<210> SEQ ID NO 901
<211> LENGTH: 19
<212> TYPE: DNA
<213> ORGANISM: Homo sapiens

<400> SEQUENCE: 901
atgggccaca tccagtatt                                              19

<210> SEQ ID NO 902
<211> LENGTH: 19
<212> TYPE: DNA
<213> ORGANISM: Homo sapiens

<400> SEQUENCE: 902
tgggccacat ccagtattt                                              19

<210> SEQ ID NO 903
<211> LENGTH: 19
<212> TYPE: DNA
<213> ORGANISM: Homo sapiens

<400> SEQUENCE: 903
agacttacct gtggccttg                                              19

<210> SEQ ID NO 904
<211> LENGTH: 19
<212> TYPE: DNA
<213> ORGANISM: Homo sapiens
```

```
<400> SEQUENCE: 904
gacttacctg tggcctttga                                              19

<210> SEQ ID NO 905
<211> LENGTH: 19
<212> TYPE: DNA
<213> ORGANISM: Homo sapiens

<400> SEQUENCE: 905
gcacctgcac agtctcaac                                               19

<210> SEQ ID NO 906
<211> LENGTH: 19
<212> TYPE: DNA
<213> ORGANISM: Homo sapiens

<400> SEQUENCE: 906
cctgctgagc agtgagggt                                               19

<210> SEQ ID NO 907
<211> LENGTH: 19
<212> TYPE: DNA
<213> ORGANISM: Homo sapiens

<400> SEQUENCE: 907
ctttctgatg aagatggcc                                               19

<210> SEQ ID NO 908
<211> LENGTH: 19
<212> TYPE: DNA
<213> ORGANISM: Homo sapiens

<400> SEQUENCE: 908
gatggccctt gacaagatc                                               19

<210> SEQ ID NO 909
<211> LENGTH: 19
<212> TYPE: DNA
<213> ORGANISM: Homo sapiens

<400> SEQUENCE: 909
gatcgccttt atccccttc                                               19

<210> SEQ ID NO 910
<211> LENGTH: 19
<212> TYPE: DNA
<213> ORGANISM: Homo sapiens

<400> SEQUENCE: 910
gcatcaccaa ggagaacta                                               19

<210> SEQ ID NO 911
<211> LENGTH: 19
<212> TYPE: DNA
<213> ORGANISM: Homo sapiens

<400> SEQUENCE: 911
ggagaactat aaccaggag                                               19

<210> SEQ ID NO 912
<211> LENGTH: 19
<212> TYPE: DNA
<213> ORGANISM: Homo sapiens
```

```
<400> SEQUENCE: 912
ctataaccag gagtggtgg                                               19

<210> SEQ ID NO 913
<211> LENGTH: 19
<212> TYPE: DNA
<213> ORGANISM: Homo sapiens

<400> SEQUENCE: 913
ggtgactttg acccagggg                                               19

<210> SEQ ID NO 914
<211> LENGTH: 19
<212> TYPE: DNA
<213> ORGANISM: Homo sapiens

<400> SEQUENCE: 914
gttccacatt ccttctagc                                               19

<210> SEQ ID NO 915
<211> LENGTH: 19
<212> TYPE: DNA
<213> ORGANISM: Homo sapiens

<400> SEQUENCE: 915
gtgtgacatc taccagtcc                                               19

<210> SEQ ID NO 916
<211> LENGTH: 19
<212> TYPE: DNA
<213> ORGANISM: Homo sapiens

<400> SEQUENCE: 916
gccatgcagc tgatcacgg                                               19

<210> SEQ ID NO 917
<211> LENGTH: 19
<212> TYPE: DNA
<213> ORGANISM: Homo sapiens

<400> SEQUENCE: 917
cgagctgcat ggggagaag                                               19

<210> SEQ ID NO 918
<211> LENGTH: 19
<212> TYPE: DNA
<213> ORGANISM: Homo sapiens

<400> SEQUENCE: 918
caggtgacag tcacccatg                                               19

<210> SEQ ID NO 919
<211> LENGTH: 19
<212> TYPE: DNA
<213> ORGANISM: Homo sapiens

<400> SEQUENCE: 919
gcagccaggc aacaaccag                                               19

<210> SEQ ID NO 920
<211> LENGTH: 19
<212> TYPE: DNA
<213> ORGANISM: Homo sapiens
```

<400> SEQUENCE: 920
caaccagcag ccagacaac                                              19

<210> SEQ ID NO 921
<211> LENGTH: 19
<212> TYPE: DNA
<213> ORGANISM: Homo sapiens

<400> SEQUENCE: 921
ccagcagcca gacaaccac                                              19

<210> SEQ ID NO 922
<211> LENGTH: 19
<212> TYPE: DNA
<213> ORGANISM: Homo sapiens

<400> SEQUENCE: 922
acctggtgac tgatgaggc                                              19

<210> SEQ ID NO 923
<211> LENGTH: 19
<212> TYPE: DNA
<213> ORGANISM: Homo sapiens

<400> SEQUENCE: 923
cctggtgact gatgaggct                                              19

<210> SEQ ID NO 924
<211> LENGTH: 19
<212> TYPE: DNA
<213> ORGANISM: Homo sapiens

<400> SEQUENCE: 924
ctggacgccg aactccgat                                              19

<210> SEQ ID NO 925
<211> LENGTH: 19
<212> TYPE: DNA
<213> ORGANISM: Homo sapiens

<400> SEQUENCE: 925
ctccgatgac ttctacaat                                              19

<210> SEQ ID NO 926
<211> LENGTH: 19
<212> TYPE: DNA
<213> ORGANISM: Homo sapiens

<400> SEQUENCE: 926
tgagaccgag accaagatc                                              19

<210> SEQ ID NO 927
<211> LENGTH: 19
<212> TYPE: DNA
<213> ORGANISM: Homo sapiens

<400> SEQUENCE: 927
gatcttcctg cagttttat                                              19

<210> SEQ ID NO 928
<211> LENGTH: 19
<212> TYPE: DNA
<213> ORGANISM: Homo sapiens

```
<400> SEQUENCE: 928
acagggattt gggaccatg                                              19

<210> SEQ ID NO 929
<211> LENGTH: 19
<212> TYPE: DNA
<213> ORGANISM: Homo sapiens

<400> SEQUENCE: 929
cagggatttg ggaccatgg                                              19

<210> SEQ ID NO 930
<211> LENGTH: 19
<212> TYPE: DNA
<213> ORGANISM: Homo sapiens

<400> SEQUENCE: 930
gcaagaggaa caagggaag                                              19

<210> SEQ ID NO 931
<211> LENGTH: 19
<212> TYPE: DNA
<213> ORGANISM: Homo sapiens

<400> SEQUENCE: 931
gaggaacaag ggaagcccc                                              19

<210> SEQ ID NO 932
<211> LENGTH: 19
<212> TYPE: DNA
<213> ORGANISM: Homo sapiens

<400> SEQUENCE: 932
caagggaagc cccagtgta                                              19

<210> SEQ ID NO 933
<211> LENGTH: 19
<212> TYPE: DNA
<213> ORGANISM: Homo sapiens

<400> SEQUENCE: 933
gggaagcccc agtgtacat                                              19

<210> SEQ ID NO 934
<211> LENGTH: 19
<212> TYPE: DNA
<213> ORGANISM: Homo sapiens

<400> SEQUENCE: 934
gccccagtgt acatgtcaa                                              19

<210> SEQ ID NO 935
<211> LENGTH: 19
<212> TYPE: DNA
<213> ORGANISM: Homo sapiens

<400> SEQUENCE: 935
agagggctgc aagctctgg                                              19

<210> SEQ ID NO 936
<211> LENGTH: 19
<212> TYPE: DNA
<213> ORGANISM: Homo sapiens
```

```
<400> SEQUENCE: 936
gccctaaact tcctccagc                                               19

<210> SEQ ID NO 937
<211> LENGTH: 19
<212> TYPE: DNA
<213> ORGANISM: Homo sapiens

<400> SEQUENCE: 937
acttcctcca gctgcacaa                                               19

<210> SEQ ID NO 938
<211> LENGTH: 19
<212> TYPE: DNA
<213> ORGANISM: Homo sapiens

<400> SEQUENCE: 938
cttcctccag ctgcacaag                                               19

<210> SEQ ID NO 939
<211> LENGTH: 19
<212> TYPE: DNA
<213> ORGANISM: Homo sapiens

<400> SEQUENCE: 939
ggacatggag aggtcccag                                               19

<210> SEQ ID NO 940
<211> LENGTH: 19
<212> TYPE: DNA
<213> ORGANISM: Homo sapiens

<400> SEQUENCE: 940
gctcttcctg gctccttct                                               19

<210> SEQ ID NO 941
<211> LENGTH: 19
<212> TYPE: DNA
<213> ORGANISM: Homo sapiens

<400> SEQUENCE: 941
ctgctgctca gtccaccat                                               19

<210> SEQ ID NO 942
<211> LENGTH: 19
<212> TYPE: DNA
<213> ORGANISM: Homo sapiens

<400> SEQUENCE: 942
caggccaaga cattttttgg                                              19

<210> SEQ ID NO 943
<211> LENGTH: 19
<212> TYPE: DNA
<213> ORGANISM: Homo sapiens

<400> SEQUENCE: 943
gtttaaccac gaagccgaa                                               19

<210> SEQ ID NO 944
<211> LENGTH: 19
<212> TYPE: DNA
<213> ORGANISM: Homo sapiens
```

```
<400> SEQUENCE: 944
ccacgaagcc gaagacctg                                           19

<210> SEQ ID NO 945
<211> LENGTH: 19
<212> TYPE: DNA
<213> ORGANISM: Homo sapiens

<400> SEQUENCE: 945
gccgaagacc tgttctatc                                           19

<210> SEQ ID NO 946
<211> LENGTH: 19
<212> TYPE: DNA
<213> ORGANISM: Homo sapiens

<400> SEQUENCE: 946
gacctgttct atcaaagtt                                           19

<210> SEQ ID NO 947
<211> LENGTH: 19
<212> TYPE: DNA
<213> ORGANISM: Homo sapiens

<400> SEQUENCE: 947
agttcacttg cttcttgga                                           19

<210> SEQ ID NO 948
<211> LENGTH: 19
<212> TYPE: DNA
<213> ORGANISM: Homo sapiens

<400> SEQUENCE: 948
gttcacttgc ttcttggaa                                           19

<210> SEQ ID NO 949
<211> LENGTH: 19
<212> TYPE: DNA
<213> ORGANISM: Homo sapiens

<400> SEQUENCE: 949
caccaatatt actgaagag                                           19

<210> SEQ ID NO 950
<211> LENGTH: 19
<212> TYPE: DNA
<213> ORGANISM: Homo sapiens

<400> SEQUENCE: 950
gagaatgtcc aaaacatga                                           19

<210> SEQ ID NO 951
<211> LENGTH: 19
<212> TYPE: DNA
<213> ORGANISM: Homo sapiens

<400> SEQUENCE: 951
aacatgaata atgctgggg                                           19

<210> SEQ ID NO 952
<211> LENGTH: 19
<212> TYPE: DNA
<213> ORGANISM: Homo sapiens
```

```
<400> SEQUENCE: 952
acatgaataa tgctgggga                                        19

<210> SEQ ID NO 953
<211> LENGTH: 19
<212> TYPE: DNA
<213> ORGANISM: Homo sapiens

<400> SEQUENCE: 953
catgaataat gctggggac                                        19

<210> SEQ ID NO 954
<211> LENGTH: 19
<212> TYPE: DNA
<213> ORGANISM: Homo sapiens

<400> SEQUENCE: 954
taatgctggg gacaaatgg                                        19

<210> SEQ ID NO 955
<211> LENGTH: 19
<212> TYPE: DNA
<213> ORGANISM: Homo sapiens

<400> SEQUENCE: 955
tgctggggac aaatggtct                                        19

<210> SEQ ID NO 956
<211> LENGTH: 19
<212> TYPE: DNA
<213> ORGANISM: Homo sapiens

<400> SEQUENCE: 956
atggtctgcc tttttaaag                                        19

<210> SEQ ID NO 957
<211> LENGTH: 19
<212> TYPE: DNA
<213> ORGANISM: Homo sapiens

<400> SEQUENCE: 957
tggtctgcct ttttaaagg                                        19

<210> SEQ ID NO 958
<211> LENGTH: 19
<212> TYPE: DNA
<213> ORGANISM: Homo sapiens

<400> SEQUENCE: 958
aggaacagtc cacacttgc                                        19

<210> SEQ ID NO 959
<211> LENGTH: 19
<212> TYPE: DNA
<213> ORGANISM: Homo sapiens

<400> SEQUENCE: 959
ggaacagtcc acacttgcc                                        19

<210> SEQ ID NO 960
<211> LENGTH: 19
<212> TYPE: DNA
<213> ORGANISM: Homo sapiens
```

```
<400> SEQUENCE: 960
cagtccacac ttgcccaaa                                                  19

<210> SEQ ID NO 961
<211> LENGTH: 19
<212> TYPE: DNA
<213> ORGANISM: Homo sapiens

<400> SEQUENCE: 961
gaaattcaga atctcacag                                                  19

<210> SEQ ID NO 962
<211> LENGTH: 19
<212> TYPE: DNA
<213> ORGANISM: Homo sapiens

<400> SEQUENCE: 962
attcagaatc tcacagtca                                                  19

<210> SEQ ID NO 963
<211> LENGTH: 19
<212> TYPE: DNA
<213> ORGANISM: Homo sapiens

<400> SEQUENCE: 963
ttcagaatct cacagtcaa                                                  19

<210> SEQ ID NO 964
<211> LENGTH: 19
<212> TYPE: DNA
<213> ORGANISM: Homo sapiens

<400> SEQUENCE: 964
tctcacagtc aagcttcag                                                  19

<210> SEQ ID NO 965
<211> LENGTH: 19
<212> TYPE: DNA
<213> ORGANISM: Homo sapiens

<400> SEQUENCE: 965
gcttcagctg caggctctt                                                  19

<210> SEQ ID NO 966
<211> LENGTH: 19
<212> TYPE: DNA
<213> ORGANISM: Homo sapiens

<400> SEQUENCE: 966
aatgggtctt cagtgctct                                                  19

<210> SEQ ID NO 967
<211> LENGTH: 19
<212> TYPE: DNA
<213> ORGANISM: Homo sapiens

<400> SEQUENCE: 967
atgggtcttc agtgctctc                                                  19

<210> SEQ ID NO 968
<211> LENGTH: 19
<212> TYPE: DNA
<213> ORGANISM: Homo sapiens
```

```
<400> SEQUENCE: 968
tgggtcttca gtgctctca                                           19

<210> SEQ ID NO 969
<211> LENGTH: 19
<212> TYPE: DNA
<213> ORGANISM: Homo sapiens

<400> SEQUENCE: 969
gacaagagca aacggttga                                           19

<210> SEQ ID NO 970
<211> LENGTH: 19
<212> TYPE: DNA
<213> ORGANISM: Homo sapiens

<400> SEQUENCE: 970
gagcaaacgg ttgaacaca                                           19

<210> SEQ ID NO 971
<211> LENGTH: 19
<212> TYPE: DNA
<213> ORGANISM: Homo sapiens

<400> SEQUENCE: 971
acggttgaac acaattcta                                           19

<210> SEQ ID NO 972
<211> LENGTH: 19
<212> TYPE: DNA
<213> ORGANISM: Homo sapiens

<400> SEQUENCE: 972
cggttgaaca caattctaa                                           19

<210> SEQ ID NO 973
<211> LENGTH: 19
<212> TYPE: DNA
<213> ORGANISM: Homo sapiens

<400> SEQUENCE: 973
atacaatgag caccatcta                                           19

<210> SEQ ID NO 974
<211> LENGTH: 19
<212> TYPE: DNA
<213> ORGANISM: Homo sapiens

<400> SEQUENCE: 974
tacaatgagc accatctac                                           19

<210> SEQ ID NO 975
<211> LENGTH: 19
<212> TYPE: DNA
<213> ORGANISM: Homo sapiens

<400> SEQUENCE: 975
tgagcaccat ctacagtac                                           19

<210> SEQ ID NO 976
<211> LENGTH: 19
<212> TYPE: DNA
<213> ORGANISM: Homo sapiens
```

```
<400> SEQUENCE: 976
gtttgtaacc cagataatc                                                19

<210> SEQ ID NO 977
<211> LENGTH: 19
<212> TYPE: DNA
<213> ORGANISM: Homo sapiens

<400> SEQUENCE: 977
cccagataat ccacaagaa                                                19

<210> SEQ ID NO 978
<211> LENGTH: 19
<212> TYPE: DNA
<213> ORGANISM: Homo sapiens

<400> SEQUENCE: 978
tgcttattac ttgaaccag                                                19

<210> SEQ ID NO 979
<211> LENGTH: 19
<212> TYPE: DNA
<213> ORGANISM: Homo sapiens

<400> SEQUENCE: 979
tggcaaacag tttagacta                                                19

<210> SEQ ID NO 980
<211> LENGTH: 19
<212> TYPE: DNA
<213> ORGANISM: Homo sapiens

<400> SEQUENCE: 980
cagtttagac tacaatgag                                                19

<210> SEQ ID NO 981
<211> LENGTH: 19
<212> TYPE: DNA
<213> ORGANISM: Homo sapiens

<400> SEQUENCE: 981
tgagaggctc tgggcttgg                                                19

<210> SEQ ID NO 982
<211> LENGTH: 19
<212> TYPE: DNA
<213> ORGANISM: Homo sapiens

<400> SEQUENCE: 982
agctggagat ctgaggtcg                                                19

<210> SEQ ID NO 983
<211> LENGTH: 19
<212> TYPE: DNA
<213> ORGANISM: Homo sapiens

<400> SEQUENCE: 983
gctggagatc tgaggtcgg                                                19

<210> SEQ ID NO 984
<211> LENGTH: 19
<212> TYPE: DNA
<213> ORGANISM: Homo sapiens
```

```
<400> SEQUENCE: 984
gcagctgagg ccattatat                                              19

<210> SEQ ID NO 985
<211> LENGTH: 19
<212> TYPE: DNA
<213> ORGANISM: Homo sapiens

<400> SEQUENCE: 985
gagtatgtgg tcttgaaaa                                              19

<210> SEQ ID NO 986
<211> LENGTH: 19
<212> TYPE: DNA
<213> ORGANISM: Homo sapiens

<400> SEQUENCE: 986
aaatgagatg gcaagagca                                              19

<210> SEQ ID NO 987
<211> LENGTH: 19
<212> TYPE: DNA
<213> ORGANISM: Homo sapiens

<400> SEQUENCE: 987
aatgagatgg caagagcaa                                              19

<210> SEQ ID NO 988
<211> LENGTH: 19
<212> TYPE: DNA
<213> ORGANISM: Homo sapiens

<400> SEQUENCE: 988
atgagatggc aagagcaaa                                              19

<210> SEQ ID NO 989
<211> LENGTH: 19
<212> TYPE: DNA
<213> ORGANISM: Homo sapiens

<400> SEQUENCE: 989
tgagatggca agagcaaat                                              19

<210> SEQ ID NO 990
<211> LENGTH: 19
<212> TYPE: DNA
<213> ORGANISM: Homo sapiens

<400> SEQUENCE: 990
gagcaaatca ttatgagga                                              19

<210> SEQ ID NO 991
<211> LENGTH: 19
<212> TYPE: DNA
<213> ORGANISM: Homo sapiens

<400> SEQUENCE: 991
atcattatga ggactatgg                                              19

<210> SEQ ID NO 992
<211> LENGTH: 19
<212> TYPE: DNA
<213> ORGANISM: Homo sapiens
```

```
<400> SEQUENCE: 992
tcattatgag gactatggg                                                 19

<210> SEQ ID NO 993
<211> LENGTH: 19
<212> TYPE: DNA
<213> ORGANISM: Homo sapiens

<400> SEQUENCE: 993
gtaaatgggg tagatggct                                                 19

<210> SEQ ID NO 994
<211> LENGTH: 19
<212> TYPE: DNA
<213> ORGANISM: Homo sapiens

<400> SEQUENCE: 994
atggggtaga tggctatga                                                 19

<210> SEQ ID NO 995
<211> LENGTH: 19
<212> TYPE: DNA
<213> ORGANISM: Homo sapiens

<400> SEQUENCE: 995
tggggtagat ggctatgac                                                 19

<210> SEQ ID NO 996
<211> LENGTH: 19
<212> TYPE: DNA
<213> ORGANISM: Homo sapiens

<400> SEQUENCE: 996
gatgtggaac ataccttttg                                                19

<210> SEQ ID NO 997
<211> LENGTH: 19
<212> TYPE: DNA
<213> ORGANISM: Homo sapiens

<400> SEQUENCE: 997
catcttcatg cctatgtga                                                 19

<210> SEQ ID NO 998
<211> LENGTH: 19
<212> TYPE: DNA
<213> ORGANISM: Homo sapiens

<400> SEQUENCE: 998
agttgatgaa tgcctatcc                                                 19

<210> SEQ ID NO 999
<211> LENGTH: 19
<212> TYPE: DNA
<213> ORGANISM: Homo sapiens

<400> SEQUENCE: 999
gttgatgaat gcctatcct                                                 19

<210> SEQ ID NO 1000
<211> LENGTH: 19
<212> TYPE: DNA
<213> ORGANISM: Homo sapiens
```

```
<400> SEQUENCE: 1000
tgcctatcct tcctatatc                                              19

<210> SEQ ID NO 1001
<211> LENGTH: 19
<212> TYPE: DNA
<213> ORGANISM: Homo sapiens

<400> SEQUENCE: 1001
ttggatgcct ccctgctca                                              19

<210> SEQ ID NO 1002
<211> LENGTH: 19
<212> TYPE: DNA
<213> ORGANISM: Homo sapiens

<400> SEQUENCE: 1002
atctgtactc tttgacagt                                              19

<210> SEQ ID NO 1003
<211> LENGTH: 19
<212> TYPE: DNA
<213> ORGANISM: Homo sapiens

<400> SEQUENCE: 1003
tctgtactct ttgacagtt                                              19

<210> SEQ ID NO 1004
<211> LENGTH: 19
<212> TYPE: DNA
<213> ORGANISM: Homo sapiens

<400> SEQUENCE: 1004
ccaaacatag atgttactg                                              19

<210> SEQ ID NO 1005
<211> LENGTH: 19
<212> TYPE: DNA
<213> ORGANISM: Homo sapiens

<400> SEQUENCE: 1005
acatagatgt tactgatgc                                              19

<210> SEQ ID NO 1006
<211> LENGTH: 19
<212> TYPE: DNA
<213> ORGANISM: Homo sapiens

<400> SEQUENCE: 1006
catagatgtt actgatgca                                              19

<210> SEQ ID NO 1007
<211> LENGTH: 19
<212> TYPE: DNA
<213> ORGANISM: Homo sapiens

<400> SEQUENCE: 1007
tattcaagga ggccgagaa                                              19

<210> SEQ ID NO 1008
<211> LENGTH: 19
<212> TYPE: DNA
<213> ORGANISM: Homo sapiens
```

```
<400> SEQUENCE: 1008
ggaggccgag aagttcttt                                           19

<210> SEQ ID NO 1009
<211> LENGTH: 19
<212> TYPE: DNA
<213> ORGANISM: Homo sapiens

<400> SEQUENCE: 1009
gttctttgta tctgttggt                                           19

<210> SEQ ID NO 1010
<211> LENGTH: 19
<212> TYPE: DNA
<213> ORGANISM: Homo sapiens

<400> SEQUENCE: 1010
tatgactcaa ggattctgg                                           19

<210> SEQ ID NO 1011
<211> LENGTH: 19
<212> TYPE: DNA
<213> ORGANISM: Homo sapiens

<400> SEQUENCE: 1011
ggattctggg aaaattcca                                           19

<210> SEQ ID NO 1012
<211> LENGTH: 19
<212> TYPE: DNA
<213> ORGANISM: Homo sapiens

<400> SEQUENCE: 1012
aattccatgc taacggacc                                           19

<210> SEQ ID NO 1013
<211> LENGTH: 19
<212> TYPE: DNA
<213> ORGANISM: Homo sapiens

<400> SEQUENCE: 1013
attccatgct aacggaccc                                           19

<210> SEQ ID NO 1014
<211> LENGTH: 19
<212> TYPE: DNA
<213> ORGANISM: Homo sapiens

<400> SEQUENCE: 1014
ttccatgcta acggaccca                                           19

<210> SEQ ID NO 1015
<211> LENGTH: 19
<212> TYPE: DNA
<213> ORGANISM: Homo sapiens

<400> SEQUENCE: 1015
cggacccagg aaatgttca                                           19

<210> SEQ ID NO 1016
<211> LENGTH: 19
<212> TYPE: DNA
<213> ORGANISM: Homo sapiens
```

<400> SEQUENCE: 1016
atgttcagaa agcagtctg                                          19

<210> SEQ ID NO 1017
<211> LENGTH: 19
<212> TYPE: DNA
<213> ORGANISM: Homo sapiens

<400> SEQUENCE: 1017
tgttcagaaa gcagtctgc                                          19

<210> SEQ ID NO 1018
<211> LENGTH: 19
<212> TYPE: DNA
<213> ORGANISM: Homo sapiens

<400> SEQUENCE: 1018
agcagtctgc catcccaca                                          19

<210> SEQ ID NO 1019
<211> LENGTH: 19
<212> TYPE: DNA
<213> ORGANISM: Homo sapiens

<400> SEQUENCE: 1019
gcagtctgcc atcccacag                                          19

<210> SEQ ID NO 1020
<211> LENGTH: 19
<212> TYPE: DNA
<213> ORGANISM: Homo sapiens

<400> SEQUENCE: 1020
gggcgacttc aggatcctt                                          19

<210> SEQ ID NO 1021
<211> LENGTH: 19
<212> TYPE: DNA
<213> ORGANISM: Homo sapiens

<400> SEQUENCE: 1021
aggtgacaat ggacgactt                                          19

<210> SEQ ID NO 1022
<211> LENGTH: 19
<212> TYPE: DNA
<213> ORGANISM: Homo sapiens

<400> SEQUENCE: 1022
ggtgacaatg gacgacttc                                          19

<210> SEQ ID NO 1023
<211> LENGTH: 19
<212> TYPE: DNA
<213> ORGANISM: Homo sapiens

<400> SEQUENCE: 1023
tggacgactt cctgacagc                                          19

<210> SEQ ID NO 1024
<211> LENGTH: 19
<212> TYPE: DNA
<213> ORGANISM: Homo sapiens

<400> SEQUENCE: 1024
ccttttctgc taagaaatg                                        19

<210> SEQ ID NO 1025
<211> LENGTH: 19
<212> TYPE: DNA
<213> ORGANISM: Homo sapiens

<400> SEQUENCE: 1025
gaaatggagc taatgaagg                                        19

<210> SEQ ID NO 1026
<211> LENGTH: 19
<212> TYPE: DNA
<213> ORGANISM: Homo sapiens

<400> SEQUENCE: 1026
atggagctaa tgaaggatt                                        19

<210> SEQ ID NO 1027
<211> LENGTH: 19
<212> TYPE: DNA
<213> ORGANISM: Homo sapiens

<400> SEQUENCE: 1027
tggagctaat gaaggattc                                        19

<210> SEQ ID NO 1028
<211> LENGTH: 19
<212> TYPE: DNA
<213> ORGANISM: Homo sapiens

<400> SEQUENCE: 1028
tgaaggattc catgaagct                                        19

<210> SEQ ID NO 1029
<211> LENGTH: 19
<212> TYPE: DNA
<213> ORGANISM: Homo sapiens

<400> SEQUENCE: 1029
ggattccatg aagctgttg                                        19

<210> SEQ ID NO 1030
<211> LENGTH: 19
<212> TYPE: DNA
<213> ORGANISM: Homo sapiens

<400> SEQUENCE: 1030
gctgttgggg aaatcatgt                                        19

<210> SEQ ID NO 1031
<211> LENGTH: 19
<212> TYPE: DNA
<213> ORGANISM: Homo sapiens

<400> SEQUENCE: 1031
atcatgtcac tttctgcag                                        19

<210> SEQ ID NO 1032
<211> LENGTH: 19
<212> TYPE: DNA
<213> ORGANISM: Homo sapiens

```
<400> SEQUENCE: 1032
tcatgtcact ttctgcagc                                              19

<210> SEQ ID NO 1033
<211> LENGTH: 19
<212> TYPE: DNA
<213> ORGANISM: Homo sapiens

<400> SEQUENCE: 1033
aatccattgg tcttctgtc                                              19

<210> SEQ ID NO 1034
<211> LENGTH: 19
<212> TYPE: DNA
<213> ORGANISM: Homo sapiens

<400> SEQUENCE: 1034
atccattggt cttctgtca                                              19

<210> SEQ ID NO 1035
<211> LENGTH: 19
<212> TYPE: DNA
<213> ORGANISM: Homo sapiens

<400> SEQUENCE: 1035
tccattggtc ttctgtcac                                              19

<210> SEQ ID NO 1036
<211> LENGTH: 19
<212> TYPE: DNA
<213> ORGANISM: Homo sapiens

<400> SEQUENCE: 1036
acagaaataa acttcctgc                                              19

<210> SEQ ID NO 1037
<211> LENGTH: 19
<212> TYPE: DNA
<213> ORGANISM: Homo sapiens

<400> SEQUENCE: 1037
cagaaataaa cttcctgct                                              19

<210> SEQ ID NO 1038
<211> LENGTH: 19
<212> TYPE: DNA
<213> ORGANISM: Homo sapiens

<400> SEQUENCE: 1038
ataaacttcc tgctcaaac                                              19

<210> SEQ ID NO 1039
<211> LENGTH: 19
<212> TYPE: DNA
<213> ORGANISM: Homo sapiens

<400> SEQUENCE: 1039
taaacttcct gctcaaaca                                              19

<210> SEQ ID NO 1040
<211> LENGTH: 19
<212> TYPE: DNA
<213> ORGANISM: Homo sapiens
```

```
<400> SEQUENCE: 1040
acttcctgct caaacaagc                                                19

<210> SEQ ID NO 1041
<211> LENGTH: 19
<212> TYPE: DNA
<213> ORGANISM: Homo sapiens

<400> SEQUENCE: 1041
cttcctgctc aaacaagca                                                19

<210> SEQ ID NO 1042
<211> LENGTH: 19
<212> TYPE: DNA
<213> ORGANISM: Homo sapiens

<400> SEQUENCE: 1042
acaagcactc acgattgtt                                                19

<210> SEQ ID NO 1043
<211> LENGTH: 19
<212> TYPE: DNA
<213> ORGANISM: Homo sapiens

<400> SEQUENCE: 1043
caagcactca cgattgttg                                                19

<210> SEQ ID NO 1044
<211> LENGTH: 19
<212> TYPE: DNA
<213> ORGANISM: Homo sapiens

<400> SEQUENCE: 1044
gcactcacga ttgttggga                                                19

<210> SEQ ID NO 1045
<211> LENGTH: 19
<212> TYPE: DNA
<213> ORGANISM: Homo sapiens

<400> SEQUENCE: 1045
gtggaggtgg atggtcttt                                                19

<210> SEQ ID NO 1046
<211> LENGTH: 19
<212> TYPE: DNA
<213> ORGANISM: Homo sapiens

<400> SEQUENCE: 1046 agggaaatt cccaaagac                                                 19

<210> SEQ ID NO 1047
<211> LENGTH: 19
<212> TYPE: DNA
<213> ORGANISM: Homo sapiens

<400> SEQUENCE: 1047
ggggaaattc ccaaagacc                                                19

<210> SEQ ID NO 1048
<211> LENGTH: 19
<212> TYPE: DNA
<213> ORGANISM: Homo sapiens
```

```
<400> SEQUENCE: 1048
attcccaaag accagtgga                                            19

<210> SEQ ID NO 1049
<211> LENGTH: 19
<212> TYPE: DNA
<213> ORGANISM: Homo sapiens

<400> SEQUENCE: 1049
ttcccaaaga ccagtggat                                            19

<210> SEQ ID NO 1050
<211> LENGTH: 19
<212> TYPE: DNA
<213> ORGANISM: Homo sapiens

<400> SEQUENCE: 1050
agaccagtgg atgaaaaag                                            19

<210> SEQ ID NO 1051
<211> LENGTH: 19
<212> TYPE: DNA
<213> ORGANISM: Homo sapiens

<400> SEQUENCE: 1051
gaccagtgga tgaaaaagt                                            19

<210> SEQ ID NO 1052
<211> LENGTH: 19
<212> TYPE: DNA
<213> ORGANISM: Homo sapiens

<400> SEQUENCE: 1052
aaagtggtgg gagatgaag                                            19

<210> SEQ ID NO 1053
<211> LENGTH: 19
<212> TYPE: DNA
<213> ORGANISM: Homo sapiens

<400> SEQUENCE: 1053
aagtggtggg agatgaagc                                            19

<210> SEQ ID NO 1054
<211> LENGTH: 19
<212> TYPE: DNA
<213> ORGANISM: Homo sapiens

<400> SEQUENCE: 1054
agtggtggga gatgaagcg                                            19

<210> SEQ ID NO 1055
<211> LENGTH: 19
<212> TYPE: DNA
<213> ORGANISM: Homo sapiens

<400> SEQUENCE: 1055
gtggtgggag atgaagcga                                            19

<210> SEQ ID NO 1056
<211> LENGTH: 19
<212> TYPE: DNA
<213> ORGANISM: Homo sapiens
```

```
<400> SEQUENCE: 1056
gcgagagata gttggggtg                                              19

<210> SEQ ID NO 1057
<211> LENGTH: 19
<212> TYPE: DNA
<213> ORGANISM: Homo sapiens

<400> SEQUENCE: 1057
cctgtgcccc atgatgaaa                                              19

<210> SEQ ID NO 1058
<211> LENGTH: 19
<212> TYPE: DNA
<213> ORGANISM: Homo sapiens

<400> SEQUENCE: 1058
acatactgtg accccgcat                                              19

<210> SEQ ID NO 1059
<211> LENGTH: 19
<212> TYPE: DNA
<213> ORGANISM: Homo sapiens

<400> SEQUENCE: 1059
catactgtga ccccgcatc                                              19

<210> SEQ ID NO 1060
<211> LENGTH: 19
<212> TYPE: DNA
<213> ORGANISM: Homo sapiens

<400> SEQUENCE: 1060
ggacccttta ccaattcca                                              19

<210> SEQ ID NO 1061
<211> LENGTH: 19
<212> TYPE: DNA
<213> ORGANISM: Homo sapiens

<400> SEQUENCE: 1061
ttccagtttc aagaagcac                                              19

<210> SEQ ID NO 1062
<211> LENGTH: 19
<212> TYPE: DNA
<213> ORGANISM: Homo sapiens

<400> SEQUENCE: 1062
gaagcacttt gtcaagcag                                              19

<210> SEQ ID NO 1063
<211> LENGTH: 19
<212> TYPE: DNA
<213> ORGANISM: Homo sapiens

<400> SEQUENCE: 1063
gcactttgtc aagcagcta                                              19

<210> SEQ ID NO 1064
<211> LENGTH: 19
<212> TYPE: DNA
<213> ORGANISM: Homo sapiens
```

```
<400> SEQUENCE: 1064
gcagctaaac atgaaggcc                                            19

<210> SEQ ID NO 1065
<211> LENGTH: 19
<212> TYPE: DNA
<213> ORGANISM: Homo sapiens

<400> SEQUENCE: 1065
acatgaaggc cctctgcac                                            19

<210> SEQ ID NO 1066
<211> LENGTH: 19
<212> TYPE: DNA
<213> ORGANISM: Homo sapiens

<400> SEQUENCE: 1066
catgaaggcc ctctgcaca                                            19

<210> SEQ ID NO 1067
<211> LENGTH: 19
<212> TYPE: DNA
<213> ORGANISM: Homo sapiens

<400> SEQUENCE: 1067
ggccctctgc acaaatgtg                                            19

<210> SEQ ID NO 1068
<211> LENGTH: 19
<212> TYPE: DNA
<213> ORGANISM: Homo sapiens

<400> SEQUENCE: 1068
atgtgacatc tcaaactct                                            19

<210> SEQ ID NO 1069
<211> LENGTH: 19
<212> TYPE: DNA
<213> ORGANISM: Homo sapiens

<400> SEQUENCE: 1069
tgtgacatct caaactcta                                            19

<210> SEQ ID NO 1070
<211> LENGTH: 19
<212> TYPE: DNA
<213> ORGANISM: Homo sapiens

<400> SEQUENCE: 1070
actctacaga agctggaca                                            19

<210> SEQ ID NO 1071
<211> LENGTH: 19
<212> TYPE: DNA
<213> ORGANISM: Homo sapiens

<400> SEQUENCE: 1071
ctctacagaa gctggacag                                            19

<210> SEQ ID NO 1072
<211> LENGTH: 19
<212> TYPE: DNA
<213> ORGANISM: Homo sapiens
```

```
<400> SEQUENCE: 1072
gctggacaga aactgttca                                                19

<210> SEQ ID NO 1073
<211> LENGTH: 19
<212> TYPE: DNA
<213> ORGANISM: Homo sapiens

<400> SEQUENCE: 1073
actgttcaat atgctgagg                                                19

<210> SEQ ID NO 1074
<211> LENGTH: 19
<212> TYPE: DNA
<213> ORGANISM: Homo sapiens

<400> SEQUENCE: 1074
ctgttcaata tgctgaggc                                                19

<210> SEQ ID NO 1075
<211> LENGTH: 19
<212> TYPE: DNA
<213> ORGANISM: Homo sapiens

<400> SEQUENCE: 1075
tatgctgagg cttggaaaa                                                19

<210> SEQ ID NO 1076
<211> LENGTH: 19
<212> TYPE: DNA
<213> ORGANISM: Homo sapiens

<400> SEQUENCE: 1076
aatcagaacc ctggaccct                                                19

<210> SEQ ID NO 1077
<211> LENGTH: 19
<212> TYPE: DNA
<213> ORGANISM: Homo sapiens

<400> SEQUENCE: 1077
atcagaaccc tggacccta                                                19

<210> SEQ ID NO 1078
<211> LENGTH: 19
<212> TYPE: DNA
<213> ORGANISM: Homo sapiens

<400> SEQUENCE: 1078
tcagaaccct ggaccctag                                                19

<210> SEQ ID NO 1079
<211> LENGTH: 19
<212> TYPE: DNA
<213> ORGANISM: Homo sapiens

<400> SEQUENCE: 1079
ccctggaccc tagcattgg                                                19

<210> SEQ ID NO 1080
<211> LENGTH: 19
<212> TYPE: DNA
<213> ORGANISM: Homo sapiens
```

```
<400> SEQUENCE: 1080
aatgttgtag gagcaaaga                                              19

<210> SEQ ID NO 1081
<211> LENGTH: 19
<212> TYPE: DNA
<213> ORGANISM: Homo sapiens

<400> SEQUENCE: 1081
atgttgtagg agcaaagaa                                              19

<210> SEQ ID NO 1082
<211> LENGTH: 19
<212> TYPE: DNA
<213> ORGANISM: Homo sapiens

<400> SEQUENCE: 1082
tgttgtagga gcaaagaac                                              19

<210> SEQ ID NO 1083
<211> LENGTH: 19
<212> TYPE: DNA
<213> ORGANISM: Homo sapiens

<400> SEQUENCE: 1083
agaacatgaa tgtaaggcc                                              19

<210> SEQ ID NO 1084
<211> LENGTH: 19
<212> TYPE: DNA
<213> ORGANISM: Homo sapiens

<400> SEQUENCE: 1084
gaacatgaat gtaaggcca                                              19

<210> SEQ ID NO 1085
<211> LENGTH: 19
<212> TYPE: DNA
<213> ORGANISM: Homo sapiens

<400> SEQUENCE: 1085
catgaatgta aggccactg                                              19

<210> SEQ ID NO 1086
<211> LENGTH: 19
<212> TYPE: DNA
<213> ORGANISM: Homo sapiens

<400> SEQUENCE: 1086
tgtaaggcca ctgctcaac                                              19

<210> SEQ ID NO 1087
<211> LENGTH: 19
<212> TYPE: DNA
<213> ORGANISM: Homo sapiens

<400> SEQUENCE: 1087
ggccactgct caactactt                                              19

<210> SEQ ID NO 1088
<211> LENGTH: 19
<212> TYPE: DNA
<213> ORGANISM: Homo sapiens
```

```
<400> SEQUENCE: 1088
ctactttgag cccttattt                                                19

<210> SEQ ID NO 1089
<211> LENGTH: 19
<212> TYPE: DNA
<213> ORGANISM: Homo sapiens

<400> SEQUENCE: 1089
agaccagaac aagaattct                                                19

<210> SEQ ID NO 1090
<211> LENGTH: 19
<212> TYPE: DNA
<213> ORGANISM: Homo sapiens

<400> SEQUENCE: 1090
gaccagaaca agaattctt                                                19

<210> SEQ ID NO 1091
<211> LENGTH: 19
<212> TYPE: DNA
<213> ORGANISM: Homo sapiens

<400> SEQUENCE: 1091
caagaattct tttgtggga                                                19

<210> SEQ ID NO 1092
<211> LENGTH: 19
<212> TYPE: DNA
<213> ORGANISM: Homo sapiens

<400> SEQUENCE: 1092
gaattctttt gtgggatgg                                                19

<210> SEQ ID NO 1093
<211> LENGTH: 19
<212> TYPE: DNA
<213> ORGANISM: Homo sapiens

<400> SEQUENCE: 1093
ttcttttgtg ggatggagt                                                19

<210> SEQ ID NO 1094
<211> LENGTH: 19
<212> TYPE: DNA
<213> ORGANISM: Homo sapiens

<400> SEQUENCE: 1094
agcatcaaag tgaggataa                                                19

<210> SEQ ID NO 1095
<211> LENGTH: 19
<212> TYPE: DNA
<213> ORGANISM: Homo sapiens

<400> SEQUENCE: 1095
gcatcaaagt gaggataag                                                19

<210> SEQ ID NO 1096
<211> LENGTH: 19
<212> TYPE: DNA
<213> ORGANISM: Homo sapiens
```

```
<400> SEQUENCE: 1096
agtgaggata agcctaaaa                                                19

<210> SEQ ID NO 1097
<211> LENGTH: 19
<212> TYPE: DNA
<213> ORGANISM: Homo sapiens

<400> SEQUENCE: 1097
gtgaggataa gcctaaaat                                                19

<210> SEQ ID NO 1098
<211> LENGTH: 19
<212> TYPE: DNA
<213> ORGANISM: Homo sapiens

<400> SEQUENCE: 1098
gcctaaaatc agctcttgg                                                19

<210> SEQ ID NO 1099
<211> LENGTH: 19
<212> TYPE: DNA
<213> ORGANISM: Homo sapiens

<400> SEQUENCE: 1099
aatcagctct tggagataa                                                19

<210> SEQ ID NO 1100
<211> LENGTH: 19
<212> TYPE: DNA
<213> ORGANISM: Homo sapiens

<400> SEQUENCE: 1100
atcagctctt ggagataaa                                                19

<210> SEQ ID NO 1101
<211> LENGTH: 19
<212> TYPE: DNA
<213> ORGANISM: Homo sapiens

<400> SEQUENCE: 1101
tcagctcttg gagataaag                                                19

<210> SEQ ID NO 1102
<211> LENGTH: 19
<212> TYPE: DNA
<213> ORGANISM: Homo sapiens

<400> SEQUENCE: 1102
agcatatgaa tggaacgac                                                19

<210> SEQ ID NO 1103
<211> LENGTH: 19
<212> TYPE: DNA
<213> ORGANISM: Homo sapiens

<400> SEQUENCE: 1103
gcatatgaat ggaacgaca                                                19

<210> SEQ ID NO 1104
<211> LENGTH: 19
<212> TYPE: DNA
<213> ORGANISM: Homo sapiens
```

```
<400> SEQUENCE: 1104
tggaacgaca atgaaatgt                                              19

<210> SEQ ID NO 1105
<211> LENGTH: 19
<212> TYPE: DNA
<213> ORGANISM: Homo sapiens

<400> SEQUENCE: 1105
cgacaatgaa atgtacctg                                              19

<210> SEQ ID NO 1106
<211> LENGTH: 19
<212> TYPE: DNA
<213> ORGANISM: Homo sapiens

<400> SEQUENCE: 1106
tgaaatgtac ctgttccga                                              19

<210> SEQ ID NO 1107
<211> LENGTH: 19
<212> TYPE: DNA
<213> ORGANISM: Homo sapiens

<400> SEQUENCE: 1107
atgtacctgt tccgatcat                                              19

<210> SEQ ID NO 1108
<211> LENGTH: 19
<212> TYPE: DNA
<213> ORGANISM: Homo sapiens

<400> SEQUENCE: 1108
tgtacctgtt ccgatcatc                                              19

<210> SEQ ID NO 1109
<211> LENGTH: 19
<212> TYPE: DNA
<213> ORGANISM: Homo sapiens

<400> SEQUENCE: 1109
tcagatgatt cttttttggg                                             19

<210> SEQ ID NO 1110
<211> LENGTH: 19
<212> TYPE: DNA
<213> ORGANISM: Homo sapiens

<400> SEQUENCE: 1110
tttgaaacca agaatctcc                                              19

<210> SEQ ID NO 1111
<211> LENGTH: 19
<212> TYPE: DNA
<213> ORGANISM: Homo sapiens

<400> SEQUENCE: 1111
tttctttgtc actgcacct                                              19

<210> SEQ ID NO 1112
<211> LENGTH: 19
<212> TYPE: DNA
<213> ORGANISM: Homo sapiens
```

```
<400> SEQUENCE: 1112
atgtgtctga tatcattcc                                          19

<210> SEQ ID NO 1113
<211> LENGTH: 19
<212> TYPE: DNA
<213> ORGANISM: Homo sapiens

<400> SEQUENCE: 1113
tgtgtctgat atcattcct                                          19

<210> SEQ ID NO 1114
<211> LENGTH: 19
<212> TYPE: DNA
<213> ORGANISM: Homo sapiens

<400> SEQUENCE: 1114
ctgaagttga aaggccat                                           19

<210> SEQ ID NO 1115
<211> LENGTH: 19
<212> TYPE: DNA
<213> ORGANISM: Homo sapiens

<400> SEQUENCE: 1115
gttgaaaagg ccatcagga                                          19

<210> SEQ ID NO 1116
<211> LENGTH: 19
<212> TYPE: DNA
<213> ORGANISM: Homo sapiens

<400> SEQUENCE: 1116
aaggccatca ggatgtccc                                          19

<210> SEQ ID NO 1117
<211> LENGTH: 19
<212> TYPE: DNA
<213> ORGANISM: Homo sapiens

<400> SEQUENCE: 1117
aggccatcag gatgtcccg                                          19

<210> SEQ ID NO 1118
<211> LENGTH: 19
<212> TYPE: DNA
<213> ORGANISM: Homo sapiens

<400> SEQUENCE: 1118
tgatgctttc cgtctgaat                                          19

<210> SEQ ID NO 1119
<211> LENGTH: 19
<212> TYPE: DNA
<213> ORGANISM: Homo sapiens

<400> SEQUENCE: 1119
tgacaacagc ctagagttt                                          19

<210> SEQ ID NO 1120
<211> LENGTH: 19
<212> TYPE: DNA
<213> ORGANISM: Homo sapiens
```

```
<400> SEQUENCE: 1120
cagcctagag tttctgggg                                                19

<210> SEQ ID NO 1121
<211> LENGTH: 19
<212> TYPE: DNA
<213> ORGANISM: Homo sapiens

<400> SEQUENCE: 1121
cacttggacc tcctaacca                                                19

<210> SEQ ID NO 1122
<211> LENGTH: 19
<212> TYPE: DNA
<213> ORGANISM: Homo sapiens

<400> SEQUENCE: 1122
ccagccccct gtttccata                                                19

<210> SEQ ID NO 1123
<211> LENGTH: 19
<212> TYPE: DNA
<213> ORGANISM: Homo sapiens

<400> SEQUENCE: 1123
aataaagcaa gaagtggag                                                19

<210> SEQ ID NO 1124
<211> LENGTH: 19
<212> TYPE: DNA
<213> ORGANISM: Homo sapiens

<400> SEQUENCE: 1124
ataaagcaag aagtggaga                                                19

<210> SEQ ID NO 1125
<211> LENGTH: 19
<212> TYPE: DNA
<213> ORGANISM: Homo sapiens

<400> SEQUENCE: 1125
taaagcaaga agtggagaa                                                19

<210> SEQ ID NO 1126
<211> LENGTH: 19
<212> TYPE: DNA
<213> ORGANISM: Homo sapiens

<400> SEQUENCE: 1126
agcaagaagt ggagaaaat                                                19

<210> SEQ ID NO 1127
<211> LENGTH: 19
<212> TYPE: DNA
<213> ORGANISM: Homo sapiens

<400> SEQUENCE: 1127
gcaagaagtg gagaaaatc                                                19

<210> SEQ ID NO 1128
<211> LENGTH: 19
<212> TYPE: DNA
<213> ORGANISM: Homo sapiens
```

```
<400> SEQUENCE: 1128
gaagtggaga aaatcctta                                                    19

<210> SEQ ID NO 1129
<211> LENGTH: 19
<212> TYPE: DNA
<213> ORGANISM: Homo sapiens

<400> SEQUENCE: 1129
gtggagaaaa tccttatgc                                                    19

<210> SEQ ID NO 1130
<211> LENGTH: 19
<212> TYPE: DNA
<213> ORGANISM: Homo sapiens

<400> SEQUENCE: 1130
aatccttatg cctccatcg                                                    19

<210> SEQ ID NO 1131
<211> LENGTH: 19
<212> TYPE: DNA
<213> ORGANISM: Homo sapiens

<400> SEQUENCE: 1131
atccttatgc ctccatcga                                                    19

<210> SEQ ID NO 1132
<211> LENGTH: 19
<212> TYPE: DNA
<213> ORGANISM: Homo sapiens

<400> SEQUENCE: 1132
tccttatgcc tccatcgat                                                    19

<210> SEQ ID NO 1133
<211> LENGTH: 19
<212> TYPE: DNA
<213> ORGANISM: Homo sapiens

<400> SEQUENCE: 1133
aggagaaaat aatccagga                                                    19

<210> SEQ ID NO 1134
<211> LENGTH: 19
<212> TYPE: DNA
<213> ORGANISM: Homo sapiens

<400> SEQUENCE: 1134
ggagaaaata atccaggat                                                    19

<210> SEQ ID NO 1135
<211> LENGTH: 19
<212> TYPE: DNA
<213> ORGANISM: Homo sapiens

<400> SEQUENCE: 1135
taatccagga ttccaaaac                                                    19

<210> SEQ ID NO 1136
<211> LENGTH: 19
<212> TYPE: DNA
<213> ORGANISM: Homo sapiens
```

<400> SEQUENCE: 1136
tccaggattc caaaacact                                            19

<210> SEQ ID NO 1137
<211> LENGTH: 19
<212> TYPE: DNA
<213> ORGANISM: Homo sapiens

<400> SEQUENCE: 1137
aacactgatg atgttcaga                                            19

<210> SEQ ID NO 1138
<211> LENGTH: 19
<212> TYPE: DNA
<213> ORGANISM: Homo sapiens

<400> SEQUENCE: 1138
acactgatga tgttcagac                                            19

<210> SEQ ID NO 1139
<211> LENGTH: 19
<212> TYPE: DNA
<213> ORGANISM: Homo sapiens

<400> SEQUENCE: 1139
cactgatgat gttcagacc                                            19

<210> SEQ ID NO 1140
<211> LENGTH: 19
<212> TYPE: DNA
<213> ORGANISM: Homo sapiens

<400> SEQUENCE: 1140
gcatggatgg atggagaag                                            19

<210> SEQ ID NO 1141
<211> LENGTH: 19
<212> TYPE: DNA
<213> ORGANISM: Homo sapiens

<400> SEQUENCE: 1141
acggatcttc ctcaagaga                                            19

<210> SEQ ID NO 1142
<211> LENGTH: 19
<212> TYPE: DNA
<213> ORGANISM: Homo sapiens

<400> SEQUENCE: 1142
cggatcttcc tcaagagaa                                            19

<210> SEQ ID NO 1143
<211> LENGTH: 19
<212> TYPE: DNA
<213> ORGANISM: Homo sapiens

<400> SEQUENCE: 1143
gagaatgccc tcaatccga                                            19

<210> SEQ ID NO 1144
<211> LENGTH: 19
<212> TYPE: DNA
<213> ORGANISM: Homo sapiens -continued

```
<400> SEQUENCE: 1144
tgccctcaat ccgagaaag                                                  19

<210> SEQ ID NO 1145
<211> LENGTH: 19
<212> TYPE: DNA
<213> ORGANISM: Homo sapiens

<400> SEQUENCE: 1145
tccgagaaag cctgaagga                                                  19

<210> SEQ ID NO 1146
<211> LENGTH: 19
<212> TYPE: DNA
<213> ORGANISM: Homo sapiens

<400> SEQUENCE: 1146
agcctgaagg aacgaggtg                                                  19

<210> SEQ ID NO 1147
<211> LENGTH: 19
<212> TYPE: DNA
<213> ORGANISM: Homo sapiens

<400> SEQUENCE: 1147
gcctgaagga acgaggtgt                                                  19

<210> SEQ ID NO 1148
<211> LENGTH: 19
<212> TYPE: DNA
<213> ORGANISM: Homo sapiens

<400> SEQUENCE: 1148
ggaacgaggt gtggacatg                                                  19

<210> SEQ ID NO 1149
<211> LENGTH: 19
<212> TYPE: DNA
<213> ORGANISM: Homo sapiens

<400> SEQUENCE: 1149
cgaggtgtgg acatggcca                                                  19

<210> SEQ ID NO 1150
<211> LENGTH: 19
<212> TYPE: DNA
<213> ORGANISM: Homo sapiens

<400> SEQUENCE: 1150
cccatgaaga ggctgacac                                                  19

<210> SEQ ID NO 1151
<211> LENGTH: 19
<212> TYPE: DNA
<213> ORGANISM: Homo sapiens

<400> SEQUENCE: 1151
gaggctgaca cttggcaac                                                  19

<210> SEQ ID NO 1152
<211> LENGTH: 19
<212> TYPE: DNA
<213> ORGANISM: Homo sapiens
```

<400> SEQUENCE: 1152
caccacctcc tccgtgatc                                           19

<210> SEQ ID NO 1153
<211> LENGTH: 19
<212> TYPE: DNA
<213> ORGANISM: Homo sapiens

<400> SEQUENCE: 1153
ctacatggac acccagtac                                           19

<210> SEQ ID NO 1154
<211> LENGTH: 19
<212> TYPE: DNA
<213> ORGANISM: Homo sapiens

<400> SEQUENCE: 1154
accttcaaag tcgtctttg                                           19

<210> SEQ ID NO 1155
<211> LENGTH: 19
<212> TYPE: DNA
<213> ORGANISM: Homo sapiens

<400> SEQUENCE: 1155
ccttcaaagt cgtctttga                                           19

<210> SEQ ID NO 1156
<211> LENGTH: 19
<212> TYPE: DNA
<213> ORGANISM: Homo sapiens

<400> SEQUENCE: 1156
agtcgtcttt gacactggt                                           19

<210> SEQ ID NO 1157
<211> LENGTH: 19
<212> TYPE: DNA
<213> ORGANISM: Homo sapiens

<400> SEQUENCE: 1157
gtcgtctttg acactggtt                                           19

<210> SEQ ID NO 1158
<211> LENGTH: 19
<212> TYPE: DNA
<213> ORGANISM: Homo sapiens

<400> SEQUENCE: 1158
tgtttgggtg ccctcctcc                                           19

<210> SEQ ID NO 1159
<211> LENGTH: 19
<212> TYPE: DNA
<213> ORGANISM: Homo sapiens

<400> SEQUENCE: 1159
gtgcagccgt ctctacact                                           19

<210> SEQ ID NO 1160
<211> LENGTH: 19
<212> TYPE: DNA
<213> ORGANISM: Homo sapiens

<400> SEQUENCE: 1160
gctcttcgat gcttcggat                    19

<210> SEQ ID NO 1161
<211> LENGTH: 19
<212> TYPE: DNA
<213> ORGANISM: Homo sapiens

<400> SEQUENCE: 1161
gcacaatgga acagaactc                    19

<210> SEQ ID NO 1162
<211> LENGTH: 19
<212> TYPE: DNA
<213> ORGANISM: Homo sapiens

<400> SEQUENCE: 1162
tggaacagaa ctcaccctc                    19

<210> SEQ ID NO 1163
<211> LENGTH: 19
<212> TYPE: DNA
<213> ORGANISM: Homo sapiens

<400> SEQUENCE: 1163
cagaactcac cctccgcta                    19

<210> SEQ ID NO 1164
<211> LENGTH: 19
<212> TYPE: DNA
<213> ORGANISM: Homo sapiens

<400> SEQUENCE: 1164
ctcaccctcc gctattcaa                    19

<210> SEQ ID NO 1165
<211> LENGTH: 19
<212> TYPE: DNA
<213> ORGANISM: Homo sapiens

<400> SEQUENCE: 1165
cagggacagt cagtggctt                    19

<210> SEQ ID NO 1166
<211> LENGTH: 19
<212> TYPE: DNA
<213> ORGANISM: Homo sapiens

<400> SEQUENCE: 1166
tcacggtgac acagatgtt                    19

<210> SEQ ID NO 1167
<211> LENGTH: 19
<212> TYPE: DNA
<213> ORGANISM: Homo sapiens

<400> SEQUENCE: 1167
caggccattg gcagggtca                    19

<210> SEQ ID NO 1168
<211> LENGTH: 19
<212> TYPE: DNA
<213> ORGANISM: Homo sapiens

```
<400> SEQUENCE: 1168
catcatctcc caagggtg                                           19

<210> SEQ ID NO 1169
<211> LENGTH: 19
<212> TYPE: DNA
<213> ORGANISM: Homo sapiens

<400> SEQUENCE: 1169
ggggtgctaa aagaggacg                                          19

<210> SEQ ID NO 1170
<211> LENGTH: 19
<212> TYPE: DNA
<213> ORGANISM: Homo sapiens

<400> SEQUENCE: 1170
aagaggacgt cttctctttt                                         19

<210> SEQ ID NO 1171
<211> LENGTH: 19
<212> TYPE: DNA
<213> ORGANISM: Homo sapiens

<400> SEQUENCE: 1171
agaggacgtc ttctctttc                                          19

<210> SEQ ID NO 1172
<211> LENGTH: 19
<212> TYPE: DNA
<213> ORGANISM: Homo sapiens

<400> SEQUENCE: 1172
gaggacgtct tctctttct                                          19

<210> SEQ ID NO 1173
<211> LENGTH: 19
<212> TYPE: DNA
<213> ORGANISM: Homo sapiens

<400> SEQUENCE: 1173
cagagattcc gagaattcc                                          19

<210> SEQ ID NO 1174
<211> LENGTH: 19
<212> TYPE: DNA
<213> ORGANISM: Homo sapiens

<400> SEQUENCE: 1174
ttcccaatcg ctgggagga                                          19

<210> SEQ ID NO 1175
<211> LENGTH: 19
<212> TYPE: DNA
<213> ORGANISM: Homo sapiens

<400> SEQUENCE: 1175
tcgctgggag gacagattg                                          19

<210> SEQ ID NO 1176
<211> LENGTH: 19
<212> TYPE: DNA
<213> ORGANISM: Homo sapiens
```

```
<400> SEQUENCE: 1176
gggaatttcc actatatca                                                19

<210> SEQ ID NO 1177
<211> LENGTH: 19
<212> TYPE: DNA
<213> ORGANISM: Homo sapiens

<400> SEQUENCE: 1177
tttccactat atcaacctc                                                19

<210> SEQ ID NO 1178
<211> LENGTH: 19
<212> TYPE: DNA
<213> ORGANISM: Homo sapiens

<400> SEQUENCE: 1178
cctcatcaag actggtgtc                                                19

<210> SEQ ID NO 1179
<211> LENGTH: 19
<212> TYPE: DNA
<213> ORGANISM: Homo sapiens

<400> SEQUENCE: 1179
gactggtgtc tggcagatt                                                19

<210> SEQ ID NO 1180
<211> LENGTH: 19
<212> TYPE: DNA
<213> ORGANISM: Homo sapiens

<400> SEQUENCE: 1180
atgaaggggg tgtctgtgg                                                19

<210> SEQ ID NO 1181
<211> LENGTH: 19
<212> TYPE: DNA
<213> ORGANISM: Homo sapiens

<400> SEQUENCE: 1181 tgaaggggt gtctgtggg                                                 19

<210> SEQ ID NO 1182
<211> LENGTH: 19
<212> TYPE: DNA
<213> ORGANISM: Homo sapiens

<400> SEQUENCE: 1182
gctcatggag gccttggga                                                19

<210> SEQ ID NO 1183
<211> LENGTH: 19
<212> TYPE: DNA
<213> ORGANISM: Homo sapiens

<400> SEQUENCE: 1183
gaagaggctg tttgattat                                                19

<210> SEQ ID NO 1184
<211> LENGTH: 19
<212> TYPE: DNA
<213> ORGANISM: Homo sapiens
```

```
<400> SEQUENCE: 1184
gaggctgttt gattatgtc                                                  19

<210> SEQ ID NO 1185
<211> LENGTH: 19
<212> TYPE: DNA
<213> ORGANISM: Homo sapiens

<400> SEQUENCE: 1185
gtgtaacgag ggccctaca                                                  19

<210> SEQ ID NO 1186
<211> LENGTH: 19
<212> TYPE: DNA
<213> ORGANISM: Homo sapiens

<400> SEQUENCE: 1186
agaatacacg ctcaccagc                                                  19

<210> SEQ ID NO 1187
<211> LENGTH: 19
<212> TYPE: DNA
<213> ORGANISM: Homo sapiens

<400> SEQUENCE: 1187
gaatacacgc tcaccagcg                                                  19

<210> SEQ ID NO 1188
<211> LENGTH: 19
<212> TYPE: DNA
<213> ORGANISM: Homo sapiens

<400> SEQUENCE: 1188
tcctacagta gtaaaaagc                                                  19

<210> SEQ ID NO 1189
<211> LENGTH: 19
<212> TYPE: DNA
<213> ORGANISM: Homo sapiens

<400> SEQUENCE: 1189
aaagctgtgc acactggcc                                                  19

<210> SEQ ID NO 1190
<211> LENGTH: 19
<212> TYPE: DNA
<213> ORGANISM: Homo sapiens

<400> SEQUENCE: 1190
aagctgtgca cactggcca                                                  19

<210> SEQ ID NO 1191
<211> LENGTH: 19
<212> TYPE: DNA
<213> ORGANISM: Homo sapiens

<400> SEQUENCE: 1191
agctgtgcac actggccat                                                  19

<210> SEQ ID NO 1192
<211> LENGTH: 19
<212> TYPE: DNA
<213> ORGANISM: Homo sapiens
```

```
<400> SEQUENCE: 1192
gctgtgcaca ctggccatc                                              19

<210> SEQ ID NO 1193
<211> LENGTH: 19
<212> TYPE: DNA
<213> ORGANISM: Homo sapiens

<400> SEQUENCE: 1193
agttctacac agagtttga                                              19

<210> SEQ ID NO 1194
<211> LENGTH: 19
<212> TYPE: DNA
<213> ORGANISM: Homo sapiens

<400> SEQUENCE: 1194
gttctacaca gagtttgat                                              19

<210> SEQ ID NO 1195
<211> LENGTH: 19
<212> TYPE: DNA
<213> ORGANISM: Homo sapiens

<400> SEQUENCE: 1195
caaccgcatt ggcttcgcc                                              19

<210> SEQ ID NO 1196
<211> LENGTH: 19
<212> TYPE: DNA
<213> ORGANISM: Homo sapiens

<400> SEQUENCE: 1196
ccgcattggc ttcgccttg                                              19

<210> SEQ ID NO 1197
<211> LENGTH: 19
<212> TYPE: DNA
<213> ORGANISM: Homo sapiens

<400> SEQUENCE: 1197
agagaaagca gatgtcctc                                              19

<210> SEQ ID NO 1198
<211> LENGTH: 19
<212> TYPE: DNA
<213> ORGANISM: Homo sapiens

<400> SEQUENCE: 1198
gagaaagcag atgtcctct                                              19

<210> SEQ ID NO 1199
<211> LENGTH: 19
<212> TYPE: DNA
<213> ORGANISM: Homo sapiens

<400> SEQUENCE: 1199
agcagatgtc ctctgccca                                              19

<210> SEQ ID NO 1200
<211> LENGTH: 19
<212> TYPE: DNA
<213> ORGANISM: Homo sapiens
```

-continued

```
<400> SEQUENCE: 1200
gcagatgtcc tctgcccag                                                  19

<210> SEQ ID NO 1201
<211> LENGTH: 19
<212> TYPE: DNA
<213> ORGANISM: Homo sapiens

<400> SEQUENCE: 1201
ttctctgtgt atgggaaca                                                  19

<210> SEQ ID NO 1202
<211> LENGTH: 19
<212> TYPE: DNA
<213> ORGANISM: Homo sapiens

<400> SEQUENCE: 1202
tcagcaactc aggggggacc                                                 19

<210> SEQ ID NO 1203
<211> LENGTH: 19
<212> TYPE: DNA
<213> ORGANISM: Homo sapiens

<400> SEQUENCE: 1203
ctcaggggga cctgtacga                                                  19

<210> SEQ ID NO 1204
<211> LENGTH: 19
<212> TYPE: DNA
<213> ORGANISM: Homo sapiens

<400> SEQUENCE: 1204
aactattcct cagtagatg                                                  19

<210> SEQ ID NO 1205
<211> LENGTH: 19
<212> TYPE: DNA
<213> ORGANISM: Homo sapiens

<400> SEQUENCE: 1205
actattcctc agtagatgc                                                  19

<210> SEQ ID NO 1206
<211> LENGTH: 19
<212> TYPE: DNA
<213> ORGANISM: Homo sapiens

<400> SEQUENCE: 1206
ctattcctca gtagatgcc                                                  19

<210> SEQ ID NO 1207
<211> LENGTH: 19
<212> TYPE: DNA
<213> ORGANISM: Homo sapiens

<400> SEQUENCE: 1207
tggcatccag tctcaaatg                                                  19

<210> SEQ ID NO 1208
<211> LENGTH: 19
<212> TYPE: DNA
<213> ORGANISM: Homo sapiens
```

```
<400> SEQUENCE: 1208
atgctttcta gatggtctg                                                    19

<210> SEQ ID NO 1209
<211> LENGTH: 19
<212> TYPE: DNA
<213> ORGANISM: Homo sapiens

<400> SEQUENCE: 1209
tgctttctag atggtctgc                                                    19

<210> SEQ ID NO 1210
<211> LENGTH: 19
<212> TYPE: DNA
<213> ORGANISM: Homo sapiens

<400> SEQUENCE: 1210
ctaaaggcaa aagtagtac                                                    19

<210> SEQ ID NO 1211
<211> LENGTH: 19
<212> TYPE: DNA
<213> ORGANISM: Homo sapiens

<400> SEQUENCE: 1211
aggcaaaagt agtacacag                                                    19

<210> SEQ ID NO 1212
<211> LENGTH: 19
<212> TYPE: DNA
<213> ORGANISM: Homo sapiens

<400> SEQUENCE: 1212
ggcaaaagta gtacacagg                                                    19

<210> SEQ ID NO 1213
<211> LENGTH: 19
<212> TYPE: DNA
<213> ORGANISM: Homo sapiens

<400> SEQUENCE: 1213
aagtagtaca caggaggcc                                                    19

<210> SEQ ID NO 1214
<211> LENGTH: 19
<212> TYPE: DNA
<213> ORGANISM: Homo sapiens

<400> SEQUENCE: 1214
agtagtacac aggaggcca                                                    19

<210> SEQ ID NO 1215
<211> LENGTH: 19
<212> TYPE: DNA
<213> ORGANISM: Homo sapiens

<400> SEQUENCE: 1215
gtagtacaca ggaggccac                                                    19

<210> SEQ ID NO 1216
<211> LENGTH: 19
<212> TYPE: DNA
<213> ORGANISM: Homo sapiens
```

```
<400> SEQUENCE: 1216
gcagtgtcca cagcacatc                                              19

<210> SEQ ID NO 1217
<211> LENGTH: 19
<212> TYPE: DNA
<213> ORGANISM: Homo sapiens

<400> SEQUENCE: 1217
caggtaaacg actaaagaa                                              19

<210> SEQ ID NO 1218
<211> LENGTH: 19
<212> TYPE: DNA
<213> ORGANISM: Homo sapiens

<400> SEQUENCE: 1218
acgactaaag aaaacaccc                                              19

<210> SEQ ID NO 1219
<211> LENGTH: 19
<212> TYPE: DNA
<213> ORGANISM: Homo sapiens

<400> SEQUENCE: 1219
cgactaaaga aaacacccg                                              19

<210> SEQ ID NO 1220
<211> LENGTH: 19
<212> TYPE: DNA
<213> ORGANISM: Homo sapiens

<400> SEQUENCE: 1220
agaaaacacc cgagaagaa                                              19

<210> SEQ ID NO 1221
<211> LENGTH: 19
<212> TYPE: DNA
<213> ORGANISM: Homo sapiens

<400> SEQUENCE: 1221
gaaaacaccc gagaagaaa                                              19

<210> SEQ ID NO 1222
<211> LENGTH: 19
<212> TYPE: DNA
<213> ORGANISM: Homo sapiens

<400> SEQUENCE: 1222
aacacccgag aagaaaact                                              19

<210> SEQ ID NO 1223
<211> LENGTH: 19
<212> TYPE: DNA
<213> ORGANISM: Homo sapiens

<400> SEQUENCE: 1223
acacccgaga agaaaactg                                              19

<210> SEQ ID NO 1224
<211> LENGTH: 19
<212> TYPE: DNA
<213> ORGANISM: Homo sapiens
```

```
<400> SEQUENCE: 1224
cacccgagaa gaaaactgg                                                  19

<210> SEQ ID NO 1225
<211> LENGTH: 19
<212> TYPE: DNA
<213> ORGANISM: Homo sapiens

<400> SEQUENCE: 1225
gattgtaaag cagacattg                                                  19

<210> SEQ ID NO 1226
<211> LENGTH: 19
<212> TYPE: DNA
<213> ORGANISM: Homo sapiens

<400> SEQUENCE: 1226
agcagacatt gcatttctg                                                  19

<210> SEQ ID NO 1227
<211> LENGTH: 19
<212> TYPE: DNA
<213> ORGANISM: Homo sapiens

<400> SEQUENCE: 1227
gcagacattg catttctga                                                  19

<210> SEQ ID NO 1228
<211> LENGTH: 19
<212> TYPE: DNA
<213> ORGANISM: Homo sapiens

<400> SEQUENCE: 1228
gctttaatat tgggcagcg                                                  19

<210> SEQ ID NO 1229
<211> LENGTH: 19
<212> TYPE: DNA
<213> ORGANISM: Homo sapiens

<400> SEQUENCE: 1229
tattgggcag cgccgattt                                                  19

<210> SEQ ID NO 1230
<211> LENGTH: 19
<212> TYPE: DNA
<213> ORGANISM: Homo sapiens

<400> SEQUENCE: 1230
ttttgttgga aaagtggct                                                  19

<210> SEQ ID NO 1231
<211> LENGTH: 19
<212> TYPE: DNA
<213> ORGANISM: Homo sapiens

<400> SEQUENCE: 1231
aagtggctct aatgttggg                                                  19

<210> SEQ ID NO 1232
<211> LENGTH: 19
<212> TYPE: DNA
<213> ORGANISM: Homo sapiens
```

```
<400> SEQUENCE: 1232
agtggctcta atgttggga                                          19

<210> SEQ ID NO 1233
<211> LENGTH: 19
<212> TYPE: DNA
<213> ORGANISM: Homo sapiens

<400> SEQUENCE: 1233
gtggctctaa tgttgggaa                                          19

<210> SEQ ID NO 1234
<211> LENGTH: 19
<212> TYPE: DNA
<213> ORGANISM: Homo sapiens

<400> SEQUENCE: 1234
tgttgggaat tggaacaga                                          19

<210> SEQ ID NO 1235
<211> LENGTH: 19
<212> TYPE: DNA
<213> ORGANISM: Homo sapiens

<400> SEQUENCE: 1235
ttggaacaga aggaccaca                                          19

<210> SEQ ID NO 1236
<211> LENGTH: 19
<212> TYPE: DNA
<213> ORGANISM: Homo sapiens

<400> SEQUENCE: 1236
cagaaggacc acatgtggg                                          19

<210> SEQ ID NO 1237
<211> LENGTH: 19
<212> TYPE: DNA
<213> ORGANISM: Homo sapiens

<400> SEQUENCE: 1237
ggaccacatg tgggccttg                                          19

<210> SEQ ID NO 1238
<211> LENGTH: 19
<212> TYPE: DNA
<213> ORGANISM: Homo sapiens

<400> SEQUENCE: 1238
gccagtgaac atcccaaaa                                          19

<210> SEQ ID NO 1239
<211> LENGTH: 19
<212> TYPE: DNA
<213> ORGANISM: Homo sapiens

<400> SEQUENCE: 1239
aactttacat cagccaaag                                          19

<210> SEQ ID NO 1240
<211> LENGTH: 19
<212> TYPE: DNA
<213> ORGANISM: Homo sapiens
```

```
<400> SEQUENCE: 1240
actttacatc agccaaaga                                                 19

<210> SEQ ID NO 1241
<211> LENGTH: 19
<212> TYPE: DNA
<213> ORGANISM: Homo sapiens

<400> SEQUENCE: 1241
ctttacatca gccaaagat                                                 19

<210> SEQ ID NO 1242
<211> LENGTH: 19
<212> TYPE: DNA
<213> ORGANISM: Homo sapiens

<400> SEQUENCE: 1242
aggaagtagg tttcagagg                                                 19

<210> SEQ ID NO 1243
<211> LENGTH: 19
<212> TYPE: DNA
<213> ORGANISM: Homo sapiens

<400> SEQUENCE: 1243
ggaagtaggt ttcagaggg                                                 19

<210> SEQ ID NO 1244
<211> LENGTH: 19
<212> TYPE: DNA
<213> ORGANISM: Homo sapiens

<400> SEQUENCE: 1244
gtaggtttca gaggggta                                                  19

<210> SEQ ID NO 1245
<211> LENGTH: 19
<212> TYPE: DNA
<213> ORGANISM: Homo sapiens

<400> SEQUENCE: 1245
ttccaataca ggaaaagcc                                                 19

<210> SEQ ID NO 1246
<211> LENGTH: 19
<212> TYPE: DNA
<213> ORGANISM: Homo sapiens

<400> SEQUENCE: 1246
tacaggaaaa gccttgaag                                                 19

<210> SEQ ID NO 1247
<211> LENGTH: 19
<212> TYPE: DNA
<213> ORGANISM: Homo sapiens

<400> SEQUENCE: 1247
aagccttgaa gcatactgc                                                 19

<210> SEQ ID NO 1248
<211> LENGTH: 19
<212> TYPE: DNA
<213> ORGANISM: Homo sapiens
```

```
<400> SEQUENCE: 1248
agccttgaag catactgct                                              19

<210> SEQ ID NO 1249
<211> LENGTH: 19
<212> TYPE: DNA
<213> ORGANISM: Homo sapiens

<400> SEQUENCE: 1249
gccttgaagc atactgctc                                              19

<210> SEQ ID NO 1250
<211> LENGTH: 19
<212> TYPE: DNA
<213> ORGANISM: Homo sapiens

<400> SEQUENCE: 1250
gcatactgct cagaaattc                                              19

<210> SEQ ID NO 1251
<211> LENGTH: 19
<212> TYPE: DNA
<213> ORGANISM: Homo sapiens

<400> SEQUENCE: 1251
attcttcacg gtagatgct                                              19

<210> SEQ ID NO 1252
<211> LENGTH: 19
<212> TYPE: DNA
<213> ORGANISM: Homo sapiens

<400> SEQUENCE: 1252
ttcttcacgg tagatgctg                                              19

<210> SEQ ID NO 1253
<211> LENGTH: 19
<212> TYPE: DNA
<213> ORGANISM: Homo sapiens

<400> SEQUENCE: 1253
gaaaagggat ccccaaagt                                              19

<210> SEQ ID NO 1254
<211> LENGTH: 19
<212> TYPE: DNA
<213> ORGANISM: Homo sapiens

<400> SEQUENCE: 1254
aagggatccc caaagtggt                                              19

<210> SEQ ID NO 1255
<211> LENGTH: 19
<212> TYPE: DNA
<213> ORGANISM: Homo sapiens

<400> SEQUENCE: 1255
agggatcccc aaagtggtg                                              19

<210> SEQ ID NO 1256
<211> LENGTH: 19
<212> TYPE: DNA
<213> ORGANISM: Homo sapiens
```

```
<400> SEQUENCE: 1256
gggatcccca aagtggtgg                                            19

<210> SEQ ID NO 1257
<211> LENGTH: 19
<212> TYPE: DNA
<213> ORGANISM: Homo sapiens

<400> SEQUENCE: 1257
agtggtggtg gtatttatt                                            19

<210> SEQ ID NO 1258
<211> LENGTH: 19
<212> TYPE: DNA
<213> ORGANISM: Homo sapiens

<400> SEQUENCE: 1258
gtggtggtgg tatttattg                                            19

<210> SEQ ID NO 1259
<211> LENGTH: 19
<212> TYPE: DNA
<213> ORGANISM: Homo sapiens

<400> SEQUENCE: 1259
gcaggcattg tggccagag                                            19

<210> SEQ ID NO 1260
<211> LENGTH: 19
<212> TYPE: DNA
<213> ORGANISM: Homo sapiens

<400> SEQUENCE: 1260
gcctatccct gaagaactg                                            19

<210> SEQ ID NO 1261
<211> LENGTH: 19
<212> TYPE: DNA
<213> ORGANISM: Homo sapiens

<400> SEQUENCE: 1261
gaactgggga tggttcagg                                            19

<210> SEQ ID NO 1262
<211> LENGTH: 19
<212> TYPE: DNA
<213> ORGANISM: Homo sapiens

<400> SEQUENCE: 1262
ctggggatgg ttcaggatg                                            19

<210> SEQ ID NO 1263
<211> LENGTH: 19
<212> TYPE: DNA
<213> ORGANISM: Homo sapiens

<400> SEQUENCE: 1263
ggctgtctgt cggaataat                                            19

<210> SEQ ID NO 1264
<211> LENGTH: 19
<212> TYPE: DNA
<213> ORGANISM: Homo sapiens
```

```
<400> SEQUENCE: 1264
taatggcttc ttctcttac                                                19

<210> SEQ ID NO 1265
<211> LENGTH: 19
<212> TYPE: DNA
<213> ORGANISM: Homo sapiens

<400> SEQUENCE: 1265
tggcttcttc tcttaccac                                                19

<210> SEQ ID NO 1266
<211> LENGTH: 19
<212> TYPE: DNA
<213> ORGANISM: Homo sapiens

<400> SEQUENCE: 1266
ctggtttggc accacaaaa                                                19

<210> SEQ ID NO 1267
<211> LENGTH: 19
<212> TYPE: DNA
<213> ORGANISM: Homo sapiens

<400> SEQUENCE: 1267
aatacgtaaa gcctctggt                                                19

<210> SEQ ID NO 1268
<211> LENGTH: 19
<212> TYPE: DNA
<213> ORGANISM: Homo sapiens

<400> SEQUENCE: 1268
atacgtaaag cctctggta                                                19

<210> SEQ ID NO 1269
<211> LENGTH: 19
<212> TYPE: DNA
<213> ORGANISM: Homo sapiens

<400> SEQUENCE: 1269
tacgtaaagc ctctggtac                                                19

<210> SEQ ID NO 1270
<211> LENGTH: 19
<212> TYPE: DNA
<213> ORGANISM: Homo sapiens

<400> SEQUENCE: 1270
agcctctggt acagaagct                                                19

<210> SEQ ID NO 1271
<211> LENGTH: 19
<212> TYPE: DNA
<213> ORGANISM: Homo sapiens

<400> SEQUENCE: 1271
gcctctggta cagaagctg                                                19

<210> SEQ ID NO 1272
<211> LENGTH: 19
<212> TYPE: DNA
<213> ORGANISM: Homo sapiens
```

```
<400> SEQUENCE: 1272
gctgtgcact catgaacaa                                               19

<210> SEQ ID NO 1273
<211> LENGTH: 19
<212> TYPE: DNA
<213> ORGANISM: Homo sapiens

<400> SEQUENCE: 1273
caaatgatgt gcagcaaga                                               19

<210> SEQ ID NO 1274
<211> LENGTH: 19
<212> TYPE: DNA
<213> ORGANISM: Homo sapiens

<400> SEQUENCE: 1274
atgatgtgca gcaagacct                                               19

<210> SEQ ID NO 1275
<211> LENGTH: 19
<212> TYPE: DNA
<213> ORGANISM: Homo sapiens

<400> SEQUENCE: 1275
tgatgtgcag caagacctg                                               19

<210> SEQ ID NO 1276
<211> LENGTH: 19
<212> TYPE: DNA
<213> ORGANISM: Homo sapiens

<400> SEQUENCE: 1276
gacctgttat aactcagtg                                               19

<210> SEQ ID NO 1277
<211> LENGTH: 19
<212> TYPE: DNA
<213> ORGANISM: Homo sapiens

<400> SEQUENCE: 1277
ctcagtgaac attgccttt                                               19

<210> SEQ ID NO 1278
<211> LENGTH: 19
<212> TYPE: DNA
<213> ORGANISM: Homo sapiens

<400> SEQUENCE: 1278
ttgatggctc cagcagtgt                                               19

<210> SEQ ID NO 1279
<211> LENGTH: 19
<212> TYPE: DNA
<213> ORGANISM: Homo sapiens

<400> SEQUENCE: 1279
tttccgcctc atgcttgaa                                               19

<210> SEQ ID NO 1280
<211> LENGTH: 19
<212> TYPE: DNA
<213> ORGANISM: Homo sapiens
```

```
<400> SEQUENCE: 1280
tttgtttcca acatagcca                                                19

<210> SEQ ID NO 1281
<211> LENGTH: 19
<212> TYPE: DNA
<213> ORGANISM: Homo sapiens

<400> SEQUENCE: 1281
catagccaag acttttgaa                                                19

<210> SEQ ID NO 1282
<211> LENGTH: 19
<212> TYPE: DNA
<213> ORGANISM: Homo sapiens

<400> SEQUENCE: 1282
gacttttgaa atctcggac                                                19

<210> SEQ ID NO 1283
<211> LENGTH: 19
<212> TYPE: DNA
<213> ORGANISM: Homo sapiens

<400> SEQUENCE: 1283
atctcggaca ttggtgcca                                                19

<210> SEQ ID NO 1284
<211> LENGTH: 19
<212> TYPE: DNA
<213> ORGANISM: Homo sapiens

<400> SEQUENCE: 1284
tctcggacat tggtgccaa                                                19

<210> SEQ ID NO 1285
<211> LENGTH: 19
<212> TYPE: DNA
<213> ORGANISM: Homo sapiens

<400> SEQUENCE: 1285
gatagctgct gtacagttt                                                19

<210> SEQ ID NO 1286
<211> LENGTH: 19
<212> TYPE: DNA
<213> ORGANISM: Homo sapiens

<400> SEQUENCE: 1286
agagaatgtc ctagctgtc                                                19

<210> SEQ ID NO 1287
<211> LENGTH: 19
<212> TYPE: DNA
<213> ORGANISM: Homo sapiens

<400> SEQUENCE: 1287
gagaatgtcc tagctgtca                                                19

<210> SEQ ID NO 1288
<211> LENGTH: 19
<212> TYPE: DNA
<213> ORGANISM: Homo sapiens
```

<400> SEQUENCE: 1288
tgtcctagct gtcatcaga                                              19

<210> SEQ ID NO 1289
<211> LENGTH: 19
<212> TYPE: DNA
<213> ORGANISM: Homo sapiens

<400> SEQUENCE: 1289
acatccgcta tatgagtgg                                              19

<210> SEQ ID NO 1290
<211> LENGTH: 19
<212> TYPE: DNA
<213> ORGANISM: Homo sapiens

<400> SEQUENCE: 1290
catccgctat atgagtggt                                              19

<210> SEQ ID NO 1291
<211> LENGTH: 19
<212> TYPE: DNA
<213> ORGANISM: Homo sapiens

<400> SEQUENCE: 1291
cagctactgg tgatgccat                                              19

<210> SEQ ID NO 1292
<211> LENGTH: 19
<212> TYPE: DNA
<213> ORGANISM: Homo sapiens

<400> SEQUENCE: 1292
atgtgtttgg ccctataag                                              19

<210> SEQ ID NO 1293
<211> LENGTH: 19
<212> TYPE: DNA
<213> ORGANISM: Homo sapiens

<400> SEQUENCE: 1293
tgtgtttggc cctataagg                                              19

<210> SEQ ID NO 1294
<211> LENGTH: 19
<212> TYPE: DNA
<213> ORGANISM: Homo sapiens

<400> SEQUENCE: 1294
gggagagccc caacaagaa                                              19

<210> SEQ ID NO 1295
<211> LENGTH: 19
<212> TYPE: DNA
<213> ORGANISM: Homo sapiens

<400> SEQUENCE: 1295
gaacttccta gtaattgtc                                              19

<210> SEQ ID NO 1296
<211> LENGTH: 19
<212> TYPE: DNA
<213> ORGANISM: Homo sapiens

```
<400> SEQUENCE: 1296
cttcctagta attgtcaca                                                   19

<210> SEQ ID NO 1297
<211> LENGTH: 19
<212> TYPE: DNA
<213> ORGANISM: Homo sapiens

<400> SEQUENCE: 1297
ttgtcacaga tgggcagtc                                                   19

<210> SEQ ID NO 1298
<211> LENGTH: 19
<212> TYPE: DNA
<213> ORGANISM: Homo sapiens

<400> SEQUENCE: 1298
tcactatctt ctctgttgg                                                   19

<210> SEQ ID NO 1299
<211> LENGTH: 19
<212> TYPE: DNA
<213> ORGANISM: Homo sapiens

<400> SEQUENCE: 1299
agatatggct tctaaaccg                                                   19

<210> SEQ ID NO 1300
<211> LENGTH: 19
<212> TYPE: DNA
<213> ORGANISM: Homo sapiens

<400> SEQUENCE: 1300
gatatggctt ctaaaccga                                                   19

<210> SEQ ID NO 1301
<211> LENGTH: 19
<212> TYPE: DNA
<213> ORGANISM: Homo sapiens

<400> SEQUENCE: 1301
accgaaggag tctcatgct                                                   19

<210> SEQ ID NO 1302
<211> LENGTH: 19
<212> TYPE: DNA
<213> ORGANISM: Homo sapiens

<400> SEQUENCE: 1302
ccgaaggagt ctcatgctt                                                   19

<210> SEQ ID NO 1303
<211> LENGTH: 19
<212> TYPE: DNA
<213> ORGANISM: Homo sapiens

<400> SEQUENCE: 1303
ggagtctcat gctttcttc                                                   19

<210> SEQ ID NO 1304
<211> LENGTH: 19
<212> TYPE: DNA
<213> ORGANISM: Homo sapiens
```

```
<400> SEQUENCE: 1304
gagagttcac aggattaga                                                19

<210> SEQ ID NO 1305
<211> LENGTH: 19
<212> TYPE: DNA
<213> ORGANISM: Homo sapiens

<400> SEQUENCE: 1305
ccaattgttt ctgatgtca                                                19

<210> SEQ ID NO 1306
<211> LENGTH: 19
<212> TYPE: DNA
<213> ORGANISM: Homo sapiens

<400> SEQUENCE: 1306
ttgtttctga tgtcatcag                                                19

<210> SEQ ID NO 1307
<211> LENGTH: 19
<212> TYPE: DNA
<213> ORGANISM: Homo sapiens

<400> SEQUENCE: 1307
tcccagcaat aatggtaac                                                19

<210> SEQ ID NO 1308
<211> LENGTH: 19
<212> TYPE: DNA
<213> ORGANISM: Homo sapiens

<400> SEQUENCE: 1308
ggcaatggac ctatgagca                                                19

<210> SEQ ID NO 1309
<211> LENGTH: 19
<212> TYPE: DNA
<213> ORGANISM: Homo sapiens

<400> SEQUENCE: 1309
tggacctatg agcagagga                                                19

<210> SEQ ID NO 1310
<211> LENGTH: 19
<212> TYPE: DNA
<213> ORGANISM: Homo sapiens

<400> SEQUENCE: 1310
gggggttgga cgtgataag                                                19

<210> SEQ ID NO 1311
<211> LENGTH: 19
<212> TYPE: DNA
<213> ORGANISM: Homo sapiens

<400> SEQUENCE: 1311
gtatgagcct gcagctgtt                                                19

<210> SEQ ID NO 1312
<211> LENGTH: 19
<212> TYPE: DNA
<213> ORGANISM: Homo sapiens
```

-continued

```
<400> SEQUENCE: 1312
caaggtgata aaaagggca                                                19

<210> SEQ ID NO 1313
<211> LENGTH: 19
<212> TYPE: DNA
<213> ORGANISM: Homo sapiens

<400> SEQUENCE: 1313
ggtgataaaa agggcaaaa                                                19

<210> SEQ ID NO 1314
<211> LENGTH: 19
<212> TYPE: DNA
<213> ORGANISM: Homo sapiens

<400> SEQUENCE: 1314
aaagggcaaa aagggcaaa                                                19

<210> SEQ ID NO 1315
<211> LENGTH: 19
<212> TYPE: DNA
<213> ORGANISM: Homo sapiens

<400> SEQUENCE: 1315
aagggcaaaa agggcaaaa                                                19

<210> SEQ ID NO 1316
<211> LENGTH: 19
<212> TYPE: DNA
<213> ORGANISM: Homo sapiens

<400> SEQUENCE: 1316
agggcaaaaa gggcaaaaa                                                19

<210> SEQ ID NO 1317
<211> LENGTH: 19
<212> TYPE: DNA
<213> ORGANISM: Homo sapiens

<400> SEQUENCE: 1317
gggcaaaaag ggcaaaaaa                                                19

<210> SEQ ID NO 1318
<211> LENGTH: 19
<212> TYPE: DNA
<213> ORGANISM: Homo sapiens

<400> SEQUENCE: 1318
aaagggcaaa aaagacagg                                                19

<210> SEQ ID NO 1319
<211> LENGTH: 19
<212> TYPE: DNA
<213> ORGANISM: Homo sapiens

<400> SEQUENCE: 1319
aagggcaaaa aagacaggg                                                19

<210> SEQ ID NO 1320
<211> LENGTH: 19
<212> TYPE: DNA
<213> ORGANISM: Homo sapiens
```

```
<400> SEQUENCE: 1320
agggcaaaaa agacaggga                                              19

<210> SEQ ID NO 1321
<211> LENGTH: 19
<212> TYPE: DNA
<213> ORGANISM: Homo sapiens

<400> SEQUENCE: 1321
gggcaaaaaa gacagggac                                              19

<210> SEQ ID NO 1322
<211> LENGTH: 19
<212> TYPE: DNA
<213> ORGANISM: Homo sapiens

<400> SEQUENCE: 1322
aaaagacagg gacatggat                                              19

<210> SEQ ID NO 1323
<211> LENGTH: 19
<212> TYPE: DNA
<213> ORGANISM: Homo sapiens

<400> SEQUENCE: 1323
aaagacaggg acatggatg                                              19

<210> SEQ ID NO 1324
<211> LENGTH: 19
<212> TYPE: DNA
<213> ORGANISM: Homo sapiens

<400> SEQUENCE: 1324
aagacaggga catggatga                                              19

<210> SEQ ID NO 1325
<211> LENGTH: 19
<212> TYPE: DNA
<213> ORGANISM: Homo sapiens

<400> SEQUENCE: 1325
agacagggac atggatgaa                                              19

<210> SEQ ID NO 1326
<211> LENGTH: 19
<212> TYPE: DNA
<213> ORGANISM: Homo sapiens

<400> SEQUENCE: 1326
gacagggaca tggatgaac                                              19

<210> SEQ ID NO 1327
<211> LENGTH: 19
<212> TYPE: DNA
<213> ORGANISM: Homo sapiens

<400> SEQUENCE: 1327
gaagtttcta tggatgatc                                              19

<210> SEQ ID NO 1328
<211> LENGTH: 19
<212> TYPE: DNA
<213> ORGANISM: Homo sapiens
```

<400> SEQUENCE: 1328
acttagcctt gatgaactt						19

<210> SEQ ID NO 1329
<211> LENGTH: 19
<212> TYPE: DNA
<213> ORGANISM: Homo sapiens

<400> SEQUENCE: 1329
cttagccttg atgaacttc						19

<210> SEQ ID NO 1330
<211> LENGTH: 19
<212> TYPE: DNA
<213> ORGANISM: Homo sapiens

<400> SEQUENCE: 1330
atatggaaca gacttgagc						19

<210> SEQ ID NO 1331
<211> LENGTH: 19
<212> TYPE: DNA
<213> ORGANISM: Homo sapiens

<400> SEQUENCE: 1331
tatggaacag acttgagcc						19

<210> SEQ ID NO 1332
<211> LENGTH: 19
<212> TYPE: DNA
<213> ORGANISM: Homo sapiens

<400> SEQUENCE: 1332
cagacttgag ccgggggatt						19

<210> SEQ ID NO 1333
<211> LENGTH: 19
<212> TYPE: DNA
<213> ORGANISM: Homo sapiens

<400> SEQUENCE: 1333
catctgctcg tgcagctga						19

<210> SEQ ID NO 1334
<211> LENGTH: 19
<212> TYPE: DNA
<213> ORGANISM: Homo sapiens

<400> SEQUENCE: 1334
tggatcaagt tttgtcggc						19

<210> SEQ ID NO 1335
<211> LENGTH: 19
<212> TYPE: DNA
<213> ORGANISM: Homo sapiens

<400> SEQUENCE: 1335
gttttgtcgg cagctcttt						19

<210> SEQ ID NO 1336
<211> LENGTH: 19
<212> TYPE: DNA
<213> ORGANISM: Homo sapiens

<400> SEQUENCE: 1336
tgttactgtg gattggagc                                        19

<210> SEQ ID NO 1337
<211> LENGTH: 19
<212> TYPE: DNA
<213> ORGANISM: Homo sapiens

<400> SEQUENCE: 1337
gctgctacag aagaggaac                                        19

<210> SEQ ID NO 1338
<211> LENGTH: 19
<212> TYPE: DNA
<213> ORGANISM: Homo sapiens

<400> SEQUENCE: 1338
gaggaacctc aaaacgata                                        19

<210> SEQ ID NO 1339
<211> LENGTH: 19
<212> TYPE: DNA
<213> ORGANISM: Homo sapiens

<400> SEQUENCE: 1339
cctcaaaacg ataatctgt                                        19

<210> SEQ ID NO 1340
<211> LENGTH: 19
<212> TYPE: DNA
<213> ORGANISM: Homo sapiens

<400> SEQUENCE: 1340
aacgataatc tgtacctgg                                        19

<210> SEQ ID NO 1341
<211> LENGTH: 19
<212> TYPE: DNA
<213> ORGANISM: Homo sapiens

<400> SEQUENCE: 1341
acgataatct gtacctggg                                        19

<210> SEQ ID NO 1342
<211> LENGTH: 19
<212> TYPE: DNA
<213> ORGANISM: Homo sapiens

<400> SEQUENCE: 1342
cgataatctg tacctgggt                                        19

<210> SEQ ID NO 1343
<211> LENGTH: 19
<212> TYPE: DNA
<213> ORGANISM: Homo sapiens

<400> SEQUENCE: 1343
tctgtacctg ggtgtggtg                                        19

<210> SEQ ID NO 1344
<211> LENGTH: 19
<212> TYPE: DNA
<213> ORGANISM: Homo sapiens

```
<400> SEQUENCE: 1344
tcataactgg ttgcttctc                                              19

<210> SEQ ID NO 1345
<211> LENGTH: 19
<212> TYPE: DNA
<213> ORGANISM: Homo sapiens

<400> SEQUENCE: 1345
ctggttgctt ctcctacta                                              19

<210> SEQ ID NO 1346
<211> LENGTH: 19
<212> TYPE: DNA
<213> ORGANISM: Homo sapiens

<400> SEQUENCE: 1346
gttcaaagat catggaatc                                              19

<210> SEQ ID NO 1347
<211> LENGTH: 19
<212> TYPE: DNA
<213> ORGANISM: Homo sapiens

<400> SEQUENCE: 1347
agatcatgga atccttcaa                                              19

<210> SEQ ID NO 1348
<211> LENGTH: 19
<212> TYPE: DNA
<213> ORGANISM: Homo sapiens

<400> SEQUENCE: 1348
gatcatggaa tccttcaaa                                              19

<210> SEQ ID NO 1349
<211> LENGTH: 19
<212> TYPE: DNA
<213> ORGANISM: Homo sapiens

<400> SEQUENCE: 1349
tccttcaaaa acatggtcc                                              19

<210> SEQ ID NO 1350
<211> LENGTH: 19
<212> TYPE: DNA
<213> ORGANISM: Homo sapiens

<400> SEQUENCE: 1350
aaacatggtc cctcagcaa                                              19

<210> SEQ ID NO 1351
<211> LENGTH: 19
<212> TYPE: DNA
<213> ORGANISM: Homo sapiens

<400> SEQUENCE: 1351
aacatggtcc ctcagcaag                                              19

<210> SEQ ID NO 1352
<211> LENGTH: 19
<212> TYPE: DNA
<213> ORGANISM: Homo sapiens
```

-continued

```
<400> SEQUENCE: 1352
acatggtccc tcagcaagc                                                19

<210> SEQ ID NO 1353
<211> LENGTH: 19
<212> TYPE: DNA
<213> ORGANISM: Homo sapiens

<400> SEQUENCE: 1353
catggtccct cagcaagcc                                                19

<210> SEQ ID NO 1354
<211> LENGTH: 19
<212> TYPE: DNA
<213> ORGANISM: Homo sapiens

<400> SEQUENCE: 1354
gcccttgtga ttcgaaatg                                                19

<210> SEQ ID NO 1355
<211> LENGTH: 19
<212> TYPE: DNA
<213> ORGANISM: Homo sapiens

<400> SEQUENCE: 1355
atggtgagaa aatgagcat                                                19

<210> SEQ ID NO 1356
<211> LENGTH: 19
<212> TYPE: DNA
<213> ORGANISM: Homo sapiens

<400> SEQUENCE: 1356
tggtgagaaa atgagcata                                                19

<210> SEQ ID NO 1357
<211> LENGTH: 19
<212> TYPE: DNA
<213> ORGANISM: Homo sapiens

<400> SEQUENCE: 1357
aatgagcata aatgcggag                                                19

<210> SEQ ID NO 1358
<211> LENGTH: 19
<212> TYPE: DNA
<213> ORGANISM: Homo sapiens

<400> SEQUENCE: 1358
atgagcataa atgcggagg                                                19

<210> SEQ ID NO 1359
<211> LENGTH: 19
<212> TYPE: DNA
<213> ORGANISM: Homo sapiens

<400> SEQUENCE: 1359
tgagcataaa tgcggagga                                                19

<210> SEQ ID NO 1360
<211> LENGTH: 19
<212> TYPE: DNA
<213> ORGANISM: Homo sapiens
```

```
<400> SEQUENCE: 1360
atgcggagga agttgtggt                                              19

<210> SEQ ID NO 1361
<211> LENGTH: 19
<212> TYPE: DNA
<213> ORGANISM: Homo sapiens

<400> SEQUENCE: 1361
tgcggaggaa gttgtggtt                                              19

<210> SEQ ID NO 1362
<211> LENGTH: 19
<212> TYPE: DNA
<213> ORGANISM: Homo sapiens

<400> SEQUENCE: 1362
gttgtggttg gggatctgg                                              19

<210> SEQ ID NO 1363
<211> LENGTH: 19
<212> TYPE: DNA
<213> ORGANISM: Homo sapiens

<400> SEQUENCE: 1363
gtaaaaggag gagaccgaa                                              19

<210> SEQ ID NO 1364
<211> LENGTH: 19
<212> TYPE: DNA
<213> ORGANISM: Homo sapiens

<400> SEQUENCE: 1364
aaggaggaga ccgaattcc                                              19

<210> SEQ ID NO 1365
<211> LENGTH: 19
<212> TYPE: DNA
<213> ORGANISM: Homo sapiens

<400> SEQUENCE: 1365
aggaggagac cgaattcct                                              19

<210> SEQ ID NO 1366
<211> LENGTH: 19
<212> TYPE: DNA
<213> ORGANISM: Homo sapiens

<400> SEQUENCE: 1366
ggaggagacc gaattcctg                                              19

<210> SEQ ID NO 1367
<211> LENGTH: 19
<212> TYPE: DNA
<213> ORGANISM: Homo sapiens

<400> SEQUENCE: 1367
ttcctgctga cctcagaat                                              19

<210> SEQ ID NO 1368
<211> LENGTH: 19
<212> TYPE: DNA
<213> ORGANISM: Homo sapiens
```

```
<400> SEQUENCE: 1368
tcatatctgc aaatggctg                                             19

<210> SEQ ID NO 1369
<211> LENGTH: 19
<212> TYPE: DNA
<213> ORGANISM: Homo sapiens

<400> SEQUENCE: 1369
atggctgcaa ggtggataa                                             19

<210> SEQ ID NO 1370
<211> LENGTH: 19
<212> TYPE: DNA
<213> ORGANISM: Homo sapiens

<400> SEQUENCE: 1370
tggctgcaag gtggataac                                             19

<210> SEQ ID NO 1371
<211> LENGTH: 19
<212> TYPE: DNA
<213> ORGANISM: Homo sapiens

<400> SEQUENCE: 1371
ggtggataac tcctcgctc                                             19

<210> SEQ ID NO 1372
<211> LENGTH: 19
<212> TYPE: DNA
<213> ORGANISM: Homo sapiens

<400> SEQUENCE: 1372
ctcctcgctc actggtgaa                                             19

<210> SEQ ID NO 1373
<211> LENGTH: 19
<212> TYPE: DNA
<213> ORGANISM: Homo sapiens

<400> SEQUENCE: 1373
tcagaacccc agactaggt                                             19

<210> SEQ ID NO 1374
<211> LENGTH: 19
<212> TYPE: DNA
<213> ORGANISM: Homo sapiens

<400> SEQUENCE: 1374
ccccagacta ggtctccag                                             19

<210> SEQ ID NO 1375
<211> LENGTH: 19
<212> TYPE: DNA
<213> ORGANISM: Homo sapiens

<400> SEQUENCE: 1375
atgaaacccc cctggagac                                             19

<210> SEQ ID NO 1376
<211> LENGTH: 19
<212> TYPE: DNA
<213> ORGANISM: Homo sapiens
```

```
<400> SEQUENCE: 1376
tgaaaacccc ctggagacg                                            19

<210> SEQ ID NO 1377
<211> LENGTH: 19
<212> TYPE: DNA
<213> ORGANISM: Homo sapiens

<400> SEQUENCE: 1377
aaccccctgg agacgagga                                            19

<210> SEQ ID NO 1378
<211> LENGTH: 19
<212> TYPE: DNA
<213> ORGANISM: Homo sapiens

<400> SEQUENCE: 1378
accccctgga gacgaggaa                                            19

<210> SEQ ID NO 1379
<211> LENGTH: 19
<212> TYPE: DNA
<213> ORGANISM: Homo sapiens

<400> SEQUENCE: 1379
cattgccttc ttttcaacc                                            19

<210> SEQ ID NO 1380
<211> LENGTH: 19
<212> TYPE: DNA
<213> ORGANISM: Homo sapiens

<400> SEQUENCE: 1380
ccaattgtgt tgaaggcac                                            19

<210> SEQ ID NO 1381
<211> LENGTH: 19
<212> TYPE: DNA
<213> ORGANISM: Homo sapiens

<400> SEQUENCE: 1381
ttgtgttgaa ggcaccgca                                            19

<210> SEQ ID NO 1382
<211> LENGTH: 19
<212> TYPE: DNA
<213> ORGANISM: Homo sapiens

<400> SEQUENCE: 1382
ggcaccgcac gtggtattg                                            19

<210> SEQ ID NO 1383
<211> LENGTH: 19
<212> TYPE: DNA
<213> ORGANISM: Homo sapiens

<400> SEQUENCE: 1383
gaattgccac acttgcttc                                            19

<210> SEQ ID NO 1384
<211> LENGTH: 19
<212> TYPE: DNA
<213> ORGANISM: Homo sapiens
```

```
<400> SEQUENCE: 1384
ttgccacact tgcttctgg                                               19

<210> SEQ ID NO 1385
<211> LENGTH: 19
<212> TYPE: DNA
<213> ORGANISM: Homo sapiens

<400> SEQUENCE: 1385
tgtgccggaa ggtttgctg                                               19

<210> SEQ ID NO 1386
<211> LENGTH: 19
<212> TYPE: DNA
<213> ORGANISM: Homo sapiens

<400> SEQUENCE: 1386
ggtttgctgg ccactgtca                                               19

<210> SEQ ID NO 1387
<211> LENGTH: 19
<212> TYPE: DNA
<213> ORGANISM: Homo sapiens

<400> SEQUENCE: 1387
acgcatggca aggaaaaac                                               19

<210> SEQ ID NO 1388
<211> LENGTH: 19
<212> TYPE: DNA
<213> ORGANISM: Homo sapiens

<400> SEQUENCE: 1388
cgcatggcaa ggaaaaact                                               19

<210> SEQ ID NO 1389
<211> LENGTH: 19
<212> TYPE: DNA
<213> ORGANISM: Homo sapiens

<400> SEQUENCE: 1389
ggaaaaactg cttagtgaa                                               19

<210> SEQ ID NO 1390
<211> LENGTH: 19
<212> TYPE: DNA
<213> ORGANISM: Homo sapiens

<400> SEQUENCE: 1390
aaactgctta gtgaagaac                                               19

<210> SEQ ID NO 1391
<211> LENGTH: 19
<212> TYPE: DNA
<213> ORGANISM: Homo sapiens

<400> SEQUENCE: 1391
aactgcttag tgaagaact                                               19

<210> SEQ ID NO 1392
<211> LENGTH: 19
<212> TYPE: DNA
<213> ORGANISM: Homo sapiens
```

-continued

```
<400> SEQUENCE: 1392
actgcttagt gaagaactt                                                   19

<210> SEQ ID NO 1393
<211> LENGTH: 19
<212> TYPE: DNA
<213> ORGANISM: Homo sapiens

<400> SEQUENCE: 1393
ctgcttagtg aagaactta                                                   19

<210> SEQ ID NO 1394
<211> LENGTH: 19
<212> TYPE: DNA
<213> ORGANISM: Homo sapiens

<400> SEQUENCE: 1394
gaacttagaa gctgtggag                                                   19

<210> SEQ ID NO 1395
<211> LENGTH: 19
<212> TYPE: DNA
<213> ORGANISM: Homo sapiens

<400> SEQUENCE: 1395
cttagaagct gtggagacc                                                   19

<210> SEQ ID NO 1396
<211> LENGTH: 19
<212> TYPE: DNA
<213> ORGANISM: Homo sapiens

<400> SEQUENCE: 1396
gctgtggaga ccttggggt                                                   19

<210> SEQ ID NO 1397
<211> LENGTH: 19
<212> TYPE: DNA
<213> ORGANISM: Homo sapiens

<400> SEQUENCE: 1397
aactggaact ctgactcag                                                   19

<210> SEQ ID NO 1398
<211> LENGTH: 19
<212> TYPE: DNA
<213> ORGANISM: Homo sapiens

<400> SEQUENCE: 1398
actggaactc tgactcaga                                                   19

<210> SEQ ID NO 1399
<211> LENGTH: 19
<212> TYPE: DNA
<213> ORGANISM: Homo sapiens

<400> SEQUENCE: 1399
ctggaactct gactcagaa                                                   19

<210> SEQ ID NO 1400
<211> LENGTH: 19
<212> TYPE: DNA
<213> ORGANISM: Homo sapiens
```

```
<400> SEQUENCE: 1400
ctctgactca gaaccggat                                              19

<210> SEQ ID NO 1401
<211> LENGTH: 19
<212> TYPE: DNA
<213> ORGANISM: Homo sapiens

<400> SEQUENCE: 1401
tcaaatccat gaagctgat                                              19

<210> SEQ ID NO 1402
<211> LENGTH: 19
<212> TYPE: DNA
<213> ORGANISM: Homo sapiens

<400> SEQUENCE: 1402
atccatgaag ctgatacga                                              19

<210> SEQ ID NO 1403
<211> LENGTH: 19
<212> TYPE: DNA
<213> ORGANISM: Homo sapiens

<400> SEQUENCE: 1403
tccatgaagc tgatacgac                                              19

<210> SEQ ID NO 1404
<211> LENGTH: 19
<212> TYPE: DNA
<213> ORGANISM: Homo sapiens

<400> SEQUENCE: 1404
gctgatacga cagagaatc                                              19

<210> SEQ ID NO 1405
<211> LENGTH: 19
<212> TYPE: DNA
<213> ORGANISM: Homo sapiens

<400> SEQUENCE: 1405
tcagagtggt gtctctttt                                              19

<210> SEQ ID NO 1406
<211> LENGTH: 19
<212> TYPE: DNA
<213> ORGANISM: Homo sapiens

<400> SEQUENCE: 1406
gacttcagct acctggctt                                              19

<210> SEQ ID NO 1407
<211> LENGTH: 19
<212> TYPE: DNA
<213> ORGANISM: Homo sapiens

<400> SEQUENCE: 1407
ttgcaggtct ttgtaacag                                              19

<210> SEQ ID NO 1408
<211> LENGTH: 19
<212> TYPE: DNA
<213> ORGANISM: Homo sapiens
```

```
<400> SEQUENCE: 1408
cagggcagtg tttcaggct                                              19

<210> SEQ ID NO 1409
<211> LENGTH: 19
<212> TYPE: DNA
<213> ORGANISM: Homo sapiens

<400> SEQUENCE: 1409
ccaggaaaac ctacctatt                                              19

<210> SEQ ID NO 1410
<211> LENGTH: 19
<212> TYPE: DNA
<213> ORGANISM: Homo sapiens

<400> SEQUENCE: 1410
aacctaccta ttcttaagc                                              19

<210> SEQ ID NO 1411
<211> LENGTH: 19
<212> TYPE: DNA
<213> ORGANISM: Homo sapiens

<400> SEQUENCE: 1411
acctacctat tcttaagcg                                              19

<210> SEQ ID NO 1412
<211> LENGTH: 19
<212> TYPE: DNA
<213> ORGANISM: Homo sapiens

<400> SEQUENCE: 1412
cctacctatt cttaagcgg                                              19

<210> SEQ ID NO 1413
<211> LENGTH: 19
<212> TYPE: DNA
<213> ORGANISM: Homo sapiens

<400> SEQUENCE: 1413
gcgggcagtt gcaggagat                                              19

<210> SEQ ID NO 1414
<211> LENGTH: 19
<212> TYPE: DNA
<213> ORGANISM: Homo sapiens

<400> SEQUENCE: 1414
agtgcataga gctgtgctg                                              19

<210> SEQ ID NO 1415
<211> LENGTH: 19
<212> TYPE: DNA
<213> ORGANISM: Homo sapiens

<400> SEQUENCE: 1415
gtgcatagag ctgtgctgt                                              19

<210> SEQ ID NO 1416
<211> LENGTH: 19
<212> TYPE: DNA
<213> ORGANISM: Homo sapiens
```

```
<400> SEQUENCE: 1416
ggagatgaga gaaagatac                                                 19

<210> SEQ ID NO 1417
<211> LENGTH: 19
<212> TYPE: DNA
<213> ORGANISM: Homo sapiens

<400> SEQUENCE: 1417
agatacgcca aaatcgtcg                                                 19

<210> SEQ ID NO 1418
<211> LENGTH: 19
<212> TYPE: DNA
<213> ORGANISM: Homo sapiens

<400> SEQUENCE: 1418
gatacgccaa aatcgtcga                                                 19

<210> SEQ ID NO 1419
<211> LENGTH: 19
<212> TYPE: DNA
<213> ORGANISM: Homo sapiens

<400> SEQUENCE: 1419
aatcgtcgag ataccccttc                                                19

<210> SEQ ID NO 1420
<211> LENGTH: 19
<212> TYPE: DNA
<213> ORGANISM: Homo sapiens

<400> SEQUENCE: 1420
atcgtcgaga tacccttca                                                 19

<210> SEQ ID NO 1421
<211> LENGTH: 19
<212> TYPE: DNA
<213> ORGANISM: Homo sapiens

<400> SEQUENCE: 1421
tcgtcgagat acccttcaa                                                 19

<210> SEQ ID NO 1422
<211> LENGTH: 19
<212> TYPE: DNA
<213> ORGANISM: Homo sapiens

<400> SEQUENCE: 1422
ctccaccaac aagtaccag                                                 19

<210> SEQ ID NO 1423
<211> LENGTH: 19
<212> TYPE: DNA
<213> ORGANISM: Homo sapiens

<400> SEQUENCE: 1423
caagtaccag ttgtctatt                                                 19

<210> SEQ ID NO 1424
<211> LENGTH: 19
<212> TYPE: DNA
<213> ORGANISM: Homo sapiens
```

```
<400> SEQUENCE: 1424
gtaccagttg tctattcat                                                    19

<210> SEQ ID NO 1425
<211> LENGTH: 19
<212> TYPE: DNA
<213> ORGANISM: Homo sapiens

<400> SEQUENCE: 1425
gaaccccaac acatcggag                                                    19

<210> SEQ ID NO 1426
<211> LENGTH: 19
<212> TYPE: DNA
<213> ORGANISM: Homo sapiens

<400> SEQUENCE: 1426
cacatcggag ccccaacac                                                    19

<210> SEQ ID NO 1427
<211> LENGTH: 19
<212> TYPE: DNA
<213> ORGANISM: Homo sapiens

<400> SEQUENCE: 1427
cacctgttgg tgatgaagg                                                    19

<210> SEQ ID NO 1428
<211> LENGTH: 19
<212> TYPE: DNA
<213> ORGANISM: Homo sapiens

<400> SEQUENCE: 1428
aggatcctag accgttgca                                                    19

<210> SEQ ID NO 1429
<211> LENGTH: 19
<212> TYPE: DNA
<213> ORGANISM: Homo sapiens

<400> SEQUENCE: 1429
ggatcctaga ccgttgcag                                                    19

<210> SEQ ID NO 1430
<211> LENGTH: 19
<212> TYPE: DNA
<213> ORGANISM: Homo sapiens

<400> SEQUENCE: 1430
agacgccttt cagaacgcc                                                    19

<210> SEQ ID NO 1431
<211> LENGTH: 19
<212> TYPE: DNA
<213> ORGANISM: Homo sapiens

<400> SEQUENCE: 1431
gacgcctttc agaacgcct                                                    19

<210> SEQ ID NO 1432
<211> LENGTH: 19
<212> TYPE: DNA
<213> ORGANISM: Homo sapiens
```

<400> SEQUENCE: 1432
cgcctatttg gagctgggg					19

<210> SEQ ID NO 1433
<211> LENGTH: 19
<212> TYPE: DNA
<213> ORGANISM: Homo sapiens

<400> SEQUENCE: 1433
cgagtcctag gtttctgcc					19

<210> SEQ ID NO 1434
<211> LENGTH: 19
<212> TYPE: DNA
<213> ORGANISM: Homo sapiens

<400> SEQUENCE: 1434
cagtttcctg aagggttcc					19

<210> SEQ ID NO 1435
<211> LENGTH: 19
<212> TYPE: DNA
<213> ORGANISM: Homo sapiens

<400> SEQUENCE: 1435
gggttccagt ttgacactg					19

<210> SEQ ID NO 1436
<211> LENGTH: 19
<212> TYPE: DNA
<213> ORGANISM: Homo sapiens

<400> SEQUENCE: 1436
tttccctatc gataatctg					19

<210> SEQ ID NO 1437
<211> LENGTH: 19
<212> TYPE: DNA
<213> ORGANISM: Homo sapiens

<400> SEQUENCE: 1437
tctgtgcttt gttgggctc					19

<210> SEQ ID NO 1438
<211> LENGTH: 19
<212> TYPE: DNA
<213> ORGANISM: Homo sapiens

<400> SEQUENCE: 1438
atgtcgaagt gctggaatt					19

<210> SEQ ID NO 1439
<211> LENGTH: 19
<212> TYPE: DNA
<213> ORGANISM: Homo sapiens

<400> SEQUENCE: 1439
tgtcgaagtg ctggaatta					19

<210> SEQ ID NO 1440
<211> LENGTH: 19
<212> TYPE: DNA
<213> ORGANISM: Homo sapiens

```
<400> SEQUENCE: 1440
gtgctggaat taaggtcat                                              19

<210> SEQ ID NO 1441
<211> LENGTH: 19
<212> TYPE: DNA
<213> ORGANISM: Homo sapiens

<400> SEQUENCE: 1441
ttaaggtcat catggtcac                                              19

<210> SEQ ID NO 1442
<211> LENGTH: 19
<212> TYPE: DNA
<213> ORGANISM: Homo sapiens

<400> SEQUENCE: 1442
ggtcatcatg gtcacagga                                              19

<210> SEQ ID NO 1443
<211> LENGTH: 19
<212> TYPE: DNA
<213> ORGANISM: Homo sapiens

<400> SEQUENCE: 1443
tcacagctaa agctattgc                                              19

<210> SEQ ID NO 1444
<211> LENGTH: 19
<212> TYPE: DNA
<213> ORGANISM: Homo sapiens

<400> SEQUENCE: 1444
agctattgcc aaaggtgtg                                              19

<210> SEQ ID NO 1445
<211> LENGTH: 19
<212> TYPE: DNA
<213> ORGANISM: Homo sapiens

<400> SEQUENCE: 1445
gctattgcca aaggtgtgg                                              19

<210> SEQ ID NO 1446
<211> LENGTH: 19
<212> TYPE: DNA
<213> ORGANISM: Homo sapiens

<400> SEQUENCE: 1446
aggtgtgggc atcatctca                                              19

<210> SEQ ID NO 1447
<211> LENGTH: 19
<212> TYPE: DNA
<213> ORGANISM: Homo sapiens

<400> SEQUENCE: 1447
ggtgtgggca tcatctcag                                              19

<210> SEQ ID NO 1448
<211> LENGTH: 19
<212> TYPE: DNA
<213> ORGANISM: Homo sapiens
```

<400> SEQUENCE: 1448
ggcaatgaga ccgtggaag                                         19

<210> SEQ ID NO 1449
<211> LENGTH: 19
<212> TYPE: DNA
<213> ORGANISM: Homo sapiens

<400> SEQUENCE: 1449
tgagaccgtg aagacatt                                          19

<210> SEQ ID NO 1450
<211> LENGTH: 19
<212> TYPE: DNA
<213> ORGANISM: Homo sapiens

<400> SEQUENCE: 1450
gacattgctg cccgcctca                                         19

<210> SEQ ID NO 1451
<211> LENGTH: 19
<212> TYPE: DNA
<213> ORGANISM: Homo sapiens

<400> SEQUENCE: 1451
catcccagtc agccaggtg                                         19

<210> SEQ ID NO 1452
<211> LENGTH: 19
<212> TYPE: DNA
<213> ORGANISM: Homo sapiens

<400> SEQUENCE: 1452
aggacatgac ctccgagca                                         19

<210> SEQ ID NO 1453
<211> LENGTH: 19
<212> TYPE: DNA
<213> ORGANISM: Homo sapiens

<400> SEQUENCE: 1453
ggacatgacc tccgagcag                                         19

<210> SEQ ID NO 1454
<211> LENGTH: 19
<212> TYPE: DNA
<213> ORGANISM: Homo sapiens

<400> SEQUENCE: 1454
gtaccacact gagatagtg                                         19

<210> SEQ ID NO 1455
<211> LENGTH: 19
<212> TYPE: DNA
<213> ORGANISM: Homo sapiens

<400> SEQUENCE: 1455
gctcatcatt gtggaaggc                                         19

<210> SEQ ID NO 1456
<211> LENGTH: 19
<212> TYPE: DNA
<213> ORGANISM: Homo sapiens -continued

<400> SEQUENCE: 1456
ggctgccaaa gacagggtg						19

<210> SEQ ID NO 1457
<211> LENGTH: 19
<212> TYPE: DNA
<213> ORGANISM: Homo sapiens

<400> SEQUENCE: 1457
agacagggtg ctatcgtgg						19

<210> SEQ ID NO 1458
<211> LENGTH: 19
<212> TYPE: DNA
<213> ORGANISM: Homo sapiens

<400> SEQUENCE: 1458
gacagggtgc tatcgtggc						19

<210> SEQ ID NO 1459
<211> LENGTH: 19
<212> TYPE: DNA
<213> ORGANISM: Homo sapiens

<400> SEQUENCE: 1459
tgactctcca gctttgaag						19

<210> SEQ ID NO 1460
<211> LENGTH: 19
<212> TYPE: DNA
<213> ORGANISM: Homo sapiens

<400> SEQUENCE: 1460
gaaagcagac attggggtt						19

<210> SEQ ID NO 1461
<211> LENGTH: 19
<212> TYPE: DNA
<213> ORGANISM: Homo sapiens

<400> SEQUENCE: 1461
agcagacatt ggggttgct						19

<210> SEQ ID NO 1462
<211> LENGTH: 19
<212> TYPE: DNA
<213> ORGANISM: Homo sapiens

<400> SEQUENCE: 1462
gcagacattg gggttgcta						19

<210> SEQ ID NO 1463
<211> LENGTH: 19
<212> TYPE: DNA
<213> ORGANISM: Homo sapiens

<400> SEQUENCE: 1463
gcaagctgct gacatgatt						19

<210> SEQ ID NO 1464
<211> LENGTH: 19
<212> TYPE: DNA
<213> ORGANISM: Homo sapiens

```
<400> SEQUENCE: 1464
gctgctgaca tgattcttc                                              19

<210> SEQ ID NO 1465
<211> LENGTH: 19
<212> TYPE: DNA
<213> ORGANISM: Homo sapiens

<400> SEQUENCE: 1465
ctttgcctca attgtgact                                              19

<210> SEQ ID NO 1466
<211> LENGTH: 19
<212> TYPE: DNA
<213> ORGANISM: Homo sapiens

<400> SEQUENCE: 1466
ttgtgactgg agtagagga                                              19

<210> SEQ ID NO 1467
<211> LENGTH: 19
<212> TYPE: DNA
<213> ORGANISM: Homo sapiens

<400> SEQUENCE: 1467
ggtcgtctga tctttgata                                              19

<210> SEQ ID NO 1468
<211> LENGTH: 19
<212> TYPE: DNA
<213> ORGANISM: Homo sapiens

<400> SEQUENCE: 1468
cttgaagaaa tccattgct                                              19

<210> SEQ ID NO 1469
<211> LENGTH: 19
<212> TYPE: DNA
<213> ORGANISM: Homo sapiens

<400> SEQUENCE: 1469
gaaatccatt gcttatacc                                              19

<210> SEQ ID NO 1470
<211> LENGTH: 19
<212> TYPE: DNA
<213> ORGANISM: Homo sapiens

<400> SEQUENCE: 1470
ccagtaacat tcccgagat                                              19

<210> SEQ ID NO 1471
<211> LENGTH: 19
<212> TYPE: DNA
<213> ORGANISM: Homo sapiens

<400> SEQUENCE: 1471
cattcccgag atcaccccg                                              19

<210> SEQ ID NO 1472
<211> LENGTH: 19
<212> TYPE: DNA
<213> ORGANISM: Homo sapiens
```

```
<400> SEQUENCE: 1472
acattccact accactggg                                              19

<210> SEQ ID NO 1473
<211> LENGTH: 19
<212> TYPE: DNA
<213> ORGANISM: Homo sapiens

<400> SEQUENCE: 1473
cattccacta ccactgggg                                              19

<210> SEQ ID NO 1474
<211> LENGTH: 19
<212> TYPE: DNA
<213> ORGANISM: Homo sapiens

<400> SEQUENCE: 1474
gagacagccc agaaatccc                                              19

<210> SEQ ID NO 1475
<211> LENGTH: 19
<212> TYPE: DNA
<213> ORGANISM: Homo sapiens

<400> SEQUENCE: 1475
atcccaaaac agacaaact                                              19

<210> SEQ ID NO 1476
<211> LENGTH: 19
<212> TYPE: DNA
<213> ORGANISM: Homo sapiens

<400> SEQUENCE: 1476
tcccaaaaca gacaaactt                                              19

<210> SEQ ID NO 1477
<211> LENGTH: 19
<212> TYPE: DNA
<213> ORGANISM: Homo sapiens

<400> SEQUENCE: 1477
acagacaaac ttgtgaatg                                              19

<210> SEQ ID NO 1478
<211> LENGTH: 19
<212> TYPE: DNA
<213> ORGANISM: Homo sapiens

<400> SEQUENCE: 1478
cagacaaact tgtgaatga                                              19

<210> SEQ ID NO 1479
<211> LENGTH: 19
<212> TYPE: DNA
<213> ORGANISM: Homo sapiens

<400> SEQUENCE: 1479
acttgtgaat gagcggctg                                              19

<210> SEQ ID NO 1480
<211> LENGTH: 19
<212> TYPE: DNA
<213> ORGANISM: Homo sapiens
```

```
<400> SEQUENCE: 1480
cttgtgaatg agcggctga                                              19

<210> SEQ ID NO 1481
<211> LENGTH: 19
<212> TYPE: DNA
<213> ORGANISM: Homo sapiens

<400> SEQUENCE: 1481
tgagcggctg atcagcatg                                              19

<210> SEQ ID NO 1482
<211> LENGTH: 19
<212> TYPE: DNA
<213> ORGANISM: Homo sapiens

<400> SEQUENCE: 1482
cggcttcctc ccaattcac                                              19

<210> SEQ ID NO 1483
<211> LENGTH: 19
<212> TYPE: DNA
<213> ORGANISM: Homo sapiens

<400> SEQUENCE: 1483
ttcacctgtt gggcctccg                                              19

<210> SEQ ID NO 1484
<211> LENGTH: 19
<212> TYPE: DNA
<213> ORGANISM: Homo sapiens

<400> SEQUENCE: 1484
cgatgtggaa gacagctac                                              19

<210> SEQ ID NO 1485
<211> LENGTH: 19
<212> TYPE: DNA
<213> ORGANISM: Homo sapiens

<400> SEQUENCE: 1485
gacagctacg ggcagcagt                                              19

<210> SEQ ID NO 1486
<211> LENGTH: 19
<212> TYPE: DNA
<213> ORGANISM: Homo sapiens

<400> SEQUENCE: 1486
aatcgtggag ttcacctgc                                              19

<210> SEQ ID NO 1487
<211> LENGTH: 19
<212> TYPE: DNA
<213> ORGANISM: Homo sapiens

<400> SEQUENCE: 1487
atcgtggagt tcacctgcc                                              19

<210> SEQ ID NO 1488
<211> LENGTH: 19
<212> TYPE: DNA
<213> ORGANISM: Homo sapiens
```

<400> SEQUENCE: 1488
tcgtggagtt cacctgcca                                                    19

<210> SEQ ID NO 1489
<211> LENGTH: 19
<212> TYPE: DNA
<213> ORGANISM: Homo sapiens

<400> SEQUENCE: 1489
gaccaggagg aattcggtc                                                    19

<210> SEQ ID NO 1490
<211> LENGTH: 19
<212> TYPE: DNA
<213> ORGANISM: Homo sapiens

<400> SEQUENCE: 1490
ttcggtcttc cagcagggg                                                    19

<210> SEQ ID NO 1491
<211> LENGTH: 19
<212> TYPE: DNA
<213> ORGANISM: Homo sapiens

<400> SEQUENCE: 1491
caagatcttg atatttggc                                                    19

<210> SEQ ID NO 1492
<211> LENGTH: 19
<212> TYPE: DNA
<213> ORGANISM: Homo sapiens

<400> SEQUENCE: 1492
gatcttgata tttggcctc                                                    19

<210> SEQ ID NO 1493
<211> LENGTH: 19
<212> TYPE: DNA
<213> ORGANISM: Homo sapiens

<400> SEQUENCE: 1493
gagacagccc tggctgctt                                                    19

<210> SEQ ID NO 1494
<211> LENGTH: 19
<212> TYPE: DNA
<213> ORGANISM: Homo sapiens

<400> SEQUENCE: 1494
tgggtgttgc tcttaggat                                                    19

<210> SEQ ID NO 1495
<211> LENGTH: 19
<212> TYPE: DNA
<213> ORGANISM: Homo sapiens

<400> SEQUENCE: 1495
acctacctgg tggttctgt                                                    19

<210> SEQ ID NO 1496
<211> LENGTH: 19
<212> TYPE: DNA
<213> ORGANISM: Homo sapiens

```
<400> SEQUENCE: 1496
cctacctggt ggttctgtg                                                  19

<210> SEQ ID NO 1497
<211> LENGTH: 19
<212> TYPE: DNA
<213> ORGANISM: Homo sapiens

<400> SEQUENCE: 1497
gtcagaaaac tcatcatca                                                  19

<210> SEQ ID NO 1498
<211> LENGTH: 19
<212> TYPE: DNA
<213> ORGANISM: Homo sapiens

<400> SEQUENCE: 1498
aactcatcat caggcgacg                                                  19

<210> SEQ ID NO 1499
<211> LENGTH: 19
<212> TYPE: DNA
<213> ORGANISM: Homo sapiens

<400> SEQUENCE: 1499
actcatcatc aggcgacgc                                                  19

<210> SEQ ID NO 1500
<211> LENGTH: 19
<212> TYPE: DNA
<213> ORGANISM: Homo sapiens

<400> SEQUENCE: 1500
ctcatcatca ggcgacgcc                                                  19

<210> SEQ ID NO 1501
<211> LENGTH: 19
<212> TYPE: DNA
<213> ORGANISM: Homo sapiens

<400> SEQUENCE: 1501 tggggcggc aagaagaaa                                                   19

<210> SEQ ID NO 1502
<211> LENGTH: 19
<212> TYPE: DNA
<213> ORGANISM: Homo sapiens

<400> SEQUENCE: 1502
gaagaaacag aaggagaag                                                  19

<210> SEQ ID NO 1503
<211> LENGTH: 19
<212> TYPE: DNA
<213> ORGANISM: Homo sapiens

<400> SEQUENCE: 1503
gaaacagaag gagaaggaa                                                  19

<210> SEQ ID NO 1504
<211> LENGTH: 19
<212> TYPE: DNA
<213> ORGANISM: Homo sapiens
```

<400> SEQUENCE: 1504
acagaaggag aaggaactg					19

<210> SEQ ID NO 1505
<211> LENGTH: 19
<212> TYPE: DNA
<213> ORGANISM: Homo sapiens

<400> SEQUENCE: 1505
cagaaggaga aggaactgg					19

<210> SEQ ID NO 1506
<211> LENGTH: 19
<212> TYPE: DNA
<213> ORGANISM: Homo sapiens

<400> SEQUENCE: 1506
ggagaaggaa ctggatgag					19

<210> SEQ ID NO 1507
<211> LENGTH: 19
<212> TYPE: DNA
<213> ORGANISM: Homo sapiens

<400> SEQUENCE: 1507
ggaactggat gagctgaag					19

<210> SEQ ID NO 1508
<211> LENGTH: 19
<212> TYPE: DNA
<213> ORGANISM: Homo sapiens

<400> SEQUENCE: 1508
ctggatgagc tgaagaagg					19

<210> SEQ ID NO 1509
<211> LENGTH: 19
<212> TYPE: DNA
<213> ORGANISM: Homo sapiens

<400> SEQUENCE: 1509
gaaggaggtg gcaatggat					19

<210> SEQ ID NO 1510
<211> LENGTH: 19
<212> TYPE: DNA
<213> ORGANISM: Homo sapiens

<400> SEQUENCE: 1510
ggaggtggca atggatgac					19

<210> SEQ ID NO 1511
<211> LENGTH: 19
<212> TYPE: DNA
<213> ORGANISM: Homo sapiens

<400> SEQUENCE: 1511
tggatgacca caagctgtc					19

<210> SEQ ID NO 1512
<211> LENGTH: 19
<212> TYPE: DNA
<213> ORGANISM: Homo sapiens

```
<400> SEQUENCE: 1512
gctgtccttg gatgagctg                                                        19

<210> SEQ ID NO 1513
<211> LENGTH: 19
<212> TYPE: DNA
<213> ORGANISM: Homo sapiens

<400> SEQUENCE: 1513
ataccaagtg gacctgtcc                                                        19

<210> SEQ ID NO 1514
<211> LENGTH: 19
<212> TYPE: DNA
<213> ORGANISM: Homo sapiens

<400> SEQUENCE: 1514
taccaagtgg acctgtcca                                                        19

<210> SEQ ID NO 1515
<211> LENGTH: 19
<212> TYPE: DNA
<213> ORGANISM: Homo sapiens

<400> SEQUENCE: 1515
cccctgagtg ggtcaagtt                                                        19

<210> SEQ ID NO 1516
<211> LENGTH: 19
<212> TYPE: DNA
<213> ORGANISM: Homo sapiens

<400> SEQUENCE: 1516
gttctgccgt cagcttttc                                                        19

<210> SEQ ID NO 1517
<211> LENGTH: 19
<212> TYPE: DNA
<213> ORGANISM: Homo sapiens

<400> SEQUENCE: 1517
ccatccaacg acaatctat                                                        19

<210> SEQ ID NO 1518
<211> LENGTH: 19
<212> TYPE: DNA
<213> ORGANISM: Homo sapiens

<400> SEQUENCE: 1518
cgacaatcta tatctgggt                                                        19

<210> SEQ ID NO 1519
<211> LENGTH: 19
<212> TYPE: DNA
<213> ORGANISM: Homo sapiens

<400> SEQUENCE: 1519
tctatatctg ggtgtggtg                                                        19

<210> SEQ ID NO 1520
<211> LENGTH: 19
<212> TYPE: DNA
<213> ORGANISM: Homo sapiens
```

```
<400> SEQUENCE: 1520
gagctccaag atcatggat                                               19

<210> SEQ ID NO 1521
<211> LENGTH: 19
<212> TYPE: DNA
<213> ORGANISM: Homo sapiens

<400> SEQUENCE: 1521
gatcatggat tccttcaag                                               19

<210> SEQ ID NO 1522
<211> LENGTH: 19
<212> TYPE: DNA
<213> ORGANISM: Homo sapiens

<400> SEQUENCE: 1522
gaacatggta cctcagcaa                                               19

<210> SEQ ID NO 1523
<211> LENGTH: 19
<212> TYPE: DNA
<213> ORGANISM: Homo sapiens

<400> SEQUENCE: 1523
catggtacct cagcaagcc                                               19

<210> SEQ ID NO 1524
<211> LENGTH: 19
<212> TYPE: DNA
<213> ORGANISM: Homo sapiens

<400> SEQUENCE: 1524
gatgcagatc aacgcagag                                               19

<210> SEQ ID NO 1525
<211> LENGTH: 19
<212> TYPE: DNA
<213> ORGANISM: Homo sapiens

<400> SEQUENCE: 1525
cgcagaggaa gtggtggtg                                               19

<210> SEQ ID NO 1526
<211> LENGTH: 19
<212> TYPE: DNA
<213> ORGANISM: Homo sapiens

<400> SEQUENCE: 1526
ggtggataac tcatcctta                                               19

<210> SEQ ID NO 1527
<211> LENGTH: 19
<212> TYPE: DNA
<213> ORGANISM: Homo sapiens

<400> SEQUENCE: 1527
ctcatcctta acaggagag                                               19

<210> SEQ ID NO 1528
<211> LENGTH: 19
<212> TYPE: DNA
<213> ORGANISM: Homo sapiens
```

```
<400> SEQUENCE: 1528
tatctgtttc ttctccacc                                                  19

<210> SEQ ID NO 1529
<211> LENGTH: 19
<212> TYPE: DNA
<213> ORGANISM: Homo sapiens

<400> SEQUENCE: 1529
ctgtgttgaa ggcactgcc                                                  19

<210> SEQ ID NO 1530
<211> LENGTH: 19
<212> TYPE: DNA
<213> ORGANISM: Homo sapiens

<400> SEQUENCE: 1530
tggagattga acacttcat                                                  19

<210> SEQ ID NO 1531
<211> LENGTH: 19
<212> TYPE: DNA
<213> ORGANISM: Homo sapiens

<400> SEQUENCE: 1531
cacttcatcc agctgatca                                                  19

<210> SEQ ID NO 1532
<211> LENGTH: 19
<212> TYPE: DNA
<213> ORGANISM: Homo sapiens

<400> SEQUENCE: 1532
gcgcatggca cggaagaac                                                  19

<210> SEQ ID NO 1533
<211> LENGTH: 19
<212> TYPE: DNA
<213> ORGANISM: Homo sapiens

<400> SEQUENCE: 1533
gaactgcctg gtgaagaac                                                  19

<210> SEQ ID NO 1534
<211> LENGTH: 19
<212> TYPE: DNA
<213> ORGANISM: Homo sapiens

<400> SEQUENCE: 1534
ctgcctggtg aagaacctg                                                  19

<210> SEQ ID NO 1535
<211> LENGTH: 19
<212> TYPE: DNA
<213> ORGANISM: Homo sapiens

<400> SEQUENCE: 1535
ccaaatccat gaggctgac                                                  19

<210> SEQ ID NO 1536
<211> LENGTH: 19
<212> TYPE: DNA
<213> ORGANISM: Homo sapiens
```

```
<400> SEQUENCE: 1536
atccatgagg ctgacacca                                                19

<210> SEQ ID NO 1537
<211> LENGTH: 19
<212> TYPE: DNA
<213> ORGANISM: Homo sapiens

<400> SEQUENCE: 1537
tccatgaggc tgacaccac                                                19

<210> SEQ ID NO 1538
<211> LENGTH: 19
<212> TYPE: DNA
<213> ORGANISM: Homo sapiens

<400> SEQUENCE: 1538
gatcagtctg gggccactt                                                19

<210> SEQ ID NO 1539
<211> LENGTH: 19
<212> TYPE: DNA
<213> ORGANISM: Homo sapiens

<400> SEQUENCE: 1539
acgatcccct acgtggacg                                                19

<210> SEQ ID NO 1540
<211> LENGTH: 19
<212> TYPE: DNA
<213> ORGANISM: Homo sapiens

<400> SEQUENCE: 1540
ttgctggtct ctgcaaccg                                                19

<210> SEQ ID NO 1541
<211> LENGTH: 19
<212> TYPE: DNA
<213> ORGANISM: Homo sapiens

<400> SEQUENCE: 1541
ggcaggacag gagaacatc                                                19

<210> SEQ ID NO 1542
<211> LENGTH: 19
<212> TYPE: DNA
<213> ORGANISM: Homo sapiens

<400> SEQUENCE: 1542
catctccgtg tctaagcgg                                                19

<210> SEQ ID NO 1543
<211> LENGTH: 19
<212> TYPE: DNA
<213> ORGANISM: Homo sapiens

<400> SEQUENCE: 1543
gcgggacaca gctggtgat                                                19

<210> SEQ ID NO 1544
<211> LENGTH: 19
<212> TYPE: DNA
<213> ORGANISM: Homo sapiens
```

```
<400> SEQUENCE: 1544
gtgcattgag ctctcctgt                                              19

<210> SEQ ID NO 1545
<211> LENGTH: 19
<212> TYPE: DNA
<213> ORGANISM: Homo sapiens

<400> SEQUENCE: 1545
aatgagagac agaaacccc                                              19

<210> SEQ ID NO 1546
<211> LENGTH: 19
<212> TYPE: DNA
<213> ORGANISM: Homo sapiens

<400> SEQUENCE: 1546
atgagagaca gaaacccca                                              19

<210> SEQ ID NO 1547
<211> LENGTH: 19
<212> TYPE: DNA
<213> ORGANISM: Homo sapiens

<400> SEQUENCE: 1547
tgagagacag aaaccccaa                                              19

<210> SEQ ID NO 1548
<211> LENGTH: 19
<212> TYPE: DNA
<213> ORGANISM: Homo sapiens

<400> SEQUENCE: 1548
accccaaggt ggcagagat                                              19

<210> SEQ ID NO 1549
<211> LENGTH: 19
<212> TYPE: DNA
<213> ORGANISM: Homo sapiens

<400> SEQUENCE: 1549
ccccaaggtg gcagagatt                                              19

<210> SEQ ID NO 1550
<211> LENGTH: 19
<212> TYPE: DNA
<213> ORGANISM: Homo sapiens

<400> SEQUENCE: 1550
ggtggcagag attcctttc                                              19

<210> SEQ ID NO 1551
<211> LENGTH: 19
<212> TYPE: DNA
<213> ORGANISM: Homo sapiens

<400> SEQUENCE: 1551
ctctaccaac aagtaccag                                              19

<210> SEQ ID NO 1552
<211> LENGTH: 19
<212> TYPE: DNA
<213> ORGANISM: Homo sapiens
```

```
<400> SEQUENCE: 1552
caagtaccag ctgtctatc                                                    19

<210> SEQ ID NO 1553
<211> LENGTH: 19
<212> TYPE: DNA
<213> ORGANISM: Homo sapiens

<400> SEQUENCE: 1553
gtaccagctg tctatccac                                                    19

<210> SEQ ID NO 1554
<211> LENGTH: 19
<212> TYPE: DNA
<213> ORGANISM: Homo sapiens

<400> SEQUENCE: 1554
ggagatcccg ctcgacaag                                                    19

<210> SEQ ID NO 1555
<211> LENGTH: 19
<212> TYPE: DNA
<213> ORGANISM: Homo sapiens

<400> SEQUENCE: 1555
ggagatgcaa gatgccttt                                                    19

<210> SEQ ID NO 1556
<211> LENGTH: 19
<212> TYPE: DNA
<213> ORGANISM: Homo sapiens

<400> SEQUENCE: 1556
gatgcctttc aaaatgcct                                                    19

<210> SEQ ID NO 1557
<211> LENGTH: 19
<212> TYPE: DNA
<213> ORGANISM: Homo sapiens

<400> SEQUENCE: 1557
aatgcctaca tggagctgg                                                    19

<210> SEQ ID NO 1558
<211> LENGTH: 19
<212> TYPE: DNA
<213> ORGANISM: Homo sapiens

<400> SEQUENCE: 1558
atgcctacat ggagctggg                                                    19

<210> SEQ ID NO 1559
<211> LENGTH: 19
<212> TYPE: DNA
<213> ORGANISM: Homo sapiens

<400> SEQUENCE: 1559
tgcctacatg gagctgggg                                                    19

<210> SEQ ID NO 1560
<211> LENGTH: 19
<212> TYPE: DNA
<213> ORGANISM: Homo sapiens
```

```
<400> SEQUENCE: 1560
ctgaatctgc catctggaa                                                  19

<210> SEQ ID NO 1561
<211> LENGTH: 19
<212> TYPE: DNA
<213> ORGANISM: Homo sapiens

<400> SEQUENCE: 1561
tctgccatct ggaaagttt                                                  19

<210> SEQ ID NO 1562
<211> LENGTH: 19
<212> TYPE: DNA
<213> ORGANISM: Homo sapiens

<400> SEQUENCE: 1562
agtttcctcg ggcttcaa                                                   19

<210> SEQ ID NO 1563
<211> LENGTH: 19
<212> TYPE: DNA
<213> ORGANISM: Homo sapiens

<400> SEQUENCE: 1563
gtttcctcgg ggcttcaaa                                                  19

<210> SEQ ID NO 1564
<211> LENGTH: 19
<212> TYPE: DNA
<213> ORGANISM: Homo sapiens

<400> SEQUENCE: 1564
attcgacacg gatgagctg                                                  19

<210> SEQ ID NO 1565
<211> LENGTH: 19
<212> TYPE: DNA
<213> ORGANISM: Homo sapiens

<400> SEQUENCE: 1565
ttcgacacgg atgagctga                                                  19

<210> SEQ ID NO 1566
<211> LENGTH: 19
<212> TYPE: DNA
<213> ORGANISM: Homo sapiens

<400> SEQUENCE: 1566
ctttcccacg gagaagctt                                                  19

<210> SEQ ID NO 1567
<211> LENGTH: 19
<212> TYPE: DNA
<213> ORGANISM: Homo sapiens

<400> SEQUENCE: 1567
gctttgcttt gtggggctc                                                  19

<210> SEQ ID NO 1568
<211> LENGTH: 19
<212> TYPE: DNA
<213> ORGANISM: Homo sapiens
```

```
<400> SEQUENCE: 1568
gcgcaggcat caaggtgat                                          19

<210> SEQ ID NO 1569
<211> LENGTH: 19
<212> TYPE: DNA
<213> ORGANISM: Homo sapiens

<400> SEQUENCE: 1569
ggtgatcatg gtaaccggg                                          19

<210> SEQ ID NO 1570
<211> LENGTH: 19
<212> TYPE: DNA
<213> ORGANISM: Homo sapiens

<400> SEQUENCE: 1570
ccggggatca ccctatcac                                          19

<210> SEQ ID NO 1571
<211> LENGTH: 19
<212> TYPE: DNA
<213> ORGANISM: Homo sapiens

<400> SEQUENCE: 1571
ggccattgcc aaaggcgtg                                          19

<210> SEQ ID NO 1572
<211> LENGTH: 19
<212> TYPE: DNA
<213> ORGANISM: Homo sapiens

<400> SEQUENCE: 1572
aggcgtgggc atcatatca                                          19

<210> SEQ ID NO 1573
<211> LENGTH: 19
<212> TYPE: DNA
<213> ORGANISM: Homo sapiens

<400> SEQUENCE: 1573
ggcgtgggca tcatatcag                                          19

<210> SEQ ID NO 1574
<211> LENGTH: 19
<212> TYPE: DNA
<213> ORGANISM: Homo sapiens

<400> SEQUENCE: 1574
cgagactgtg gaggacatt                                          19

<210> SEQ ID NO 1575
<211> LENGTH: 19
<212> TYPE: DNA
<213> ORGANISM: Homo sapiens

<400> SEQUENCE: 1575
cattcccatg agtcaagtc                                          19

<210> SEQ ID NO 1576
<211> LENGTH: 19
<212> TYPE: DNA
<213> ORGANISM: Homo sapiens
```

-continued

```
<400> SEQUENCE: 1576
gtcaacccca gagaagcca                                                    19

<210> SEQ ID NO 1577
<211> LENGTH: 19
<212> TYPE: DNA
<213> ORGANISM: Homo sapiens

<400> SEQUENCE: 1577
ccccagagaa gccaaggca                                                    19

<210> SEQ ID NO 1578
<211> LENGTH: 19
<212> TYPE: DNA
<213> ORGANISM: Homo sapiens

<400> SEQUENCE: 1578
ggacatgaca tcggagcag                                                    19

<210> SEQ ID NO 1579
<211> LENGTH: 19
<212> TYPE: DNA
<213> ORGANISM: Homo sapiens

<400> SEQUENCE: 1579
gaaccacaca gagatcgtc                                                    19

<210> SEQ ID NO 1580
<211> LENGTH: 19
<212> TYPE: DNA
<213> ORGANISM: Homo sapiens

<400> SEQUENCE: 1580
ccacacagag atcgtcttt                                                    19

<210> SEQ ID NO 1581
<211> LENGTH: 19
<212> TYPE: DNA
<213> ORGANISM: Homo sapiens

<400> SEQUENCE: 1581
cgtctcccca gcagaagct                                                    19

<210> SEQ ID NO 1582
<211> LENGTH: 19
<212> TYPE: DNA
<213> ORGANISM: Homo sapiens

<400> SEQUENCE: 1582
gctcatcatt gtggaggga                                                    19

<210> SEQ ID NO 1583
<211> LENGTH: 19
<212> TYPE: DNA
<213> ORGANISM: Homo sapiens

<400> SEQUENCE: 1583
cgactcccct gcattgaag                                                    19

<210> SEQ ID NO 1584
<211> LENGTH: 19
<212> TYPE: DNA
<213> ORGANISM: Homo sapiens
```

```
<400> SEQUENCE: 1584
gaaggctgac attggcatt                                        19

<210> SEQ ID NO 1585
<211> LENGTH: 19
<212> TYPE: DNA
<213> ORGANISM: Homo sapiens

<400> SEQUENCE: 1585
ggctgacatt ggcattgcc                                        19

<210> SEQ ID NO 1586
<211> LENGTH: 19
<212> TYPE: DNA
<213> ORGANISM: Homo sapiens

<400> SEQUENCE: 1586
gcaggcagcc gacatgatc                                        19

<210> SEQ ID NO 1587
<211> LENGTH: 19
<212> TYPE: DNA
<213> ORGANISM: Homo sapiens

<400> SEQUENCE: 1587
ctttgcctcc atcgtcacg                                        19

<210> SEQ ID NO 1588
<211> LENGTH: 19
<212> TYPE: DNA
<213> ORGANISM: Homo sapiens

<400> SEQUENCE: 1588
cttgaagaaa tccatcgcc                                        19

<210> SEQ ID NO 1589
<211> LENGTH: 19
<212> TYPE: DNA
<213> ORGANISM: Homo sapiens

<400> SEQUENCE: 1589
gaaatccatc gcctacacc                                        19

<210> SEQ ID NO 1590
<211> LENGTH: 19
<212> TYPE: DNA
<213> ORGANISM: Homo sapiens

<400> SEQUENCE: 1590
atccatcgcc tacaccctg                                        19

<210> SEQ ID NO 1591
<211> LENGTH: 19
<212> TYPE: DNA
<213> ORGANISM: Homo sapiens

<400> SEQUENCE: 1591
tccatcgcct acaccctga                                        19

<210> SEQ ID NO 1592
<211> LENGTH: 19
<212> TYPE: DNA
<213> ORGANISM: Homo sapiens
```

```
<400> SEQUENCE: 1592
actcccagac ggacaagct                                            19

<210> SEQ ID NO 1593
<211> LENGTH: 19
<212> TYPE: DNA
<213> ORGANISM: Homo sapiens

<400> SEQUENCE: 1593
ctcccagacg gacaagctg                                            19

<210> SEQ ID NO 1594
<211> LENGTH: 19
<212> TYPE: DNA
<213> ORGANISM: Homo sapiens

<400> SEQUENCE: 1594
gctggtgaat gagaggctc                                            19

<210> SEQ ID NO 1595
<211> LENGTH: 19
<212> TYPE: DNA
<213> ORGANISM: Homo sapiens

<400> SEQUENCE: 1595
tgagaggctc atcagcatg                                            19

<210> SEQ ID NO 1596
<211> LENGTH: 19
<212> TYPE: DNA
<213> ORGANISM: Homo sapiens

<400> SEQUENCE: 1596
cggtttcctg ccatcacgg                                            19

<210> SEQ ID NO 1597
<211> LENGTH: 19
<212> TYPE: DNA
<213> ORGANISM: Homo sapiens

<400> SEQUENCE: 1597
tccgcctcga ctgggatga                                            19

<210> SEQ ID NO 1598
<211> LENGTH: 19
<212> TYPE: DNA
<213> ORGANISM: Homo sapiens

<400> SEQUENCE: 1598
tgatctggag gacagctat                                            19

<210> SEQ ID NO 1599
<211> LENGTH: 19
<212> TYPE: DNA
<213> ORGANISM: Homo sapiens

<400> SEQUENCE: 1599
ggtggtggag ttcacgtgc                                            19

<210> SEQ ID NO 1600
<211> LENGTH: 19
<212> TYPE: DNA
<213> ORGANISM: Homo sapiens
```

```
<400> SEQUENCE: 1600
ctcagtcttc cagcagggc                                              19

<210> SEQ ID NO 1601
<211> LENGTH: 19
<212> TYPE: DNA
<213> ORGANISM: Homo sapiens

<400> SEQUENCE: 1601
caagatcctg atttttggg                                              19

<210> SEQ ID NO 1602
<211> LENGTH: 19
<212> TYPE: DNA
<213> ORGANISM: Homo sapiens

<400> SEQUENCE: 1602
gatcctgatt tttgggctc                                              19

<210> SEQ ID NO 1603
<211> LENGTH: 19
<212> TYPE: DNA
<213> ORGANISM: Homo sapiens

<400> SEQUENCE: 1603
agtcacctgg tggttctgc                                              19

<210> SEQ ID NO 1604
<211> LENGTH: 19
<212> TYPE: DNA
<213> ORGANISM: Homo sapiens

<400> SEQUENCE: 1604
gtcacctggt ggttctgcg                                              19

<210> SEQ ID NO 1605
<211> LENGTH: 19
<212> TYPE: DNA
<213> ORGANISM: Homo sapiens

<400> SEQUENCE: 1605
agctcatcct gcggcggta                                              19

<210> SEQ ID NO 1606
<211> LENGTH: 19
<212> TYPE: DNA
<213> ORGANISM: Homo sapiens

<400> SEQUENCE: 1606
gctcatcctg cggcggtat                                              19

<210> SEQ ID NO 1607
<211> LENGTH: 19
<212> TYPE: DNA
<213> ORGANISM: Homo sapiens

<400> SEQUENCE: 1607 gatggggac aagaaagat                                               19

<210> SEQ ID NO 1608
<211> LENGTH: 19
<212> TYPE: DNA
<213> ORGANISM: Homo sapiens
```

<400> SEQUENCE: 1608
gaaagatgac aaggactca                                                    19

<210> SEQ ID NO 1609
<211> LENGTH: 19
<212> TYPE: DNA
<213> ORGANISM: Homo sapiens

<400> SEQUENCE: 1609
agatgacaag gactcaccc                                                    19

<210> SEQ ID NO 1610
<211> LENGTH: 19
<212> TYPE: DNA
<213> ORGANISM: Homo sapiens

<400> SEQUENCE: 1610
gatgacaagg actcaccca                                                    19

<210> SEQ ID NO 1611
<211> LENGTH: 19
<212> TYPE: DNA
<213> ORGANISM: Homo sapiens

<400> SEQUENCE: 1611
ggactcaccc aagaagaac                                                    19

<210> SEQ ID NO 1612
<211> LENGTH: 19
<212> TYPE: DNA
<213> ORGANISM: Homo sapiens

<400> SEQUENCE: 1612
gaagaacaag ggcaaggag                                                    19

<210> SEQ ID NO 1613
<211> LENGTH: 19
<212> TYPE: DNA
<213> ORGANISM: Homo sapiens

<400> SEQUENCE: 1613
gaacaagggc aaggagcgc                                                    19

<210> SEQ ID NO 1614
<211> LENGTH: 19
<212> TYPE: DNA
<213> ORGANISM: Homo sapiens

<400> SEQUENCE: 1614
gaaggaggtg gctatgaca                                                    19

<210> SEQ ID NO 1615
<211> LENGTH: 19
<212> TYPE: DNA
<213> ORGANISM: Homo sapiens

<400> SEQUENCE: 1615
ggaggtggct atgacagag                                                    19

<210> SEQ ID NO 1616
<211> LENGTH: 19
<212> TYPE: DNA
<213> ORGANISM: Homo sapiens

```
<400> SEQUENCE: 1616
gatgtcagtg gaagaggtc                                            19

<210> SEQ ID NO 1617
<211> LENGTH: 19
<212> TYPE: DNA
<213> ORGANISM: Homo sapiens

<400> SEQUENCE: 1617
gaggtctgcc ggaaataca                                            19

<210> SEQ ID NO 1618
<211> LENGTH: 19
<212> TYPE: DNA
<213> ORGANISM: Homo sapiens

<400> SEQUENCE: 1618
atacaacaca gactgtgtg                                            19

<210> SEQ ID NO 1619
<211> LENGTH: 19
<212> TYPE: DNA
<213> ORGANISM: Homo sapiens

<400> SEQUENCE: 1619
tacaacacag actgtgtgc                                            19

<210> SEQ ID NO 1620
<211> LENGTH: 19
<212> TYPE: DNA
<213> ORGANISM: Homo sapiens

<400> SEQUENCE: 1620
cacagactgt gtgcagggt                                            19

<210> SEQ ID NO 1621
<211> LENGTH: 19
<212> TYPE: DNA
<213> ORGANISM: Homo sapiens

<400> SEQUENCE: 1621
gttttgccgg cagctcttc                                            19

<210> SEQ ID NO 1622
<211> LENGTH: 19
<212> TYPE: DNA
<213> ORGANISM: Homo sapiens

<400> SEQUENCE: 1622
cctgtacctg ggcatcgtg                                            19

<210> SEQ ID NO 1623
<211> LENGTH: 19
<212> TYPE: DNA
<213> ORGANISM: Homo sapiens

<400> SEQUENCE: 1623
gagctccaag atcatggag                                            19

<210> SEQ ID NO 1624
<211> LENGTH: 19
<212> TYPE: DNA
<213> ORGANISM: Homo sapiens
```

```
<400> SEQUENCE: 1624
gatcatggag tccttcaag                                              19

<210> SEQ ID NO 1625
<211> LENGTH: 19
<212> TYPE: DNA
<213> ORGANISM: Homo sapiens

<400> SEQUENCE: 1625
gaacatggtg ccccagcaa                                              19

<210> SEQ ID NO 1626
<211> LENGTH: 19
<212> TYPE: DNA
<213> ORGANISM: Homo sapiens

<400> SEQUENCE: 1626
ggtgagaaga tgcaggtga                                              19

<210> SEQ ID NO 1627
<211> LENGTH: 19
<212> TYPE: DNA
<213> ORGANISM: Homo sapiens

<400> SEQUENCE: 1627
gatgcaggtg aacgctgag                                              19

<210> SEQ ID NO 1628
<211> LENGTH: 19
<212> TYPE: DNA
<213> ORGANISM: Homo sapiens

<400> SEQUENCE: 1628
ggtggacaac tcctccctg                                              19

<210> SEQ ID NO 1629
<211> LENGTH: 19
<212> TYPE: DNA
<213> ORGANISM: Homo sapiens

<400> SEQUENCE: 1629
ctcctccctg actggcgaa                                              19

<210> SEQ ID NO 1630
<211> LENGTH: 19
<212> TYPE: DNA
<213> ORGANISM: Homo sapiens

<400> SEQUENCE: 1630 cccctttggag actcggaac                                             19

<210> SEQ ID NO 1631
<211> LENGTH: 19
<212> TYPE: DNA
<213> ORGANISM: Homo sapiens

<400> SEQUENCE: 1631
catcaccttc ttttccacc                                              19

<210> SEQ ID NO 1632
<211> LENGTH: 19
<212> TYPE: DNA
<213> ORGANISM: Homo sapiens
```

-continued

```
<400> SEQUENCE: 1632
ctgtgtggaa ggcacggct                                                19

<210> SEQ ID NO 1633
<211> LENGTH: 19
<212> TYPE: DNA
<213> ORGANISM: Homo sapiens

<400> SEQUENCE: 1633
tgtcccagag ggtctgctg                                                19

<210> SEQ ID NO 1634
<211> LENGTH: 19
<212> TYPE: DNA
<213> ORGANISM: Homo sapiens

<400> SEQUENCE: 1634
gaactgcctg gtgaagaac                                                19

<210> SEQ ID NO 1635
<211> LENGTH: 19
<212> TYPE: DNA
<213> ORGANISM: Homo sapiens

<400> SEQUENCE: 1635
ctgcctggtg aagaacctg                                                19

<210> SEQ ID NO 1636
<211> LENGTH: 19
<212> TYPE: DNA
<213> ORGANISM: Homo sapiens

<400> SEQUENCE: 1636
gaacctggag gctgtagaa                                                19

<210> SEQ ID NO 1637
<211> LENGTH: 19
<212> TYPE: DNA
<213> ORGANISM: Homo sapiens

<400> SEQUENCE: 1637
cctggaggct gtagaaacc                                                19

<210> SEQ ID NO 1638
<211> LENGTH: 19
<212> TYPE: DNA
<213> ORGANISM: Homo sapiens

<400> SEQUENCE: 1638
gacagggacc ctcactcag                                                19

<210> SEQ ID NO 1639
<211> LENGTH: 19
<212> TYPE: DNA
<213> ORGANISM: Homo sapiens

<400> SEQUENCE: 1639
ccagatccac gaggctgac                                                19

<210> SEQ ID NO 1640
<211> LENGTH: 19
<212> TYPE: DNA
<213> ORGANISM: Homo sapiens
```

<400> SEQUENCE: 1640
gagttcgcac acctgggtg                                        19

<210> SEQ ID NO 1641
<211> LENGTH: 19
<212> TYPE: DNA
<213> ORGANISM: Homo sapiens

<400> SEQUENCE: 1641
tcgcgctgtc ttcaagggt                                        19

<210> SEQ ID NO 1642
<211> LENGTH: 19
<212> TYPE: DNA
<213> ORGANISM: Homo sapiens

<400> SEQUENCE: 1642
gggtggtcag gacaacatc                                        19

<210> SEQ ID NO 1643
<211> LENGTH: 19
<212> TYPE: DNA
<213> ORGANISM: Homo sapiens

<400> SEQUENCE: 1643
catccctgtg ctcaagagg                                        19

<210> SEQ ID NO 1644
<211> LENGTH: 19
<212> TYPE: DNA
<213> ORGANISM: Homo sapiens

<400> SEQUENCE: 1644
gagggatgtg gctggggat                                        19

<210> SEQ ID NO 1645
<211> LENGTH: 19
<212> TYPE: DNA
<213> ORGANISM: Homo sapiens

<400> SEQUENCE: 1645
gtgcatcgag ctgtcctct                                        19

<210> SEQ ID NO 1646
<211> LENGTH: 19
<212> TYPE: DNA
<213> ORGANISM: Homo sapiens

<400> SEQUENCE: 1646
gctgatgcgt gaacgcaac                                        19

<210> SEQ ID NO 1647
<211> LENGTH: 19
<212> TYPE: DNA
<213> ORGANISM: Homo sapiens

<400> SEQUENCE: 1647
cgcaacaaga aagtggctg                                        19

<210> SEQ ID NO 1648
<211> LENGTH: 19
<212> TYPE: DNA
<213> ORGANISM: Homo sapiens

```
<400> SEQUENCE: 1648
caagaaagtg gctgagatt                                                  19

<210> SEQ ID NO 1649
<211> LENGTH: 19
<212> TYPE: DNA
<213> ORGANISM: Homo sapiens

<400> SEQUENCE: 1649
gaaagtggct gagattccc                                                  19

<210> SEQ ID NO 1650
<211> LENGTH: 19
<212> TYPE: DNA
<213> ORGANISM: Homo sapiens

<400> SEQUENCE: 1650
agtggctgag attcccttc                                                  19

<210> SEQ ID NO 1651
<211> LENGTH: 19
<212> TYPE: DNA
<213> ORGANISM: Homo sapiens

<400> SEQUENCE: 1651
gtggctgaga ttcccttca                                                  19

<210> SEQ ID NO 1652
<211> LENGTH: 19
<212> TYPE: DNA
<213> ORGANISM: Homo sapiens

<400> SEQUENCE: 1652
ttccaccaac aaataccag                                                  19

<210> SEQ ID NO 1653
<211> LENGTH: 19
<212> TYPE: DNA
<213> ORGANISM: Homo sapiens

<400> SEQUENCE: 1653
caaataccag ctctccatc                                                  19

<210> SEQ ID NO 1654
<211> LENGTH: 19
<212> TYPE: DNA
<213> ORGANISM: Homo sapiens

<400> SEQUENCE: 1654
ataccagctc tccatccat                                                  19

<210> SEQ ID NO 1655
<211> LENGTH: 19
<212> TYPE: DNA
<213> ORGANISM: Homo sapiens

<400> SEQUENCE: 1655
taccagctct ccatccatg                                                  19

<210> SEQ ID NO 1656
<211> LENGTH: 19
<212> TYPE: DNA
<213> ORGANISM: Homo sapiens
```

```
<400> SEQUENCE: 1656
cgacaaccga tacctgctg                                              19

<210> SEQ ID NO 1657
<211> LENGTH: 19
<212> TYPE: DNA
<213> ORGANISM: Homo sapiens

<400> SEQUENCE: 1657
ccgatacctg ctggtgatg                                              19

<210> SEQ ID NO 1658
<211> LENGTH: 19
<212> TYPE: DNA
<213> ORGANISM: Homo sapiens

<400> SEQUENCE: 1658
atgaaggagg ccttccaga                                              19

<210> SEQ ID NO 1659
<211> LENGTH: 19
<212> TYPE: DNA
<213> ORGANISM: Homo sapiens

<400> SEQUENCE: 1659
tgaaggaggc cttccagaa                                              19

<210> SEQ ID NO 1660
<211> LENGTH: 19
<212> TYPE: DNA
<213> ORGANISM: Homo sapiens

<400> SEQUENCE: 1660
ggaggccttc cagaatgcc                                              19

<210> SEQ ID NO 1661
<211> LENGTH: 19
<212> TYPE: DNA
<213> ORGANISM: Homo sapiens

<400> SEQUENCE: 1661
tgcctacctt gagctcggt                                              19

<210> SEQ ID NO 1662
<211> LENGTH: 19
<212> TYPE: DNA
<213> ORGANISM: Homo sapiens

<400> SEQUENCE: 1662
gggctttgcc ttcgactgt                                              19

<210> SEQ ID NO 1663
<211> LENGTH: 19
<212> TYPE: DNA
<213> ORGANISM: Homo sapiens

<400> SEQUENCE: 1663
cttcaccacg gacaacctc                                              19

<210> SEQ ID NO 1664
<211> LENGTH: 19
<212> TYPE: DNA
<213> ORGANISM: Homo sapiens
```

```
<400> SEQUENCE: 1664
cctctgcttt gtgggcctc                                              19

<210> SEQ ID NO 1665
<211> LENGTH: 19
<212> TYPE: DNA
<213> ORGANISM: Homo sapiens

<400> SEQUENCE: 1665
ggtcatcatg gtcaccggc                                              19

<210> SEQ ID NO 1666
<211> LENGTH: 19
<212> TYPE: DNA
<213> ORGANISM: Homo sapiens

<400> SEQUENCE: 1666
ggccattgcc aagggtgtg                                              19

<210> SEQ ID NO 1667
<211> LENGTH: 19
<212> TYPE: DNA
<213> ORGANISM: Homo sapiens

<400> SEQUENCE: 1667
gggtgtgggc atcatctct                                              19

<210> SEQ ID NO 1668
<211> LENGTH: 19
<212> TYPE: DNA
<213> ORGANISM: Homo sapiens

<400> SEQUENCE: 1668
cgagactgtg gaggacatc                                              19

<210> SEQ ID NO 1669
<211> LENGTH: 19
<212> TYPE: DNA
<213> ORGANISM: Homo sapiens

<400> SEQUENCE: 1669
cattcccgtc agccaggtt                                              19

<210> SEQ ID NO 1670
<211> LENGTH: 19
<212> TYPE: DNA
<213> ORGANISM: Homo sapiens

<400> SEQUENCE: 1670
ggacttcacc tccgagcaa                                              19

<210> SEQ ID NO 1671
<211> LENGTH: 19
<212> TYPE: DNA
<213> ORGANISM: Homo sapiens

<400> SEQUENCE: 1671
atcgacgaga tcctgcaga                                              19

<210> SEQ ID NO 1672
<211> LENGTH: 19
<212> TYPE: DNA
<213> ORGANISM: Homo sapiens
```

```
<400> SEQUENCE: 1672
tcgacgagat cctgcagaa                                               19

<210> SEQ ID NO 1673
<211> LENGTH: 19
<212> TYPE: DNA
<213> ORGANISM: Homo sapiens

<400> SEQUENCE: 1673
tcacaccgag atcgtcttc                                               19

<210> SEQ ID NO 1674
<211> LENGTH: 19
<212> TYPE: DNA
<213> ORGANISM: Homo sapiens

<400> SEQUENCE: 1674
gctcatcatt gtggagggc                                               19

<210> SEQ ID NO 1675
<211> LENGTH: 19
<212> TYPE: DNA
<213> ORGANISM: Homo sapiens

<400> SEQUENCE: 1675
ttgtggctgt gaccgggga                                               19

<210> SEQ ID NO 1676
<211> LENGTH: 19
<212> TYPE: DNA
<213> ORGANISM: Homo sapiens

<400> SEQUENCE: 1676
gaaggccgac attggggtg                                               19

<210> SEQ ID NO 1677
<211> LENGTH: 19
<212> TYPE: DNA
<213> ORGANISM: Homo sapiens

<400> SEQUENCE: 1677
gcaggcagct gacatgatc                                               19

<210> SEQ ID NO 1678
<211> LENGTH: 19
<212> TYPE: DNA
<213> ORGANISM: Homo sapiens

<400> SEQUENCE: 1678
ctttgcctcc atcgtcaca                                               19

<210> SEQ ID NO 1679
<211> LENGTH: 19
<212> TYPE: DNA
<213> ORGANISM: Homo sapiens

<400> SEQUENCE: 1679
cctaaagaag tccattgcc                                               19

<210> SEQ ID NO 1680
<211> LENGTH: 19
<212> TYPE: DNA
<213> ORGANISM: Homo sapiens
```

```
<400> SEQUENCE: 1680
agaagtccat tgcctacac                                              19

<210> SEQ ID NO 1681
<211> LENGTH: 19
<212> TYPE: DNA
<213> ORGANISM: Homo sapiens

<400> SEQUENCE: 1681
gaagtccatt gcctacacc                                              19

<210> SEQ ID NO 1682
<211> LENGTH: 19
<212> TYPE: DNA
<213> ORGANISM: Homo sapiens

<400> SEQUENCE: 1682
gtccattgcc tacaccctg                                              19

<210> SEQ ID NO 1683
<211> LENGTH: 19
<212> TYPE: DNA
<213> ORGANISM: Homo sapiens

<400> SEQUENCE: 1683
tatcccggag atcacgccc                                              19

<210> SEQ ID NO 1684
<211> LENGTH: 19
<212> TYPE: DNA
<213> ORGANISM: Homo sapiens

<400> SEQUENCE: 1684
agcgacatca tgaagagac                                              19

<210> SEQ ID NO 1685
<211> LENGTH: 19
<212> TYPE: DNA
<213> ORGANISM: Homo sapiens

<400> SEQUENCE: 1685
gcgacatcat gaagagaca                                              19

<210> SEQ ID NO 1686
<211> LENGTH: 19
<212> TYPE: DNA
<213> ORGANISM: Homo sapiens

<400> SEQUENCE: 1686
cccgcggacg gacaaattg                                              19

<210> SEQ ID NO 1687
<211> LENGTH: 19
<212> TYPE: DNA
<213> ORGANISM: Homo sapiens

<400> SEQUENCE: 1687
attggtcaat gagagactc                                              19

<210> SEQ ID NO 1688
<211> LENGTH: 19
<212> TYPE: DNA
<213> ORGANISM: Homo sapiens
```

```
<400> SEQUENCE: 1688
ttggtcaatg agagactca                                              19

<210> SEQ ID NO 1689
<211> LENGTH: 19
<212> TYPE: DNA
<213> ORGANISM: Homo sapiens

<400> SEQUENCE: 1689
tgagagactc atcagcatg                                              19

<210> SEQ ID NO 1690
<211> LENGTH: 19
<212> TYPE: DNA
<213> ORGANISM: Homo sapiens

<400> SEQUENCE: 1690
tgatccaggc tctcggtgg                                              19

<210> SEQ ID NO 1691
<211> LENGTH: 19
<212> TYPE: DNA
<213> ORGANISM: Homo sapiens

<400> SEQUENCE: 1691
aatggcttct tgcccggca                                              19

<210> SEQ ID NO 1692
<211> LENGTH: 19
<212> TYPE: DNA
<213> ORGANISM: Homo sapiens

<400> SEQUENCE: 1692
atggcttctt gcccggcaa                                              19

<210> SEQ ID NO 1693
<211> LENGTH: 19
<212> TYPE: DNA
<213> ORGANISM: Homo sapiens

<400> SEQUENCE: 1693
tggcttcttg cccggcaac                                              19

<210> SEQ ID NO 1694
<211> LENGTH: 19
<212> TYPE: DNA
<213> ORGANISM: Homo sapiens

<400> SEQUENCE: 1694
tgacctggaa gacagttac                                              19

<210> SEQ ID NO 1695
<211> LENGTH: 19
<212> TYPE: DNA
<213> ORGANISM: Homo sapiens

<400> SEQUENCE: 1695
gacagttacg ggcagcagt                                              19

<210> SEQ ID NO 1696
<211> LENGTH: 19
<212> TYPE: DNA
<213> ORGANISM: Homo sapiens
```

```
<400> SEQUENCE: 1696
ggtggtggag ttcacctgc                                               19

<210> SEQ ID NO 1697
<211> LENGTH: 19
<212> TYPE: DNA
<213> ORGANISM: Homo sapiens

<400> SEQUENCE: 1697
gaacaagatc ctgatcttc                                               19

<210> SEQ ID NO 1698
<211> LENGTH: 19
<212> TYPE: DNA
<213> ORGANISM: Homo sapiens

<400> SEQUENCE: 1698
caagatcctg atcttcggg                                               19

<210> SEQ ID NO 1699
<211> LENGTH: 19
<212> TYPE: DNA
<213> ORGANISM: Homo sapiens

<400> SEQUENCE: 1699
gatcctgatc ttcgggctg                                               19

<210> SEQ ID NO 1700
<211> LENGTH: 19
<212> TYPE: DNA
<213> ORGANISM: Homo sapiens

<400> SEQUENCE: 1700
gcccagctgg tggttctgt                                               19

<210> SEQ ID NO 1701
<211> LENGTH: 19
<212> TYPE: DNA
<213> ORGANISM: Homo sapiens

<400> SEQUENCE: 1701
atccgcaaac tcatcctgc                                               19

<210> SEQ ID NO 1702
<211> LENGTH: 19
<212> TYPE: DNA
<213> ORGANISM: Homo sapiens

<400> SEQUENCE: 1702
tccgcaaact catcctgcg                                               19

<210> SEQ ID NO 1703
<211> LENGTH: 19
<212> TYPE: DNA
<213> ORGANISM: Homo sapiens

<400> SEQUENCE: 1703
actcatcctg cgcaggaac                                               19

<210> SEQ ID NO 1704
<211> LENGTH: 19
<212> TYPE: DNA
<213> ORGANISM: Homo sapiens
```

-continued

```
<400> SEQUENCE: 1704
ctcatcctgc gcaggaacc                                                19

<210> SEQ ID NO 1705
<211> LENGTH: 19
<212> TYPE: DNA
<213> ORGANISM: Homo sapiens

<400> SEQUENCE: 1705
ggaaacctac tactgacct                                                19

<210> SEQ ID NO 1706
<211> LENGTH: 19
<212> TYPE: DNA
<213> ORGANISM: Homo sapiens

<400> SEQUENCE: 1706
aaattaaatt ttaagtgac                                                19

<210> SEQ ID NO 1707
<211> LENGTH: 19
<212> TYPE: DNA
<213> ORGANISM: Homo sapiens

<400> SEQUENCE: 1707
aattaaattt taagtgaca                                                19

<210> SEQ ID NO 1708
<211> LENGTH: 19
<212> TYPE: DNA
<213> ORGANISM: Homo sapiens

<400> SEQUENCE: 1708
attaaatttt aagtgacac                                                19

<210> SEQ ID NO 1709
<211> LENGTH: 19
<212> TYPE: DNA
<213> ORGANISM: Homo sapiens

<400> SEQUENCE: 1709 ttaaattta agtgacact                                                 19

<210> SEQ ID NO 1710
<211> LENGTH: 19
<212> TYPE: DNA
<213> ORGANISM: Homo sapiens

<400> SEQUENCE: 1710
gaaattcatc tggaactca                                                19

<210> SEQ ID NO 1711
<211> LENGTH: 19
<212> TYPE: DNA
<213> ORGANISM: Homo sapiens

<400> SEQUENCE: 1711
attcatctgg aactcagag                                                19

<210> SEQ ID NO 1712
<211> LENGTH: 19
<212> TYPE: DNA
<213> ORGANISM: Homo sapiens
```

```
<400> SEQUENCE: 1712
ttcatctgga actcagaga                                            19

<210> SEQ ID NO 1713
<211> LENGTH: 19
<212> TYPE: DNA
<213> ORGANISM: Homo sapiens

<400> SEQUENCE: 1713
ctcagagaag aaggagttt                                            19

<210> SEQ ID NO 1714
<211> LENGTH: 19
<212> TYPE: DNA
<213> ORGANISM: Homo sapiens

<400> SEQUENCE: 1714
gaaggagttt ctgggcagg                                            19

<210> SEQ ID NO 1715
<211> LENGTH: 19
<212> TYPE: DNA
<213> ORGANISM: Homo sapiens

<400> SEQUENCE: 1715
ggagtttctg ggcaggacc                                            19

<210> SEQ ID NO 1716
<211> LENGTH: 19
<212> TYPE: DNA
<213> ORGANISM: Homo sapiens

<400> SEQUENCE: 1716
gatccttcta ttctacgta                                            19

<210> SEQ ID NO 1717
<211> LENGTH: 19
<212> TYPE: DNA
<213> ORGANISM: Homo sapiens

<400> SEQUENCE: 1717
tattttatgg ctgcctggc                                            19

<210> SEQ ID NO 1718
<211> LENGTH: 19
<212> TYPE: DNA
<213> ORGANISM: Homo sapiens

<400> SEQUENCE: 1718
ccatccaagt gatgctgct                                            19

<210> SEQ ID NO 1719
<211> LENGTH: 19
<212> TYPE: DNA
<213> ORGANISM: Homo sapiens

<400> SEQUENCE: 1719
gtgatgctgc tcaccatca                                            19

<210> SEQ ID NO 1720
<211> LENGTH: 19
<212> TYPE: DNA
<213> ORGANISM: Homo sapiens
```

```
<400> SEQUENCE: 1720
tttaagccca catatcagg                                                    19

<210> SEQ ID NO 1721
<211> LENGTH: 19
<212> TYPE: DNA
<213> ORGANISM: Homo sapiens

<400> SEQUENCE: 1721
gcccacatat caggaccga                                                    19

<210> SEQ ID NO 1722
<211> LENGTH: 19
<212> TYPE: DNA
<213> ORGANISM: Homo sapiens

<400> SEQUENCE: 1722
cacagattcc tcagatcca                                                    19

<210> SEQ ID NO 1723
<211> LENGTH: 19
<212> TYPE: DNA
<213> ORGANISM: Homo sapiens

<400> SEQUENCE: 1723
gactgaaatt tcctttcgt                                                    19

<210> SEQ ID NO 1724
<211> LENGTH: 19
<212> TYPE: DNA
<213> ORGANISM: Homo sapiens

<400> SEQUENCE: 1724
atttcctttc gtcctaatg                                                    19

<210> SEQ ID NO 1725
<211> LENGTH: 19
<212> TYPE: DNA
<213> ORGANISM: Homo sapiens

<400> SEQUENCE: 1725
tttcctttcg tcctaatga                                                    19

<210> SEQ ID NO 1726
<211> LENGTH: 19
<212> TYPE: DNA
<213> ORGANISM: Homo sapiens

<400> SEQUENCE: 1726
tgatcccaag agctatgag                                                    19

<210> SEQ ID NO 1727
<211> LENGTH: 19
<212> TYPE: DNA
<213> ORGANISM: Homo sapiens

<400> SEQUENCE: 1727
gagctatgag gcatatgta                                                    19

<210> SEQ ID NO 1728
<211> LENGTH: 19
<212> TYPE: DNA
<213> ORGANISM: Homo sapiens
```

<400> SEQUENCE: 1728
catagttagg ttcctggaa                                          19

<210> SEQ ID NO 1729
<211> LENGTH: 19
<212> TYPE: DNA
<213> ORGANISM: Homo sapiens

<400> SEQUENCE: 1729
aagtacaaag attcagccc                                          19

<210> SEQ ID NO 1730
<211> LENGTH: 19
<212> TYPE: DNA
<213> ORGANISM: Homo sapiens

<400> SEQUENCE: 1730
agtacaaaga ttcagccca                                          19

<210> SEQ ID NO 1731
<211> LENGTH: 19
<212> TYPE: DNA
<213> ORGANISM: Homo sapiens

<400> SEQUENCE: 1731
gtacaaagat tcagcccag                                          19

<210> SEQ ID NO 1732
<211> LENGTH: 19
<212> TYPE: DNA
<213> ORGANISM: Homo sapiens

<400> SEQUENCE: 1732
agattcagcc cagagggat                                          19

<210> SEQ ID NO 1733
<211> LENGTH: 19
<212> TYPE: DNA
<213> ORGANISM: Homo sapiens

<400> SEQUENCE: 1733
gattcagccc agagggatg                                          19

<210> SEQ ID NO 1734
<211> LENGTH: 19
<212> TYPE: DNA
<213> ORGANISM: Homo sapiens

<400> SEQUENCE: 1734
gattgtggcg atgtgccca                                          19

<210> SEQ ID NO 1735
<211> LENGTH: 19
<212> TYPE: DNA
<213> ORGANISM: Homo sapiens

<400> SEQUENCE: 1735
ccgaaagaac gaggagact                                          19

<210> SEQ ID NO 1736
<211> LENGTH: 19
<212> TYPE: DNA
<213> ORGANISM: Homo sapiens

```
<400> SEQUENCE: 1736
agaacgagga gactttaat                                              19

<210> SEQ ID NO 1737
<211> LENGTH: 19
<212> TYPE: DNA
<213> ORGANISM: Homo sapiens

<400> SEQUENCE: 1737
gaacgaggag actttaatc                                              19

<210> SEQ ID NO 1738
<211> LENGTH: 19
<212> TYPE: DNA
<213> ORGANISM: Homo sapiens

<400> SEQUENCE: 1738
cgaggagact taatcatg                                               19

<210> SEQ ID NO 1739
<211> LENGTH: 19
<212> TYPE: DNA
<213> ORGANISM: Homo sapiens

<400> SEQUENCE: 1739
tcatgaacga ggagagcga                                              19

<210> SEQ ID NO 1740
<211> LENGTH: 19
<212> TYPE: DNA
<213> ORGANISM: Homo sapiens

<400> SEQUENCE: 1740
cgaggagagc gaaaggtct                                              19

<210> SEQ ID NO 1741
<211> LENGTH: 19
<212> TYPE: DNA
<213> ORGANISM: Homo sapiens

<400> SEQUENCE: 1741
aggtctgcag attcaagct                                              19

<210> SEQ ID NO 1742
<211> LENGTH: 19
<212> TYPE: DNA
<213> ORGANISM: Homo sapiens

<400> SEQUENCE: 1742
ggtctgcaga ttcaagctt                                              19

<210> SEQ ID NO 1743
<211> LENGTH: 19
<212> TYPE: DNA
<213> ORGANISM: Homo sapiens

<400> SEQUENCE: 1743
gcttgaatgg ctgggaaat                                              19

<210> SEQ ID NO 1744
<211> LENGTH: 19
<212> TYPE: DNA
<213> ORGANISM: Homo sapiens
```

```
<400> SEQUENCE: 1744
tggctgggaa attgctctg                                          19

<210> SEQ ID NO 1745
<211> LENGTH: 19
<212> TYPE: DNA
<213> ORGANISM: Homo sapiens

<400> SEQUENCE: 1745
tgatgaaact tatggctac                                          19

<210> SEQ ID NO 1746
<211> LENGTH: 19
<212> TYPE: DNA
<213> ORGANISM: Homo sapiens

<400> SEQUENCE: 1746
acttatggct acaaagagg                                          19

<210> SEQ ID NO 1747
<211> LENGTH: 19
<212> TYPE: DNA
<213> ORGANISM: Homo sapiens

<400> SEQUENCE: 1747
cttatggcta caaagaggg                                          19

<210> SEQ ID NO 1748
<211> LENGTH: 19
<212> TYPE: DNA
<213> ORGANISM: Homo sapiens

<400> SEQUENCE: 1748
agagggcaaa ccgtgcatt                                          19

<210> SEQ ID NO 1749
<211> LENGTH: 19
<212> TYPE: DNA
<213> ORGANISM: Homo sapiens

<400> SEQUENCE: 1749
gagggcaaac cgtgcatta                                          19

<210> SEQ ID NO 1750
<211> LENGTH: 19
<212> TYPE: DNA
<213> ORGANISM: Homo sapiens

<400> SEQUENCE: 1750
ccgtgcatta ttataaagc                                          19

<210> SEQ ID NO 1751
<211> LENGTH: 19
<212> TYPE: DNA
<213> ORGANISM: Homo sapiens

<400> SEQUENCE: 1751
agctcaaccg agttctagg                                          19

<210> SEQ ID NO 1752
<211> LENGTH: 19
<212> TYPE: DNA
<213> ORGANISM: Homo sapiens
```

```
<400> SEQUENCE: 1752
gctcaaccga gttctaggc                                              19

<210> SEQ ID NO 1753
<211> LENGTH: 19
<212> TYPE: DNA
<213> ORGANISM: Homo sapiens

<400> SEQUENCE: 1753
ccgagttcta ggcttcaaa                                              19

<210> SEQ ID NO 1754
<211> LENGTH: 19
<212> TYPE: DNA
<213> ORGANISM: Homo sapiens

<400> SEQUENCE: 1754
acctaagcct cccaagaat                                              19

<210> SEQ ID NO 1755
<211> LENGTH: 19
<212> TYPE: DNA
<213> ORGANISM: Homo sapiens

<400> SEQUENCE: 1755
cctaagcctc ccaagaatg                                              19

<210> SEQ ID NO 1756
<211> LENGTH: 19
<212> TYPE: DNA
<213> ORGANISM: Homo sapiens

<400> SEQUENCE: 1756
gcctcccaag aatgagtcc                                              19

<210> SEQ ID NO 1757
<211> LENGTH: 19
<212> TYPE: DNA
<213> ORGANISM: Homo sapiens

<400> SEQUENCE: 1757
gaatgagtcc ttggagact                                              19

<210> SEQ ID NO 1758
<211> LENGTH: 19
<212> TYPE: DNA
<213> ORGANISM: Homo sapiens

<400> SEQUENCE: 1758
tgagtccttg gagacttac                                              19

<210> SEQ ID NO 1759
<211> LENGTH: 19
<212> TYPE: DNA
<213> ORGANISM: Homo sapiens

<400> SEQUENCE: 1759
gtataaccca aatgtcctt                                              19

<210> SEQ ID NO 1760
<211> LENGTH: 19
<212> TYPE: DNA
<213> ORGANISM: Homo sapiens
```

```
<400> SEQUENCE: 1760
cccaaatgtc cttcccgtt                                                19

<210> SEQ ID NO 1761
<211> LENGTH: 19
<212> TYPE: DNA
<213> ORGANISM: Homo sapiens

<400> SEQUENCE: 1761
atgtccttcc cgttcagtg                                                19

<210> SEQ ID NO 1762
<211> LENGTH: 19
<212> TYPE: DNA
<213> ORGANISM: Homo sapiens

<400> SEQUENCE: 1762
tgtccttccc gttcagtgc                                                19

<210> SEQ ID NO 1763
<211> LENGTH: 19
<212> TYPE: DNA
<213> ORGANISM: Homo sapiens

<400> SEQUENCE: 1763
gcgagatgaa gataaggat                                                19

<210> SEQ ID NO 1764
<211> LENGTH: 19
<212> TYPE: DNA
<213> ORGANISM: Homo sapiens

<400> SEQUENCE: 1764
ggataaagtt ggaaatgtg                                                19

<210> SEQ ID NO 1765
<211> LENGTH: 19
<212> TYPE: DNA
<213> ORGANISM: Homo sapiens

<400> SEQUENCE: 1765
agttggaaat gtggagtat                                                19

<210> SEQ ID NO 1766
<211> LENGTH: 19
<212> TYPE: DNA
<213> ORGANISM: Homo sapiens

<400> SEQUENCE: 1766
gttggaaatg tggagtatt                                                19

<210> SEQ ID NO 1767
<211> LENGTH: 19
<212> TYPE: DNA
<213> ORGANISM: Homo sapiens

<400> SEQUENCE: 1767
atgtggagta ttttggact                                                19

<210> SEQ ID NO 1768
<211> LENGTH: 19
<212> TYPE: DNA
<213> ORGANISM: Homo sapiens
```

```
<400> SEQUENCE: 1768
tgtggagtat tttggactg                                                19

<210> SEQ ID NO 1769
<211> LENGTH: 19
<212> TYPE: DNA
<213> ORGANISM: Homo sapiens

<400> SEQUENCE: 1769
ctcccctggt tttcctctg                                                19

<210> SEQ ID NO 1770
<211> LENGTH: 19
<212> TYPE: DNA
<213> ORGANISM: Homo sapiens

<400> SEQUENCE: 1770
actcctgcag cccaaatac                                                19

<210> SEQ ID NO 1771
<211> LENGTH: 19
<212> TYPE: DNA
<213> ORGANISM: Homo sapiens

<400> SEQUENCE: 1771
ctcctgcagc ccaaatacc                                                19

<210> SEQ ID NO 1772
<211> LENGTH: 19
<212> TYPE: DNA
<213> ORGANISM: Homo sapiens

<400> SEQUENCE: 1772
atacctgcag cccctgctg                                                19

<210> SEQ ID NO 1773
<211> LENGTH: 19
<212> TYPE: DNA
<213> ORGANISM: Homo sapiens

<400> SEQUENCE: 1773
tcttaccatg gacactgaa                                                19

<210> SEQ ID NO 1774
<211> LENGTH: 19
<212> TYPE: DNA
<213> ORGANISM: Homo sapiens

<400> SEQUENCE: 1774
attcgcatag agtgtaagg                                                19

<210> SEQ ID NO 1775
<211> LENGTH: 19
<212> TYPE: DNA
<213> ORGANISM: Homo sapiens

<400> SEQUENCE: 1775
ttcgcataga gtgtaaggc                                                19

<210> SEQ ID NO 1776
<211> LENGTH: 19
<212> TYPE: DNA
<213> ORGANISM: Homo sapiens
```

```
<400> SEQUENCE: 1776
ggcgtacggt gagaacatt                                                   19

<210> SEQ ID NO 1777
<211> LENGTH: 19
<212> TYPE: DNA
<213> ORGANISM: Homo sapiens

<400> SEQUENCE: 1777
cattgggtac agtgagaaa                                                   19

<210> SEQ ID NO 1778
<211> LENGTH: 19
<212> TYPE: DNA
<213> ORGANISM: Homo sapiens

<400> SEQUENCE: 1778
agaccgtttt cagggacgt                                                   19

<210> SEQ ID NO 1779
<211> LENGTH: 19
<212> TYPE: DNA
<213> ORGANISM: Homo sapiens

<400> SEQUENCE: 1779
gaccgttttc agggacgtt                                                   19

<210> SEQ ID NO 1780
<211> LENGTH: 19
<212> TYPE: DNA
<213> ORGANISM: Homo sapiens

<400> SEQUENCE: 1780
ttgaagttaa gagctgatc                                                   19

<210> SEQ ID NO 1781
<211> LENGTH: 19
<212> TYPE: DNA
<213> ORGANISM: Homo sapiens

<400> SEQUENCE: 1781
gatggtcatc cagaaagag                                                   19

<210> SEQ ID NO 1782
<211> LENGTH: 19
<212> TYPE: DNA
<213> ORGANISM: Homo sapiens

<400> SEQUENCE: 1782
agagaagaag agctgcggg                                                   19

<210> SEQ ID NO 1783
<211> LENGTH: 19
<212> TYPE: DNA
<213> ORGANISM: Homo sapiens

<400> SEQUENCE: 1783
gagaagaaga gctgcgggc                                                   19

<210> SEQ ID NO 1784
<211> LENGTH: 19
<212> TYPE: DNA
<213> ORGANISM: Homo sapiens
```

```
<400> SEQUENCE: 1784
ggagttcgtg tggaacccg                                              19

<210> SEQ ID NO 1785
<211> LENGTH: 19
<212> TYPE: DNA
<213> ORGANISM: Homo sapiens

<400> SEQUENCE: 1785
cccgaggacg caccagttt                                              19

<210> SEQ ID NO 1786
<211> LENGTH: 19
<212> TYPE: DNA
<213> ORGANISM: Homo sapiens

<400> SEQUENCE: 1786
gactgagaac cttgatgtc                                              19

<210> SEQ ID NO 1787
<211> LENGTH: 19
<212> TYPE: DNA
<213> ORGANISM: Homo sapiens

<400> SEQUENCE: 1787
ccttgatgtc attgtcaat                                              19

<210> SEQ ID NO 1788
<211> LENGTH: 19
<212> TYPE: DNA
<213> ORGANISM: Homo sapiens

<400> SEQUENCE: 1788
tgtcagtgac actgaaagc                                              19

<210> SEQ ID NO 1789
<211> LENGTH: 19
<212> TYPE: DNA
<213> ORGANISM: Homo sapiens

<400> SEQUENCE: 1789
agctgggacc agcatgttc                                              19

<210> SEQ ID NO 1790
<211> LENGTH: 19
<212> TYPE: DNA
<213> ORGANISM: Homo sapiens

<400> SEQUENCE: 1790
gctgggacca gcatgttca                                              19

<210> SEQ ID NO 1791
<211> LENGTH: 19
<212> TYPE: DNA
<213> ORGANISM: Homo sapiens

<400> SEQUENCE: 1791
gctcaacaag ttcttggag                                              19

<210> SEQ ID NO 1792
<211> LENGTH: 19
<212> TYPE: DNA
<213> ORGANISM: Homo sapiens
```

```
<400> SEQUENCE: 1792
caagttcttg gagccttac                                              19

<210> SEQ ID NO 1793
<211> LENGTH: 19
<212> TYPE: DNA
<213> ORGANISM: Homo sapiens

<400> SEQUENCE: 1793
gttcttggag ccttacaac                                              19

<210> SEQ ID NO 1794
<211> LENGTH: 19
<212> TYPE: DNA
<213> ORGANISM: Homo sapiens

<400> SEQUENCE: 1794
cgactctatc caagcccaa                                              19

<210> SEQ ID NO 1795
<211> LENGTH: 19
<212> TYPE: DNA
<213> ORGANISM: Homo sapiens

<400> SEQUENCE: 1795
gcccaaaaga atgatgtct                                              19

<210> SEQ ID NO 1796
<211> LENGTH: 19
<212> TYPE: DNA
<213> ORGANISM: Homo sapiens

<400> SEQUENCE: 1796
aagaatgatg tctgccgcc                                              19

<210> SEQ ID NO 1797
<211> LENGTH: 19
<212> TYPE: DNA
<213> ORGANISM: Homo sapiens

<400> SEQUENCE: 1797
agaatgatgt ctgccgccc                                              19

<210> SEQ ID NO 1798
<211> LENGTH: 19
<212> TYPE: DNA
<213> ORGANISM: Homo sapiens

<400> SEQUENCE: 1798
gaatgatgtc tgccgccct                                              19

<210> SEQ ID NO 1799
<211> LENGTH: 19
<212> TYPE: DNA
<213> ORGANISM: Homo sapiens

<400> SEQUENCE: 1799
cagccagata atggagtcc                                              19

<210> SEQ ID NO 1800
<211> LENGTH: 19
<212> TYPE: DNA
<213> ORGANISM: Homo sapiens
```

```
<400> SEQUENCE: 1800
tggagtcctc aactacccc                                                19

<210> SEQ ID NO 1801
<211> LENGTH: 19
<212> TYPE: DNA
<213> ORGANISM: Homo sapiens

<400> SEQUENCE: 1801
ctaccccaaa cgtgcctgc                                                19

<210> SEQ ID NO 1802
<211> LENGTH: 19
<212> TYPE: DNA
<213> ORGANISM: Homo sapiens

<400> SEQUENCE: 1802
acgtgcctgc caattcaac                                                19

<210> SEQ ID NO 1803
<211> LENGTH: 19
<212> TYPE: DNA
<213> ORGANISM: Homo sapiens

<400> SEQUENCE: 1803
cgtgcctgcc aattcaacc                                                19

<210> SEQ ID NO 1804
<211> LENGTH: 19
<212> TYPE: DNA
<213> ORGANISM: Homo sapiens

<400> SEQUENCE: 1804
ttcaaccgga cccagctgg                                                19

<210> SEQ ID NO 1805
<211> LENGTH: 19
<212> TYPE: DNA
<213> ORGANISM: Homo sapiens

<400> SEQUENCE: 1805
gatgaaccgg gtcatcaac                                                19

<210> SEQ ID NO 1806
<211> LENGTH: 19
<212> TYPE: DNA
<213> ORGANISM: Homo sapiens

<400> SEQUENCE: 1806
ccgggtcatc aacttctat                                                19

<210> SEQ ID NO 1807
<211> LENGTH: 19
<212> TYPE: DNA
<213> ORGANISM: Homo sapiens

<400> SEQUENCE: 1807
cttctatgca ggagcaaac                                                19

<210> SEQ ID NO 1808
<211> LENGTH: 19
<212> TYPE: DNA
<213> ORGANISM: Homo sapiens
```

```
<400> SEQUENCE: 1808
accagagcat gaatgttac                                              19

<210> SEQ ID NO 1809
<211> LENGTH: 19
<212> TYPE: DNA
<213> ORGANISM: Homo sapiens

<400> SEQUENCE: 1809
ccagagcatg aatgttacc                                              19

<210> SEQ ID NO 1810
<211> LENGTH: 19
<212> TYPE: DNA
<213> ORGANISM: Homo sapiens

<400> SEQUENCE: 1810
tgttacctgt gctgggaag                                              19

<210> SEQ ID NO 1811
<211> LENGTH: 19
<212> TYPE: DNA
<213> ORGANISM: Homo sapiens

<400> SEQUENCE: 1811
gcgagatgaa gatgctgag                                              19

<210> SEQ ID NO 1812
<211> LENGTH: 19
<212> TYPE: DNA
<213> ORGANISM: Homo sapiens

<400> SEQUENCE: 1812
gatgctgaga atctcggca                                              19

<210> SEQ ID NO 1813
<211> LENGTH: 19
<212> TYPE: DNA
<213> ORGANISM: Homo sapiens

<400> SEQUENCE: 1813
tctcggcaac ttcgtcatg                                              19

<210> SEQ ID NO 1814
<211> LENGTH: 19
<212> TYPE: DNA
<213> ORGANISM: Homo sapiens

<400> SEQUENCE: 1814
cttcgtcatg ttccccgcc                                              19

<210> SEQ ID NO 1815
<211> LENGTH: 19
<212> TYPE: DNA
<213> ORGANISM: Homo sapiens

<400> SEQUENCE: 1815
cggcaacatc gacctcatg                                              19

<210> SEQ ID NO 1816
<211> LENGTH: 19
<212> TYPE: DNA
<213> ORGANISM: Homo sapiens
```

<400> SEQUENCE: 1816
catcgacctc atgtacttc                                              19

<210> SEQ ID NO 1817
<211> LENGTH: 19
<212> TYPE: DNA
<213> ORGANISM: Homo sapiens

<400> SEQUENCE: 1817
aaagttccac gtgaactac                                              19

<210> SEQ ID NO 1818
<211> LENGTH: 19
<212> TYPE: DNA
<213> ORGANISM: Homo sapiens

<400> SEQUENCE: 1818
aagttccacg tgaactaca                                              19

<210> SEQ ID NO 1819
<211> LENGTH: 19
<212> TYPE: DNA
<213> ORGANISM: Homo sapiens

<400> SEQUENCE: 1819
agttccacgt gaactacac                                              19

<210> SEQ ID NO 1820
<211> LENGTH: 19
<212> TYPE: DNA
<213> ORGANISM: Homo sapiens

<400> SEQUENCE: 1820
gttccacgtg aactacaca                                              19

<210> SEQ ID NO 1821
<211> LENGTH: 19
<212> TYPE: DNA
<213> ORGANISM: Homo sapiens

<400> SEQUENCE: 1821
ctacacacag cccctggtg                                              19

<210> SEQ ID NO 1822
<211> LENGTH: 19
<212> TYPE: DNA
<213> ORGANISM: Homo sapiens

<400> SEQUENCE: 1822
gttcctgaat gtgaccccc                                              19

<210> SEQ ID NO 1823
<211> LENGTH: 19
<212> TYPE: DNA
<213> ORGANISM: Homo sapiens

<400> SEQUENCE: 1823
tgtgaccccc aacgtggag                                              19

<210> SEQ ID NO 1824
<211> LENGTH: 19
<212> TYPE: DNA
<213> ORGANISM: Homo sapiens

```
<400> SEQUENCE: 1824
cgtggaggtg aatgtagaa                                                19

<210> SEQ ID NO 1825
<211> LENGTH: 19
<212> TYPE: DNA
<213> ORGANISM: Homo sapiens

<400> SEQUENCE: 1825
tgtagaatgt cgcatcaac                                                19

<210> SEQ ID NO 1826
<211> LENGTH: 19
<212> TYPE: DNA
<213> ORGANISM: Homo sapiens

<400> SEQUENCE: 1826
tgtcgcatca acgccgcca                                                19

<210> SEQ ID NO 1827
<211> LENGTH: 19
<212> TYPE: DNA
<213> ORGANISM: Homo sapiens

<400> SEQUENCE: 1827
catcgccaca gacgatgag                                                19

<210> SEQ ID NO 1828
<211> LENGTH: 19
<212> TYPE: DNA
<213> ORGANISM: Homo sapiens

<400> SEQUENCE: 1828
actccgcatc aacaaaacc                                                19

<210> SEQ ID NO 1829
<211> LENGTH: 19
<212> TYPE: DNA
<213> ORGANISM: Homo sapiens

<400> SEQUENCE: 1829
ctccgcatca acaaaacct                                                19
```

TREATMENT OF EYE DISORDERS CHARACTERIZED BY AN ELEVATED INTRAOCULAR PRESSURE BY SIRNAS

FIELD OF THE INVENTION

The present invention relates to methods and compositions for the treatment of eye disorders; in particular but not exclusively to the treatment of glaucoma. In preferred embodiments, the invention relates to the use of RNAI technology to downregulate the expression of aqueous formation genes and aqueous outflow genes. Methods and compositions for the treatment of eye disorders are also provided.

BACKGROUND OF THE INVENTION

RNAI as a Tool to Downregulate Gene Expression

Gene targeting by homologous recombination is commonly used to determine gene function in mammals, but this is a costly and time-consuming process. Alternatively, the functions of many genes can be determined after mRNA inhibition with ribozyme or antisense technologies, Although successful in some situations these technologies have been difficult to apply universally. The advent of siRNA-directed "knockdown" has sparked a revolution In somatic cell genetics, allowing the inexpensive and rapid analysis of gene function in mammals.

Establishing a convenient and reliable method to knockout gene expression at the mRNA level has been a recurrent theme in molecular biology over the last 15 years. In efforts to generate loss-of function cells or organisms, various molecules that included, for example, antisense sequences, ribozymes, and chimeric oligonucleotides have been tested, but the design of such molecules was based on trial and error, depending on the properties of the target gene.

Moreover, the desired effects were difficult to predict, and often only weak suppression achieved (Braasch & Corey, 2002).

After the discovery of the phenomenon in plants in the early 1990s, in 1998 Andy Fire and Craig Mello for the first time demonstrated with the worm *Caenorhabditis elegans* that dsRNA (double-stranded RNA) may specifically and selectively inhibit gene expression in an extremely efficient manner (Fire et al., 1998). In their experiment, the sequence of the first strand (the so-called sense RNA) coincides with that of the corresponding region of the target messenger RNA (mRNA). The second strand (antisense RNA) is complementary to this mRNA. The resulting dsRNA turned out to be far more (several orders of magnitude) efficient than the corresponding single-stranded RNA molecules (in particular, antisense RNA). Fire et al., 1998 named the phenomenon RNAi for RNA interference. This powerful gene silencing mechanism has been shown to operate in several species among most phylogenetic phyla.

RNAi begins when an enzyme named DICER encounters dsRNA and chops it into pieces called small-interfering RNAs or siRNAs. This protein belongs to the RNase III nuclease family. A complex of proteins gathers up these RNA remains and uses their code as a guide to search out and destroy any RNAs in the cell with a matching sequence, such as target mRNA (for review see Bosher & Labouesse, 2000).

The RNAi phenomenon (Akashi et al., 2001) might be summarized as follows:
  Step 1: dsRNA recognition and scanning process.
  Step 2: dsRNA cleavage through RNase III activity and production of siRNAs.
  Step 3: association of the siRNAs and associated factors in RISC complexes.
  Step 4: recognition of the complementary target mRNA.
  Step 5: cleavage of the target mRNA in the centre of the region complementary to the siRNA.
  Step 6: degradation of the target mRNA and recycling of the RISC complex.

In trying to apply the RNAI phenomenon as a technology for gene knockdown, it was soon realized that mammalian cells have developed various protective phenomena against viral infections that could impede the use of this approach. Indeed, the presence of extremely low levels of viral dsRNA triggers an interferon response, resulting in a global non-specific suppression of translation, which in turn triggers apoptosis (Williams, 1997, Gil & Esteban, 2000).

In 2000, a first attempt with dsRNA resulted in the specific inhibition of 3 genes (MmGFP under the control of the Elongation Factor 1a, E-cadherin, and c-mos) in the mouse oocyte and early embryo. Translational arrest, and thus a PKR response, was not observed as the embryos continued to develop (Wianny & Zernicka-Goetz, 2000). One year later, research at Ribopharma AG (Kulmbach, Germany) first demonstrated the functionality of RNAi in mammalian cells. Using short (20-24 base pairs) dsRNAs—which are called SIRPLEX™—they specifically switched off genes even in human cells without initiating the acute-phase response. Similar experiments carried out later by other research groups (Elbashir et al., 2001; Caplen et al., 2001) further confirmed these results.

A year later, Paddison et. al. (Paddison et al, 2002) tried to use small RNAs folded in hairpin structures to inhibit the function of specific genes. This work was inspired by previous studies showing that some genes in *Caenorhabditis elegans* naturally regulate other genes through RNAi by coding for hairpin-structured RNAs. Tested in a variety of normal and cancer human and mouse cell lines, short hairpin RNAs (shRNAs) are able to silence genes as efficiently as their siRNA counterparts. Moreover, shRNAs exhibit better reassociation kinetics in vivo than equivalent duplexes. Even more important, these authors generated transgenic cell lines engineered to synthesize shRNAs that exhibit a long-lasting suppressing effect throughout cell divisions (Eurogentec). Recently, another group of small RNAs (also comprised in the range of 21-25 nt) was shown to mediate downregulation of gene expression. These RNAs, known as small temporally regulated RNAs (stRNAs), have been described in *Caenorhabditis elegans* were they regulate timing of gene expression during development. It should be noted that stRNAs and siRNAs, despite obvious similarities, proceed through different modes of action (for review see Banedjee & Slack, 2002. In contrast with siRNAs, 22 nt long stRNAs downregulate expression of target mRNA after translational initiation without affecting mRNA integrity. Recent studies indicate that the two stRNAs first described in nematodes are the members of a huge family with hundreds of additional micro-RNAs (miRNAs) existing in metazoans (Grosshans & Slack, 2002).

Scientists have initially used RNAi in several systems, including *Caenorhabditis elegans,* Drosophilia, trypanosomes, and various other invertebrates. Moreover, using this approach, several groups have recently presented the specific suppression of protein biosynthesis in different mammalian cell lines—specifically in HeLa cells—showing that RNAi is a broadly applicable method for gene silencing in vitro. Based on these results, RNAi has rapidly become a well recognized tool for validating (identifying and assigning) gene functions.

RNA interference employing short dsRNA oligonucleotides will, moreover, permit to decipher the function of genes being only partially sequenced. RNAi will therefore become inevitable in studies such as:

Inhibition of gene expression at the post-transcriptional level in eukaryotic cells. In this context, RNAi is a straight-forward tool to rapidly assess gene function and reveal null phenotypes.

Development of the RNAi technology for use in post-implantation embryos.

The predominant economic significance of RNA interference is established by its application as a therapeutic principle. As so, RNAi may yield RNA-based drugs to treat human diseases.

Glaucoma

Glaucoma is one of the leading causes of blindness, Approximately 15% of cases of blindness world-wide result from glaucoma. The most common type, primary open-angle glaucoma, has a prevalence of 1/200 in the general population over 40 years of age.

Glaucoma has been simply defined as the process of ocular tissue destruction caused by a sustained elevation of the Intra Ocular Pressure (IOP) above its normal physiological limits.

It is becoming increasingly clear that many forms of glaucoma have a genetic component, and much current research is focused on identifying chromosomal regions and genes that contribute to glaucoma. It is likely that the aetiology of OAG is multifactorial, resulting from a combination of mutations in more than one gene and as yet unidentified environmental factors. With regard to juvenile and adult-onset OAG, several loci have been identified. However, only one gene is known, namely the myocilin/TIGR (trabecular meshwork inducible glucocorticoid response) gene at the GLC1A locus on chromosome 1q21-q31. More than thirty mutations of this gene have been identified in ethnically diverse populations worldwide. Studies have shown that it is responsible for only about 5% of OAG overall (See reviews in Wirtz & Samples, 2003, and Khaw et al, 2004a).

Pathogenesis

Most glaucomas are characterised by an elevated IOP, although the level of elevation may vary. In those glaucomas in which the elevation is initially low (i.e., open angle glaucoma, melanocytic glaucoma) and some secondary glaucoma, retinal ganglion cell and optic nerve damage are slow to progress. In angle-closure glaucoma the sudden high rise in IOP often renders the eye blind, undoubtedly primarily due to a cessation of axoplasmic flow at the level of the lamina cribrosa.

In human studies, it has been widely accepted that tissue ischaemia has a part to play in the initiation or progression of the optic disc damage that occurs in glaucoma. Retinal ganglion cell degeneration may be necrosis, but the possibility that it is apoptosis triggered by the rise in IOP is plausible, and the respective roles of nitric oxide and glutamate are thought to be relevant during progression of the disease (For a recent review on the subject see Osborne et al, 2003).

Treatment

Although several aetiologies are involved in the glaucoma complex, the absolute determinant in therapy selection is the amount of primary and/or induced change in pressure within the iridocorneal angle.

Current therapies include medications or surgeries aimed at lowering this pressure, although the pathophysiological mechanisms by which elevated IOP leads to neuronal damage in glaucoma are unknown.

Medical suppression of an elevated IOP can be attempted using four types of drugs: the aqueous formation suppressors (among them, carbonic anhydrase inhibitors, beta-adrenergic blocking agents, or alpha2-adrenoreceptor agonists) miotics (i.e. parasympathomimetics—cholinergics-, or anticholinesterase inhibitors); uveoscleral outflow enhancers; and the hyperosmotic agents (that produce an osmotic pressure gradient across the blood/aqueous barrier within the ciliary epithelium). All four are used in the treatment of glaucoma, the first three commonly as emergency treatment and in long term control while the hyperosmotic agents are invaluable as emergency and preoperative treatment. A fifth category of drugs, the neuroprotection agents, is beginning to emerge as an important possible addition to medical therapy. Indeed, observation that the NOS and glutamate levels are elevated in glaucoma and that they are involved in retinal ganglion cell necrosis or apoptosis has raised the possibility of neuroprotective therapies and even neuroregeneration. Thus NOS inhibitors, exciting amino acid antagonists, glutamate receptor antagonists, apoptosis inhibitors and calcium channel blockers are all potential candidates in the development of future glaucoma therapies. The calcium channel blockers may reduce the effect of impaired microcirculation to the optic nerve head whilst potentially increasing outflow facility at the level of the trabecular cells.

Reviews of various eye disorders and their treatments are given in the references, in particular in Bunce (2005), Costagliola (1995, 2000), Cullinane (2002), Sakaguchi (2002), Shah (2000), and Wang (2005).

Currently our existing therapies must fall short of the mark and the practical difficulties associated with the assessment of outflow facility, the accurate monitoring of therapy and the complexity of surgical techniques all combine to confound the prognosis. The overriding factor in all glaucoma is the degeneration of the retinal ganglion cell, thus neuroprotection through effective ocular hypotension is the essential requirement of any therapy we utilise (for a recent review on the subject, see Khaw et al 2004b).

BRIEF SUMMARY OF THE INVENTION

In the present invention we describe a method for the treatment of eye conditions characterised by an altered IOP in animals, including humans. In particular, the eye conditions may Include glaucoma, uveitis, and inflammation. The method is based on the downregulation of expression of genes involved in aqueous formation or aqueous outflow in the eye. Downregulation may be effected by the use of double stranded nucleic acid moieties, named siNA or small interfering NA that are directed at interfering with the mRNA expression of various candidate genes. The siNA are preferably siRNA, although modified nucleic acids or similar chemically synthesised entities are also included within the scope of the invention.

Preferred embodiments of the invention relate to topical application of siNA. Embodiments of the invention also provide pharmaceutical compositions for use in the treatment of eye conditions. The invention may be used within the fields of local eye treatments, of target genes involved in glaucoma pathogenesis, as well as the use of chemically synthesized entities to treat animal (including humans) diseases.

In addition to the treatment of glaucoma, the present method is also suitable for the treatment of other diseases of the anterior chamber of the eye. In particular, the method may be applied to the treatment of diseases characterised by altered aqueous formation or outflow in the eye. Examples of conditions which may be treated include local conditions such as infections or inflammations, and general conditions such as uveitis or expression of systemic diseases. Further, certain embodiments of the invention provide treatment for diabetic retinopathy.

BRIEF DESCRIPTION OF THE DRAWINGS

FIG. 1 shows GenBank Accession Numbers corresponding to selected human target genes.

FIG. 2 shows selected oligonucleotide sequences against which RNAi is directed.

DETAILED DESCRIPTION OF THE INVENTION

Target Genes

Figure 3:
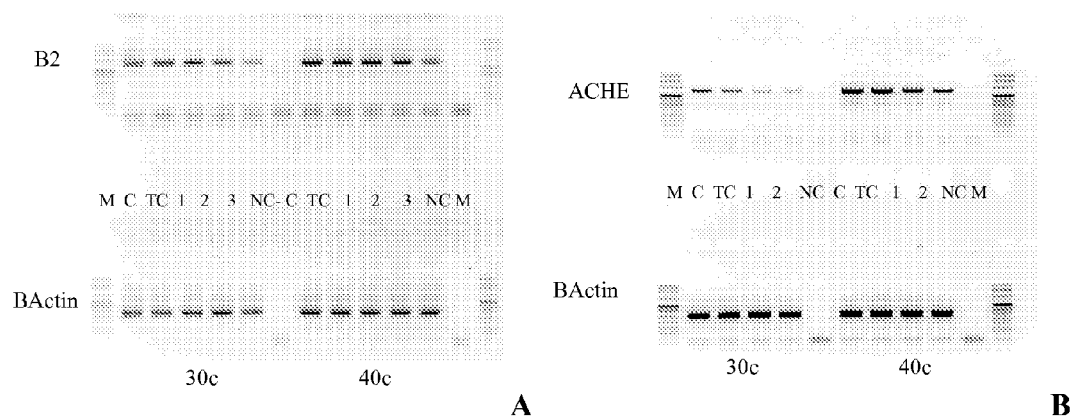
FIG. 3 shows representative semiquantitative gels demonstrating the effects of siRNAs on target genes of the invention.

In the present invention, we define a list of target genes, whose expression levels may alter IOP. These genes can fall within the groups of genes involved in aqueous formation or the group of genes involved in aqueous outflow. Here is a list of our target genes:
  Carbonic Anhydrases II, IV and XII
  Adrenergic Receptors: beta1 and 2 and alpha 1A, 1B and 1D
  Acetylcholinesterase
  Cyclooxygenases 1 and 2
  ATPases: alpha1, alpha2, alpha3, beta1, beta2
  Endothelial Leukocyte Adhesion Molecule I (ELAM-1)
  Angiotensin System: Angiotensin II, Angiotensin II Converting Enzymes (ACE I and ACE II), Angiotensin II Receptors (ATR1 and ATR2) and Renin
  Cochlin Design of siNA Although the mechanisms for RNAi remain unknown, the steps required to generate the specific dsRNA oligonucleotides are clear. It has been shown that dsRNA duplex strands that are 21-26 nucleotides in length work most effectively in producing RNA interference. Selecting the right homologous region within the gene is also important. Factors such as the distance from start codon, the G/C content and the location of adenosine dimers are important when considering the generation of dsRNA for RNAi. One consequence of this, however, is that one may need to test several different sequences for the most efficient RNAi and this may become costly.

In 1999, Tuschl et al. deciphered the silencing effect of siRNAs showing that their efficiency is a function of the length of the duplex, the length of the 3'-end overhangs, and the sequence in these overhangs. Based on this founder work, Eurogentec recommends that the target mRNA region, and hence the sequence of the siRNA duplex, should be chosen using the following guidelines:
  Since RNAi relies on the establishment of complex protein interactions, it is obvious that the mRNA target should be devoided of unrelated bound factors. In this context, both the 5' and 3' untranslated regions (UTRs) and regions close to the start codon should be avoided as they may be richer in regulatory protein binding sites. The sequence of the siRNA is therefore selected as follows:
  In the mRNA sequence, a region located 50 to 100 nt downstream of the AUG start codon or upstream of stop codon is selected.
  In this region, the following sequences are searched for: AA(N19), CA(N19).
  The G/C percentage for each identified sequence is calculated. Ideally, the G/C content is 50% but it must less than 70% and greater than 30%.
  Preferably, sequences containing following repetitions are avoided: AAA, CCC, GGG, TTT, AAAA, CCCC, GGGG, TTTT.
  An accessibility prediction according to the secondary structure of the mRNA is carried out as well.
  A BLAST is also performed (i.e. NCBI ESrs database) with the nucleotide sequence fitting best the previous criteria to ensure that only one gene will be inactivated.
  In order to maximize the result's interpretation, the following precautions should be taken when using siRNAs:
  Always test the sense and antisense single strands in separate experiments.
  Try a scramble siRNA duplex. This should have the same nucleotide composition as your siRNA but lack significant sequence homology to any other gene (including yours).
  If possible, knock-down the same gene with two independent siRNA duplexes to control the specificity of the silencing process.

Practically, each of the selected genes is introduced as a nucleotide sequence in a prediction program that takes into account all the variables described above for the design of optimal oligonucleotides. This program scans any mRNA nucleotide sequence for regions susceptible to be targeted by siRNAs. The output of this analysis is a score of possible siRNA oligonucleotides. The highest scores are used to design double stranded RNA oligonucleotides (typically 21 bp long, although other lengths are also possible) that are typically made by chemical synthesis.

In addition to siRNA, modified nucleotides may also be used. We plan to test several chemical modifications that are well known in the art. These modifications are aimed at increasing stability or availability of the siNA. Examples of suitable modifications are described in the publications referenced below, each of which is incorporated herein by reference.

Studies show that replacing the 3'-terminal nucleotide overhanging segments of a 21-mer siRNA duplex having two -nucleotide 3'-overhangs with deoxyribonucleotides does not have an adverse effect on RNAi activity. Replacing up to four nucleotides on each end of the siRNA with deoxyribonucleotides has been reported to be well tolerated, whereas complete substitution with deoxyribonucleotides results in no RNAi activity (Elbashir 2001). In addition, Elbashir et al. also report that substitution of siRNA with 2'-O-methyl nucleotides completely abolishes RNAi activity.

Affinity modified nucleosides as described in WO2005/044976 may be used. This publication describes oligonucleotides comprising nucleosides modified so as to have increased or decreased affinity for their complementary nucleotide in the target mRNA and/or in the complementary siNA strand.

GB2406568 describes alternative modified oligonucleotides chemically modified to provide improved resistance to degradation or improved uptake. Examples of such modifications include phosphorothioate internucleotide linkages, 2'-O-methyl ribonucleotides, 2'-deoxy-fluoro ribonucleotides, 2'-deoxy ribonucleotides, "universal base" nucleotides, 5-C-methyl nucleotides, and inverted deoxyabasic residue incorporation.

WO2004/029212 describes oligonucleotides modified to enhance the stability of the siRNA or to increase targeting efficiency. Modifications include chemical cross linking between the two complementary strands of an siRNA and chemical modification of a 3' terminus of a strand of an siRNA. Preferred modifications are internal modifications, for example, sugar modifications, nucleobase modifications and/or backbone modifications. 2'-fluoro modified ribonucleotides and 2'-deoxy ribonucleotides are described.

WO2005/040537 further recites modified oligonucleotides which may be used in the invention.

As well as making use of dsNA and modified dsNA, the present invention may use short hairpin NA (shNA); the two strands of the siNA molecule may be connected by a linker region, which may be a nucleotide linker or a non-nucleotide linker.

In addition to siNA which is perfectly complementary to the target region, degenerate siNA sequences may be used to target homologous regions. WO2005/045037 describes the design of siNA molecules to target such homologous sequences, for example by incorporating non-canonical base pairs, for example mismatches and/or wobble base pairs, that can provide additional target sequences. In instances where mismatches are identified, non-canonical base pairs (for example, mismatches and/or wobble bases) can be used to generate siNA molecules that target more than one gene sequence. In a non-limiting example, non-canonical base pairs such as UU and CC base pairs are used to generate siNA molecules that are capable of targeting sequences for differing targets that share sequence homology. As such, one advantage of using siNAs of the invention is that a single siNA can be designed to include nucleic acid sequence that is complementary to the nucleotide sequence that is conserved between homologous genes. In this approach, a single siNA can be used to inhibit expression of more than one gene instead of using more than one siNA molecule to target different genes.

Preferred siNA molecules of the invention are double stranded. A siNA molecule of the invention may comprise blunt ends, that is, ends that do not include any overhanging nucleotides. In one embodiment, an siNA molecule of the invention can comprise one or more blunt ends. In preferred embodiments, the siNA molecules have 3' overhangs. siNA molecules of the invention may comprise duplex nucleic acid molecules with 3' overhangs of n nucleotides ($5 \geq n \geq 1$). Elbashir (2001) shows that 21-nucleotide siRNA duplexes are most active when containing 3'-terminal dinucleotide overhangs.

Candidate oligonucleotides are further filtered for interspecies sequence conservation in order to facilitate the transition from animal to human clinical studies. In preferred embodiments of the invention, conserved oligonucleotides are used; this allows a single oligonucleotide sequence to be used in both animal models and human clinical trials.

GenBank Accession Numbers corresponding to our selected human target genes are shown in FIG. 1. In some of these genes, alternative splicing produces a family of transcripts that differ in exon content. The present invention allows individual targeting of each transcript form.

Selected oligonucleotide sequences against which RNAi is directed are shown in FIGS. 2A-2R. Displayed sequences are the DNA sequences targeted by the siNA. Therefore, the invention would make use of NA duplexes with sequences complementary to the indicated DNA sequences.

The sequences shown in FIGS. 2A-2R are not limiting. As a matter of fact, target DNA need not necessarily be preceded by AA or CA. Further, target DNA could be constituted by sequences included in FIGS. 2A-2R flanked by any contiguous sequence.

In vitro and Animal Studies
Obtaining siRNA Duplexes
RNAs are preferably chemically synthesized using appropriately protected ribonucleoside phosphoramidites and a conventional DNA/RNA synthesizer. Substitution of one or both strands of a siRNA duplex by 2'-deoxy or 2'-O-methyl oligoribonucleotides abolished silencing in fly extract (Elbashir et al. 2001). In mammalian cells, however, it seems possible to substitute the sense siRNA by a 2'-O-methyl oligoribonucleotide (Ge et al. 2003).

Most conveniently, siRNAs are obtained from commercial RNA oligo synthesis suppliers, which sell RNA-synthesis products of different quality and costs. In general, 21-nt RNAs are not too difficult to synthesize and are readily provided in a quality suitable for RNAi.

Suppliers of RNA synthesis reagents include Proligo (Hamburg, Germany), Dharmacon Research (Lafayette, Col., USA), Glen Research (Sterling, Va., USA), ChemGenes (Ashland, Mass., USA), and Cruachem (Glasgow, UK), Qiagen (Germany), Ambion (USA) and Invitrogen (Scotland). The previous custom RNA synthesis companies are entitled to provide siRNAs with a license for target validation. In particular, our siRNA suppliers are Ambion, Dharmacon and Invitrogen, companies that offer the traditional custom chemical synthesis service for siRNA, and supply the siRNA with HPLC purification and delivered in dry form along with RNase-free water. A central web-based resource for RNAi and siRNA methodologies, along with links to additional siRNA related products and services, can be found on the website of above-mentioned suppliers.

An annealing step is necessary when working with single-stranded RNA molecules. It is critical that all handling steps be conducted under sterile, Rnase free conditions. To anneal the RNAs, the oligos must first be quantified by UV absorption at 260 nanometers (nm). The following protocol based on Elbashir et al. (2001) is then used for annealing:

Separately aliquot and dilute each RNA oligo to a concentration of 50 µM.

Combine 30 µl of each RNA oligo solution and 15 µl of 5× annealing buffer. Final buffer concentration is: 100 mM potassium acetate, 30 mM HEPES-KOH pH 7.4, 2 mM magnesium acetate. Final volume is 75 µl.

Incubate the solution for 1 minute at 90° C., centrifuge the tube for 15 seconds, let sit for 1 hour at 37° C., then use at ambient temperature. The solution can be stored frozen at −20° C. and freeze-thawed up to 5 times. The final concentration of siRNA duplex is usually 20 µM.

Alternatively, already annealed dsRNAs may be purchased from the suppliers.

Chemically modified nucleic acids may also be used. For example, an overview of the types of modification which may be used is given in WO03/070744, the contents of which are incorporated herein by reference. Particular attention is drawn to pages 11 to 21 of this publication. Other possible modifications are as described above. The skilled person will be aware of other types of chemical modification which may be incorporated into RNA molecules.

In vitro System

To check the specificity of the siRNA interference different cell cultures that express the target genes were employed. The cells used for these experiments were: rabbit non-pigmented ciliary epithelium cells NPE, human ciliary epithelium cells OMDC, and human embryonic kidney cells HEK293. The cells are incubated with the corresponding siRNA duplexes, and analysis of the downregulation of expression of the target gene is carried out. For linking siRNA knockdown to specific phenotypes in cultured cells, it is necessary to demonstrate the reduction of targeted protein or at least demonstrate the reduction of the targeted mRNA.

mRNA levels of the target gene can be quantitated by real-time quantitative PCR (RT-PCR). Further, the protein levels can be determined in a variety of ways well known in the art, such as Western blot analysis with specific antibodies to the different target allow direct monitoring of the reduction of targeted protein.

Transfection of siRNA Duplexes

Several examples of techniques well known in the art are as follows: We can perform a single transfection of siRNA duplex using a cationic lipid, such as RNAiFect Transfection Reagent (Qiagen) and Lipofectamine 2000 Reagent (Invitrogen) and assay for silencing 24, 48 and 72 hours after transfection.

A typical transfection protocol can be performed as follows: For one well of a 6-well plate, we transfect using 100 nM as final concentration of siRNA. Following RNAiFect protocol, we seed, the day before transfection, $2-4\times10^5$ cells per well in 3 ml of an appropriate growth medium, containing DMEM, 10% serum, antibiotics and glutamine, and incubate cells under normal growth conditions (37° C. and 5% $CO_2$). On the day of transfection, cells have to be at 30-50% confluence. We dilute 15 ul of 20 uM siRNA duplex (corresponding to 100 nM final concentration) in 85 ul of Buffer EC-R, to give a final volume of 100 ul, and mix by vortexing. For complex formation, we add 19 ul of RNAiFect Transfection Reagent to the diluted siRNA and mix by pipetting or vortexing. After incubating the samples for 10-15 minutes at room temperature to allow formation of transfection complexes, we add the complexes drop-wise onto the cells with 2.9 ml of fresh growth medium low in antibiotics. After swirling the plates to ensure uniform distribution of the transfection complexes, we incubate the cells under their normal growth conditions. The day after, the complexes are removed and fresh and complete growth medium is added. To monitor gene silencing, cells are collected at 24, 48 and 72 hours post-transfection. The Lipofectamine 2000 Reagent protocol is quite similar. The day before transfection, we seed $2-4\times10^5$ cells per well in 3 ml of an appropriate growth medium, containing DMEM, 10% serum, antibiotics and glutamine, and incubate cells under normal growth conditions (37° C. and 5% $CO_2$). On the day of transfection, cells have to be at 30-50% confluence. We dilute 12.5 ul of 20 uM siRNA duplex (corresponding to 100 nM final concentration) in 250 ul of DMEM, to give a final volume of 262.5 ul, and mix. Also, 6 ul of Lipofectamine 2000 is diluted in 250 ul of DMEM and mixed. After a 5 minutes incubation at room temperature, the diluted oligomer and the diluted Lipofectamine are combined to allow complex formation during a 20 minutes incubation at room temperature. Afterwards, we add the complexes drop-wise onto the cells with 2 ml of fresh growth medium low in antibiotics and mix gently by rocking the plate back and forth, to ensure uniform distribution of the transfection complexes. We incubate the cells under their normal growth conditions and the day after, the complexes are removed and fresh and complete growth medium is added. To monitor gene silencing, cells are collected at 24, 48 and 72 hours post-transfection.

The efficiency of transfection may depend on the cell type, but also on the passage number and the confluency of the cells. The time and the manner of formation of siRNA-liposome complexes (e.g. inversion versus vortexing) are also critical. Low transfection efficiencies are the most frequent cause of unsuccessful silencing. Good transfection is a non-trivial issue and needs to be carefully examined for each new cell line to be used. Transfection efficiency may be tested transfecting reporter genes, for example a CMV-driven EGFP-expression plasmid (e.g. from Clontech) or a B-Gal expression plasmid, and then assessed by phase contrast and/or fluorescence microscopy the next day.

Testing of siRNA Duplexes

Depending on the abundance and the life time (or turnover) of the targeted protein, a knock-down phenotype may become apparent after 1 to 3 days, or even later. In cases where no phenotype is observed, depletion of the protein may be observed by immunofluorescence or Western blotting.

After transfections, total RNA fractions extracted from cells were pre-treated with DNase I and used for reverse transcribed using a random primer. PCR is amplified with a specific primer pair covering at least one exon-exon junction in order to control for amplification of pre-mRNAs. RT/PCR of a non-targeted mRNA is also needed as control. Effective depletion of the mRNA yet undetectable reduction of target protein may indicate that a large reservoir of stable protein may exist in the cell. Alternatively, RealTime PCR amplification can be used to test in a more precise way the mRNA decrease or disappearance. Real-time reverse-transcriptase (RT) PCR quantitates the initial amount of the template most specifically, sensitively and reproducibly. Real-time PCR monitors the fluorescence emitted during the reaction as an indicator of amplicon production during each PCR cycle. This signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template.

To verify the interference pattern of the differentially expressing genes identified in the cell cultures, qRT-PCR was performed according to the manufacturer protocol. For quantitative RT-PCR (qRT-PCR), approximately 250 ng of total RNA were used for reverse transcription followed by PCR amplification with specific primers for each gene in reaction mixture containing Master SYBR Green I. Basic PCR conditions comprised an initial step of 30 minutes at 91° C., followed by 40 cyles of 5 s at 95° C., 10 s at 62° C. and 15 s at 72° C. Specific primer sequences corresponding to each target gene were used. Quantification of b-actin mRNA was used as a control for data normalization. Relative gene expression comparisons work best when the gene expression of the chosen endogenous/internal control is more abundant and remains constant, in proportion to total RNA, among the samples. By using an invariant endogenous control as an active reference, quantitation of an mRNA target can be normalised for differences in the amount of total RNA added to each reaction.

Pharmaceutical Formulations

The present invention may comprise the administration of one or more species of siNA molecule simultaneously. These species may be selected to target one or more target genes.

The siNA molecules of the Invention and formulations or compositions thereof may be administered directly or topically (e.g., locally) to the eye as is generally known In the art. For example, a siNA molecule can comprise a delivery vehicle, including liposomes, for administration to a subject. Carriers and diluents and their salts can be present in pharmaceutically acceptable formulations. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins poly (lactic-co-glycolic) acid (PLGA) and PLCA microspheres, biodegradable nanocapsules, and bioadhesive microspheres, or by proteinaceous vectors. In another embodiment, the nucleic add molecules of the invention can also be formulated or complexed with polyethyleneimine and derivatives thereof, such as polyethylene-imine-polyethyleneglycol-N-acetylgalactosamine (PEI- PEG-GAL) or polyethyleneimine-polyethyleneglycol-tri-N-acetylgalactosamine (PEI-PEG-triGAL) derivatives.

A siNA molecule of the invention may be complexed with membrane disruptive agents and/or a cationic lipid or helper lipid molecule.

Delivery systems which may be used with the invention include, for example, aqueous and non aqueous gels, creams, multiple emulsions, microemulsions, liposomes, ointments, aqueous and non aqueous solutions, lotions, aerosols, hydrocarbon bases and powders, and can contain excipients such as solubilizers, permeation enhancers (e. g., fatty acids, fatty acid esters, fatty alcohols and amino acids), and hydrophilic polymers (e. g., polycarbophil and polyvinylpyrolidone). In one embodiment, the pharmaceutically acceptable carrier is a liposome or a transdermal enhancer.

A pharmaceutical formulation of the invention is in a form suitable for administration, e.g., systemic or local administration, into a cell or subject, including for example a human. Suitable forms, in part, depend upon the use or the route of entry, for example oral, transdermal, or by injection. Other factors are known in the art, and include considerations such as toxicity and forms that prevent the composition or formulation from exerting its effect.

The present invention also includes compositions prepared for storage or administration that include a pharmaceutically effective amount of the desired compounds in a pharmaceutically acceptable carrier or diluent. Acceptable carriers or diluents for therapeutic use are well known in the pharmaceutical art. For example, preservatives, stabilizers, dyes and flavouring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose dependes on the type of disease, the composition used, the route of administration, the type of mammal being treated, the physical characteristics of the specific mammal under consideration, concurrent medication, and other factors that those skilled in the medical arts will recognize Generally, an amount between 0.1 mg/kg and 100 mg/kg body weight/day of active ingredients is administered.

The formulations of the invention can be administered in dosage unit formulations containing conventional non-toxic pharmaceutically acceptable carriers, adjuvants and/or vehicles. Formulations can be in a form suitable for oral use, for example, as tablets, troches, lozenges, aqueous or oily suspensions, dispersible powders or granules, emulsion, hard or soft capsules, or syrups or elixirs. Compositions intended for oral use can be prepared according to any method known to the art for the manufacture of pharmaceutical compositions and such compositions can contain one or more such sweetening agents, flavouring agents, colouring agents or preservative agents in order to provide pharmaceutically elegant and palatable preparations. Tablets contain the active ingredient in admixture with non-toxic pharmaceutically acceptable excipients that are suitable for the manufacture of tablets.

These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules wherein the active ingredient is mixed with an inert solid diluent, for example, calcium carbonate, caldum phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more colouring agents, one or more flavouring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavouring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavouring and colouring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavouring agents.

Syrups and elixirs can be formulated with sweetening agents, for example glycerol, propylene glycol, sorbitol, glucose or sucrose. Such formulations can also contain a demulcent, a preservative and flavouring and colouring agents. The pharmaceutical compositions can be in the form of a sterile injectable aqueous or oleaginous suspension.

This suspension can be formulated according to the known art using those suitable dispersing or wetting agents and suspending agents that have been mentioned above.

A sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The nucleic acid molecules of the invention can also be administered in the form of suppositories, e. g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

Alternatively, certain siNA molecules of the invention can be expressed within cells from eukaryotic promoters. Recombinant vectors capable of expressing the siNA molecules can be delivered and persist in target cells. Alternatively, vectors can be used that provide for transient expression of nucleic add molecules. Such vectors can be repeatedly administered as necessary. Once expressed, the siNA molecule interacts with the target mRNA and generates an RNAi response. Delivery of siNA molecule expressing vectors can be systemic, such as by intravenous or intramuscular administration, by administration to target cells ex-planted from a subject followed by reintroduction into the subject, or by any other means that would allow for introduction into the desired target cell.

Animal Studies

The New Zealand rabbit is the gold standard in experimental platforms designed to study IOP. It is easy to handle and it has a big eye, similar in size to the human organ. In addition, present equipment to measure IOP is not suited to use in animals with small eyes such as mice or rats. Finally, rabbits have an IOP (around 23 mm Hg) that can be brought down to up to 40% its value using local commercial hypotensive medication. Thus, although it is possible to generate rabbit glaucoma models (for example, surgically blocking episclerotic veins or artificially occluding the trabecular meshwork), we have used normotensive rabbits since, in our hands, the pharmacological decrease in IOP can be easily and reproducibly measured.

Experimental Protocol

Normotensive New Zealand White rabbits (males, 2-3 kg) were used. The animals were kept in individual cages with free access to food and water. They were submitted to artificial 12 hours light/darkness cycles, to avoid uncontrolled circadian oscillations of IOP Animal handling and treatment were carried out in accordance with the European Communities Council Directive (86/609/EEC) and the statement of the Association for Research in Vision and Ophthalmology on the Use of Animals in Ophthalmic and Vision Research.

The drugs were typically administered by instilling a small volume (typically 40 μL) on the corneal surface. Contralateral eyes were treated with the vehicle alone and could be used as controls in each experiment lest there is a sympathy phenomenon with the other eye. Multiple experiments in the same animal should be abolished.

IOP measurements were done using a contact tonometer (TONOPEN XL, Mentor, Norwell, Mass.). The TonoPen tonometer is very convenient due to its reliability and small size. Measurements with this instrument were performed delicately applying the tonometer's sensor to the corneal surface. This device has been shown to be the tonometer of choice for measuring intraocular pressures within the range of 3 to 30 mm Hg in rabbits (Abrams et al., 1996). All measurements fell within this interval: the mean baseline value of intraocular pressure was $17.0 \pm 0.39$ mm Hg (n=100). Because IOP changes from the night to day, all the experiments were performed at the same time to allow IOP more stable and permit an objective comparison with vehicle treatment. In order to avoid distress to the animal, rabbits were topically anesthetized (oxibuprocaine/tetracaine, 0.4%/1%, in a saline solution (1/4 v:v). The solution was applied (10 μl) to the cornea before each measurement of intraocular pressure was made. siRNA or saline was applied topically to the cornea in volumes of 40 μl.

The standard protocol for the siRNA application in rabbit was as follows. Doses of siRNA in saline solution (0.9% w/v) to a final volume of 40 ul, were applied to one eye each day during four consecutive days. The opposite eye was taken as a control and 40 ul of sterile saline (0.9% w/v) were instilled on it, at the same time points. The IOP was measured before each application and at 2 h, 4 h and 6 h following the instillation, during 10 days. Maximum responses were observed between second and third day. To compare the effect of siRNA with other hypotensive compounds, Xalatan (latanoprost 0.005%) and Trustop (Dorzolamide 2%) were assayed and IOP measured in the same conditions.

Results

EXAMPLE 1

In vitro Assays

To determine the inhibition of the different targets involved in glaucoma using RNAi technology, the first step was to perform experiments in cell cultures. For each target, several siRNAs were designed using a specific software according to the rules described before. Those with the best characteristics were selected to be tested. The siRNAs were applied to cell cultures, such as NPE, OMDC and HEK293. The effect of siRNAs over the target gene was analyzed by real time PCR and semi-quantitative PCR according to standard protocols. The gene target transcript levels were normalized using actin as housekeeping gene. Table I below shows representative results of real time PCR experiments for some of the target genes described previously. The values represent the mean of the percentage of siRNA interference over each gene expression once normalized with the control cells and their standard deviations. Compared to the control cells, the level of the different transcripts at both 24 and 48 h time points was significantly reduced after the siRNA treatment. In the Table are included some of the different siRNAs that were tested and their different efficacies in the interference of the target gene. The siRNAs used in the Table correspond to the listed human siRNA targets given in FIGS. 2A-2R as follows.

AC2:
siRNA1: rabbit sequence homologous to human SEQ. ID. 73
siRNA2: rabbit sequence identical to human SEQ. ID. 54
siRNA3: rabbit sequence identical to human SEQ. ID. 66

PTGS1
siRNA1: rabbit sequence homologous to human SEQ. ID. 353
siRNA2: rabbit sequence homologous to human SEQ. ID. 369

PTGS2
siRNA1: rabbit sequence identical to human SEQ. ID. 426
siRNA2: rabbit sequence homologous to human SEQ. ID. 421
siRNA3: rabbit sequence homologous to human SEQ. ID. 477

TABLE I siRNA treatment reduces the levels or target gene transcripts. RNA was prepared from cells treated with different siRNAs for 24 and 48 h. The samples were analyzed by real time PCR using specific primers. The values show the mean expression levels of different transcripts normalized to actin relative to cell control.

| Target | | % of gene transcript level | |
|---|---|---|---|
| | | 24 h | 48 h |
| AC2 | siRNA1 | 76.25 ± 12.60 | 84.57 ± 14.70 |
| | siRNA2 | 37.97 ± 9.78 | 61.45 ± 9.62 |
| | siRNA3 | 35.30 ± 9.73 | 51.14 ± 16.49 |
| PTGS1 | siRNA1 | 42.25 ± 13.76 | 42.68 ± 17.00 |
| | siRNA2 | 34.98 ± 14.33 | 26.30 ± 10.91 |
| PTGS2 | siRNA1 | 68.68 ± 12.48 | 70.17 ± 19.21 |
| | siRNA2 | 81.00 ± 13.54 | 66.85 ± 18.67 |
| | siRNA3 | 75.45 ± 14.71 | 61.83 ± 16.96 |

FIG. 3 shows some representative semi-quantitative gels for some of the targets described above. The decrease of the gene expression for each target gene depends on the efficiency in siRNA silencing. For each target, the most effective siRNA obtained by in vitro studies was administered to the animal model. RNA was prepared from cells treated with different siRNAs. The samples were analyzed by semi-quantitative PCR using specific primers. The figure shows a representative semi-quantitative gel for Beta Adrenergic Receptor 2 expression (A) and other for Acetylcholinesterase expression (B). M: MW Marker; C: Control cells; TC: Transfection Control; 1: siRNA1; 2: siRNA2; 3: siRNA3; NC: Negative Control. The expression levels for each target depends on the efficiency in siRNA silencing. The siRNAs used in the Figure correspond to the human targets given in FIGS. 2A-2R as follows:

Panel A (Beta Adrenergic Receptor 2)
1: rabbit sequence homologous to human SEQ. ID. 122
2: rabbit sequence identical to human SEQ. ID. 125
3: rabbit sequence homologous to human SEQ. ID. 139

Panel B (Acetyicholinesterase)
1: rabbit sequence homologous to human SEQ. ID. 162
2: rabbit sequence homologous to human SEQ. ID. 177

EXAMPLE 2

In vivo Assays

Previously to the siRNA therapeutical application, the in vivo assays were validated to determine the proper siRNA delivery.

Those siRNAs selected by the in vitro assays were applied to the animal model, following the protocol previously described. To avoid the effect of IOP fluctuations due to circadian cycles, all the applications were performed at the same time. To determine the siRNA effect, intraocular pressures (IOPs) were measured as previously mentioned.

Since glaucoma pathology presents an increase in the intraocular pressure, the aim was to obtain a decrease in its levels following siRNA application.

Most of the results for the different targets showed a significant decrease in IOP levels comparing with controls and also with commercial drugs (Latanoprost and Dorzolamide) and the animals treated with vehicle alone (negative control) didn't present any significant change in their IOP baseline. The data are summarized in table II where values represent the mean of the maximum percentage of IOP reduction after siRNA treatment once normalized and their standard deviations. The decrease in IOP was statistically significant for all the treated targets. These results indicate that siRNAs and commercial drugs act in a similar way, reducing IOP levels around 20%, although siRNAs present a more maintained effect. No secondary effects were observed in the animals along the experimental protocols. The siRNAs used in these experiments correspond to the human targets given in FIGS. 2A-2R as follows:

AC2: rabbit sequence homologous to human SEQ. ID. 73
AC4: rabbit sequence identical to human SEQ. ID. 5
AC12: rabbit sequence identical to human SEQ. ID. 522
ADRB1: rabbit sequence identical to human SEQ. ID. 105
ADRB2: rabbit sequence homologous to human SEQ. ID. 139
ADRA1A: rabbit sequence homologous to human SEQ. ID. 546
ADRA1B: rabbit sequence homologous to human SEQ. ID. 619
ACHE: rabbit sequence homologous to human SEQ. ID. 189
PTGS1: rabbit sequence homologous to human SEQ. ID. 322
PTGS2: rabbit sequence identical to human SEQ. ID. 426
SELE: rabbit sequence homologous to human SEQ. ID. 262
ACE1: rabbit sequence homologous to human SEQ. ID. 866
10 AGTR1: rabbit sequence homologous to human SEQ. ID. 705
AGTR2: rabbit sequence identical to human SEQ. ID. 774
ATP1A1: rabbit sequence identical to human SEQ. ID. 1399
ATP1B2: rabbit sequence identical to human SEQ. ID. 1820

TABLE II

Effect of siRNAs on the reduction of IOP in normotensive New Zealand rabbit. The values represent the mean of the percentage of IOP reduction over the control (contralateral eye with vehicle alone) and their standard error (SEM).

| Target | IOP reduction (% of the control) |
|---|---|
| AC2 | 24.84 ± 3.41 |
| AC4 | 14.47 ± 5.00 |
| AC12 | 24.30 ± 1.29 |
| ADRB1 | 28.04 ± 2.98 |
| ADRB2 | 21.18 ± 1.88 |
| ADRA1A | 9.51 ± 1.04 |
| ADRA1B | 17.48 ± 1.30 |
| ACHE | 25.25 ± 2.70 |
| PTGS1 | 14.62 ± 1.93 |
| PTGS2 | 23.78 ± 2.27 |
| SELE | 21.80 ± 1.74 |
| ACE1 | 17.51 ± 1.28 |
| AGTR1 | 9.72 ± 1.35 |
| AGTR2 | 11.22 ± 1.53 |
| ATP1A1 | 18.13 ± 1.39 |
| ATP1B2 | 16.32 ± 0.91 |
| Latanoprost | 25.46 ± 5.24 |
| Dorzolamide | 16.41 ± 2.38 |

REFERENCES

Abrams L S, Vitale S, Jampel H D. Comparison of three tonometers for measuring intraocular pressure in rabbits. Invest Ophthalmol Vis Sci. 1996 April;37(5):940-4.

Akashi H, Miyagishi M, Taira K. Suppression of gene expression by RNA interference in cultured plant cells. Antisense Nucleic Acid Drug Dev, 2001, 11(6):359-67.

Banerjee D, Slack F. Control of developmental timing by small temporal RNAs: a paradigm for RNA-mediated regulation of gene expression. Bioessays, 2002, 24(2):119-29.

Bhattacharya S K, Annangudi S P, Salomon R G, Kuchtey R W, Peachey N S, Crabb J W. Cochlin deposits in the trabecular meshwork of the glaucomatous DBA/2J mouse. Exp Eye Res. 2005a May;80(5):741-4.

Bhattacharya S K, Rockwood E J, Smith S D, Bonilha V L, Crabb J S, Kuchtey R W, Robertson N G, Peachey N S, Morton C C, Crabb J W. Proteomics reveal Cochlin deposits associated with glaucomatous trabecular meshwork. J Biol Chem. 2005b Feb. 18;280(7):6080-4. Epub 2004 Dec. 3.

Bosher J M, Labouesse M. RNA interference: genetic wand and genetic watchdog. Nat Cell Biol, 2000, 2(2):E31-6.

Braasch D A, Corey D R. Novel antisense and peptide nucleic acid strategies for controlling gene expression. Biochemistry, 2002, 41(14):4503-10

Bunce C, Hitchings R A, Van Duijn C M, De Jong P T, Vingerling J R. Associations between the deletion polymorphism of the angiotensin 1-converting enzyme gene and ocular signs of primary open-angle glaucoma. Graefes Arch Clin Exp Ophthalmol. 2005 April; 243(4):294-9. Epub 2004 Oct. 13.

Caplen, N. J., Parrish, S., Imani, F., Fire, A. & Morgan, R. A. Specific inhibition of gene expression by small double stranded RNAs in invertebrate and vertebrate systems. Proc. Natl. Acad. Sci. USA, 2001, 98: 9742-9747.

Costagliola C, Verolino M, De Rosa M L, Iaccarino G, Ciancaglini M, Mastropasqua L. Effect of oral iosartan potassium administration on intraocular pressure in normotensive and glaucomatous human subjects. Exp Eye Res. 2000 August;71(2):167-71.

Costagliola C, Di Benedetto R. De Caprio L, Verde R, Mastropasqua L. Effect of oral captopril (SQ 14225) on intraocular pressure in man. Eur J Ophthalmol. 1995 January-March;5(1):19-25.

Cullinane A B, Leung P S, Ortego J, Coca-Prados M, Harvey B J. Renin-angiotensin system expression and secretory function in cultured human ciliary body non-pigmented epithelium. Br J Ophthalmol. 2002 June;86(6):676-83.

Elbashir S M, Lendeckel W, Tuschl T. RNA interference is mediated by 21- and 22-nucleotide RNAS. Genes Dev, 2001, 15(2):188-200.

Fire A, Xu S, Montgomery M K, Kostas S A, Driver S E, Mello C C. Potent and specific genetic interference by double stranded RNA in Caenorhabditis elegans. Nature, 1998, 391(6669):806-11.

Ge Q, McManus M T, Nguyen T, Shen C H, Sharp P A, Eisen H N, Chen J. RNA interference of influenza virus production by directly targeting mRNA for degradation and indirectly inhibiting all viral RNA transcription. Proc Natl Acad Sci USA., 2003; 100(5):2718-23.

Gil J, Esteban M. Induction of apoptosis by the dsRNA-dependent protein kinase (PKR): mechanism of action. Apoptosis, 2000, 5(2):107-14.

Grosshans H, Slack F J. Micro-RNAs: small is plentiful. J Cell Biol, 2002, 156(1):17-21.

Hara H, Ichikawa M, Oku H, Shimazawa M, Araie M. Bunazosin, a selective alpha1-adrenoceptor antagonist, as an anti-glaucoma drug: effects on ocular circulation and retinal neuronal damage. Cardiovasc Drug Rev. 2005 Spring;23(1):43-56.

Khaw P T, Shah P, Elkington A R. Glaucoma-1: diagnosis. BMJ, 2004a, 328:97-9.

Khaw P T, Shah P, Elkington A R. Glaucoma-2: treatment. BMJ, 2004b, 328:156-8.

Osborne N N, Chidlow G, Wood J, Casson R. Some current ideas on the pathogenesis and the role of neuroprotection in glaucomatous optic neuropathy. Eur J Ophthalmol. 2003 April; 13 Suppl 3:S19-26.

Paddison P J, Caudy A A, Bernstein E, Hannon G J, Conklin D S. Short hairpin RNAs (shRNAs) induce sequence-specific silencing in mammalian cells. Genes Dev, 2002, 16(8):948-58.

Sakaguchi H, Takai S, Sakaguchi M, Sugiyama T, Ishihara T, Yao Y, Miyazaki M, Ikeda T. Chymase and angiotensin converting enzyme activities in a hamster model of glaucoma filtering surgery. Curr Eye Res, 2002 May;24(5):325-31.

Shah G B, Sharma S, Mehta A A, Goyal R K. Oculohypotensive effect of angiotensin-converting enzyme inhibitors in acute and chronic models of glaucoma. J Cardiovasc Pharmacol. 2000 August;36(2):169-75.

Tuschl T, Zamore P D, Lehmann R, Bartel D P, Sharp P A. Targeted mRNA degradation by double-stranded RNA in vitro. Genes Dev., 1999; 13(24):3191-7.

Wang R F, Podos S M, Mittag T W, Yokoyoma T. Effect of CS-088, an angiotensin AT1 receptor antagonist, on intraocular pressure in glaucomatous monkey eyes. Exp Eye Res. 2005 May;80(5):629-32. Epub 2005 Jan. 4.

Wianny F, Zernicka-Goetz M. Specific interference with gene function by double-stranded RNA in early mouse development. Nat Cell Biol, 2000, 2(2):70-5.

Williams B R. Role of the double-stranded RNA-activated protein kinase (PKR) in cell regulation. Biochem Soc Trans, 1997, 25(2):509-13.

Wirtz M K, Samples J R. The genetic loci of open-angle glaucoma. Ophthalmol Clin North Am. 2003 16:505-14

The invention claimed is:

1. A method of treating an eye condition characterized by increased intra-ocular pressure (IOP), said method comprising topically administering to the corneal surface of the eye of a patient in need thereof a short interfering nucleic acid (siNA) molecule that downregulates expression in the eye of a target gene, the target gene being selected from aqueous formation genes and aqueous outflow genes.

2. The method of claim 1, wherein the eye condition is selected from the group consisting of glaucoma, infection, inflammation, and uveitis.

3. The method of claim 1, wherein the eye condition is glaucoma.

4. The method of claim 1, wherein the eye condition is diabetic retinopathy.

5. The method of claim 1, wherein the siNA is siRNA.

6. The method of claim 1, wherein said topically administering consists of instilling said siNA molecule on said corneal surface.

7. The method of claim 1, wherein said siNA molecule is unmodified.

* * * * *